(12) United States Patent
Kakitani et al.

(10) Patent No.: US 9,700,594 B2
(45) Date of Patent: Jul. 11, 2017

(54) PHARMACEUTICAL COMPOSITION FOR TREATING BONE DISEASES WHICH COMPRISES PROTEIN COMPRISING FRIZZLED1, FRIZZLED2 OR FRIZZLED7 EXTRACELLULAR CYSTEINE-RICH DOMAIN

(71) Applicant: KYOWA HAKKO KIRIN CO., LTD, Tokyo (JP)

(72) Inventors: Makoto Kakitani, Tokyo (JP); Kazuma Tomizuka, Tokyo (JP)

(73) Assignee: KYOWA HAKKO KIRIN CO., LTD, Tokyo (JP)

( * ) Notice: Subject to any disclaimer, the term of this patent is extended or adjusted under 35 U.S.C. 154(b) by 226 days.

(21) Appl. No.: 13/869,083

(22) Filed: Apr. 24, 2013

(65) Prior Publication Data

US 2013/0230520 A1 Sep. 5, 2013

Related U.S. Application Data

(62) Division of application No. 13/121,637, filed as application No. PCT/JP2009/066996 on Sep. 30, 2009, now abandoned.

(30) Foreign Application Priority Data

Sep. 30, 2008 (JP) ................................ 2008-255804
May 29, 2009 (JP) ................................ 2009-131449

(51) Int. Cl.
*A61K 38/17* (2006.01)
*A61K 38/18* (2006.01)
*A61P 19/08* (2006.01)
*A61K 31/70* (2006.01)
*A61K 45/06* (2006.01)
*C07K 14/71* (2006.01)
*A01K 67/027* (2006.01)
*A61K 47/48* (2006.01)
*C07K 14/72* (2006.01)
*A61K 31/7088* (2006.01)
*A61K 39/395* (2006.01)
*A61K 48/00* (2006.01)

(52) U.S. Cl.
CPC .......... *A61K 38/177* (2013.01); *A01K 67/027* (2013.01); *A01K 67/0271* (2013.01); *A61K 31/7088* (2013.01); *A61K 38/1709* (2013.01); *A61K 39/3955* (2013.01); *A61K 45/06* (2013.01); *A61K 47/48215* (2013.01); *A61K 47/48507* (2013.01); *C07K 14/723* (2013.01); *A01K 2207/12* (2013.01); *A01K 2207/30* (2013.01); *A01K 2217/072* (2013.01); *A01K 2227/105* (2013.01); *A01K 2267/035* (2013.01); *A61K 48/00* (2013.01); *C07K 2319/30* (2013.01)

(58) Field of Classification Search
None
See application file for complete search history.

(56) References Cited

U.S. PATENT DOCUMENTS

| 7,713,526 | B2 | 5/2010 | Rhee et al. | |
|---|---|---|---|---|
| 2003/0103986 | A1 | 6/2003 | Rixon et al. | |
| 2003/0165500 | A1* | 9/2003 | Rhee et al. | 424/143.1 |
| 2006/0034852 | A1 | 2/2006 | Rixon et al. | |
| 2006/0134109 | A1 | 6/2006 | Gaitanaris | |
| 2007/0072238 | A1 | 3/2007 | Bhat | |
| 2007/0117751 | A1* | 5/2007 | Gurney et al. | 514/12 |
| 2008/0299136 | A1 | 12/2008 | Ernst et al. | |
| 2009/0209006 | A1 | 8/2009 | Rixon et al. | |

FOREIGN PATENT DOCUMENTS

| JP | 2004535182 | 11/2004 |
|---|---|---|
| WO | 02094852 | 11/2002 |
| WO | 2008031009 | 3/2008 |
| WO | 2008031013 | 5/2008 |

OTHER PUBLICATIONS

Gross, et al. "TACI-Ig Neutralizes Molecules Critical for B Cell Development and Autoimmune Disease: Impaired B Cell Maturation in Mice Lacking BLyS", Immunity, 15:289-302 (2001).
Daroszewska et al., "Mechanisms of Disease: genetics of Paget's disease of bone and related disorders", Nature Clinical Practice Rheumatology, 2(5):270-277 (2006).
Tamai et al., "LDL-receptor-related proteins in Wnt signal transduction", Nature, 407:530-535 (2000).
Masiakowski et al., "The Wnt receptor CRD domain is also found in MuSK and related orphan receptor tyrosine kinases", Curr. biol., 8:R407 (1998).

(Continued)

Primary Examiner — Xiaozhen Xie
(74) Attorney, Agent, or Firm — Sughrue Mion, PLLC

(57) ABSTRACT

This invention relates to a pharmaceutical composition for treatment of a bone disease comprising, as an active ingredient, a protein comprising an extracellular cysteine-rich domain, which is from the Frizzled receptor selected from the group consisting of mammalian animal-derived Frizzled 1, Frizzled 2, and Frizzled 7 and has activity of increasing bone mass, bone density, and/or bone strength, or a mutant of such domain having sequence identity of 85% or higher to the amino acid sequence of the domain and having activity of increasing bone mass, bone density, and/or bone strength, or a vector comprising a nucleic acid encoding the protein.

13 Claims, 25 Drawing Sheets

(56) References Cited

OTHER PUBLICATIONS

Dann et al., "Insights into Wnt binding and signaling from the structures of two Frizzled cysteine-rich domains", *Nature*, 412:86-90 (2001).
Rawadi et al., "Wnt signaling pathway: a new target for the treatment of osteoporosis", Oncologic, Endocrine & Metabolic, *Expert Opinion Therapeutics Targets*, 9(5):1063-1077 (2005).
Semenov et al., "SOST is a ligand for LRP5/LRP6 and a Wnt Signaling Inhibitor", J. B. C., 280(29):26770-26775 (2005).
Li et al., "Targeted Deletion of the Sclerostin Gene in Mice Results in Increased Bone Formation and Bone Strength", *J. of Bone and Mineral Research*, 23(6):860-869 (2008).
Yaccoby, "Antibody-based inhibition of DKK1 suppresses tumor-induced bone resorption and multiple myeloma growth in vivo", Blood, 109:2106-2111 (2007).
Nakanishi et al., "Secreted Frizzled-related Protein 4 is a negative regulator of Peak BMD in SAMP6 Mice", J. of Bone and Mineral Research, 21:1713-1721 (2006).
Trevat et al., "Expression of Secreted Frizzled Related Protein 1, A Wnt Antagonists, in Brain, Kidney, and Skeleton in Dispensable for Normal Embryonic Development", J. Cell Physiol., 217:113-126 (2008).
Wang et al., "A Large family of Putative Transmembrane Receptors Homologous to the Product of the *Drosophila* Tissue Polarity Gene Frizzled" J. B. C., 271(8):4468-4476 (1996).
Huang et al., "The Frizzled family: receptors for multiple signal transduction pathways", Genome Biology, 5(234):1-7 (2004).
Wheeler et al., "Inducible gene expression in transgenic Xenopus embryos", Current Biology, 10:849-852 (2000).
Matsumoto et al., "Wnt9a secreted from the walls of hepatic sinusoids is essential for morphogenesis, proliferation, and glycogen accumulation of chick hepatic epithelium", Dev. Biol., 319(2):234-247 (2008).
Gregorieff et al., "Expression Pattern of Wnt Signaling Components in the Adult Intestine", Gastroenterology, 129:626-638 (2005).
Katoh et al., "Comparative integromics on FZD7 orthologs: Conserved binding sites for PU.1, SP1, CCAAT-box and TCF/LEF/SOX transcription factors within 5'-promoter region of mammalian FZD7 orthologs", Int. J. Mol. Med., 19:529-533 (2007).
Sagara et al., "Molecular Cloning, Differential Expression, and Chromosomal Localization of Human Frizzled-1, Frizzled-2, and Frizzled-7", Biochemical and Biophysical Research Communications, 252:117-122 (1998).
Kemp et al., "Expression of Frizzled5, Frizzled7, and Frizzled10 during early mouse development and Interactions with Canonical Wnt Signaling", Dev. Dynamics., 236:2011-2019 (2007).
Merle et al., "Oncogenic role of the Frizzled-7/β-catenin pathway in hepatocellular carcinoma", J. of Hepatology, 43(5):854-862 (2005).
Vincan et al., "Frizzled-7 Receptors ectodomain expression in a colon cancer cell line induces Morphological change and attenuates tumor growth", Differentiation, 73:142-153 (2005).
Chacon et al., "Frizzled-1 is involved in the Neuroprotective Effect of Wnt3a Against Aβ Oligomers", J. Cellular Physiology, 217:215-227 (2008).
Holcombe et al., "Expression of Wnt ligands and Frizzled receptors in colonic mucosa and in colon carcinoma", *Mol. Pathol.*, 55:220-226 (2006).
Milovanovic et al., "Expression of Wng genes and frizzled 1 and 2 receptors in normal breast epithelium and infiltrating breast carcinoma", *Int. J. Oncology*, 25:1337-1342 (2004).
Deltagen, Inc., "NIH initiative supporting placement of Deltagene, Inc. mice into public repositories" MGI Direct Data Submission 2005 (http://www.informatics.jax.org/javawi2/serylet/WIFetch?page=alleleDetail&key=40116), last database update Sep. 12, 2012.
European Communication for EP 09817788 dated Sep. 4, 2012, with Supplementary European Search Report dated Aug. 29, 2012.
International Search Report for PCT/JP2009/066996 dated Nov. 2, 2009.

* cited by examiner

SEQUENCE LISTING

<160> NUMBER OF SEQ ID NOS: 73

<210> SEQ ID NO 1
<211> LENGTH: 1719
<212> TYPE: DNA
<213> ORGANISM: Mus musculus

<400> SEQUENCE: 1

| | | | | | |
|---|---|---|---|---|---|
| atgcggggcc | ccggcacggc | ggcgtcgcac | tcgcccctgg | gcctctgcgc | cctggtgctt | 60 |
| gctcttctgt | gcgcgctgcc | cacggacacc | cgggctcagc | catatcacgg | cgagaaaggc | 120 |
| atctcggtac | cggaccacgg | cttctgccag | cccatctcca | tcccgttgtg | cacggatatc | 180 |
| gcctacaacc | agaccatcct | gcccaacctg | ctgggccaca | cgaaccaaga | ggacgcgggc | 240 |
| ctcgaggtgc | accagttcta | ccctctggta | aggtgcagt | gttctcctga | gctacgcttc | 300 |
| ttcttatgct | ctatgtacgc | acccgtgtgc | accgtgctcg | accaagccat | tcctccgtgc | 360 |
| cgttccttgt | gcgagcgcgc | ccgacagggc | tgcgaggcgc | tcatgaacaa | gttcggcttc | 420 |
| cagtggccag | agcggttgcg | ctgcgagaac | ttcccagtgc | acggtgccgg | cgagatctgc | 480 |
| gtggggcaga | cacgtccga | cggctcccggg | ggcgcgggcg | gcagtccac | cgcctaccct | 540 |
| actgctccct | acctgccaga | cccacctttc | actgcgatgt | cccctcaga | tggcagaggc | 600 |
| cgcttgtctt | tccccttctc | gtgtccgcgc | cagctcaagg | tgccccccta | cctgggctac | 660 |
| cgcttcctag | gtgagcgtga | ctgcggtgcc | ccgtgtgagc | cgggccgtgc | taacggcctc | 720 |
| atgtacttta | agaagagga | gagacggttc | gcccgcctct | gggtgggtgt | gtggtcagtg | 780 |
| ctgtgctgcg | cctcgacgct | cttcacggtg | ctcacctacc | tagtggacat | gcgtcgcttc | 840 |
| agctatccag | agcgacccat | catcttcctg | tcgggttgct | acttcatggt | ggcagtggcg | 900 |
| cacgtggcag | gcttcctgct | agaggaccgt | gccgtgtgcg | tggagcgctt | ctcggacgat | 960 |
| ggctaccgca | cggtggcgca | gggcaccaag | aaggagggct | gcaccatcct | cttcatggtg | 1020 |
| ctttacttct | tcggtatggc | cagctccatc | tggtgggtca | ttctgtccct | cacttggttc | 1080 |
| ctggcagctg | gcatgaagtg | gggccacgag | gccatcgagg | ccaactcgca | gtactttcat | 1140 |
| ctggccgcgt | gggctgtgcc | agcggtcaag | acaatcacca | ttttggccat | gggccaggtg | 1200 |
| gatggtgacc | tactcagtgg | agtgtgctac | gtgggcctgt | ctagtgtgga | tgcattgcgg | 1260 |
| ggcttcgtgc | tggcgccctt | gttcgtctac | ctcttcatcg | gacgtccttt | cctgttggcc | 1320 |
| ggctttgtgt | ctctctttcg | catccgcacc | atcatgaagc | acgacggcac | caagacagag | 1380 |
| aagctggaga | agctgatggt | gcgcatcggc | gtcttcagcg | tgctctacac | ggtgccggcc | 1440 |
| accatcgtgt | tggcctgcta | cttttatgag | caggccttcc | gagagcactg | ggaacgcacc | 1500 |
| tggctcctgc | agacttgcaa | gagctacgct | gtgccctgcc | ctccgggcca | cttctctccc | 1560 |
| atgagccccg | actttacagt | cttcatgatc | aagtacctga | tgaccatgat | cgtgggcatc | 1620 |
| actacgggct | tctggatctg | gtcgggcaag | accctgcagt | catggcgtcg | cttctaccac | 1680 |
| agactcagcc | acagcagcaa | gggggaaact | gcggtatga | | | 1719 |

<210> SEQ ID NO 2
<211> LENGTH: 572
<212> TYPE: PRT
<213> ORGANISM: Mus musculus

<400> SEQUENCE: 2

Met Arg Gly Pro Gly Thr Ala Ala Ser His Ser Pro Leu Gly Leu Cys
1               5                   10                  15

```
Ala Leu Val Leu Ala Leu Leu Cys Ala Leu Pro Thr Asp Thr Arg Ala
             20                  25                  30

Gln Pro Tyr His Gly Glu Lys Gly Ile Ser Val Pro Asp His Gly Phe
         35                  40                  45

Cys Gln Pro Ile Ser Ile Pro Leu Cys Thr Asp Ile Ala Tyr Asn Gln
     50                  55                  60

Thr Ile Leu Pro Asn Leu Leu Gly His Thr Asn Gln Glu Asp Ala Gly
 65                  70                  75                  80

Leu Glu Val His Gln Phe Tyr Pro Leu Val Lys Val Gln Cys Ser Pro
                 85                  90                  95

Glu Leu Arg Phe Phe Leu Cys Ser Met Tyr Ala Pro Val Cys Thr Val
             100                 105                 110

Leu Asp Gln Ala Ile Pro Pro Cys Arg Ser Leu Cys Glu Arg Ala Arg
         115                 120                 125

Gln Gly Cys Glu Ala Leu Met Asn Lys Phe Gly Phe Gln Trp Pro Glu
     130                 135                 140

Arg Leu Arg Cys Glu Asn Phe Pro Val His Gly Ala Gly Glu Ile Cys
145                 150                 155                 160

Val Gly Gln Asn Thr Ser Asp Gly Ser Gly Gly Ala Gly Gly Ser Pro
                 165                 170                 175

Thr Ala Tyr Pro Thr Ala Pro Tyr Leu Pro Asp Pro Pro Phe Thr Ala
             180                 185                 190

Met Ser Pro Ser Asp Gly Arg Gly Arg Leu Ser Phe Pro Phe Ser Cys
         195                 200                 205

Pro Arg Gln Leu Lys Val Pro Pro Tyr Leu Gly Tyr Arg Phe Leu Gly
     210                 215                 220

Glu Arg Asp Cys Gly Ala Pro Cys Glu Pro Gly Arg Ala Asn Gly Leu
225                 230                 235                 240

Met Tyr Phe Lys Glu Glu Arg Arg Phe Ala Arg Leu Trp Val Gly
                 245                 250                 255

Val Trp Ser Val Leu Cys Cys Ala Ser Thr Leu Phe Thr Val Leu Thr
             260                 265                 270

Tyr Leu Val Asp Met Arg Arg Phe Ser Tyr Pro Glu Arg Pro Ile Ile
         275                 280                 285

Phe Leu Ser Gly Cys Tyr Phe Met Val Ala Val Ala His Val Ala Gly
     290                 295                 300

Phe Leu Leu Glu Asp Arg Ala Val Cys Val Glu Arg Phe Ser Asp Asp
305                 310                 315                 320

Gly Tyr Arg Thr Val Ala Gln Gly Thr Lys Lys Glu Gly Cys Thr Ile
                 325                 330                 335

Leu Phe Met Val Leu Tyr Phe Phe Gly Met Ala Ser Ser Ile Trp Trp
             340                 345                 350

Val Ile Leu Ser Leu Thr Trp Phe Leu Ala Ala Gly Met Lys Trp Gly
         355                 360                 365

His Glu Ala Ile Glu Ala Asn Ser Gln Tyr Phe His Leu Ala Ala Trp
     370                 375                 380

Ala Val Pro Ala Val Lys Thr Ile Thr Ile Leu Ala Met Gly Gln Val
385                 390                 395                 400

Asp Gly Asp Leu Leu Ser Gly Val Cys Tyr Val Gly Leu Ser Ser Val
                 405                 410                 415

Asp Ala Leu Arg Gly Phe Val Leu Ala Pro Leu Phe Val Tyr Leu Phe
             420                 425                 430

Ile Gly Thr Ser Phe Leu Leu Ala Gly Phe Val Ser Leu Phe Arg Ile
```

```
                435                 440                 445
Arg Thr Ile Met Lys His Asp Gly Thr Lys Thr Glu Lys Leu Glu Lys
            450                 455                 460

Leu Met Val Arg Ile Gly Val Phe Ser Val Leu Tyr Thr Val Pro Ala
465                 470                 475                 480

Thr Ile Val Leu Ala Cys Tyr Phe Tyr Glu Gln Ala Phe Arg Glu His
                485                 490                 495

Trp Glu Arg Thr Trp Leu Leu Gln Thr Cys Lys Ser Tyr Ala Val Pro
            500                 505                 510

Cys Pro Pro Gly His Phe Ser Pro Met Ser Pro Asp Phe Thr Val Phe
        515                 520                 525

Met Ile Lys Tyr Leu Met Thr Met Ile Val Gly Ile Thr Thr Gly Phe
    530                 535                 540

Trp Ile Trp Ser Gly Lys Thr Leu Gln Ser Trp Arg Arg Phe Tyr His
545                 550                 555                 560

Arg Leu Ser His Ser Ser Lys Gly Glu Thr Ala Val
                565                 570
```

<210> SEQ ID NO 3
<211> LENGTH: 702
<212> TYPE: DNA
<213> ORGANISM: Artificial
<220> FEATURE:
<223> OTHER INFORMATION: human IgG1 Fc variant

<400> SEQUENCE: 3

```
gccgagccta ggtcttcaga caaaactcac acatgcccac cgtgcccagc acctgaagcc     60
gagggggccc cgtcagtctt cctcttcccc ccaaaaccca aggacaccct catgatctcc    120
cggacccctg aggtcacatg cgtggtggtg gacgtgagcc acgaagaccc tgaggtcaag    180
ttcaactggt acgtggacgg cgtggaggtg cataatgcca agacaaagcc gcgggaggag    240
cagtacaaca gcacgtaccg tgtggtcagc gtcctcaccg tcctgcacca ggactggctg    300
aatggcaagg agtacaagtg cgccgtctcc aacaaagccc tcccagcctc catcgagaaa    360
accatctcca aagccaaagg gcagcccgga gaaccacagg tgtacaccct gcccccatcc    420
cgggatgagc tgaccaagaa ccaggtcagc ctgacctgcc tggtcaaagg cttctatccc    480
agcgacatcg ccgtggagtg ggagagcaat gggcagccgg agaacaacta caagaccacg    540
cctcccgtgc tggactccga cggctccttc ttcctctaca gcaagctcac cgtggacaag    600
agcaggtggc agcaggggaa cgtcttctca tgctccgtga tgcatgaggc tctgcacaac    660
cactacacgc agaagagcct ctccctgtct ccgggtaaat ga                       702
```

<210> SEQ ID NO 4
<211> LENGTH: 233
<212> TYPE: PRT
<213> ORGANISM: Artificial
<220> FEATURE:
<223> OTHER INFORMATION: human IgG1 Fc variant

<400> SEQUENCE: 4

```
Ala Glu Pro Arg Ser Ser Asp Lys Thr His Thr Cys Pro Pro Cys Pro
1               5                   10                  15

Ala Pro Glu Ala Glu Gly Ala Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45
```

```
Val Val Asp Val Ser His Glu Asp Pro Glu Val Lys Phe Asn Trp Tyr
 50                  55                  60

Val Asp Gly Val Glu Val His Asn Ala Lys Thr Lys Pro Arg Glu Glu
 65                  70                  75                  80

Gln Tyr Asn Ser Thr Tyr Arg Val Val Ser Val Leu Thr Val Leu His
                 85                  90                  95

Gln Asp Trp Leu Asn Gly Lys Glu Tyr Lys Cys Ala Val Ser Asn Lys
            100                 105                 110

Ala Leu Pro Ala Ser Ile Glu Lys Thr Ile Ser Lys Ala Lys Gly Gln
            115                 120                 125

Pro Arg Glu Pro Gln Val Tyr Thr Leu Pro Pro Ser Arg Asp Glu Leu
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
            195                 200                 205

Phe Ser Cys Ser Val Met His Glu Ala Leu His Asn His Tyr Thr Gln
210                 215                 220

Lys Ser Leu Ser Leu Ser Pro Gly Lys
225                 230

<210> SEQ ID NO 5
<211> LENGTH: 1462
<212> TYPE: DNA
<213> ORGANISM: Artificial
<220> FEATURE:
<223> OTHER INFORMATION: DNA encoding fusion protein

<400> SEQUENCE: 5
atggagacag acacactcct gttatgggta ctgctgctct gggttccagg tgagagtgca      60
gagaagtgtt ggatgcaacc tctgtggcca ttatgatact ccatgcctct ctgttcttga    120
tcactataat tagggcattt gtcactggtt ttaagtttcc ccagtcccct gaattttcca    180
ttttctcaga gtgatgtcca aaattattct taaaaattta ataaaaaagg tcctctgctg    240
tgaaggcttt tatacatata taacaataat ctttgtgttt atcattccag gttccactgg    300
ccagccatat cacggcgaga aaggcatctc ggtaccggac acggcttct gccagcccat     360 ctccatcccg ttgtgcacgg atatcgccta caaccagacc atcctgccca acctgctggg    420
ccacacgaac caagaggacg cgggcctcga ggtgcaccag ttctaccctc tggtaaaggt    480
gcagtgttct cctgagctac gcttcttctt atgctctatg tacgcacccg tgtgcaccgt    540
gctcgaccaa gccattcctc cgtgccgttc cttgtgcgag cgcgcccgac agggctgcga    600
ggcgctcatg aacaagttcg gcttccagtg gccagagcgg ttgcgctgcg agaacttccc    660
agtgcacggt gccggcgaga tctgcgtggg gcagaacacg tccgacggct ccggggcgc    720 gggcggcagt cccaccgcct accctactgc tccctacctg gccgagccta ggtcttcaga    780
caaaactcac acatgcccac cgtgcccagc acctgaagcc gagggggccc cgtcagtctt    840
cctcttcccc ccaaaaccca aggacaccct catgatctcc cggaccctg aggtcacatg     900 cgtggtggtg gacgtgagcc acgaagaccc tgaggtcaag ttcaactggt acgtggacgg    960
cgtggaggtg cataatgcca agacaaagcc gcgggaggag cagtacaaca gcacgtaccg   1020
```

-continued

```
tgtggtcagc gtcctcaccg tcctgcacca ggactggctg aatggcaagg agtacaagtg    1080
cgccgtctcc aacaaagccc tcccagcctc catcgagaaa accatctcca aagccaaagg    1140
gcagccccga aaccacagg tgtacaccct gcccccatcc cgggatgagc tgaccaagaa     1200
ccaggtcagc ctgacctgcc tggtcaaagg cttctatccc agcgacatcg ccgtggagtg    1260
ggagagcaat gggcagccgg agaacaacta caagaccacg cctcccgtgc tggactccga    1320
cggctccttc ttcctctaca gcaagctcac cgtggacaag agcaggtggc agcaggggaa    1380
cgtcttctca tgctccgtga tgcatgaggc tctgcacaac cactacacgc agaagagcct    1440
ctccctgtct ccgggtaaat ga                                             1462
```

<210> SEQ ID NO 6
<211> LENGTH: 406
<212> TYPE: PRT
<213> ORGANISM: Artificial
<220> FEATURE:
<223> OTHER INFORMATION: fusion protein

<400> SEQUENCE: 6

```
Met Glu Thr Asp Thr Leu Leu Leu Trp Val Leu Leu Leu Trp Val Pro
1               5                   10                  15

Gly Ser Thr Gly Gln Pro Tyr His Gly Glu Lys Gly Ile Ser Val Pro
            20                  25                  30

Asp His Gly Phe Cys Gln Pro Ile Ser Ile Pro Leu Cys Thr Asp Ile
        35                  40                  45

Ala Tyr Asn Gln Thr Ile Leu Pro Asn Leu Leu Gly His Thr Asn Gln
    50                  55                  60

Glu Asp Ala Gly Leu Glu Val His Gln Phe Tyr Pro Leu Val Lys Val
65                  70                  75                  80

Gln Cys Ser Pro Glu Leu Arg Phe Phe Leu Cys Ser Met Tyr Ala Pro
                85                  90                  95

Val Cys Thr Val Leu Asp Gln Ala Ile Pro Pro Cys Arg Ser Leu Cys
            100                 105                 110

Glu Arg Ala Arg Gln Gly Cys Glu Ala Leu Met Asn Lys Phe Gly Phe
        115                 120                 125

Gln Trp Pro Glu Arg Leu Arg Cys Glu Asn Phe Pro Val His Gly Ala
    130                 135                 140

Gly Glu Ile Cys Val Gly Gln Asn Thr Ser Asp Gly Ser Gly Gly Ala
145                 150                 155                 160

Gly Gly Ser Pro Thr Ala Tyr Pro Thr Ala Pro Tyr Leu Ala Glu Pro
                165                 170                 175

Arg Ser Ser Asp Lys Thr His Thr Cys Pro Pro Cys Pro Ala Pro Glu
            180                 185                 190

Ala Glu Gly Ala Pro Ser Val Phe Leu Phe Pro Pro Lys Pro Lys Asp
        195                 200                 205

Thr Leu Met Ile Ser Arg Thr Pro Glu Val Thr Cys Val Val Val Asp
    210                 215                 220

Val Ser His Glu Asp Pro Glu Val Lys Phe Asn Trp Tyr Val Asp Gly
225                 230                 235                 240

Val Glu Val His Asn Ala Lys Thr Lys Pro Arg Glu Glu Gln Tyr Asn
                245                 250                 255

Ser Thr Tyr Arg Val Val Ser Val Leu Thr Val Leu His Gln Asp Trp
            260                 265                 270

Leu Asn Gly Lys Glu Tyr Lys Cys Ala Val Ser Asn Lys Ala Leu Pro
```

```
            275                 280                 285
Ala Ser Ile Glu Lys Thr Ile Ser Lys Ala Lys Gly Gln Pro Arg Glu
    290                 295                 300

Pro Gln Val Tyr Thr Leu Pro Pro Ser Arg Asp Glu Leu Thr Lys Asn
305                 310                 315                 320

Gln Val Ser Leu Thr Cys Leu Val Lys Gly Phe Tyr Pro Ser Asp Ile
                325                 330                 335

Ala Val Glu Trp Glu Ser Asn Gly Gln Pro Glu Asn Asn Tyr Lys Thr
            340                 345                 350

Thr Pro Pro Val Leu Asp Ser Asp Gly Ser Phe Phe Leu Tyr Ser Lys
        355                 360                 365

Leu Thr Val Asp Lys Ser Arg Trp Gln Gln Gly Asn Val Phe Ser Cys
    370                 375                 380

Ser Val Met His Glu Ala Leu His Asn His Tyr Thr Gln Lys Ser Leu
385                 390                 395                 400

Ser Leu Ser Pro Gly Lys
            405

<210> SEQ ID NO 7
<211> LENGTH: 1725
<212> TYPE: DNA
<213> ORGANISM: Homo sapiens

<400> SEQUENCE: 7
atgcgggacc ccggcgcggc cgctccgctt cgtccctgg gcctctgtgc cctggtgctg      60
gcgctgctgg gcgcactgtc cgcgggcgcc ggggcgcagc cgtaccacgg agagaagggc    120
atctccgtgc cggaccacgg cttctgccag cccatctcca tcccgctgtg cacggacatc    180
gcctacaacc agaccatcct gcccaacctg ctgggccaca cgaaccaaga ggacgcgggc    240
ctcgaggtgc accagttcta cccgctggtg aaggtgcagt gttctcccga actccgcttt    300
ttcttatgct ccatgtatgc gcccgtgtgc accgtgctcg atcaggccat ccgccgtgt    360 cgttctctgt gcgagcgcgc ccgccagggc tgcgaggcgc tcatgaacaa gttcggcttc    420
cagtggcccg agcggctgcg ctgcgagaac ttcccggtgc acggtgcggg cgagatctgc    480
gtgggccaga cacgtcgga cggctccggg ggcccaggcg gcggccccac tgcctaccct    540
accgcgccct acctgccgga cctgcccttc acgcgctgc cccgggggc ctcagatggc    600 aggggggcgtc ccgccttccc cttctcatgc cccgtcagc tcaaggtgcc cccgtacctg    660
ggctaccgct tcctgggtga gcgcgattgt ggcgccccgt gcgaaccggg ccgtgccaac    720
ggcctgatgt actttaagga ggaggagagg cgcttcgccc gcctctgggt gggcgtgtgg    780
tccgtgctgt gctgcgcctc gacgctcttt accgttctca cctacctggt ggacatgcgg    840
cgcttcagct acccagagcg gcccatcatc ttcctgtcgg gctgctactt catggtggcc    900
gtggcgcacg tggccggctt ccttctagag gaccgcgccg tgtgcgtgga gcgcttctcg    960
gacgatggct accgcacggt ggcgcagggc accaagaagg agggctgcac catcctcttc   1020
atggtgctct acttcttcgg catggccagc tccatctggt gggtcattct gtctctcact   1080
tggttcctgg cggccggcat gaagtgggc cacgaggcca tcgaggccaa ctcgcagtac   1140
ttccacctgg ccgcgtgggc cgtgcccgcc gtcaagacca tcactatcct ggccatgggc   1200
caggtagacg gggaccctgct gagcggggtg tgctacgttg gcctctccag tgtggacgcg   1260
ctgcggggct tcgtgctggc gcctctgttc gtctacctct tcataggcac gtccttcttg   1320
ctggccggct tcgtgtccct cttccgtatc cgcaccatca tgaaacacga cggcaccaag   1380
```

```
accgagaagc tggagaagct catggtgcgc atcggcgtct tcagcgtgct ctacacagtg    1440
cccgccacca tcgtcctggc ctgctacttc tacgagcagg ccttccgcga gcactgggag    1500
cgcacctggc tcctgcagac gtgcaagagc tatgccgtgc cctgcccgcc cggccacttc    1560
ccgcccatga gccccgactt caccgtcttc atgatcaagt acctgatgac catgatcgtc    1620
ggcatcacca ctggcttctg gatctggtcg ggcaagaccc tgcagtcgtg gcgccgcttc    1680
taccacagac ttagccacag cagcaagggg gagactgcgg tatga                    1725
```

<210> SEQ ID NO 8
<211> LENGTH: 574
<212> TYPE: PRT
<213> ORGANISM: Homo sapiens

<400> SEQUENCE: 8

```
Met Arg Asp Pro Gly Ala Ala Pro Leu Ser Ser Leu Gly Leu Cys
1               5                   10                  15

Ala Leu Val Leu Ala Leu Leu Gly Ala Leu Ser Ala Gly Ala Gly Ala
                20                  25                  30

Gln Pro Tyr His Gly Glu Lys Gly Ile Ser Val Pro Asp His Gly Phe
            35                  40                  45

Cys Gln Pro Ile Ser Ile Pro Leu Cys Thr Asp Ile Ala Tyr Asn Gln
        50                  55                  60

Thr Ile Leu Pro Asn Leu Leu Gly His Thr Asn Gln Glu Asp Ala Gly
65                  70                  75                  80

Leu Glu Val His Gln Phe Tyr Pro Leu Val Lys Val Gln Cys Ser Pro
                85                  90                  95

Glu Leu Arg Phe Phe Leu Cys Ser Met Tyr Ala Pro Val Cys Thr Val
            100                 105                 110

Leu Asp Gln Ala Ile Pro Pro Cys Arg Ser Leu Cys Glu Arg Ala Arg
        115                 120                 125

Gln Gly Cys Glu Ala Leu Met Asn Lys Phe Gly Phe Gln Trp Pro Glu
    130                 135                 140

Arg Leu Arg Cys Glu Asn Phe Pro Val His Gly Ala Gly Glu Ile Cys
145                 150                 155                 160

Val Gly Gln Asn Thr Ser Asp Gly Ser Gly Gly Pro Gly Gly Gly Pro
                165                 170                 175

Thr Ala Tyr Pro Thr Ala Pro Tyr Leu Pro Asp Leu Pro Phe Thr Ala
            180                 185                 190

Leu Pro Pro Gly Ala Ser Asp Gly Arg Gly Arg Pro Ala Phe Pro Phe
        195                 200                 205

Ser Cys Pro Arg Gln Leu Lys Val Pro Pro Tyr Leu Gly Tyr Arg Phe
    210                 215                 220

Leu Gly Glu Arg Asp Cys Gly Ala Pro Cys Glu Pro Gly Arg Ala Asn
225                 230                 235                 240

Gly Leu Met Tyr Phe Lys Glu Glu Arg Arg Phe Ala Arg Leu Trp
                245                 250                 255

Val Gly Val Trp Ser Val Leu Cys Cys Ala Ser Thr Leu Phe Thr Val
            260                 265                 270

Leu Thr Tyr Leu Val Asp Met Arg Arg Phe Ser Tyr Pro Glu Arg Pro
        275                 280                 285

Ile Ile Phe Leu Ser Gly Cys Tyr Phe Met Val Ala Val Ala His Val
    290                 295                 300

Ala Gly Phe Leu Leu Glu Asp Arg Ala Val Cys Val Glu Arg Phe Ser
```

```
            305                 310                 315                 320
Asp Asp Gly Tyr Arg Thr Val Ala Gln Gly Thr Lys Lys Glu Gly Cys
                    325                 330                 335

Thr Ile Leu Phe Met Val Leu Tyr Phe Phe Gly Met Ala Ser Ser Ile
                340                 345                 350

Trp Trp Val Ile Leu Ser Leu Thr Trp Phe Leu Ala Ala Gly Met Lys
                355                 360                 365

Trp Gly His Glu Ala Ile Glu Ala Asn Ser Gln Tyr Phe His Leu Ala
            370                 375                 380

Ala Trp Ala Val Pro Ala Val Lys Thr Ile Thr Ile Leu Ala Met Gly
385                 390                 395                 400

Gln Val Asp Gly Asp Leu Leu Ser Gly Val Cys Tyr Val Gly Leu Ser
                    405                 410                 415

Ser Val Asp Ala Leu Arg Gly Phe Val Leu Ala Pro Leu Phe Val Tyr
                420                 425                 430

Leu Phe Ile Gly Thr Ser Phe Leu Leu Ala Gly Phe Val Ser Leu Phe
            435                 440                 445

Arg Ile Arg Thr Ile Met Lys His Asp Gly Thr Lys Thr Glu Lys Leu
        450                 455                 460

Glu Lys Leu Met Val Arg Ile Gly Val Phe Ser Val Leu Tyr Thr Val
465                 470                 475                 480

Pro Ala Thr Ile Val Leu Ala Cys Tyr Phe Tyr Glu Gln Ala Phe Arg
                    485                 490                 495

Glu His Trp Glu Arg Thr Trp Leu Leu Gln Thr Cys Lys Ser Tyr Ala
                500                 505                 510

Val Pro Cys Pro Pro Gly His Phe Pro Pro Met Ser Pro Asp Phe Thr
            515                 520                 525

Val Phe Met Ile Lys Tyr Leu Met Thr Met Ile Val Gly Ile Thr Thr
        530                 535                 540

Gly Phe Trp Ile Trp Ser Gly Lys Thr Leu Gln Ser Trp Arg Arg Phe
545                 550                 555                 560

Tyr His Arg Leu Ser His Ser Ser Lys Gly Glu Thr Ala Val
                    565                 570

<210> SEQ ID NO 9
<211> LENGTH: 1462
<212> TYPE: DNA
<213> ORGANISM: Artificial
<220> FEATURE:
<223> OTHER INFORMATION: DNA encoding fusion protein

<400> SEQUENCE: 9
atggagacag acacactcct gttatgggta ctgctgctct ggttccaggt gagagtgca      60 gagaagtgtt ggatgcaacc tctgtggcca ttatgatact ccatgcctct ctgttcttga    120
tcactataat tagggcattt gtcactggtt ttaagtttcc ccagtcccct gaattttcca    180
ttttctcaga gtgatgtcca aaattattct taaaaattta ataaaaagg tcctctgctg     240 tgaaggcttt tatacatata taacaataat ctttgtgttt atcattccag gttccactgg    300
ccagccgtac cacggagaga agggcatctc cgtgccggac cacggcttct gccagcccat    360
ctccatcccg ctgtgcacgg acatcgccta caaccagacc atcctgccca acctgctggg    420
ccacacgaac caagaggacg cgggcctcga ggtgcaccag ttctaccgc tggtgaaggt     480 gcagtgttct cccgaactcc gcttttctt atgctccatg tatgcgcccg tgtgcaccgt    540
gctcgatcag gccatcccgc cgtgtcgttc tctgtgcgag cgcgcccgcc agggctgcga    600
```

```
ggcgctcatg aacaagttcg gcttccagtg gcccgagcgg ctgcgctgcg agaacttccc    660
ggtgcacggt gcgggcgaga tctgcgtggg ccagaacacg tcggacggct ccggggggccc    720 aggcggcggc cccactgcct accctaccgc ccctacctg ccgagccta ggtcttcaga    780 caaaactcac acatgcccac cgtgcccagc acctgaagcc gagggggccc cgtcagtctt    840
cctcttcccc ccaaaaccca aggacaccct catgatctcc cggacccctg aggtcacatg    900
cgtggtggtg gacgtgagcc acgaagaccc tgaggtcaag ttcaactggt acgtggacgg    960
cgtggaggtg cataatgcca agacaaagcc gcgggaggag cagtacaaca gcacgtaccg   1020
tgtggtcagc gtcctcaccg tcctgcacca ggactggctg aatggcaagg agtacaagtg   1080
cgccgtctcc aacaaagccc tcccagcctc catcgagaaa accatctcca agccaaagg   1140 gcagccccga gaaccacagg tgtacaccct gcccccatcc cgggatgagc tgaccaagaa   1200
ccaggtcagc ctgacctgcc tggtcaaagg cttctatccc agcgacatcg ccgtggagtg   1260
ggagagcaat gggcagccgg agaacaacta caagaccacg cctcccgtgc tggactccga   1320
cggctccttc ttcctctaca gcaagctcac cgtggacaag agcaggtggc agcaggggaa   1380
cgtcttctca tgctccgtga tgcatgaggc tctgcacaac cactacacgc agaagagcct   1440
ctccctgtct ccgggtaaat ga                                           1462
```

<210> SEQ ID NO 10
<211> LENGTH: 406
<212> TYPE: PRT
<213> ORGANISM: Artificial
<220> FEATURE:
<223> OTHER INFORMATION: fusion protein

<400> SEQUENCE: 10

```
Met Glu Thr Asp Thr Leu Leu Leu Trp Val Leu Leu Leu Trp Val Pro
1               5                   10                  15

Gly Ser Thr Gly Gln Pro Tyr His Gly Glu Lys Gly Ile Ser Val Pro
            20                  25                  30

Asp His Gly Phe Cys Gln Pro Ile Ser Ile Pro Leu Cys Thr Asp Ile
        35                  40                  45

Ala Tyr Asn Gln Thr Ile Leu Pro Asn Leu Leu Gly His Thr Asn Gln
    50                  55                  60

Glu Asp Ala Gly Leu Glu Val His Gln Phe Tyr Pro Leu Val Lys Val
65                  70                  75                  80

Gln Cys Ser Pro Glu Leu Arg Phe Phe Leu Cys Ser Met Tyr Ala Pro
                85                  90                  95

Val Cys Thr Val Leu Asp Gln Ala Ile Pro Pro Cys Arg Ser Leu Cys
            100                 105                 110

Glu Arg Ala Arg Gln Gly Cys Glu Ala Leu Met Asn Lys Phe Gly Phe
        115                 120                 125

Gln Trp Pro Glu Arg Leu Arg Cys Glu Asn Phe Pro Val His Gly Ala
    130                 135                 140

Gly Glu Ile Cys Val Gly Gln Asn Thr Ser Asp Gly Ser Gly Gly Pro
145                 150                 155                 160

Gly Gly Gly Pro Thr Ala Tyr Pro Thr Ala Pro Tyr Leu Ala Glu Pro
                165                 170                 175

Arg Ser Ser Asp Lys Thr His Thr Cys Pro Pro Cys Pro Ala Pro Glu
            180                 185                 190

Ala Glu Gly Ala Pro Ser Val Phe Leu Phe Pro Pro Lys Pro Lys Asp
        195                 200                 205
```

```
Thr Leu Met Ile Ser Arg Thr Pro Glu Val Thr Cys Val Val Asp
    210                 215                 220
Val Ser His Glu Asp Pro Glu Val Lys Phe Asn Trp Tyr Val Asp Gly
225                 230                 235                 240
Val Glu Val His Asn Ala Lys Thr Lys Pro Arg Glu Glu Gln Tyr Asn
            245                 250                 255
Ser Thr Tyr Arg Val Val Ser Val Leu Thr Val Leu His Gln Asp Trp
        260                 265                 270
Leu Asn Gly Lys Glu Tyr Lys Cys Ala Val Ser Asn Lys Ala Leu Pro
    275                 280                 285
Ala Ser Ile Glu Lys Thr Ile Ser Lys Ala Lys Gly Gln Pro Arg Glu
290                 295                 300
Pro Gln Val Tyr Thr Leu Pro Pro Ser Arg Asp Glu Leu Thr Lys Asn
305                 310                 315                 320
Gln Val Ser Leu Thr Cys Leu Val Lys Gly Phe Tyr Pro Ser Asp Ile
            325                 330                 335
Ala Val Glu Trp Glu Ser Asn Gly Gln Pro Glu Asn Asn Tyr Lys Thr
        340                 345                 350
Thr Pro Pro Val Leu Asp Ser Asp Gly Ser Phe Phe Leu Tyr Ser Lys
    355                 360                 365
Leu Thr Val Asp Lys Ser Arg Trp Gln Gln Gly Asn Val Phe Ser Cys
370                 375                 380
Ser Val Met His Glu Ala Leu His Asn His Tyr Thr Gln Lys Ser Leu
385                 390                 395                 400
Ser Leu Ser Pro Gly Lys
            405

<210> SEQ ID NO 11
<211> LENGTH: 1929
<212> TYPE: DNA
<213> ORGANISM: Mus musculus

<400> SEQUENCE: 11
atggctgagg aggcggcgcc tagcgagtcc cgggccgccg ccggctgag cttggaactt      60 tgtgccgaag cactcccggg ccggcgggag gaggtggggc acgaggacac ggccagccac     120
cgccgccccc gggctgatcc ccggcgttgg gctagcgggc tgctgctgct gctttggttg     180
ctggaggctc ctctgctttt ggggggtccga gcgcaggcgg cgggccaggt atccggggccg   240 ggccagcaag ccccgccgcc gccccagccc agcagagcg gcagcagta caacggcgaa       300 cggggcatct ccatcccgga ccacggctac tgccagccca tctccatccc gctgtgcacg     360
gacatcgcgt acaaccagac catcatgccc aacctgctgg ccacacgaa tcaggaggac     420 gccggtctgg aggtgcacca gttctaccct ctggtgaagg tgcagtgctc cgccgagctc    480
aagttcttcc tgtgctccat gtacgcgcct gtgtgcaccg tactggagca ggcgctaccg    540
ccctgccgct ccctgtgcga gcgcgcacgc cagggctgcg aggcgctcat gaacaagttc    600
ggcttccagt ggccagacac actcaagtgc gagaagttcc cggtgcacgg cgcaggagag    660
ctgtgcgtgg gccagaacac gtccgacaaa ggcaccccaa ctccctcctt gctaccagag    720
ttctggacca gtaatccgca gcacggcggc ggtggttacc gcggcggcta cccgggggggt   780 gccgggacgg tggagcgggg aaagttctcc tgcccgcgcg ccctcagggt gccctcctac    840
ctcaactacc actttctggg ggagaaggac tgcggcgcac cctgcgaacc caccaaggtt    900
tacgggctca tgtacttcgg gccagaggag ctgcgcttct cgcgcacctg gataggcatc    960
```

-continued

```
tggtccgtgc tgtgctgcgc ctccacgctc ttcacggtgc tcacgtacct agtggacatg    1020
cggcgcttca gctacccgga acggcccatc attttcctgt ccggctgtta cacagcggtg    1080
gcggtggcct acatcgctgg ctttctgttg gaggaccggg tggtgtgcaa cgacaagttt    1140
gcagaggacg gggcgcgcac ggtggcgcag ggcactaaga aagaaggctg cactatactc    1200
tttatgatgc tctacttctt cagcatggcc agctccatct ggtgggtgat cctgtccctc    1260
acctggttcc tggcagccgg catgaagtgg ggccacgaag ccatcgaggc caactcacag    1320
tatttccatt tagccgcctg ggctgtgcca gccatcaaaa ctataaccat cttggcgttg    1380
ggccaggtgg atggcgacgt actgagcgga gtgtgttttg tggggctcaa caacgtggac    1440
gcactgcgtg gctttgtgct ggcgcctctc ttcgtttatc tgttcattgg cacttctttc    1500
ctgctggccg gtttcgtgtc actcttccgc atccgcacca tcatgaagca tgacggcacc    1560
aagacagaga agctggagaa gctcatggtg cgcatcggag tcttcagtgt cctctacact    1620
gtgccggcca ccatcgtcat cgcctgctac ttctatgaac aggcctttcg ggaccagtgg    1680
gagcgcagct gggtggccca gagctgcaag agttatgcca tcccttgccc tcacctccag    1740
ggaggtggag gagtcccacc acacccgccc atgagcccag actttacagt cttcatgatc    1800
aagtatctca tgacgctgat tgtgggcatc acatcgggct tctggatctg gtccggcaag    1860
acactgaatt cctggaggaa gttctacacg aggcttacca acagcaaaca gggggagact    1920
accgtctga                                                              1929
```

<210> SEQ ID NO 12
<211> LENGTH: 642
<212> TYPE: PRT
<213> ORGANISM: Mus musculus

<400> SEQUENCE: 12

```
Met Ala Glu Glu Ala Ala Pro Ser Glu Ser Arg Ala Ala Gly Arg Leu
1               5                   10                  15

Ser Leu Glu Leu Cys Ala Glu Ala Leu Pro Gly Arg Arg Glu Glu Val
            20                  25                  30

Gly His Glu Asp Thr Ala Ser His Arg Pro Arg Ala Asp Pro Arg
        35                  40                  45

Arg Trp Ala Ser Gly Leu Leu Leu Leu Trp Leu Leu Glu Ala Pro
    50                  55                  60

Leu Leu Leu Gly Val Arg Ala Gln Ala Gly Gln Val Ser Gly Pro
65                  70                  75                  80

Gly Gln Gln Ala Pro Pro Pro Gln Pro Gln Ser Gly Gln Gln
            85                  90                  95

Tyr Asn Gly Glu Arg Gly Ile Ser Ile Pro Asp His Gly Tyr Cys Gln
            100                 105                 110

Pro Ile Ser Ile Pro Leu Cys Thr Asp Ile Ala Tyr Asn Gln Thr Ile
        115                 120                 125

Met Pro Asn Leu Leu Gly His Thr Asn Gln Glu Asp Ala Gly Leu Glu
    130                 135                 140

Val His Gln Phe Tyr Pro Leu Val Lys Val Gln Cys Ser Ala Glu Leu
145                 150                 155                 160

Lys Phe Phe Leu Cys Ser Met Tyr Ala Pro Val Cys Thr Val Leu Glu
                165                 170                 175

Gln Ala Leu Pro Pro Cys Arg Ser Leu Cys Glu Arg Ala Arg Gln Gly
            180                 185                 190
```

-continued

```
Cys Glu Ala Leu Met Asn Lys Phe Gly Phe Gln Trp Pro Asp Thr Leu
        195                 200                 205
Lys Cys Glu Lys Phe Pro Val His Gly Ala Gly Glu Leu Cys Val Gly
210                 215                 220
Gln Asn Thr Ser Asp Lys Gly Thr Pro Thr Pro Ser Leu Leu Pro Glu
225                 230                 235                 240
Phe Trp Thr Ser Asn Pro Gln His Gly Gly Gly Tyr Arg Gly Gly
                245                 250                 255
Tyr Pro Gly Gly Ala Gly Thr Val Glu Arg Gly Lys Phe Ser Cys Pro
            260                 265                 270
Arg Ala Leu Arg Val Pro Ser Tyr Leu Asn Tyr His Phe Leu Gly Glu
        275                 280                 285
Lys Asp Cys Gly Ala Pro Cys Glu Pro Thr Lys Val Tyr Gly Leu Met
290                 295                 300
Tyr Phe Gly Pro Glu Glu Leu Arg Phe Ser Arg Thr Trp Ile Gly Ile
305                 310                 315                 320
Trp Ser Val Leu Cys Cys Ala Ser Thr Leu Phe Thr Val Leu Thr Tyr
                325                 330                 335
Leu Val Asp Met Arg Arg Phe Ser Tyr Pro Glu Arg Pro Ile Ile Phe
            340                 345                 350
Leu Ser Gly Cys Tyr Thr Ala Val Ala Val Ala Tyr Ile Ala Gly Phe
        355                 360                 365
Leu Leu Glu Asp Arg Val Val Cys Asn Asp Lys Phe Ala Glu Asp Gly
        370                 375                 380
Ala Arg Thr Val Ala Gln Gly Thr Lys Lys Glu Gly Cys Thr Ile Leu
385                 390                 395                 400
Phe Met Met Leu Tyr Phe Phe Ser Met Ala Ser Ser Ile Trp Trp Val
                405                 410                 415
Ile Leu Ser Leu Thr Trp Phe Leu Ala Ala Gly Met Lys Trp Gly His
            420                 425                 430
Glu Ala Ile Glu Ala Asn Ser Gln Tyr Phe His Leu Ala Ala Trp Ala
        435                 440                 445
Val Pro Ala Ile Lys Thr Ile Thr Ile Leu Ala Leu Gly Gln Val Asp
450                 455                 460
Gly Asp Val Leu Ser Gly Val Cys Phe Val Gly Leu Asn Asn Val Asp
465                 470                 475                 480
Ala Leu Arg Gly Phe Val Leu Ala Pro Leu Phe Val Tyr Leu Phe Ile
                485                 490                 495
Gly Thr Ser Phe Leu Leu Ala Gly Phe Val Ser Leu Phe Arg Ile Arg
            500                 505                 510
Thr Ile Met Lys His Asp Gly Thr Lys Thr Glu Lys Leu Glu Lys Leu
        515                 520                 525
Met Val Arg Ile Gly Val Phe Ser Val Leu Tyr Thr Val Pro Ala Thr
        530                 535                 540
Ile Val Ile Ala Cys Tyr Phe Tyr Glu Gln Ala Phe Arg Asp Gln Trp
545                 550                 555                 560
Glu Arg Ser Trp Val Ala Gln Ser Cys Lys Ser Tyr Ala Ile Pro Cys
                565                 570                 575
Pro His Leu Gln Gly Gly Gly Val Pro Pro His Pro Pro Met Ser
            580                 585                 590
Pro Asp Phe Thr Val Phe Met Ile Lys Tyr Leu Met Thr Leu Ile Val
        595                 600                 605
Gly Ile Thr Ser Gly Phe Trp Ile Trp Ser Gly Lys Thr Leu Asn Ser
```

Trp Arg Lys Phe Tyr Thr Arg Leu Thr Asn Ser Lys Gln Gly Glu Thr
625                 630                 635                 640

Thr Val

<210> SEQ ID NO 13
<211> LENGTH: 1534
<212> TYPE: DNA
<213> ORGANISM: Artificial
<220> FEATURE:
<223> OTHER INFORMATION: DNA encoding fusion protein

<400> SEQUENCE: 13

```
atggagacag acacactcct gttatgggta ctgctgctct ggttccagg  tgagagtgca      60
gagaagtgtt ggatgcaacc tctgtggcca ttatgatact ccatgcctct ctgttcttga    120
tcactataat tagggcattt gtcactggtt ttaagtttcc ccagtcccct gaattttcca    180
ttttctcaga gtgatgtcca aaattattct taaaaattta ataaaaagg  tcctctgctg    240
tgaaggcttt tatacatata taacaataat cttttgtgttt atcattccag gttccactgg    300
ccaggcggcg ggccaggtat ccgggccggg ccagcaagcc cgccgccgc  cccagcccca    360
gcagagcggg cagcagtaca acggcgaacg gggcatctcc atcccggacc acggctactg    420
ccagcccatc tccatcccgc tgtgcacgga catcgcgtac aaccagacca tcatgcccaa    480
cctgctgggc cacacgaatc aggaggacgc cggtctggag gtgcaccagt tctaccctct    540
ggtgaaggtg cagtgctccg ccgagctcaa gttcttcctg tgctccatgt acgcgcctgt    600
gtgcaccgta ctggagcagg cgctaccgcc ctgccgctcc ctgtgcgagc gcgcacgcca    660
gggctgcgag gcgctcatga acaagttcgg cttccagtgg ccagacacac tcaagtgcga    720
gaagttcccg gtgcacggcg caggagagct gtgcgtgggc cagaacacgt ccgacaaagg    780
cacccccaact ccctccttgc taccagagtt ctggaccagt aatccgcagc acgccgagcc    840
taggtcttca gacaaaactc acacatgccc accgtgccca gcacctgaag ccgaggggc     900
cccgtcagtc ttcctcttcc ccccaaaacc caaggacacc ctcatgatct cccggacccc    960
tgaggtcaca tgcgtggtgg tggacgtgag ccacgaagac cctgaggtca gttcaactg    1020
gtacgtggac ggcgtggagg tgcataatgc caagacaaag ccgcgggag  agcagtacaa   1080
cagcacgtac cgtgtggtca gcgtcctcac cgtcctgcac caggactggc tgaatggcaa   1140
ggagtacaag tgcgccgtct ccaacaaagc cctcccagcc tccatcgaga aaaccatctc   1200
caaagccaaa gggcagcccc gagaaccaca ggtgtacacc ctgcccccat cccgggatga   1260
gctgaccaag aaccaggtca gcctgacctg cctggtcaaa ggcttctatc cagcgacat    1320
cgccgtggag tgggagagca atgggcagcc ggagaacaac tacaagacca cgcctcccgt    1380
gctggactcc gacggctcct tcttcctcta cagcaagctc accgtggaca gagcaggtg    1440
gcagcagggg aacgtcttct catgctccgt gatgcatgag gctctgcaca accactacac   1500
gcagaagagc ctctccctgt ctccgggtaa atga                                1534
```

<210> SEQ ID NO 14
<211> LENGTH: 430
<212> TYPE: PRT
<213> ORGANISM: Artificial
<220> FEATURE:
<223> OTHER INFORMATION: fusion protein

<400> SEQUENCE: 14

```
Met Glu Thr Asp Thr Leu Leu Leu Trp Val Leu Leu Leu Trp Val Pro
1               5                   10                  15
Gly Ser Thr Gly Gln Ala Ala Gly Gln Val Ser Gly Pro Gly Gln Gln
            20                  25                  30
Ala Pro Pro Pro Gln Pro Gln Gln Ser Gly Gln Gln Tyr Asn Gly
        35                  40                  45
Glu Arg Gly Ile Ser Ile Pro Asp His Gly Tyr Cys Gln Pro Ile Ser
50                  55                  60
Ile Pro Leu Cys Thr Asp Ile Ala Tyr Asn Gln Thr Ile Met Pro Asn
65                  70                  75                  80
Leu Leu Gly His Thr Asn Gln Glu Asp Ala Gly Leu Glu Val His Gln
                85                  90                  95
Phe Tyr Pro Leu Val Lys Val Gln Cys Ser Ala Glu Leu Lys Phe Phe
            100                 105                 110
Leu Cys Ser Met Tyr Ala Pro Val Cys Thr Val Leu Glu Gln Ala Leu
        115                 120                 125
Pro Pro Cys Arg Ser Leu Cys Glu Arg Ala Arg Gln Gly Cys Glu Ala
    130                 135                 140
Leu Met Asn Lys Phe Gly Phe Gln Trp Pro Asp Thr Leu Lys Cys Glu
145                 150                 155                 160
Lys Phe Pro Val His Gly Ala Gly Glu Leu Cys Val Gly Gln Asn Thr
                165                 170                 175
Ser Asp Lys Gly Thr Pro Thr Pro Ser Leu Leu Pro Glu Phe Trp Thr
            180                 185                 190
Ser Asn Pro Gln His Ala Glu Pro Arg Ser Ser Asp Lys Thr His Thr
        195                 200                 205
Cys Pro Pro Cys Pro Ala Pro Glu Ala Glu Gly Ala Pro Ser Val Phe
    210                 215                 220
Leu Phe Pro Pro Lys Pro Lys Asp Thr Leu Met Ile Ser Arg Thr Pro
225                 230                 235                 240
Glu Val Thr Cys Val Val Val Asp Val Ser His Glu Asp Pro Glu Val
                245                 250                 255
Lys Phe Asn Trp Tyr Val Asp Gly Val Glu Val His Asn Ala Lys Thr
            260                 265                 270
Lys Pro Arg Glu Glu Gln Tyr Asn Ser Thr Tyr Arg Val Val Ser Val
        275                 280                 285
Leu Thr Val Leu His Gln Asp Trp Leu Asn Gly Lys Glu Tyr Lys Cys
    290                 295                 300
Ala Val Ser Asn Lys Ala Leu Pro Ala Ser Ile Glu Lys Thr Ile Ser
305                 310                 315                 320
Lys Ala Lys Gly Gln Pro Arg Glu Pro Gln Val Tyr Thr Leu Pro Pro
                325                 330                 335
Ser Arg Asp Glu Leu Thr Lys Asn Gln Val Ser Leu Thr Cys Leu Val
            340                 345                 350
Lys Gly Phe Tyr Pro Ser Asp Ile Ala Val Glu Trp Glu Ser Asn Gly
        355                 360                 365
Gln Pro Glu Asn Asn Tyr Lys Thr Thr Pro Pro Val Leu Asp Ser Asp
    370                 375                 380
Gly Ser Phe Phe Leu Tyr Ser Lys Leu Thr Val Asp Lys Ser Arg Trp
385                 390                 395                 400
Gln Gln Gly Asn Val Phe Ser Cys Ser Val Met His Glu Ala Leu His
                405                 410                 415
Asn His Tyr Thr Gln Lys Ser Leu Ser Leu Ser Pro Gly Lys
```

<210> SEQ ID NO 15
<211> LENGTH: 1944
<212> TYPE: DNA
<213> ORGANISM: Homo sapiens

<400> SEQUENCE: 15

| | | | | | |
|---|---|---|---|---|---|
| atggctgagg | aggaggcgcc | taagaagtcc | cgggccgccg | gcggtggcgc | gagctgggaa | 60 |
| ctttgtgccg | gggcgctctc | ggcccggctg | gcggaggagg | gcagcgggga | cgccggtggc | 120 |
| cgccgccgcc | cgccagttga | cccccggcga | ttggcgcgcc | agctgctgct | gctgctttgg | 180 |
| ctgctggagg | ctccgctgct | gctggggggtc | cgggcccagg | cggcgggcca | ggggccaggc | 240 |
| caggggcccg | gccgggggca | gcaaccgccg | ccgccgcctc | agcagcaaca | gagcgggcag | 300 |
| cagtacaacg | gcgagcgggg | catctccgtc | ccggaccacg | gctattgcca | gcccatctcc | 360 |
| atcccgctgt | gcacggacat | cgcgtacaac | cagaccatca | tgcccaacct | gctgggccac | 420 |
| acgaaccagg | aggacgcggg | cctggaggtg | caccagttct | accctctagt | gaaagtgcag | 480 |
| tgttccgctg | agctcaagtt | cttcctgtgc | tccatgtacg | cgcccgtgtg | caccgtgcta | 540 |
| gagcaggcgc | tgccgccctg | ccgctccctg | tgcgagcgcg | cgcgccaggg | ctgcgaggcg | 600 |
| ctcatgaaca | agttcggctt | ccagtggcca | gacacgctca | gtgtgagaa | gttcccggtg | 660 |
| cacggcgccg | cgagctgtg | cgtgggccag | aacacgtccg | acaagggcac | ccgacgccc | 720 |
| tcgctgcttc | cagagttctg | gaccagcaac | cctcagcacg | gcggcggagg | gcaccgtggc | 780 |
| ggcttcccgg | ggggcgccgg | cgcgtcgagc | gaggcaagt | tctcctgccc | gcgcgccctc | 840 |
| aaggtgccct | cctacctcaa | ctaccacttc | ctgggggaga | aggactgcgg | cgcaccttgt | 900 |
| gagccgacca | ggtgtatgg | gctcatgtac | ttcgggcccg | aggagctgcg | cttctcgcgc | 960 |
| acctggattg | gcatttggtc | agtgctgtgc | tgcgcctcca | cgctcttcac | ggtgcttacg | 1020 |
| tacctggtgg | acatgcggcg | cttcagctac | ccggagcggc | ccatcatctt | cttgtccggc | 1080 |
| tgttacacgg | ccgtggccgt | ggcctacatc | gccggcttcc | tcctggaaga | ccgagtggtg | 1140 |
| tgtaatgaca | gttcgccga | ggacgggggca | cgcactgtgg | cgcagggcac | caagaaggag | 1200 |
| ggctgcacca | tcctcttcat | gatgctctac | ttcttcagca | tggccagctc | catctggtgg | 1260 |
| gtgatcctgt | cgctcacctg | gttcctggcg | gctggcatga | agtggggcca | cgaggccatc | 1320 |
| gaagccaact | cacagtattt | tcacctggcc | gcctgggctg | tgccggccat | caagaccatc | 1380 |
| accatcctgg | cgctgggcca | ggtggacggc | gatgtgctga | gcggagtgtg | cttcgtgggg | 1440 |
| cttaacaacg | tggacgcgct | gcgtggcttc | gtgctggcgc | ccctcttcgt | gtacctgttt | 1500 |
| atcggcacgt | cctttctgct | ggccggcttt | gtgtcgctct | ccgcatccg | caccatcatg | 1560 |
| aagcacgatg | gcaccaagac | cgagaagctg | gagaagctca | tggtgcgcat | ggcgtcttc | 1620 |
| agcgtgctgt | acactgtgcc | agccaccatc | gtcatcgcct | gctacttcta | cgagcaggcc | 1680 |
| ttccgggacc | agtgggaacg | cagctgggtg | gcccagagct | gcaagagcta | cgctatcccc | 1740 |
| tgccctcacc | tccaggcggg | cggaggcgcc | ccgccgcacc | cgcccatgag | cccggacttc | 1800 |
| acggtcttca | tgattaagta | ccttatgacg | ctgatcgtgg | gcatcacgtc | gggcttctgg | 1860 |
| atctggtccg | gcaagaccct | caactcctgg | aggaagttct | acacgaggct | caccaacagc | 1920 |
| aaacaagggg | agactacagt | ctga | | | | 1944 |

<210> SEQ ID NO 16
<211> LENGTH: 647

```
<212> TYPE: PRT
<213> ORGANISM: Homo sapiens

<400> SEQUENCE: 16

Met Ala Glu Glu Ala Pro Lys Lys Ser Arg Ala Ala Gly Gly Gly
1               5                   10                  15

Ala Ser Trp Glu Leu Cys Ala Gly Ala Leu Ser Ala Arg Leu Ala Glu
            20                  25                  30

Glu Gly Ser Gly Asp Ala Gly Gly Arg Arg Pro Pro Val Asp Pro
            35                  40                  45

Arg Arg Leu Ala Arg Gln Leu Leu Leu Leu Trp Leu Leu Glu Ala
        50                  55                  60

Pro Leu Leu Leu Gly Val Arg Ala Gln Ala Ala Gly Gln Gly Pro Gly
65                  70                  75                  80

Gln Gly Pro Gly Pro Gly Gln Gln Pro Pro Pro Gln Gln Gln
                85                  90                  95

Gln Ser Gly Gln Gln Tyr Asn Gly Glu Arg Gly Ile Ser Val Pro Asp
            100                 105                 110

His Gly Tyr Cys Gln Pro Ile Ser Ile Pro Leu Cys Thr Asp Ile Ala
        115                 120                 125

Tyr Asn Gln Thr Ile Met Pro Asn Leu Leu Gly His Thr Asn Gln Glu
    130                 135                 140

Asp Ala Gly Leu Glu Val His Gln Phe Tyr Pro Leu Val Lys Val Gln
145                 150                 155                 160

Cys Ser Ala Glu Leu Lys Phe Phe Leu Cys Ser Met Tyr Ala Pro Val
            165                 170                 175

Cys Thr Val Leu Glu Gln Ala Leu Pro Pro Cys Arg Ser Leu Cys Glu
        180                 185                 190

Arg Ala Arg Gln Gly Cys Glu Ala Leu Met Asn Lys Phe Gly Phe Gln
    195                 200                 205

Trp Pro Asp Thr Leu Lys Cys Glu Lys Phe Pro Val His Gly Ala Gly
210                 215                 220

Glu Leu Cys Val Gly Gln Asn Thr Ser Asp Lys Gly Thr Pro Thr Pro
225                 230                 235                 240

Ser Leu Leu Pro Glu Phe Trp Thr Ser Asn Pro Gln His Gly Gly Gly
            245                 250                 255

Gly His Arg Gly Gly Phe Pro Gly Gly Ala Gly Ala Ser Glu Arg Gly
        260                 265                 270

Lys Phe Ser Cys Pro Arg Ala Leu Lys Val Pro Ser Tyr Leu Asn Tyr
    275                 280                 285

His Phe Leu Gly Glu Lys Asp Cys Gly Ala Pro Cys Glu Pro Thr Lys
    290                 295                 300

Val Tyr Gly Leu Met Tyr Phe Gly Pro Glu Glu Leu Arg Phe Ser Arg
305                 310                 315                 320

Thr Trp Ile Gly Ile Trp Ser Val Leu Cys Cys Ala Ser Thr Leu Phe
            325                 330                 335

Thr Val Leu Thr Tyr Leu Val Asp Met Arg Arg Phe Ser Tyr Pro Glu
        340                 345                 350

Arg Pro Ile Ile Phe Leu Ser Gly Cys Tyr Thr Ala Val Ala Val Ala
    355                 360                 365

Tyr Ile Ala Gly Phe Leu Leu Glu Asp Arg Val Val Cys Asn Asp Lys
    370                 375                 380

Phe Ala Glu Asp Gly Ala Arg Thr Val Ala Gln Gly Thr Lys Lys Glu
385                 390                 395                 400
```

Gly Cys Thr Ile Leu Phe Met Met Leu Tyr Phe Phe Ser Met Ala Ser
            405                 410                 415

Ser Ile Trp Trp Val Ile Leu Ser Leu Thr Trp Phe Leu Ala Ala Gly
        420                 425                 430

Met Lys Trp Gly His Glu Ala Ile Glu Ala Asn Ser Gln Tyr Phe His
        435                 440                 445

Leu Ala Ala Trp Ala Val Pro Ala Ile Lys Thr Ile Thr Ile Leu Ala
    450                 455                 460

Leu Gly Gln Val Asp Gly Asp Val Leu Ser Gly Val Cys Phe Val Gly
465                 470                 475                 480

Leu Asn Asn Val Asp Ala Leu Arg Gly Phe Val Leu Ala Pro Leu Phe
                485                 490                 495

Val Tyr Leu Phe Ile Gly Thr Ser Phe Leu Leu Ala Gly Phe Val Ser
            500                 505                 510

Leu Phe Arg Ile Arg Thr Ile Met Lys His Asp Gly Thr Lys Thr Glu
        515                 520                 525

Lys Leu Glu Lys Leu Met Val Arg Ile Gly Val Phe Ser Val Leu Tyr
    530                 535                 540

Thr Val Pro Ala Thr Ile Val Ile Ala Cys Tyr Phe Tyr Glu Gln Ala
545                 550                 555                 560

Phe Arg Asp Gln Trp Glu Arg Ser Trp Val Ala Gln Ser Cys Lys Ser
                565                 570                 575

Tyr Ala Ile Pro Cys Pro His Leu Gln Ala Gly Gly Ala Pro Pro
            580                 585                 590

His Pro Pro Met Ser Pro Asp Phe Thr Val Phe Met Ile Lys Tyr Leu
        595                 600                 605

Met Thr Leu Ile Val Gly Ile Thr Ser Gly Phe Trp Ile Trp Ser Gly
    610                 615                 620

Lys Thr Leu Asn Ser Trp Arg Lys Phe Tyr Thr Arg Leu Thr Asn Ser
625                 630                 635                 640

Lys Gln Gly Glu Thr Thr Val
                645

<210> SEQ ID NO 17
<211> LENGTH: 1546
<212> TYPE: DNA
<213> ORGANISM: Artificial
<220> FEATURE:
<223> OTHER INFORMATION: DNA encoding fusion protein

<400> SEQUENCE: 17

```
atggagacag acacactcct gttatgggta ctgctgctct gggttccagg tgagagtgca      60
gagaagtgtt ggatgcaacc tctgtggcca ttatgatact ccatgcctct ctgttcttga     120
tcactataat tagggcattt gtcactggtt ttaagtttcc ccagtcccct gaattttcca     180
ttttctcaga gtgatgtcca aaattattct taaaaattta ataaaaagg tcctctgctg      240
tgaaggcttt tatacatata taacaataat ctttgtgttt atcattccag gttccactgg     300
ccaggcggcg ggccaggggc caggccaggg gcccgggccg ggcagcaac cgccgccgcc      360
gcctcagcag caacagagcg ggcagcagta acggcgag cggggcatct ccgtcccgga       420
ccacggctat tgccagccca tctccatccc gctgtgcacg acatcgcgt acaaccagac      480
catcatgccc aacctgctgg ccacacgaa ccaggaggac gcgggcctgg aggtgcacca      540
gttctaccct ctagtgaaag tgcagtgttc cgctgagctc aagttcttcc tgtgctccat    600
```

```
gtacgcgccc gtgtgcaccg tgctagagca ggcgctgccg ccctgccgct ccctgtgcga   660
gcgcgcgcgc cagggctgcg aggcgctcat gaacaagttc ggcttccagt ggccagacac   720
gctcaagtgt gagaagttcc cggtgcacgg cgccggcgag ctgtgcgtgg gccagaacac   780
gtccgacaag ggcaccccga cgccctcgct gcttccagag ttctggacca gcaaccctca   840
gcacgccgag cctaggtctt cagacaaaac tcacacatgc ccaccgtgcc cagcacctga   900
agccgagggg gccccgtcag tcttcctctt ccccccaaaa cccaaggaca ccctcatgat   960
ctcccggacc cctgaggtca catgcgtggt ggtggacgtg agccacgaag accctgaggt  1020
caagttcaac tggtacgtgg acggcgtgga ggtgcataat gccaagacaa agccgcggga  1080
ggagcagtac aacagcacgt accgtgtggt cagcgtcctc accgtcctgc accaggactg  1140
gctgaatggc aaggagtaca agtgcgccgt ctccaacaaa gccctcccag cctccatcga  1200
gaaaaccatc tccaaagcca agggcagccc cgagaaccag gtgtacaccc tgcccccc    1260 atcccgggat gagctgacca gaaccaggt cagcctgacc tgcctggtca aaggcttcta  1320
tcccagcgac atcgccgtgg agtgggagag caatgggcag ccggagaaca actacaagac  1380
cacgcctccc gtgctggact ccgacggctc cttcttcctc tacagcaagc tcaccgtgga  1440
caagagcagg tggcagcagg ggaacgtctt ctcatgctcc gtgatgcatg aggctctgca  1500
caaccactac acgcagaaga gcctctccct gtctccgggt aaatga                1546

<210> SEQ ID NO 18
<211> LENGTH: 434
<212> TYPE: PRT
<213> ORGANISM: Artificial
<220> FEATURE:
<223> OTHER INFORMATION: fusion protein

<400> SEQUENCE: 18

Met Glu Thr Asp Thr Leu Leu Leu Trp Val Leu Leu Leu Trp Val Pro
1               5                   10                  15

Gly Ser Thr Gly Gln Ala Ala Gly Gln Gly Pro Gly Gln Gly Pro Gly
                20                  25                  30

Pro Gly Gln Gln Pro Pro Pro Gln Gln Gln Ser Gly Gln
            35                  40                  45

Gln Tyr Asn Gly Glu Arg Gly Ile Ser Val Pro Asp His Gly Tyr Cys
    50                  55                  60

Gln Pro Ile Ser Ile Pro Leu Cys Thr Asp Ile Ala Tyr Asn Gln Thr
65                  70                  75                  80

Ile Met Pro Asn Leu Leu Gly His Thr Asn Gln Glu Asp Ala Gly Leu
                85                  90                  95

Glu Val His Gln Phe Tyr Pro Leu Val Lys Val Gln Cys Ser Ala Glu
            100                 105                 110

Leu Lys Phe Phe Leu Cys Ser Met Tyr Ala Pro Val Cys Thr Val Leu
        115                 120                 125

Glu Gln Ala Leu Pro Pro Cys Arg Ser Leu Cys Glu Arg Ala Arg Gln
    130                 135                 140

Gly Cys Glu Ala Leu Met Asn Lys Phe Gly Phe Gln Trp Pro Asp Thr
145                 150                 155                 160

Leu Lys Cys Glu Lys Phe Pro Val His Gly Ala Gly Glu Leu Cys Val
                165                 170                 175

Gly Gln Asn Thr Ser Asp Lys Gly Thr Pro Thr Pro Ser Leu Leu Pro
            180                 185                 190

Glu Phe Trp Thr Ser Asn Pro Gln His Ala Glu Pro Arg Ser Ser Asp
```

```
         195                 200                 205
Lys Thr His Thr Cys Pro Pro Cys Pro Ala Pro Glu Ala Glu Gly Ala
    210                 215                 220

Pro Ser Val Phe Leu Phe Pro Pro Lys Pro Lys Asp Thr Leu Met Ile
225                 230                 235                 240

Ser Arg Thr Pro Glu Val Thr Cys Val Val Val Asp Val Ser His Glu
                245                 250                 255

Asp Pro Glu Val Lys Phe Asn Trp Tyr Val Asp Gly Val Glu Val His
            260                 265                 270

Asn Ala Lys Thr Lys Pro Arg Glu Glu Gln Tyr Asn Ser Thr Tyr Arg
        275                 280                 285

Val Val Ser Val Leu Thr Val Leu His Gln Asp Trp Leu Asn Gly Lys
    290                 295                 300

Glu Tyr Lys Cys Ala Val Ser Asn Lys Ala Leu Pro Ala Ser Ile Glu
305                 310                 315                 320

Lys Thr Ile Ser Lys Ala Lys Gly Gln Pro Arg Glu Pro Gln Val Tyr
                325                 330                 335

Thr Leu Pro Pro Ser Arg Asp Glu Leu Thr Lys Asn Gln Val Ser Leu
            340                 345                 350

Thr Cys Leu Val Lys Gly Phe Tyr Pro Ser Asp Ile Ala Val Glu Trp
        355                 360                 365

Glu Ser Asn Gly Gln Pro Glu Asn Asn Tyr Lys Thr Thr Pro Pro Val
    370                 375                 380

Leu Asp Ser Asp Gly Ser Phe Phe Leu Tyr Ser Lys Leu Thr Val Asp
385                 390                 395                 400

Lys Ser Arg Trp Gln Gln Gly Asn Val Phe Ser Cys Ser Val Met His
                405                 410                 415

Glu Ala Leu His Asn His Tyr Thr Gln Lys Ser Leu Ser Leu Ser Pro
            420                 425                 430

Gly Lys

<210> SEQ ID NO 19
<211> LENGTH: 153
<212> TYPE: PRT
<213> ORGANISM: Homo sapiens

<400> SEQUENCE: 19

Gln Pro Tyr His Gly Glu Lys Gly Ile Ser Val Pro Asp His Gly Phe
1               5                   10                  15

Cys Gln Pro Ile Ser Ile Pro Leu Cys Thr Asp Ile Ala Tyr Asn Gln
                20                  25                  30

Thr Ile Leu Pro Asn Leu Leu Gly His Thr Asn Gln Glu Asp Ala Gly
            35                  40                  45

Leu Glu Val His Gln Phe Tyr Pro Leu Val Lys Val Gln Cys Ser Pro
    50                  55                  60

Glu Leu Arg Phe Phe Leu Cys Ser Met Tyr Ala Pro Val Cys Thr Val
65                  70                  75                  80

Leu Asp Gln Ala Ile Pro Pro Cys Arg Ser Leu Cys Glu Arg Ala Arg
                85                  90                  95

Gln Gly Cys Glu Ala Leu Met Asn Lys Phe Gly Phe Gln Trp Pro Glu
            100                 105                 110

Arg Leu Arg Cys Glu Asn Phe Pro Val His Gly Ala Gly Glu Ile Cys
        115                 120                 125

Val Gly Gln Asn Thr Ser Asp Gly Ser Gly Gly Pro Gly Gly Gly Pro
```

```
                130                 135                 140

Thr Ala Tyr Pro Thr Ala Pro Tyr Leu
145                 150

<210> SEQ ID NO 20
<211> LENGTH: 153
<212> TYPE: PRT
<213> ORGANISM: Mus musculus

<400> SEQUENCE: 20

Gln Pro Tyr His Gly Glu Lys Gly Ile Ser Val Pro Asp His Gly Phe
1               5                   10                  15

Cys Gln Pro Ile Ser Ile Pro Leu Cys Thr Asp Ile Ala Tyr Asn Gln
            20                  25                  30

Thr Ile Leu Pro Asn Leu Leu Gly His Thr Asn Gln Glu Asp Ala Gly
        35                  40                  45

Leu Glu Val His Gln Phe Tyr Pro Leu Val Lys Val Gln Cys Ser Pro
    50                  55                  60

Glu Leu Arg Phe Phe Leu Cys Ser Met Tyr Ala Pro Val Cys Thr Val
65                  70                  75                  80

Leu Asp Gln Ala Ile Pro Pro Cys Arg Ser Leu Cys Glu Arg Ala Arg
                85                  90                  95

Gln Gly Cys Glu Ala Leu Met Asn Lys Phe Gly Phe Gln Trp Pro Glu
            100                 105                 110

Arg Leu Arg Cys Glu Asn Phe Pro Val His Gly Ala Gly Glu Ile Cys
        115                 120                 125

Val Gly Gln Asn Thr Ser Asp Gly Ser Gly Ala Gly Gly Ser Pro
    130                 135                 140

Thr Ala Tyr Pro Thr Ala Pro Tyr Leu
145                 150

<210> SEQ ID NO 21
<211> LENGTH: 112
<212> TYPE: PRT
<213> ORGANISM: Homo sapiens

<400> SEQUENCE: 21

Cys Gln Pro Ile Ser Ile Pro Leu Cys Thr Asp Ile Ala Tyr Asn Gln
1               5                   10                  15

Thr Ile Leu Pro Asn Leu Leu Gly His Thr Asn Gln Glu Asp Ala Gly
            20                  25                  30

Leu Glu Val His Gln Phe Tyr Pro Leu Val Lys Val Gln Cys Ser Pro
        35                  40                  45

Glu Leu Arg Phe Phe Leu Cys Ser Met Tyr Ala Pro Val Cys Thr Val
    50                  55                  60

Leu Asp Gln Ala Ile Pro Pro Cys Arg Ser Leu Cys Glu Arg Ala Arg
65                  70                  75                  80

Gln Gly Cys Glu Ala Leu Met Asn Lys Phe Gly Phe Gln Trp Pro Glu
                85                  90                  95

Arg Leu Arg Cys Glu Asn Phe Pro Val His Gly Ala Gly Glu Ile Cys
            100                 105                 110

<210> SEQ ID NO 22
<211> LENGTH: 181
<212> TYPE: PRT
<213> ORGANISM: Homo sapiens

<400> SEQUENCE: 22
```

```
Gln Ala Ala Gly Gln Gly Pro Gly Gln Gly Pro Gly Pro Gly Gln Gln
1               5                   10                  15

Pro Pro Pro Pro Gln Gln Gln Ser Gly Gln Gln Tyr Asn Gly
            20                  25                  30

Glu Arg Gly Ile Ser Val Pro Asp His Gly Tyr Cys Gln Pro Ile Ser
        35                  40                  45

Ile Pro Leu Cys Thr Asp Ile Ala Tyr Asn Gln Thr Ile Met Pro Asn
50                  55                  60

Leu Leu Gly His Thr Asn Gln Glu Asp Ala Gly Leu Glu Val His Gln
65                  70                  75                  80

Phe Tyr Pro Leu Val Lys Val Gln Cys Ser Ala Glu Leu Lys Phe Phe
                85                  90                  95

Leu Cys Ser Met Tyr Ala Pro Val Cys Thr Val Leu Glu Gln Ala Leu
            100                 105                 110

Pro Pro Cys Arg Ser Leu Cys Glu Arg Ala Arg Gln Gly Cys Glu Ala
        115                 120                 125

Leu Met Asn Lys Phe Gly Phe Gln Trp Pro Asp Thr Leu Lys Cys Glu
130                 135                 140

Lys Phe Pro Val His Gly Ala Gly Glu Leu Cys Val Gly Gln Asn Thr
145                 150                 155                 160

Ser Asp Lys Gly Thr Pro Thr Pro Ser Leu Leu Pro Glu Phe Trp Thr
                165                 170                 175

Ser Asn Pro Gln His
            180

<210> SEQ ID NO 23
<211> LENGTH: 177
<212> TYPE: PRT
<213> ORGANISM: Mus musculus

<400> SEQUENCE: 23

Gln Ala Ala Gly Gln Val Ser Gly Pro Gly Gln Gln Ala Pro Pro Pro
1               5                   10                  15

Pro Gln Pro Gln Gln Ser Gly Gln Gln Tyr Asn Gly Glu Arg Gly Ile
            20                  25                  30

Ser Ile Pro Asp His Gly Tyr Cys Gln Pro Ile Ser Ile Pro Leu Cys
        35                  40                  45

Thr Asp Ile Ala Tyr Asn Gln Thr Ile Met Pro Asn Leu Leu Gly His
50                  55                  60

Thr Asn Gln Glu Asp Ala Gly Leu Glu Val His Gln Phe Tyr Pro Leu
65                  70                  75                  80

Val Lys Val Gln Cys Ser Ala Glu Leu Lys Phe Phe Leu Cys Ser Met
                85                  90                  95

Tyr Ala Pro Val Cys Thr Val Leu Glu Gln Ala Leu Pro Pro Cys Arg
            100                 105                 110

Ser Leu Cys Glu Arg Ala Arg Gln Gly Cys Glu Ala Leu Met Asn Lys
        115                 120                 125

Phe Gly Phe Gln Trp Pro Asp Thr Leu Lys Cys Glu Lys Phe Pro Val
130                 135                 140

His Gly Ala Gly Glu Leu Cys Val Gly Gln Asn Thr Ser Asp Lys Gly
145                 150                 155                 160

Thr Pro Thr Pro Ser Leu Leu Pro Glu Phe Trp Thr Ser Asn Pro Gln
                165                 170                 175

His
```

<210> SEQ ID NO 24
<211> LENGTH: 112
<212> TYPE: PRT
<213> ORGANISM: Homo sapiens

<400> SEQUENCE: 24

Cys Gln Pro Ile Ser Ile Pro Leu Cys Thr Asp Ile Ala Tyr Asn Gln
1               5                   10                  15

Thr Ile Met Pro Asn Leu Leu Gly His Thr Asn Gln Glu Asp Ala Gly
            20                  25                  30

Leu Glu Val His Gln Phe Tyr Pro Leu Val Lys Val Gln Cys Ser Ala
        35                  40                  45

Glu Leu Lys Phe Phe Leu Cys Ser Met Tyr Ala Pro Val Cys Thr Val
50                  55                  60

Leu Glu Gln Ala Leu Pro Pro Cys Arg Ser Leu Cys Glu Arg Ala Arg
65                  70                  75                  80

Gln Gly Cys Glu Ala Leu Met Asn Lys Phe Gly Phe Gln Trp Pro Asp
                85                  90                  95

Thr Leu Lys Cys Glu Lys Phe Pro Val His Gly Ala Gly Glu Leu Cys
            100                 105                 110

<210> SEQ ID NO 25
<211> LENGTH: 140
<212> TYPE: PRT
<213> ORGANISM: Homo sapiens

<400> SEQUENCE: 25

Gln Phe His Gly Glu Lys Gly Ile Ser Ile Pro Asp His Gly Phe Cys
1               5                   10                  15

Gln Pro Ile Ser Ile Pro Leu Cys Thr Asp Ile Ala Tyr Asn Gln Thr
            20                  25                  30

Ile Met Pro Asn Leu Leu Gly His Thr Asn Gln Glu Asp Ala Gly Leu
        35                  40                  45

Glu Val His Gln Phe Tyr Pro Leu Val Lys Val Gln Cys Ser Pro Glu
50                  55                  60

Leu Arg Phe Phe Leu Cys Ser Met Tyr Ala Pro Val Cys Thr Val Leu
65                  70                  75                  80

Glu Gln Ala Ile Pro Pro Cys Arg Ser Ile Cys Glu Arg Ala Arg Gln
                85                  90                  95

Gly Cys Glu Ala Leu Met Asn Lys Phe Gly Phe Gln Trp Pro Glu Arg
            100                 105                 110

Leu Arg Cys Glu His Phe Pro Arg His Gly Ala Glu Gln Ile Cys Val
        115                 120                 125

Gly Gln Asn His Ser Glu Asp Gly Ala Pro Ala Leu
    130                 135                 140

<210> SEQ ID NO 26
<211> LENGTH: 112
<212> TYPE: PRT
<213> ORGANISM: Homo sapiens

<400> SEQUENCE: 26

Cys Gln Pro Ile Ser Ile Pro Leu Cys Thr Asp Ile Ala Tyr Asn Gln
1               5                   10                  15

Thr Ile Met Pro Asn Leu Leu Gly His Thr Asn Gln Glu Asp Ala Gly
            20                  25                  30

```
Leu Glu Val His Gln Phe Tyr Pro Leu Val Lys Val Gln Cys Ser Pro
             35                  40                  45

Glu Leu Arg Phe Phe Leu Cys Ser Met Tyr Ala Pro Val Cys Thr Val
 50                  55                  60

Leu Glu Gln Ala Ile Pro Pro Cys Arg Ser Ile Cys Glu Arg Ala Arg
 65                  70                  75                  80

Gln Gly Cys Glu Ala Leu Met Asn Lys Phe Gly Phe Gln Trp Pro Glu
             85                  90                  95

Arg Leu Arg Cys Glu His Phe Pro Arg His Gly Ala Glu Gln Ile Cys
            100                 105                 110
```

<210> SEQ ID NO 27
<211> LENGTH: 386
<212> TYPE: PRT
<213> ORGANISM: Artificial
<220> FEATURE:
<223> OTHER INFORMATION: fusion protein

<400> SEQUENCE: 27

```
Gln Pro Tyr His Gly Glu Lys Gly Ile Ser Val Pro Asp His Gly Phe
 1               5                  10                  15

Cys Gln Pro Ile Ser Ile Pro Leu Cys Thr Asp Ile Ala Tyr Asn Gln
             20                  25                  30

Thr Ile Leu Pro Asn Leu Leu Gly His Thr Asn Gln Glu Asp Ala Gly
             35                  40                  45

Leu Glu Val His Gln Phe Tyr Pro Leu Val Lys Val Gln Cys Ser Pro
 50                  55                  60

Glu Leu Arg Phe Phe Leu Cys Ser Met Tyr Ala Pro Val Cys Thr Val
 65                  70                  75                  80

Leu Asp Gln Ala Ile Pro Pro Cys Arg Ser Leu Cys Glu Arg Ala Arg
             85                  90                  95

Gln Gly Cys Glu Ala Leu Met Asn Lys Phe Gly Phe Gln Trp Pro Glu
            100                 105                 110

Arg Leu Arg Cys Glu Asn Phe Pro Val His Gly Ala Gly Glu Ile Cys
            115                 120                 125

Val Gly Gln Asn Thr Ser Asp Gly Ser Gly Pro Gly Gly Pro
            130                 135                 140

Thr Ala Tyr Pro Thr Ala Pro Tyr Leu Ala Glu Pro Arg Ser Ser Asp
145                 150                 155                 160

Lys Thr His Thr Cys Pro Pro Cys Pro Ala Pro Glu Ala Glu Gly Ala
                    165                 170                 175

Pro Ser Val Phe Leu Phe Pro Pro Lys Pro Lys Asp Thr Leu Met Ile
                180                 185                 190

Ser Arg Thr Pro Glu Val Thr Cys Val Val Val Asp Val Ser His Glu
                195                 200                 205

Asp Pro Glu Val Lys Phe Asn Trp Tyr Val Asp Gly Val Glu Val His
        210                 215                 220

Asn Ala Lys Thr Lys Pro Arg Glu Glu Gln Tyr Asn Ser Thr Tyr Arg
225                 230                 235                 240

Val Val Ser Val Leu Thr Val Leu His Gln Asp Trp Leu Asn Gly Lys
                    245                 250                 255

Glu Tyr Lys Cys Ala Val Ser Asn Lys Ala Leu Pro Ala Ser Ile Glu
                260                 265                 270

Lys Thr Ile Ser Lys Ala Lys Gly Gln Pro Arg Glu Pro Gln Val Tyr
                275                 280                 285
```

```
Thr Leu Pro Pro Ser Arg Asp Glu Leu Thr Lys Asn Gln Val Ser Leu
290                 295                 300

Thr Cys Leu Val Lys Gly Phe Tyr Pro Ser Asp Ile Ala Val Glu Trp
305                 310                 315                 320

Glu Ser Asn Gly Gln Pro Glu Asn Asn Tyr Lys Thr Thr Pro Pro Val
            325                 330                 335

Leu Asp Ser Asp Gly Ser Phe Phe Leu Tyr Ser Lys Leu Thr Val Asp
            340                 345                 350

Lys Ser Arg Trp Gln Gln Gly Asn Val Phe Ser Cys Ser Val Met His
        355                 360                 365

Glu Ala Leu His Asn His Tyr Thr Gln Lys Ser Leu Ser Leu Ser Pro
370                 375                 380

Gly Lys
385

<210> SEQ ID NO 28
<211> LENGTH: 386
<212> TYPE: PRT
<213> ORGANISM: Artificial
<220> FEATURE:
<223> OTHER INFORMATION: fusion protein

<400> SEQUENCE: 28

Gln Pro Tyr His Gly Glu Lys Gly Ile Ser Val Pro Asp His Gly Phe
1               5                   10                  15

Cys Gln Pro Ile Ser Ile Pro Leu Cys Thr Asp Ile Ala Tyr Asn Gln
                20                  25                  30

Thr Ile Leu Pro Asn Leu Leu Gly His Thr Asn Gln Glu Asp Ala Gly
            35                  40                  45

Leu Glu Val His Gln Phe Tyr Pro Leu Val Lys Val Gln Cys Ser Pro
50                  55                  60

Glu Leu Arg Phe Phe Leu Cys Ser Met Tyr Ala Pro Val Cys Thr Val
65                  70                  75                  80

Leu Asp Gln Ala Ile Pro Pro Cys Arg Ser Leu Cys Glu Arg Ala Arg
                85                  90                  95

Gln Gly Cys Glu Ala Leu Met Asn Lys Phe Gly Phe Gln Trp Pro Glu
            100                 105                 110

Arg Leu Arg Cys Glu Asn Phe Pro Val His Gly Ala Gly Glu Ile Cys
        115                 120                 125

Val Gly Gln Asn Thr Ser Asp Gly Ser Gly Gly Ala Gly Gly Ser Pro
130                 135                 140

Thr Ala Tyr Pro Thr Ala Pro Tyr Leu Ala Glu Pro Arg Ser Ser Asp
145                 150                 155                 160

Lys Thr His Thr Cys Pro Pro Cys Pro Ala Pro Glu Ala Glu Gly Ala
                165                 170                 175

Pro Ser Val Phe Leu Phe Pro Pro Lys Pro Lys Asp Thr Leu Met Ile
            180                 185                 190

Ser Arg Thr Pro Glu Val Thr Cys Val Val Val Asp Val Ser His Glu
        195                 200                 205

Asp Pro Glu Val Lys Phe Asn Trp Tyr Val Asp Gly Val Glu Val His
210                 215                 220

Asn Ala Lys Thr Lys Pro Arg Glu Glu Gln Tyr Asn Ser Thr Tyr Arg
225                 230                 235                 240

Val Val Ser Val Leu Thr Val Leu His Gln Asp Trp Leu Asn Gly Lys
                245                 250                 255
```

```
Glu Tyr Lys Cys Ala Val Ser Asn Lys Ala Leu Pro Ala Ser Ile Glu
                260                 265                 270

Lys Thr Ile Ser Lys Ala Lys Gly Gln Pro Arg Glu Pro Gln Val Tyr
            275                 280                 285

Thr Leu Pro Pro Ser Arg Asp Glu Leu Thr Lys Asn Gln Val Ser Leu
        290                 295                 300

Thr Cys Leu Val Lys Gly Phe Tyr Pro Ser Asp Ile Ala Val Glu Trp
305                 310                 315                 320

Glu Ser Asn Gly Gln Pro Glu Asn Asn Tyr Lys Thr Thr Pro Pro Val
                325                 330                 335

Leu Asp Ser Asp Gly Ser Phe Phe Leu Tyr Ser Lys Leu Thr Val Asp
            340                 345                 350

Lys Ser Arg Trp Gln Gln Gly Asn Val Phe Ser Cys Ser Val Met His
        355                 360                 365

Glu Ala Leu His Asn His Tyr Thr Gln Lys Ser Leu Ser Leu Ser Pro
370                 375                 380

Gly Lys
385

<210> SEQ ID NO 29
<211> LENGTH: 414
<212> TYPE: PRT
<213> ORGANISM: Artificial
<220> FEATURE:
<223> OTHER INFORMATION: fusion protein

<400> SEQUENCE: 29

Gln Ala Ala Gly Gln Gly Pro Gly Gln Gly Pro Gly Pro Gly Gln Gln
1               5                   10                  15

Pro Pro Pro Pro Gln Gln Gln Gln Ser Gly Gln Gln Tyr Asn Gly
            20                  25                  30

Glu Arg Gly Ile Ser Val Pro Asp His Gly Tyr Cys Gln Pro Ile Ser
            35                  40                  45

Ile Pro Leu Cys Thr Asp Ile Ala Tyr Asn Gln Thr Ile Met Pro Asn
50                  55                  60

Leu Leu Gly His Thr Asn Gln Glu Asp Ala Gly Leu Glu Val His Gln
65                  70                  75                  80

Phe Tyr Pro Leu Val Lys Val Gln Cys Ser Ala Glu Leu Lys Phe Phe
                85                  90                  95

Leu Cys Ser Met Tyr Ala Pro Val Cys Thr Val Leu Glu Gln Ala Leu
            100                 105                 110

Pro Pro Cys Arg Ser Leu Cys Glu Arg Ala Arg Gln Gly Cys Glu Ala
        115                 120                 125

Leu Met Asn Lys Phe Gly Phe Gln Trp Pro Asp Thr Leu Lys Cys Glu
130                 135                 140

Lys Phe Pro Val His Gly Ala Gly Glu Leu Cys Val Gly Gln Asn Thr
145                 150                 155                 160

Ser Asp Lys Gly Thr Pro Thr Pro Ser Leu Leu Pro Glu Phe Trp Thr
                165                 170                 175

Ser Asn Pro Gln His Ala Glu Pro Arg Ser Ser Asp Lys Thr His Thr
            180                 185                 190

Cys Pro Pro Cys Pro Ala Pro Glu Ala Glu Gly Ala Pro Ser Val Phe
        195                 200                 205

Leu Phe Pro Pro Lys Pro Lys Asp Thr Leu Met Ile Ser Arg Thr Pro
210                 215                 220
```

```
Glu Val Thr Cys Val Val Asp Val Ser His Glu Asp Pro Glu Val
225                 230                 235                 240

Lys Phe Asn Trp Tyr Val Asp Gly Val Glu Val His Asn Ala Lys Thr
                245                 250                 255

Lys Pro Arg Glu Glu Gln Tyr Asn Ser Thr Tyr Arg Val Val Ser Val
            260                 265                 270

Leu Thr Val Leu His Gln Asp Trp Leu Asn Gly Lys Glu Tyr Lys Cys
            275                 280                 285

Ala Val Ser Asn Lys Ala Leu Pro Ala Ser Ile Glu Lys Thr Ile Ser
            290                 295                 300

Lys Ala Lys Gly Gln Pro Arg Glu Pro Gln Val Tyr Thr Leu Pro Pro
305                 310                 315                 320

Ser Arg Asp Glu Leu Thr Lys Asn Gln Val Ser Leu Thr Cys Leu Val
                325                 330                 335

Lys Gly Phe Tyr Pro Ser Asp Ile Ala Val Glu Trp Glu Ser Asn Gly
                340                 345                 350

Gln Pro Glu Asn Asn Tyr Lys Thr Thr Pro Pro Val Leu Asp Ser Asp
            355                 360                 365

Gly Ser Phe Phe Leu Tyr Ser Lys Leu Thr Val Asp Lys Ser Arg Trp
370                 375                 380

Gln Gln Gly Asn Val Phe Ser Cys Ser Val Met His Glu Ala Leu His
385                 390                 395                 400

Asn His Tyr Thr Gln Lys Ser Leu Ser Leu Ser Pro Gly Lys
                405                 410

<210> SEQ ID NO 30
<211> LENGTH: 410
<212> TYPE: PRT
<213> ORGANISM: Artificial
<220> FEATURE:
<223> OTHER INFORMATION: fusion protein

<400> SEQUENCE: 30

Gln Ala Ala Gly Gln Val Ser Gly Pro Gly Gln Gln Ala Pro Pro Pro
1               5                   10                  15

Pro Gln Pro Gln Gln Ser Gly Gln Gln Tyr Asn Gly Glu Arg Gly Ile
            20                  25                  30

Ser Ile Pro Asp His Gly Tyr Cys Gln Pro Ile Ser Ile Pro Leu Cys
        35                  40                  45

Thr Asp Ile Ala Tyr Asn Gln Thr Ile Met Pro Asn Leu Leu Gly His
    50                  55                  60

Thr Asn Gln Glu Asp Ala Gly Leu Glu Val His Gln Phe Tyr Pro Leu
65                  70                  75                  80

Val Lys Val Gln Cys Ser Ala Glu Leu Lys Phe Phe Leu Cys Ser Met
                85                  90                  95

Tyr Ala Pro Val Cys Thr Val Leu Glu Gln Ala Leu Pro Pro Cys Arg
            100                 105                 110

Ser Leu Cys Glu Arg Ala Arg Gln Gly Cys Glu Ala Leu Met Asn Lys
            115                 120                 125

Phe Gly Phe Gln Trp Pro Asp Thr Leu Lys Cys Glu Lys Phe Pro Val
        130                 135                 140

His Gly Ala Gly Glu Leu Cys Val Gly Gln Asn Thr Ser Asp Lys Gly
145                 150                 155                 160

Thr Pro Thr Pro Ser Leu Leu Pro Glu Phe Trp Thr Ser Asn Pro Gln
                165                 170                 175
```

His Ala Glu Pro Arg Ser Ser Asp Lys Thr His Thr Cys Pro Cys
            180                 185                 190

Pro Ala Pro Glu Ala Glu Gly Ala Pro Ser Val Phe Leu Phe Pro Pro
        195                 200                 205

Lys Pro Lys Asp Thr Leu Met Ile Ser Arg Thr Pro Glu Val Thr Cys
210                 215                 220

Val Val Val Asp Val Ser His Glu Asp Pro Glu Val Lys Phe Asn Trp
225                 230                 235                 240

Tyr Val Asp Gly Val Glu Val His Asn Ala Lys Thr Lys Pro Arg Glu
            245                 250                 255

Glu Gln Tyr Asn Ser Thr Tyr Arg Val Val Ser Val Leu Thr Val Leu
        260                 265                 270

His Gln Asp Trp Leu Asn Gly Lys Glu Tyr Lys Cys Ala Val Ser Asn
    275                 280                 285

Lys Ala Leu Pro Ala Ser Ile Glu Lys Thr Ile Ser Lys Ala Lys Gly
290                 295                 300

Gln Pro Arg Glu Pro Gln Val Tyr Thr Leu Pro Pro Ser Arg Asp Glu
305                 310                 315                 320

Leu Thr Lys Asn Gln Val Ser Leu Thr Cys Leu Val Lys Gly Phe Tyr
            325                 330                 335

Pro Ser Asp Ile Ala Val Glu Trp Glu Ser Asn Gly Gln Pro Glu Asn
        340                 345                 350

Asn Tyr Lys Thr Thr Pro Pro Val Leu Asp Ser Asp Gly Ser Phe Phe
    355                 360                 365

Leu Tyr Ser Lys Leu Thr Val Asp Lys Ser Arg Trp Gln Gln Gly Asn
370                 375                 380

Val Phe Ser Cys Ser Val Met His Glu Ala Leu His Asn His Tyr Thr
385                 390                 395                 400

Gln Lys Ser Leu Ser Leu Ser Pro Gly Lys
            405                 410

<210> SEQ ID NO 31
<211> LENGTH: 373
<212> TYPE: PRT
<213> ORGANISM: Artificial
<220> FEATURE:
<223> OTHER INFORMATION: fusion protein

<400> SEQUENCE: 31

Gln Phe His Gly Glu Lys Gly Ile Ser Ile Pro Asp His Gly Phe Cys
1               5                   10                  15

Gln Pro Ile Ser Ile Pro Leu Cys Thr Asp Ile Ala Tyr Asn Gln Thr
            20                  25                  30

Ile Met Pro Asn Leu Leu Gly His Thr Asn Gln Glu Asp Ala Gly Leu
        35                  40                  45

Glu Val His Gln Phe Tyr Pro Leu Val Lys Val Gln Cys Ser Pro Glu
    50                  55                  60

Leu Arg Phe Phe Leu Cys Ser Met Tyr Ala Pro Val Cys Thr Val Leu
65                  70                  75                  80

Glu Gln Ala Ile Pro Pro Cys Arg Ser Ile Cys Glu Arg Ala Arg Gln
            85                  90                  95

Gly Cys Glu Ala Leu Met Asn Lys Phe Gly Phe Gln Trp Pro Glu Arg
        100                 105                 110

Leu Arg Cys Glu His Phe Pro Arg His Gly Ala Glu Gln Ile Cys Val
    115                 120                 125

Gly Gln Asn His Ser Glu Asp Gly Ala Pro Ala Leu Ala Glu Pro Arg
130                 135                 140

Ser Ser Asp Lys Thr His Thr Cys Pro Cys Pro Ala Pro Glu Ala
145                 150                 155                 160

Glu Gly Ala Pro Ser Val Phe Leu Phe Pro Lys Pro Lys Asp Thr
            165                 170                 175

Leu Met Ile Ser Arg Thr Pro Glu Val Thr Cys Val Val Asp Val
            180                 185                 190

Ser His Glu Asp Pro Glu Val Lys Phe Asn Trp Tyr Val Asp Gly Val
            195                 200                 205

Glu Val His Asn Ala Lys Thr Lys Pro Arg Glu Glu Gln Tyr Asn Ser
210                 215                 220

Thr Tyr Arg Val Val Ser Val Leu Thr Val Leu His Gln Asp Trp Leu
225                 230                 235                 240

Asn Gly Lys Glu Tyr Lys Cys Ala Val Ser Asn Lys Ala Leu Pro Ala
            245                 250                 255

Ser Ile Glu Lys Thr Ile Ser Lys Ala Lys Gly Gln Pro Arg Glu Pro
            260                 265                 270

Gln Val Tyr Thr Leu Pro Pro Ser Arg Asp Glu Leu Thr Lys Asn Gln
            275                 280                 285

Val Ser Leu Thr Cys Leu Val Lys Gly Phe Tyr Pro Ser Asp Ile Ala
290                 295                 300

Val Glu Trp Glu Ser Asn Gly Gln Pro Glu Asn Asn Tyr Lys Thr Thr
305                 310                 315                 320

Pro Pro Val Leu Asp Ser Asp Gly Ser Phe Phe Leu Tyr Ser Lys Leu
            325                 330                 335

Thr Val Asp Lys Ser Arg Trp Gln Gln Gly Asn Val Phe Ser Cys Ser
            340                 345                 350

Val Met His Glu Ala Leu His Asn His Tyr Thr Gln Lys Ser Leu Ser
            355                 360                 365

Leu Ser Pro Gly Lys
    370

<210> SEQ ID NO 32
<211> LENGTH: 555
<212> TYPE: DNA
<213> ORGANISM: Mus musculus

<400> SEQUENCE: 32
atgcggggcc ccggcacggc ggcgtcgcac tcgcccctgg gcctctgcgc cctggtgctt      60
gctcttctgt gcgcgctgcc cacggacacc cgggctcagc catatcacgg cgagaaaggc     120
atctcggtac cggaccacgg cttctgccag cccatctcca tcccgttgtg cacggatatc     180
gcctacaacc agaccatcct gcccaacctg ctgggccaca cgaaccaaga ggacgcgggc     240
ctcgaggtgc accagttcta ccctctggta aaggtgcagt gttctcctga gctacgcttc     300
ttcttatgct ctatgtacgc acccgtgtgc accgtgctcg accaagccat tcctccgtgc     360
cgttccttgt gcgagcgcgc ccgacagggc tgcgaggcgc tcatgaacaa gttcggcttc     420
cagtggccag agcggttgcg ctgcgagaac ttcccagtgc acgtgccgg cgagatctgc     480 gtggggcaga acacgtccga cggctccggg ggcgcgggcg gcagtccac cgcctaccct     540 actgctccct acctg                                                      555

<210> SEQ ID NO 33
<211> LENGTH: 555

<212> TYPE: DNA
<213> ORGANISM: Homo sapiens

<400> SEQUENCE: 33

```
atgcgggacc ccggcgcggc cgctccgctt tcgtccctgg gcctctgtgc cctggtgctg      60
gcgctgctgg gcgcactgtc cgcgggcgcc ggggcgcagc cgtaccacgg agagaagggc     120
atctccgtgc cggaccacgg cttctgccag cccatctcca tcccgctgtg cacggacatc     180
gcctacaacc agaccatcct gcccaacctg ctgggccaca cgaaccaaga ggacgcgggc     240
ctcgaggtgc accagttcta cccgctggtg aaggtgcagt gttctcccga actccgcttt     300
ttcttatgct ccatgtatgc gcccgtgtgc accgtgctcg atcaggccat cccgccgtgt     360
cgttctctgt gcgagcgcgc ccgccagggc tgcgaggcgc tcatgaacaa gttcggcttc     420
cagtggcccg agcggctgcg ctgcgagaac ttcccggtgc acggtgcggg cgagatctgc     480
gtgggccaga acacgtcgga cggctccggg ggcccaggcg gcggcccac tgcctaccct      540
accgcgccct acctg                                                      555
```

<210> SEQ ID NO 34
<211> LENGTH: 744
<212> TYPE: DNA
<213> ORGANISM: Mus musculus

<400> SEQUENCE: 34

```
atggctgagg aggcggcgcc tagcgagtcc cgggccgccg gccggctgag cttggaactt      60
tgtgccgaag cactcccggg ccggcggag gaggtgggc acgaggacac ggccagccac       120
cgccgccccc gggctgatcc ccggcgttgg gctagcgggc tgctgctgct gctttggttg     180
ctggaggctc ctctgctttt gggggtccga gcgcaggcgg cgggccaggt atccggccg      240
ggccagcaag ccccgccgcc gccccagccc agcagagcg ggcagcagta caacggcgaa      300
cggggcatct ccatcccgga ccacggctac tgccagccca tctccatccc gctgtgcacg     360
gacatcgcgt acaaccagac catcatgccc aacctgctgg ccacacgaa tcaggaggac      420
gccggtctgg aggtgcacca gttctaccct ctggtgaagg tgcagtgctc cgccgagctc     480
aagttcttcc tgtgctccat gtacgcgcct gtgtgcaccg tactgagca ggcgctaccg      540
ccctgccgct ccctgtgcga gcgcgcacgc cagggctgcg aggcgctcat gaacaagttc     600
ggcttccagt ggccagacac actcaagtgc gagaagttcc cggtgcacgg cgcaggagag     660
ctgtgcgtgg gccagaacac gtccgacaaa ggcaccccaa ctccctcctt gctaccagag     720
ttctggacca gtaatccgca gcac                                            744
```

<210> SEQ ID NO 35
<211> LENGTH: 759
<212> TYPE: DNA
<213> ORGANISM: Homo sapiens

<400> SEQUENCE: 35

```
atggctgagg aggaggcgcc taagaagtcc cgggccgccg gcggtggcgc gagctgggaa     60
ctttgtgccg gggcgctctc ggcccggct gcggaggagg gcagcgggga cgccggtggc     120
cgccgccgcc cgccagttga cccccggcga ttggcgcgca agctgctgct gctgctttgg     180
ctgctggagg ctccgctgct gctggggtc cgggcccagg cggcgggcca ggggccaggc     240
caggggcccg ggcggggca gcaaccgccg ccgccgcctc agcagcaaca gagcgggcag     300
cagtacaacg gcgagcgggg catctccgtc ccggaccacg gctattgcca gcccatctcc     360
```

| | |
|---|---|
| atcccgctgt gcacggacat cgcgtacaac cagaccatca tgcccaacct gctgggccac | 420 |
| acgaaccagg aggacgcggg cctggaggtg caccagttct accctctagt gaaagtgcag | 480 |
| tgttccgctg agctcaagtt cttcctgtgc tccatgtacg cgcccgtgtg caccgtgcta | 540 |
| gagcaggcgc tgccgccctg ccgctccctg tgcgagcgcg cgcgccaggg ctgcgaggcg | 600 |
| ctcatgaaca agttcggctt ccagtggcca gacacgctca agtgtgagaa gttcccggtg | 660 |
| cacggcgccg cgtgggccag aacacgtccg acaagggcac cccgacgccc | 720 |
| tcgctgcttc cagagttctg gaccagcaac cctcagcac | 759 |

<210> SEQ ID NO 36
<211> LENGTH: 504
<212> TYPE: DNA
<213> ORGANISM: Mus musculus

<400> SEQUENCE: 36

| | |
|---|---|
| atgcgggccc gcagcgccct gccccgcagc gccctgcccc gcctgctgct gccactgctg | 60 |
| ctgctgccgg ccgccggacc ggcccagttc acggggagga agggcatctc catcccggac | 120 |
| cacggcttct gccagcccat ctccatcccg ctgtgcacgg acatcgccta aaccagacc | 180 |
| atcatgccca accttcttgg ccacacgaac caggaagacg cgggcctgga ggtgcatcag | 240 |
| ttctacccgc tggtgaaggt gcagtgctcg cccgagctgc gcttcttcct gtgctccatg | 300 |
| tacgcgccgg tgtgcacagt gctggagcag gccatcccgc cgtgccgctc catctgcgag | 360 |
| cgcgcgcgcc aaggctgcga ggcgctcatg aacaagttcg gcttccaatg gcccgagcgc | 420 |
| ctccgctgcg agcatttccc cgtcacggc gcggagcaga tctgcgtggg ccagaaccac | 480 |
| tcggaggacg gagctcctgc gcta | 504 |

<210> SEQ ID NO 37
<211> LENGTH: 489
<212> TYPE: DNA
<213> ORGANISM: Homo sapiens

<400> SEQUENCE: 37

| | |
|---|---|
| atgcggcccc gcagcgccct gccccgcctg ctgctgccgc tgctgctgct gcccgccgcc | 60 |
| gggccggccc agttccacgg ggagaagggc atctccatcc cggaccacgg cttctgccag | 120 |
| cccatctcca tcccgctgtg cacggacatc gcctacaacc agaccatcat gcccaacctt | 180 |
| ctgggccaca cgaaccagga ggacgcaggc ctagaggtgc accagttcta tccgctggtg | 240 |
| aaggtgcagt gctcgcccga actgcgcttc ttcctgtgct ccatgtacgc acccgtgtgc | 300 |
| accgtgctgg aacaggccat cccgccgtgc cgctctatct gtgagcgcgc gcgccagggc | 360 |
| tgcgaagccc tcatgaacaa gttcggtttt cagtggcccg agcgcctgcg ctgcgagcac | 420 |
| ttcccgcgcc acgcgccga gcagatctgc gtcggccaga accactccga ggacggagct | 480 |
| cccgcgcta | 489 |

<210> SEQ ID NO 38
<211> LENGTH: 1161
<212> TYPE: DNA
<213> ORGANISM: Artificial
<220> FEATURE:
<223> OTHER INFORMATION: DNA encoding fusion protein

<400> SEQUENCE: 38

| | |
|---|---|
| cagccatatc acggcgagaa aggcatctcg gtaccggacc acggcttctg ccagcccatc | 60 |
| tccatcccgt tgtgcacgga tatcgcctac aaccagacca tcctgcccaa cctgctgggc | 120 |

```
cacacgaacc aagaggacgc gggcctcgag gtgcaccagt tctaccctct ggtaaaggtg      180
cagtgttctc ctgagctacg cttcttctta tgctctatgt acgcacccgt gtgcaccgtg      240
ctcgaccaag ccattcctcc gtgccgttcc ttgtgcgagc gcgcccgaca gggctgcgag      300
gcgctcatga acaagttcgg cttccagtgg ccagagcggt tgcgctgcga aacttcccca      360
gtgcacggtg ccggcgagat ctgcgtgggg cagaacacgt ccgacggctc cggggggcgcg    420 ggcggcagtc ccaccgccta ccctactgct ccctacctgg ccgagcctag gtcttcagac      480
aaaactcaca catgcccacc gtgcccagca cctgaagccg agggggcccc gtcagtcttc      540
ctcttccccc caaaacccaa ggacaccctc atgatctccc ggacccctga ggtcacatgc      600
gtggtggtgg acgtgagcca cgaagaccct gaggtcaagt tcaactggta cgtggacggc      660
gtggaggtgc ataatgccaa gacaaagccg cgggaggagc agtacaacag cacgtaccgt      720
gtggtcagcg tcctcaccgt cctgcaccag gactggctga atggcaagga gtacaagtgc      780
gccgtctcca acaaagccct cccagcctcc atcgagaaaa ccatctccaa agccaaaggg      840
cagccccgag aaccacaggt gtacaccctg cccccatccc gggatgagct gaccaagaac      900
caggtcagcc tgacctgcct ggtcaaaggc ttctatccca gcgacatcgc cgtggagtgg      960
gagagcaatg ggcagccgga gaacaactac aagaccacgc ctcccgtgct ggactccgac     1020
ggctccttct tcctctacag caagctcacc gtggacaaga gcaggtggca gcaggggaac     1080
gtcttctcat gctccgtgat gcatgaggct ctgcacaacc actacacgca gaagagcctc     1140
tccctgtctc cgggtaaatg a                                               1161

<210> SEQ ID NO 39
<211> LENGTH: 1161
<212> TYPE: DNA
<213> ORGANISM: Artificial
<220> FEATURE:
<223> OTHER INFORMATION: DNA encoding fusion protein

<400> SEQUENCE: 39
cagccgtacc acggagagaa gggcatctcc gtgccggacc acggcttctg ccagcccatc       60
tccatcccgc tgtgcacgga catcgcctac aaccagacca tcctgcccaa cctgctgggc      120
cacacgaacc aagaggacgc gggcctcgag gtgcaccagt tctacccgct ggtgaaggtg      180
cagtgttctc ccgaactccg cttttttctta tgctccatgt atgcgcccgt gtgcaccgtg     240
ctcgatcagg ccatcccgcc gtgtcgttct ctgtgcgagc gcgcccgcca gggctgcgag      300
gcgctcatga acaagttcgg cttccagtgg cccgagcggt tgcgctgcga aacttcccg       360 gtgcacggtg cgggcgagat ctgcgtgggc cagaacacgt cggacggctc cggggggccca    420 ggcggcggcc ccactgccta ccctaccgcg ccctacctgg ccgagcctag gtcttcagac      480
aaaactcaca catgcccacc gtgcccagca cctgaagccg agggggcccc gtcagtcttc      540
ctcttccccc caaaacccaa ggacaccctc atgatctccc ggacccctga ggtcacatgc      600
gtggtggtgg acgtgagcca cgaagaccct gaggtcaagt tcaactggta cgtggacggc      660
gtggaggtgc ataatgccaa gacaaagccg cgggaggagc agtacaacag cacgtaccgt      720
gtggtcagcg tcctcaccgt cctgcaccag gactggctga atggcaagga gtacaagtgc      780
gccgtctcca acaaagccct cccagcctcc atcgagaaaa ccatctccaa agccaaaggg      840
cagccccgag aaccacaggt gtacaccctg cccccatccc gggatgagct gaccaagaac      900
caggtcagcc tgacctgcct ggtcaaaggc ttctatccca gcgacatcgc cgtggagtgg      960
```

```
gagagcaatg ggcagccgga gaacaactac aagaccacgc ctcccgtgct ggactccgac    1020
ggctccttct tcctctacag caagctcacc gtggacaaga gcaggtggca gcagggaac     1080 gtcttctcat gctccgtgat gcatgaggct ctgcacaacc actacacgca gaagagcctc    1140
tccctgtctc cgggtaaatg a                                              1161
```

<210> SEQ ID NO 40
<211> LENGTH: 1233
<212> TYPE: DNA
<213> ORGANISM: Artificial
<220> FEATURE:
<223> OTHER INFORMATION: DNA encoding fusion protein

<400> SEQUENCE: 40

```
caggcggcgg gccaggtatc cgggccgggc cagcaagccc cgccgccgcc ccagccccag      60
cagagcgggc agcagtacaa cggcgaacgg ggcatctcca tcccggacca cggctactgc    120
cagcccatct ccatcccgct gtgcacggac atcgcgtaca accagaccat catgcccaac    180
ctgctgggcc acacgaatca ggaggacgcc ggtctggagg tgcaccagtt ctaccctctg    240
gtgaaggtgc agtgctccgc cgagctcaag ttcttcctgt gctccatgta cgcgcctgtg    300
tgcaccgtac tggagcaggc gctaccgccc tgccgctccc tgtgcgagcg cgcacgccag    360
ggctgcgagg cgctcatgaa caagttcggc ttccagtggc cagacacact caagtgcgag    420
aagttcccgg tgcacggcgc aggagagctg tgcgtgggcc agaacacgtc cgacaaaggc    480
accccaactc cctccttgct accagagttc tggaccagta atccgcagca cgccgagcct    540
aggtcttcag acaaaactca cacatgccca ccgtgcccag cacctgaagc cgaggggggcc    600 ccgtcagtct tcctcttccc cccaaaaccc aaggacaccc tcatgatctc ccggacccct    660
gaggtcacat gcgtggtggt ggacgtgagc cacgaagacc ctgaggtcaa gttcaactgg    720
tacgtggacg gcgtggaggt gcataatgcc aagacaaagc cgcgggagga gcagtacaac    780
agcacgtacc gtgtggtcag cgtcctcacc gtcctgcacc aggactggct gaatggcaag    840
gagtacaagt gcgccgtctc caacaaagcc ctcccagcct ccatcgagaa aaccatctcc    900
aaagccaaag ggcagccccg agaaccacag gtgtacaccc tgcccccatc ccgggatgag    960
ctgaccaaga accaggtcag cctgacctgc ctggtcaaag gcttctatcc cagcgacatc   1020
gccgtggagt gggagagcaa tgggcagccg gagaacaact acaagaccac gcctcccgtg   1080
ctggactccg acggctcctt cttcctctac agcaagctca ccgtggacaa gagcaggtgg   1140
cagcagggga acgtcttctc atgctccgtg atgcatgagg ctctgcacaa ccactacacg   1200
cagaagagcc tctccctgtc tccgggtaaa tga                                1233
```

<210> SEQ ID NO 41
<211> LENGTH: 1245
<212> TYPE: DNA
<213> ORGANISM: Artificial
<220> FEATURE:
<223> OTHER INFORMATION: DNA encoding fusion protein

<400> SEQUENCE: 41

```
caggcggcgg gccagggggcc aggccagggg cccggggccgg ggcagcaacc gccgccgccg     60
cctcagcagc aacagagcgg gcagcagtac aacggcgagc ggggcatctc cgtcccggac    120
cacggctatt gccagcccat ctccatcccg ctgtgcacgg acatcgcgta caaccagacc    180
atcatgccca acctgctggg ccacacgaac caggaggacg cgggcctgga ggtgcaccag    240
ttctaccctc tagtgaaagt gcagtgttcc gctgagctca agttcttcct gtgctccatg    300
```

```
tacgcgcccg tgtgcaccgt gctagagcag gcgctgccgc cctgccgctc cctgtgcgag    360
cgcgcgcgcc agggctgcga ggcgctcatg aacaagttcg gcttccagtg gccagacacg    420
ctcaagtgtg agaagttccc ggtgcacggc gccggcgagc tgtgcgtggg ccagaacacg    480
tccgacaagg gcaccccgac gccctcgctg cttccagagt tctggaccag caaccctcag    540
cacgccgagc ctaggtcttc agacaaaact cacacatgcc caccgtgccc agcacctgaa    600
gccgaggggg ccccgtcagt cttcctcttc cccccaaaac ccaaggacac cctcatgatc    660
tcccggaccc ctgaggtcac atgcgtggtg gtggacgtga gccacgaaga ccctgaggtc    720
aagttcaact ggtacgtgga cggcgtggag gtgcataatg ccaagacaaa gccgcgggag    780
gagcagtaca acagcacgta ccgtgtggtc agcgtcctca ccgtcctgca ccaggactgg    840
ctgaatggca aggagtacaa gtgcgccgtc tccaacaaag ccctcccagc tccatcgag    900 aaaaccatct ccaaagccaa agggcagccc cgagaaccac aggtgtacac cctgcccca    960 tcccgggatg agctgaccaa gaaccaggtc agcctgacct gcctggtcaa aggcttctat   1020
cccagcgaca tcgccgtgga gtgggagagc aatgggcagc cggagaacaa ctacaagacc   1080
acgcctcccg tgctggactc cgacggctcc ttcttcctct acagcaagct caccgtggac   1140
aagagcaggt ggcagcaggg gaacgtcttc tcatgctccg tgatgcatga ggctctgcac   1200
aaccactaca cgcagaagag cctctccctg tctccgggta aatga                   1245

<210> SEQ ID NO 42
<211> LENGTH: 1122
<212> TYPE: DNA
<213> ORGANISM: Artificial
<220> FEATURE:
<223> OTHER INFORMATION: DNA encoding fusion protein

<400> SEQUENCE: 42
cagttccacg gggagaaggg catctccatc ccggaccacg gcttctgcca gcccatctcc     60
atcccgctgt gcacggacat cgcctacaac cagaccatca tgcccaacct tcttggccac    120
acgaaccagg aagacgcggg cctggaggtg catcagttct accgctggt gaaggtgcag    180 tgctcgcccg agctgcgctt cttcctgtgc tccatgtacg cgccggtgtg cacagtgctg    240
gagcaggcca tccgccgtg ccgctccatc tgcgagcgcg cgcgccaagg ctgcgaggcg    300
ctcatgaaca agttcggctt ccaatggccc gagcgcctcc gctgcgagca tttcccgcgt    360
cacggcgcgg agcagatctg cgtgggccag aaccactcgg aggacggagc tcctgcgcta    420
gccgagccta ggtcttcaga caaaactcac acatgcccac cgtgcccagc acctgaagcc    480
gagggggccc cgtcagtctt cctcttcccc ccaaaaccca aggacaccct catgatctcc    540
cggacccctg aggtcacatg cgtggtggtg gacgtgagcc acgaagaccc tgaggtcaag    600
ttcaactggt acgtggacgg cgtggaggtg cataatgcca agacaaagcc gcgggaggag    660
cagtacaaca gcacgtaccg tgtggtcagc gtcctcaccg tcctgcacca ggactggctg    720
aatggcaagg agtacaagtg cgccgtctcc aacaaagccc tcccagcctc catcgagaaa    780
accatctcca aagccaaagg gcagccccga gaaccacagg tgtacaccct gcccccatcc    840
cgggatgagc tgaccaagaa ccaggtcagc ctgacctgcc tggtcaaagg cttctatccc    900
agcgacatcg ccgtggagtg ggagagcaat gggcagccgg agaacaacta caagaccacg    960
cctcccgtgc tggactccga cggctccttc ttcctctaca gcaagctcac cgtggacaag   1020
agcaggtggc agcaggggaa cgtcttctca tgctccgtga tgcatgaggc tctgcacaac   1080
```

```
cactacacgc agaagagcct ctccctgtct ccgggtaaat ga                     1122
```

<210> SEQ ID NO 43
<211> LENGTH: 1122
<212> TYPE: DNA
<213> ORGANISM: Artificial
<220> FEATURE:
<223> OTHER INFORMATION: DNA encoding fusion protein

<400> SEQUENCE: 43

```
cagttccacg gggagaaggg catctccatc ccggaccacg gcttctgcca gcccatctcc    60
atcccgctgt gcacggacat cgcctacaac cagaccatca tgcccaacct tctgggccac   120
acgaaccagg aggacgcagg cctagaggtg caccagttct atccgctggt gaaggtgcag   180
tgctcgcccg aactgcgctt cttcctgtgc tccatgtacg cacccgtgtg caccgtgctg   240
gaacaggcca tcccgccgtg ccgctctatc tgtgagcgcg cgcgccaggg ctgcgaagcc   300
ctcatgaaca agttcggttt tcagtggccc gagcgcctgc gctgcgagca cttcccgcgc   360
cacggcgccg agcagatctg cgtcggccag aaccactccg aggacggagc tcccgcgcta   420
gccgagccta ggtcttcaga caaaactcac acatgcccac cgtgcccagc acctgaagcc   480
gaggggggccc cgtcagtctt cctcttcccc ccaaaaccca aggacaccct catgatctcc   540
cggacccctg aggtcacatg cgtggtggtg gacgtgagcc acgaagaccc tgaggtcaag   600
ttcaactggt acgtggacgg cgtggaggtg cataatgcca agacaaagcc gcgggaggag   660
cagtacaaca gcacgtaccg tgtggtcagc gtcctcaccg tcctgcacca ggactggctg   720
aatggcaagg agtacaagtg cgccgtctcc aacaaagccc tcccagcctc catcgagaaa   780
accatctcca aagccaaagg gcagccccga gaaccacagg tgtacaccct gcccccatcc   840
cgggatgagc tgaccaagaa ccaggtcagc ctgacctgcc tggtcaaagg cttctatccc   900
agcgacatcg ccgtggagtg ggagagcaat gggcagccgg agaacaacta caagaccacg   960
cctcccgtgc tggactccga cggctccttc ttcctctaca gcaagctcac cgtggacaag  1020
agcaggtggc agcaggggaa cgtcttctca tgctccgtga tgcatgaggc tctgcacaac  1080
cactacacgc agaagagcct ctccctgtct ccgggtaaat ga                    1122
```

<210> SEQ ID NO 44
<211> LENGTH: 336
<212> TYPE: DNA
<213> ORGANISM: Mus musculus

<400> SEQUENCE: 44

```
tgccagccca tctccatccc gttgtgcacg gatatcgcct acaaccagac catcctgccc    60
aacctgctgg ccacacgaa ccaagaggac gcgggcctcg aggtgcacca gttctaccct   120
ctggtaaagg tgcagtgttc tcctgagcta cgcttcttct tatgctctat gtacgcaccc   180
gtgtgcaccg tgctcgacca agccattcct ccgtgccgtt ccttgtgcga gcgcgcccga   240
cagggctgcg aggcgctcat gaacaagttc ggcttccagt ggccagagcg gttgcgctgc   300
gagaacttcc cagtgcacgg tgccggcgag atctgc                            336
```

<210> SEQ ID NO 45
<211> LENGTH: 336
<212> TYPE: DNA
<213> ORGANISM: Homo sapiens

<400> SEQUENCE: 45

```
tgccagccca tctccatccc gctgtgcacg gacatcgcct acaaccagac catcctgccc    60
```

```
aacctgctgg gccacacgaa ccaagaggac gcgggcctcg aggtgcacca gttctacccg    120
ctggtgaagg tgcagtgttc tcccgaactc cgcttttct tatgctccat gtatgcgccc    180
gtgtgcaccg tgctcgatca ggccatcccg ccgtgtcgtt ctctgtgcga gcgcgcccgc    240
cagggctgcg aggcgctcat gaacaagttc ggcttccagt ggcccgagcg gctgcgctgc    300
gagaacttcc cggtgcacgg tgcgggcgag atctgc                              336
```

```
<210> SEQ ID NO 46
<211> LENGTH: 336
<212> TYPE: DNA
<213> ORGANISM: Mus musculus

<400> SEQUENCE: 46
tgccagccca tctccatccc gctgtgcacg gacatcgcgt acaaccagac catcatgccc    60
aacctgctgg gccacacgaa tcaggaggac gccggtctgg aggtgcacca gttctaccct   120
ctggtgaagg tgcagtgctc cgccgagctc aagttcttcc tgtgctccat gtacgcgcct   180
gtgtgcaccg tactggagca ggcgctaccg ccctgccgct ccctgtgcga gcgcgcacgc   240
cagggctgcg aggcgctcat gaacaagttc ggcttccagt ggccagacac actcaagtgc   300
gagaagttcc cggtgcacgg cgcaggagag ctgtgc                             336
```

```
<210> SEQ ID NO 47
<211> LENGTH: 336
<212> TYPE: DNA
<213> ORGANISM: Homo sapiens

<400> SEQUENCE: 47
tgccagccca tctccatccc gctgtgcacg gacatcgcgt acaaccagac catcatgccc    60
aacctgctgg gccacacgaa ccaggaggac gcgggcctgg aggtgcacca gttctaccct   120
ctagtgaaag tgcagtgttc cgctgagctc aagttcttcc tgtgctccat gtacgcgccc   180
gtgtgcaccg tgctagagca ggcgctgccg ccctgccgct ccctgtgcga gcgcgcgcgc   240
cagggctgcg aggcgctcat gaacaagttc ggcttccagt ggccagacac gctcaagtgt   300
gagaagttcc cggtgcacgg cgccggcgag ctgtgc                             336
```

```
<210> SEQ ID NO 48
<211> LENGTH: 336
<212> TYPE: DNA
<213> ORGANISM: Mus musculus

<400> SEQUENCE: 48
tgccagccca tctccatccc gctgtgcacg gacatcgcct acaaccagac catcatgccc    60
aaccttcttg gccacacgaa ccaggaagac gcgggcctgg aggtgcatca gttctacccg   120
ctggtgaagg tgcagtgctc gcccgagctg cgcttcttcc tgtgctccat gtacgcgccg   180
gtgtgcacag tgctggagca ggccatcccg ccgtgccgct ccatctgcga gcgcgcgcgc   240
caaggctgcg aggcgctcat gaacaagttc ggcttccaat ggcccgagcg cctccgctgc   300
gagcatttcc cgcgtcacgg cgcggagcag atctgc                             336
```

```
<210> SEQ ID NO 49
<211> LENGTH: 336
<212> TYPE: DNA
<213> ORGANISM: Homo sapiens

<400> SEQUENCE: 49
```

```
tgccagccca tctccatccc gctgtgcacg gacatcgcct acaaccagac catcatgccc    60
aaccttctgg gccacacgaa ccaggaggac gcaggcctag aggtgcacca gttctatccg   120
ctggtgaagg tgcagtgctc gcccgaactg cgcttcttcc tgtgctccat gtacgcaccc   180
gtgtgcaccg tgctggaaca ggccatcccg ccgtgccgct ctatctgtga gcgcgcgcgc   240
cagggctgcg aagccctcat gaacaagttc ggttttcagt ggcccgagcg cctgcgctgc   300
gagcacttcc cgcgccacgg cgccgagcag atctgc                             336
```

```
<210> SEQ ID NO 50
<211> LENGTH: 63
<212> TYPE: DNA
<213> ORGANISM: Artificial
<220> FEATURE:
<223> OTHER INFORMATION: sense oligoDNA

<400> SEQUENCE: 50
gatccgctag cgtcgacggt aagcctatcc ctaaccctct cctcggtctc gattctacgt    60
gac                                                                  63

<210> SEQ ID NO 51
<211> LENGTH: 63
<212> TYPE: DNA
<213> ORGANISM: Artificial
<220> FEATURE:
<223> OTHER INFORMATION: antisense oligoDNA

<400> SEQUENCE: 51
tcgagtcacg tagaatcgag accgaggaga gggttaggga taggcttacc gtcgacgcta    60
gcg                                                                  63

<210> SEQ ID NO 52
<211> LENGTH: 40
<212> TYPE: DNA
<213> ORGANISM: Artificial
<220> FEATURE:
<223> OTHER INFORMATION: primer

<400> SEQUENCE: 52
taaaggatcc cggccaccat gcggggcccc ggcacggcgg                           40

<210> SEQ ID NO 53
<211> LENGTH: 40
<212> TYPE: DNA
<213> ORGANISM: Artificial
<220> FEATURE:
<223> OTHER INFORMATION: primer

<400> SEQUENCE: 53
gtctgaagac ctaggctcgg ccaggtaggg agcagtaggg                           40

<210> SEQ ID NO 54
<211> LENGTH: 21
<212> TYPE: DNA
<213> ORGANISM: Artificial
<220> FEATURE:
<223> OTHER INFORMATION: primer

<400> SEQUENCE: 54
gccgagccta ggtcttcaga c                                              21

<210> SEQ ID NO 55
<211> LENGTH: 30
```

```
<212> TYPE: DNA
<213> ORGANISM: Artificial
<220> FEATURE:
<223> OTHER INFORMATION: primer

<400> SEQUENCE: 55
taaagtcgac tcatttaccc ggagacaggg                                         30

<210> SEQ ID NO 56
<211> LENGTH: 1257
<212> TYPE: DNA
<213> ORGANISM: Artificial
<220> FEATURE:
<223> OTHER INFORMATION: DNA encoding fusion protein

<400> SEQUENCE: 56
atgcggggcc ccggcacggc ggcgtcgcac tcgcccctgg gcctctgcgc cctggtgctt        60
gctcttctgt gcgcgctgcc cacggacacc cgggctcagc catatcacgg cgagaaaggc       120
atctcggtac cggaccacgg cttctgccag cccatctcca tcccgttgtg cacggatatc       180
gcctacaacc agaccatcct gcccaacctg ctgggccaca cgaaccaaga ggacgcgggc       240
ctcgaggtgc accagttcta ccctctggta aaggtgcagt gttctcctga gctacgcttc       300
ttcttatgct ctatgtacgc accgtgtgc accgtgctcg accaagccat tcctccgtgc        360
cgttccttgt gcgagcgcgc ccgacagggc tgcgaggcgc tcatgaacaa gttcggcttc       420
cagtggccag agcggttgcg ctgcgagaac ttcccagtgc acggtgccgg cgagatctgc       480
gtggggcaga acacgtccga cggctccggg ggcgcgggcg gcagtccac cgcctaccct        540 actgctccct acctggccga gcctaggtct tcagacaaaa ctcacacatg cccaccgtgc       600
ccagcacctg aagccgaggg ggccccgtca gtcttcctct ccccccaaa acccaaggac        660 accctcatga tctcccggac ccctgaggtc acatgcgtgt ggtggacgt gagccacgaa        720 gaccctgagg tcaagttcaa ctggtacgtg gacggcgtgg aggtgcataa tgccaagaca       780
aagccgcggg aggagcagta caacagcacg taccgtgtgg tcagcgtcct caccgtcctg       840
caccaggact ggctgaatgg caaggagtac aagtgcgccg tctccaacaa agccctccca       900
gcctccatcg agaaaaccat ctccaaagcc aaagggcagc ccgagaacc acaggtgtac        960 accctgcccc catcccggga tgagctgacc aagaaccagg tcagcctgac ctgcctggtc      1020
aaaggcttct atcccagcga catcgccgtg gagtgggaga gcaatgggca gccggagaac      1080
aactacaaga ccacgcctcc cgtgctggac tccgacggct ccttcttcct ctacagcaag      1140
ctcaccgtgg acaagagcag gtggcagcag gggaacgtct tctcatgctc cgtgatgcat      1200
gaggctctgc acaaccacta cacgcagaag agcctctccc tgtctccggg taaatga         1257

<210> SEQ ID NO 57
<211> LENGTH: 418
<212> TYPE: PRT
<213> ORGANISM: Artificial
<220> FEATURE:
<223> OTHER INFORMATION: fusion protein

<400> SEQUENCE: 57

Met Arg Gly Pro Gly Thr Ala Ala Ser His Ser Pro Leu Gly Leu Cys
1               5                   10                  15

Ala Leu Val Leu Ala Leu Leu Cys Ala Leu Pro Thr Asp Thr Arg Ala
            20                  25                  30

Gln Pro Tyr His Gly Glu Lys Gly Ile Ser Val Pro Asp His Gly Phe
        35                  40                  45
```

Cys Gln Pro Ile Ser Ile Pro Leu Cys Thr Asp Ile Ala Tyr Asn Gln
 50                  55                  60

Thr Ile Leu Pro Asn Leu Leu Gly His Thr Asn Gln Glu Asp Ala Gly
 65                  70                  75                  80

Leu Glu Val His Gln Phe Tyr Pro Leu Val Lys Val Gln Cys Ser Pro
                 85                  90                  95

Glu Leu Arg Phe Phe Leu Cys Ser Met Tyr Ala Pro Val Cys Thr Val
             100                 105                 110

Leu Asp Gln Ala Ile Pro Pro Cys Arg Ser Leu Cys Glu Arg Ala Arg
         115                 120                 125

Gln Gly Cys Glu Ala Leu Met Asn Lys Phe Gly Phe Gln Trp Pro Glu
 130                 135                 140

Arg Leu Arg Cys Glu Asn Phe Pro Val His Gly Ala Gly Glu Ile Cys
145                  150                 155                 160

Val Gly Gln Asn Thr Ser Asp Gly Ser Gly Ala Gly Gly Ser Pro
                 165                 170                 175

Thr Ala Tyr Pro Thr Ala Pro Tyr Leu Ala Glu Pro Arg Ser Ser Asp
             180                 185                 190

Lys Thr His Thr Cys Pro Pro Cys Pro Ala Pro Glu Ala Glu Gly Ala
                 195                 200                 205

Pro Ser Val Phe Leu Phe Pro Pro Lys Pro Lys Asp Thr Leu Met Ile
210                  215                 220

Ser Arg Thr Pro Glu Val Thr Cys Val Val Val Asp Val Ser His Glu
225                  230                 235                 240

Asp Pro Glu Val Lys Phe Asn Trp Tyr Val Asp Gly Val Glu Val His
                 245                 250                 255

Asn Ala Lys Thr Lys Pro Arg Glu Glu Gln Tyr Asn Ser Thr Tyr Arg
             260                 265                 270

Val Val Ser Val Leu Thr Val Leu His Gln Asp Trp Leu Asn Gly Lys
         275                 280                 285

Glu Tyr Lys Cys Ala Val Ser Asn Lys Ala Leu Pro Ala Ser Ile Glu
 290                 295                 300

Lys Thr Ile Ser Lys Ala Lys Gly Gln Pro Arg Glu Pro Gln Val Tyr
305                  310                 315                 320

Thr Leu Pro Pro Ser Arg Asp Glu Leu Thr Lys Asn Gln Val Ser Leu
                 325                 330                 335

Thr Cys Leu Val Lys Gly Phe Tyr Pro Ser Asp Ile Ala Val Glu Trp
             340                 345                 350

Glu Ser Asn Gly Gln Pro Glu Asn Asn Tyr Lys Thr Thr Pro Pro Val
         355                 360                 365

Leu Asp Ser Asp Gly Ser Phe Phe Leu Tyr Ser Lys Leu Thr Val Asp
 370                 375                 380

Lys Ser Arg Trp Gln Gln Gly Asn Val Phe Ser Cys Ser Val Met His
385                  390                 395                 400

Glu Ala Leu His Asn His Tyr Thr Gln Lys Ser Leu Ser Leu Ser Pro
                 405                 410                 415

Gly Lys

<210> SEQ ID NO 58
<211> LENGTH: 1713
<212> TYPE: DNA
<213> ORGANISM: Mus musculus

<400> SEQUENCE: 58

-continued

```
atgcgggccc gcagcgccct gccccgcagc gccctgcccc gcctgctgct gccactgctg     60
ctgctgccgg ccgccggacc ggcccagttc cacggggaga agggcatctc catcccggac    120
cacggcttct gccagcccat ctccatcccg ctgtgcacgg acatcgccta caaccagacc    180
atcatgccca accttcttgg ccacacgaac caggaagacg cgggcctgga ggtgcatcag    240
ttctacccgc tggtgaaggt gcagtgctcg cccgagctgc gcttcttcct gtgctccatg    300
tacgcgccgc tgtgcacagt gctggagcag gccatcccgc cgtgccgctc catctgcgag    360
cgcgcgcgcc aaggctgcga ggcgctcatg aacaagttcg gcttccaatg ccccgagcgc    420
ctccgctgcg agcatttccc gcgtcacggc gcggagcaga tctgcgtggg ccagaaccac    480
tcggaggacg gagctcctgc gctactcacc accgcgccac cttctgggct gcagcccggc    540
gcgggtggca ccccggggcgg ccctggcggt ggtggctcgc caccgcgtta cgccactctg    600
gagcacccct tccactgtcc ccgcgtcctc aaggtgccgt cctatctcag ctataagttt    660
ctgggtgagc gcgattgtgc cgcgccctgc gagcccgcac ggcccgacgg ctctatgttc    720
ttctcgcaag aggagactcg ttttgcccgt ctctggatcc tcacatggtc ggtgttgtgc    780
tgcgcttcca ctttcttcac ggtcaccacc tatttagtgg acatgcagcg atttcgctac    840
ccagagcggc ccatcatctt tctgtccggc tgctacacca tggtgtcagt ggcctacatt    900
gcgggcttcg ttctccagga gcgcgtggta tgcaatgagc gcttctcaga ggacggttat    960
cgcacggtgg tgcagggcac taagaaagaa ggctgcacta tactcttcat gatgctctac   1020
ttcttcagca tggccagctc catctggtgg gtgattctgt ccctcacctg gttcctggca   1080
gccggaatga agtggggcca cgaggccatc gaggccaatt cgcagtactt ccacctggcc   1140
gcctgggccg tgccggccgt caaaaccatc accatcttgg ccatgggcca gatcgacggc   1200
gacctgctga gcggcgtgtg cttcgtgggc ctcaatagcc tggaccccgct gcggggcttc   1260 gtgctggcgc cgctcttcgt ataccgtgttc atcggtacat ccttcctgct ggccggcttc   1320
gtgtcactct tccgcatccg caccatcatg aagcacgacg gcaccaagac ggagaagctg   1380
gagaggctca tggtgcgcat tggcgtcttc tcggtgctct acacggtacc ggccaccatc   1440
gtcatcgcct gctacttcta tgagcaggcc ttccgcgagc actgggagcg ctcctgggta   1500
agccagcact gcaagagcct agccatcccc tgcccggccc actacacgcc ccgcatgtcg   1560
cccgacttca cagtctacat gatcaaatac ctcatgacgc tcatcgtggg catcacgtcg   1620
ggcttctgga tctggtccgg caagacactg cactcgtgga ggaagttcta cactcgtctc   1680
accaacagcc ggcatggcga gaccactgtg tga                                1713
```

<210> SEQ ID NO 59
<211> LENGTH: 570
<212> TYPE: PRT
<213> ORGANISM: Mus musculus

<400> SEQUENCE: 59

```
Met Arg Ala Arg Ser Ala Leu Pro Arg Ser Ala Leu Pro Arg Leu Leu
1               5                   10                  15

Leu Pro Leu Leu Leu Leu Pro Ala Ala Gly Pro Ala Gln Phe His Gly
            20                  25                  30

Glu Lys Gly Ile Ser Ile Pro Asp His Gly Phe Cys Gln Pro Ile Ser
        35                  40                  45

Ile Pro Leu Cys Thr Asp Ile Ala Tyr Asn Gln Thr Ile Met Pro Asn
    50                  55                  60
```

```
Leu Leu Gly His Thr Asn Gln Glu Asp Ala Gly Leu Glu Val His Gln
 65                  70                  75                  80

Phe Tyr Pro Leu Val Lys Val Gln Cys Ser Pro Glu Leu Arg Phe Phe
             85                  90                  95

Leu Cys Ser Met Tyr Ala Pro Val Cys Thr Val Leu Glu Gln Ala Ile
            100                 105                 110

Pro Pro Cys Arg Ser Ile Cys Glu Arg Ala Arg Gln Gly Cys Glu Ala
            115                 120                 125

Leu Met Asn Lys Phe Gly Phe Gln Trp Pro Glu Arg Leu Arg Cys Glu
        130                 135                 140

His Phe Pro Arg His Gly Ala Glu Gln Ile Cys Val Gly Gln Asn His
145                 150                 155                 160

Ser Glu Asp Gly Ala Pro Ala Leu Leu Thr Thr Ala Pro Pro Ser Gly
                165                 170                 175

Leu Gln Pro Gly Ala Gly Gly Thr Pro Gly Gly Pro Gly Gly Gly Gly
            180                 185                 190

Ser Pro Pro Arg Tyr Ala Thr Leu Glu His Pro Phe His Cys Pro Arg
        195                 200                 205

Val Leu Lys Val Pro Ser Tyr Leu Ser Tyr Lys Phe Leu Gly Glu Arg
        210                 215                 220

Asp Cys Ala Ala Pro Cys Glu Pro Ala Arg Pro Asp Gly Ser Met Phe
225                 230                 235                 240

Phe Ser Gln Glu Glu Thr Arg Phe Ala Arg Leu Trp Ile Leu Thr Trp
                245                 250                 255

Ser Val Leu Cys Cys Ala Ser Thr Phe Phe Thr Val Thr Thr Tyr Leu
            260                 265                 270

Val Asp Met Gln Arg Phe Arg Tyr Pro Glu Arg Pro Ile Ile Phe Leu
        275                 280                 285

Ser Gly Cys Tyr Thr Met Val Ser Val Ala Tyr Ile Ala Gly Phe Val
        290                 295                 300

Leu Gln Glu Arg Val Val Cys Asn Glu Arg Phe Ser Glu Asp Gly Tyr
305                 310                 315                 320

Arg Thr Val Val Gln Gly Thr Lys Lys Glu Gly Cys Thr Ile Leu Phe
                325                 330                 335

Met Met Leu Tyr Phe Phe Ser Met Ala Ser Ser Ile Trp Trp Val Ile
            340                 345                 350

Leu Ser Leu Thr Trp Phe Leu Ala Ala Gly Met Lys Trp Gly His Glu
        355                 360                 365

Ala Ile Glu Ala Asn Ser Gln Tyr Phe His Leu Ala Ala Trp Ala Val
        370                 375                 380

Pro Ala Val Lys Thr Ile Thr Ile Leu Ala Met Gly Gln Ile Asp Gly
385                 390                 395                 400

Asp Leu Leu Ser Gly Val Cys Phe Val Gly Leu Asn Ser Leu Asp Pro
                405                 410                 415

Leu Arg Gly Phe Val Leu Ala Pro Leu Phe Val Tyr Leu Phe Ile Gly
            420                 425                 430

Thr Ser Phe Leu Leu Ala Gly Phe Val Ser Leu Phe Arg Ile Arg Thr
        435                 440                 445

Ile Met Lys His Asp Gly Thr Lys Thr Glu Lys Leu Glu Arg Leu Met
        450                 455                 460

Val Arg Ile Gly Val Phe Ser Val Leu Tyr Thr Val Pro Ala Thr Ile
465                 470                 475                 480

Val Ile Ala Cys Tyr Phe Tyr Glu Gln Ala Phe Arg Glu His Trp Glu
```

```
                485                 490                 495
Arg Ser Trp Val Ser Gln His Cys Lys Ser Leu Ala Ile Pro Cys Pro
                500                 505                 510

Ala His Tyr Thr Pro Arg Met Ser Pro Asp Phe Thr Val Tyr Met Ile
                515                 520                 525

Lys Tyr Leu Met Thr Leu Ile Val Gly Ile Thr Ser Gly Phe Trp Ile
            530                 535                 540

Trp Ser Gly Lys Thr Leu His Ser Trp Arg Lys Phe Tyr Thr Arg Leu
545                 550                 555                 560

Thr Asn Ser Arg His Gly Glu Thr Thr Val
                565                 570

<210> SEQ ID NO 60
<211> LENGTH: 1423
<212> TYPE: DNA
<213> ORGANISM: Mus musculus

<400> SEQUENCE: 60
atggagacag acacactcct gttatgggta ctgctgctct gggttccagg tgagagtgca        60
gagaagtgtt ggatgcaacc tctgtggcca ttatgatact ccatgcctct ctgttcttga      120
tcactataat tagggcattt gtcactggtt ttaagtttcc ccagtcccct gaattttcca      180
ttttctcaga gtgatgtcca aaattattct taaaaattta ataaaaaagg tcctctgctg      240
tgaaggcttt tatacatata taacaataat ctttgtgttt atcattccag gttccactgg      300
ccagttccac ggggagaagg gcatctccat cccggaccac ggcttctgcc agcccatctc      360
catcccgctg tgcacggaca tcgcctacaa ccagaccatc atgcccaacc ttcttggcca      420
cacgaaccag gaagacgcgg gcctggaggt gcatcagttc tacccgctgg tgaaggtgca      480
gtgctcgccc gagctgcgct tcttcctgtg ctccatgtac gcgccggtgt gcacagtgct      540
ggagcaggcc atcccgccgt gccgctccat ctgcgagcgc gcgcgccaag gctgcgaggc      600
gctcatgaac aagttcggct ccaatggccc gagcgcctc cgctgcgagc atttcccgcg       660
tcacggcgcg gagcagatct gcgtgggcca gaaccactcg gaggacggag ctcctgcgct      720
agccgagcct aggtcttcag acaaaactca cacatgccca ccgtgcccag cacctgaagc      780
cgagggggcc ccgtcagtct tcctcttccc cccaaaaccc aaggacaccc tcatgatctc      840 ccggaccct gaggtcacat gcgtggtggt ggacgtgagc cacgaagacc ctgaggtcaa       900
gttcaactgg tacgtggacg gcgtggaggt gcataatgcc aagacaaagc cgcgggagga      960
gcagtacaac agcacgtacc gtgtggtcag cgtcctcacc gtcctgcacc aggactggct     1020
gaatggcaag gagtacaagt gcgccgtctc caacaaagcc ctcccagcct ccatcgagaa     1080
aaccatctcc aaagccaaag gcagccccg agaaccacag gtgtacaccc tgcccccatc      1140
ccgggatgag ctgaccaaga accaggtcag cctgacctgc ctggtcaaag gcttctatcc     1200
cagcgacatc gccgtggagt gggagagcaa tgggcagccg gagaacaact acaagaccac     1260
gcctcccgtg ctggactccg acggctcctt cttcctctac agcaagctca ccgtggacaa     1320
gagcaggtgg cagcagggga acgtcttctc atgctccgtg atgcatgagg ctctgcacaa     1380
ccactacacg cagaagagcc tctccctgtc tccgggtaaa tga                       1423

<210> SEQ ID NO 61
<211> LENGTH: 393
<212> TYPE: PRT
<213> ORGANISM: Mus musculus
```

<400> SEQUENCE: 61

```
Met Glu Thr Asp Thr Leu Leu Leu Trp Val Leu Leu Leu Trp Val Pro
1               5                   10                  15

Gly Ser Thr Gly Gln Phe His Gly Glu Lys Gly Ile Ser Ile Pro Asp
            20                  25                  30

His Gly Phe Cys Gln Pro Ile Ser Ile Pro Leu Cys Thr Asp Ile Ala
        35                  40                  45

Tyr Asn Gln Thr Ile Met Pro Asn Leu Leu Gly His Thr Asn Gln Glu
    50                  55                  60

Asp Ala Gly Leu Glu Val His Gln Phe Tyr Pro Leu Val Lys Val Gln
65                  70                  75                  80

Cys Ser Pro Glu Leu Arg Phe Phe Leu Cys Ser Met Tyr Ala Pro Val
                85                  90                  95

Cys Thr Val Leu Glu Gln Ala Ile Pro Pro Cys Arg Ser Ile Cys Glu
            100                 105                 110

Arg Ala Arg Gln Gly Cys Glu Ala Leu Met Asn Lys Phe Gly Phe Gln
        115                 120                 125

Trp Pro Glu Arg Leu Arg Cys Glu His Phe Pro Arg His Gly Ala Glu
    130                 135                 140

Gln Ile Cys Val Gly Gln Asn His Ser Glu Asp Gly Ala Pro Ala Leu
145                 150                 155                 160

Ala Glu Pro Arg Ser Ser Asp Lys Thr His Thr Cys Pro Pro Cys Pro
                165                 170                 175

Ala Pro Glu Ala Glu Gly Ala Pro Ser Val Phe Leu Phe Pro Pro Lys
            180                 185                 190

Pro Lys Asp Thr Leu Met Ile Ser Arg Thr Pro Glu Val Thr Cys Val
        195                 200                 205

Val Val Asp Val Ser His Glu Asp Pro Glu Val Lys Phe Asn Trp Tyr
    210                 215                 220

Val Asp Gly Val Glu Val His Asn Ala Lys Thr Lys Pro Arg Glu Glu
225                 230                 235                 240

Gln Tyr Asn Ser Thr Tyr Arg Val Val Ser Val Leu Thr Val Leu His
                245                 250                 255

Gln Asp Trp Leu Asn Gly Lys Glu Tyr Lys Cys Ala Val Ser Asn Lys
            260                 265                 270

Ala Leu Pro Ala Ser Ile Glu Lys Thr Ile Ser Lys Ala Lys Gly Gln
        275                 280                 285

Pro Arg Glu Pro Gln Val Tyr Thr Leu Pro Pro Ser Arg Asp Glu Leu
    290                 295                 300

Thr Lys Asn Gln Val Ser Leu Thr Cys Leu Val Lys Gly Phe Tyr Pro
305                 310                 315                 320

Ser Asp Ile Ala Val Glu Trp Glu Ser Asn Gly Gln Pro Glu Asn Asn
                325                 330                 335

Tyr Lys Thr Thr Pro Pro Val Leu Asp Ser Asp Gly Ser Phe Phe Leu
            340                 345                 350

Tyr Ser Lys Leu Thr Val Asp Lys Ser Arg Trp Gln Gln Gly Asn Val
        355                 360                 365

Phe Ser Cys Ser Val Met His Glu Ala Leu His Asn His Tyr Thr Gln
    370                 375                 380

Lys Ser Leu Ser Leu Ser Pro Gly Lys
385                 390
```

<210> SEQ ID NO 62

```
<211> LENGTH: 38
<212> TYPE: DNA
<213> ORGANISM: Artificial
<220> FEATURE:
<223> OTHER INFORMATION: primer

<400> SEQUENCE: 62
taaaggatcc cggccaccat ggctgaggag gcggcgcc                              38

<210> SEQ ID NO 63
<211> LENGTH: 41
<212> TYPE: DNA
<213> ORGANISM: Artificial
<220> FEATURE:
<223> OTHER INFORMATION: primer

<400> SEQUENCE: 63
gtctgaagac ctaggctcgg cgtgctgcgg attactggtc c                         41

<210> SEQ ID NO 64
<211> LENGTH: 1446
<212> TYPE: DNA
<213> ORGANISM: Artificial
<220> FEATURE:
<223> OTHER INFORMATION: DNA encoding fusion protein

<400> SEQUENCE: 64
atggctgagg aggcggcgcc tagcgagtcc cgggccgccg ccggctgag cttggaactt      60
tgtgccgaag cactcccggg ccggcgggag gaggtggggc acgaggacac ggccagccac    120
cgccgccccc gggctgatcc ccggcgttgg gctagcgggc tgctgctgct gctttggttg    180
ctggaggctc ctctgctttt gggggtccga gcgcaggcgg cgggccaggt atccgggccg    240
ggccagcaag ccccgccgcc gccccagccc agcagagcg gcagcagta caacggcgaa      300
cggggcatct ccatcccgga ccacggctac tgccagccca tctccatccc gctgtgcacg    360
gacatcgcgt acaaccagac catcatgccc aacctgctgg ccacacgaa tcaggaggac     420
gccggtctgg aggtgcacca gttctaccct ctggtgaagg tgcagtgctc cgccgagctc    480
aagttcttcc tgtgctccat gtacgcgcct gtgtgcaccg tactggagca ggcgctaccg    540
ccctgccgct ccctgtgcga gcgcgcacgc cagggctgcg aggcgctcat gaacaagttc    600
ggcttccagt ggccagacac actcaagtgc gagaagttcc cggtgcacgg cgcaggagag    660
ctgtgcgtgg gccagaacac gtccgacaaa ggcaccccaa ctccctcctt gctaccagag    720
ttctggacca gtaatccgca gcacgccgag cctaggtctt cagacaaaac tcacacatgc    780
ccaccgtgcc cagcacctga gccgagggg gccccgtcag tcttcctctt ccccccaaaa    840
cccaaggaca ccctcatgat ctcccggacc cctgaggtca catgcgtggt ggtgacgtg    900
agccacgaag accctgaggt caagttcaac tggtacgtgg acggcgtgga ggtgcataat    960
gccaagacaa agccgcggga ggagcagtac aacagcacgt accgtgtggt cagcgtcctc   1020
accgtcctgc accaggactg gctgaatggc aaggagtaca agtgcgccgt ctccaacaaa   1080
gccctcccag cctccatcga gaaaaccatc tccaaagcca agggcagcc ccgagaacca    1140
caggtgtaca ccctgccccc atcccgggat gagctgacca agaaccaggt cagcctgacc   1200
tgcctggtca aaggcttcta tcccagcgac atcgccgtgg agtgggagag caatgggcag   1260
ccggagaaca actacaagac cacgcctccc gtgctggact ccgacggctc cttcttcctc   1320
tacagcaagc tcaccgtgga caagagcagg tggcagcagg ggaacgtctt ctcatgctcc   1380
gtgatgcatg aggctctgca caaccactac acgcagaaga gcctctccct gtctccgggt   1440
```

```
aaatga                                                       1446
```

<210> SEQ ID NO 65
<211> LENGTH: 481
<212> TYPE: PRT
<213> ORGANISM: Artificial
<220> FEATURE:
<223> OTHER INFORMATION: fusion protein

<400> SEQUENCE: 65

```
Met Ala Glu Glu Ala Ala Pro Ser Glu Ser Arg Ala Ala Gly Arg Leu
1               5                   10                  15

Ser Leu Glu Leu Cys Ala Glu Ala Leu Pro Gly Arg Arg Glu Glu Val
            20                  25                  30

Gly His Glu Asp Thr Ala Ser His Arg Arg Pro Arg Ala Asp Pro Arg
        35                  40                  45

Arg Trp Ala Ser Gly Leu Leu Leu Leu Trp Leu Leu Glu Ala Pro
    50                  55                  60

Leu Leu Leu Gly Val Arg Ala Gln Ala Ala Gly Gln Val Ser Gly Pro
65                  70                  75                  80

Gly Gln Gln Ala Pro Pro Pro Gln Pro Gln Gln Ser Gly Gln Gln
                85                  90                  95

Tyr Asn Gly Glu Arg Gly Ile Ser Ile Pro Asp His Gly Tyr Cys Gln
            100                 105                 110

Pro Ile Ser Ile Pro Leu Cys Thr Asp Ile Ala Tyr Asn Gln Thr Ile
        115                 120                 125

Met Pro Asn Leu Leu Gly His Thr Asn Gln Glu Asp Ala Gly Leu Glu
    130                 135                 140

Val His Gln Phe Tyr Pro Leu Val Lys Val Gln Cys Ser Ala Glu Leu
145                 150                 155                 160

Lys Phe Phe Leu Cys Ser Met Tyr Ala Pro Val Cys Thr Val Leu Glu
                165                 170                 175

Gln Ala Leu Pro Pro Cys Arg Ser Leu Cys Glu Arg Ala Arg Gln Gly
            180                 185                 190

Cys Glu Ala Leu Met Asn Lys Phe Gly Phe Gln Trp Pro Asp Thr Leu
        195                 200                 205

Lys Cys Glu Lys Phe Pro Val His Gly Ala Gly Glu Leu Cys Val Gly
    210                 215                 220

Gln Asn Thr Ser Asp Lys Gly Thr Pro Thr Pro Ser Leu Leu Pro Glu
225                 230                 235                 240

Phe Trp Thr Ser Asn Pro Gln His Ala Glu Pro Arg Ser Ser Asp Lys
                245                 250                 255

Thr His Thr Cys Pro Pro Cys Pro Ala Pro Glu Ala Glu Gly Ala Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350
```

-continued

```
Tyr Lys Cys Ala Val Ser Asn Lys Ala Leu Pro Ala Ser Ile Glu Lys
            355                 360                 365

Thr Ile Ser Lys Ala Lys Gly Gln Pro Arg Glu Pro Gln Val Tyr Thr
    370                 375                 380

Leu Pro Pro Ser Arg Asp Glu Leu Thr Lys Asn Gln Val Ser Leu Thr
385                 390                 395                 400

Cys Leu Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Tyr Ser Lys Leu Thr Val Asp Lys
        435                 440                 445

Ser Arg Trp Gln Gln Gly Asn Val Phe Ser Cys Ser Val Met His Glu
    450                 455                 460

Ala Leu His Asn His Tyr Thr Gln Lys Ser Leu Ser Leu Ser Pro Gly
465                 470                 475                 480

Lys
```

<210> SEQ ID NO 66
<211> LENGTH: 40
<212> TYPE: DNA
<213> ORGANISM: Artificial
<220> FEATURE:
<223> OTHER INFORMATION: primer

<400> SEQUENCE: 66
taaaggatcc cggccaccat gcgggcccgc agcgccctgc           40

<210> SEQ ID NO 67
<211> LENGTH: 40
<212> TYPE: DNA
<213> ORGANISM: Artificial
<220> FEATURE:
<223> OTHER INFORMATION: primer

<400> SEQUENCE: 67
gtctgaagac ctaggctcgg ctagcgcagg agctccgtcc           40

<210> SEQ ID NO 68
<211> LENGTH: 35
<212> TYPE: DNA
<213> ORGANISM: Artificial
<220> FEATURE:
<223> OTHER INFORMATION: primer

<400> SEQUENCE: 68
atagtttagc ggccgctcat ttacccggag acagg                35

<210> SEQ ID NO 69
<211> LENGTH: 1206
<212> TYPE: DNA
<213> ORGANISM: Artificial
<220> FEATURE:
<223> OTHER INFORMATION: DNA encoding fusion protein

<400> SEQUENCE: 69
atgcgggccc gcagcgccct gccccgcagc gccctgcccc gctgctgct gccactgctg     60 ctgctgccgg ccgccggacc ggcccagttc acggggaga agggcatctc catcccggac    120
cacggcttct gccagcccat ctccatcccg ctgtgcacgg acatcgccta caaccagacc    180
atcatgccca accttcttgg ccacacgaac caggaagacg cgggcctgga ggtgcatcag    240

```
ttctacccgc tggtgaaggt gcagtgctcg cccgagctgc gcttcttcct gtgctccatg     300
tacgcgccgg tgtgcacagt gctggagcag gccatcccgc cgtgccgctc catctgcgag     360
cgcgcgcgcc aaggctgcga ggcgctcatg aacaagttcg gcttccaatg gcccgagcgc     420
ctccgctgcg agcatttccc gcgtcacggc gcggagcaga tctgcgtggg ccagaaccac     480
tcggaggacg gagctcctgc gctagccgag cctaggtctt cagacaaaac tcacacatgc     540
ccaccgtgcc cagcacctga agccgagggg gccccgtcag tcttcctctt ccccccaaaa     600
cccaaggaca cctcatgat ctcccggacc cctgaggtca catgcgtggt ggtggacgtg     660
agccacgaag accctgaggt caagttcaac tggtacgtgg acggcgtgga ggtgcataat     720
gccaagacaa agccgcggga ggagcagtac aacagcacgt accgtgtggt cagcgtcctc     780
accgtcctgc accaggactg gctgaatggc aaggagtaca agtgcgccgt ctccaacaaa     840
gccctcccag cctccatcga gaaaaccatc tccaaagcca agggcagcc cgagaaccac     900
caggtgtaca ccctgccccc atcccgggat gagctgacca agaaccaggt cagcctgacc     960
tgcctggtca aaggcttcta tcccagcgac atcgccgtgg agtgggagag caatgggcag    1020
ccggagaaca actacaagac cacgcctccc gtgctggact ccgacggctc cttcttcctc    1080
tacagcaagc tcaccgtgga caagagcagg tggcagcagg ggaacgtctt ctcatgctcc    1140
gtgatgcatg aggctctgca caaccactac acgcagaaga gcctctccct gtctccgggt    1200
aaatga                                                               1206
```

<210> SEQ ID NO 70
<211> LENGTH: 401
<212> TYPE: PRT
<213> ORGANISM: Artificial
<220> FEATURE:
<223> OTHER INFORMATION: fusion protein

<400> SEQUENCE: 70

```
Met Arg Ala Arg Ser Ala Leu Pro Arg Ser Ala Leu Pro Arg Leu Leu
1               5                   10                  15

Leu Pro Leu Leu Leu Leu Pro Ala Ala Gly Pro Ala Gln Phe His Gly
            20                  25                  30

Glu Lys Gly Ile Ser Ile Pro Asp His Gly Phe Cys Gln Pro Ile Ser
        35                  40                  45

Ile Pro Leu Cys Thr Asp Ile Ala Tyr Asn Gln Thr Ile Met Pro Asn
    50                  55                  60

Leu Leu Gly His Thr Asn Gln Glu Asp Ala Gly Leu Glu Val His Gln
65                  70                  75                  80

Phe Tyr Pro Leu Val Lys Val Gln Cys Ser Pro Glu Leu Arg Phe Phe
                85                  90                  95

Leu Cys Ser Met Tyr Ala Pro Val Cys Thr Val Leu Glu Gln Ala Ile
            100                 105                 110

Pro Pro Cys Arg Ser Ile Cys Glu Arg Ala Arg Gln Gly Cys Glu Ala
        115                 120                 125

Leu Met Asn Lys Phe Gly Phe Gln Trp Pro Glu Arg Leu Arg Cys Glu
    130                 135                 140

His Phe Pro Arg His Gly Ala Glu Gln Ile Cys Val Gly Gln Asn His
145                 150                 155                 160

Ser Glu Asp Gly Ala Pro Ala Leu Ala Glu Pro Arg Ser Ser Asp Lys
                165                 170                 175

Thr His Thr Cys Pro Pro Cys Pro Ala Pro Glu Ala Glu Gly Ala Pro
```

```
            180                 185                 190
Ser Val Phe Leu Phe Pro Pro Lys Pro Lys Asp Thr Leu Met Ile Ser
                195                 200                 205
Arg Thr Pro Glu Val Thr Cys Val Val Asp Val Ser His Glu Asp
        210                 215                 220
Pro Glu Val Lys Phe Asn Trp Tyr Val Asp Gly Val Glu Val His Asn
225                 230                 235                 240
Ala Lys Thr Lys Pro Arg Glu Glu Gln Tyr Asn Ser Thr Tyr Arg Val
                245                 250                 255
Val Ser Val Leu Thr Val Leu His Gln Asp Trp Leu Asn Gly Lys Glu
            260                 265                 270
Tyr Lys Cys Ala Val Ser Asn Lys Ala Leu Pro Ala Ser Ile Glu Lys
        275                 280                 285
Thr Ile Ser Lys Ala Lys Gly Gln Pro Arg Glu Pro Gln Val Tyr Thr
    290                 295                 300
Leu Pro Pro Ser Arg Asp Glu Leu Thr Lys Asn Gln Val Ser Leu Thr
305                 310                 315                 320
Cys Leu Val Lys Gly Phe Tyr Pro Ser Asp Ile Ala Val Glu Trp Glu
                325                 330                 335
Ser Asn Gly Gln Pro Glu Asn Asn Tyr Lys Thr Thr Pro Pro Val Leu
            340                 345                 350
Asp Ser Asp Gly Ser Phe Phe Leu Tyr Ser Lys Leu Thr Val Asp Lys
        355                 360                 365
Ser Arg Trp Gln Gln Gly Asn Val Phe Ser Cys Ser Val Met His Glu
    370                 375                 380
Ala Leu His Asn His Tyr Thr Gln Lys Ser Leu Ser Leu Ser Pro Gly
385                 390                 395                 400
Lys

<210> SEQ ID NO 71
<211> LENGTH: 39
<212> TYPE: DNA
<213> ORGANISM: Artificial
<220> FEATURE:
<223> OTHER INFORMATION: primer

<400> SEQUENCE: 71
taaaggatcc cggccaccat ggagacagac acactcctg                              39

<210> SEQ ID NO 72
<211> LENGTH: 1339
<212> TYPE: DNA
<213> ORGANISM: Artificial
<220> FEATURE:
<223> OTHER INFORMATION: DNA encoding fusion protein

<400> SEQUENCE: 72
atggagacag acacactcct gttatgggta ctgctgctct ggttccaggt gagagtgca        60 gagaagtgtt ggatgcaacc tctgtggcca ttatgatact ccatgcctct ctgttcttga      120
tcactataat tagggcattt gtcactggtt ttaagtttcc ccagtcccct gaattttcca      180
ttttctcaga gtgatgtcca aaattattct taaaaattta ataaaaagg tcctctgctg       240 tgaaggcttt tatacatata taacaataat ctttgtgttt atcattccag gttccactgg      300
ctgccagccc atctccatcc cgttgtgcac ggatatcgcc tacaaccaga ccatcctgcc      360
caacctgctg ggccacacga accaagagga cgcgggcctc gaggtgcacc agttctaccc     420
```

```
tctggtaaag gtgcagtgtt ctcctgagct acgcttcttc ttatgctcta tgtacgcacc    480
cgtgtgcacc gtgctcgacc aagccattcc tccgtgccgt tccttgtgcg agcgcgcccg    540
acagggctgc gaggcgctca tgaacaagtt cggcttccag tggccagagc ggttgcgctg    600
cgagaacttc ccagtgcacg gtgccggcga gatctgcgcc gagcctaggt cttcagacaa    660
aactcacaca tgcccaccgt gcccagcacc tgaagccgag ggggcccgt cagtcttcct    720 cttccccca aaacccaagg acaccctcat gatctcccgg acccctgagg tcacatgcgt    780
ggtggtggac gtgagccacg aagaccctga ggtcaagttc aactggtacg tggacggcgt    840
ggaggtgcat aatgccaaga caaagccgcg ggaggagcag tacaacagca cgtaccgtgt    900
ggtcagcgtc ctcaccgtcc tgcaccagga ctggctgaat ggcaaggagt acaagtgcgc    960
cgtctccaac aaagccctcc cagcctccat cgagaaaacc atctccaaag ccaagggca   1020 gccccgagaa ccacaggtgt acaccctgcc cccatcccgg gatgagctga ccaagaacca   1080
ggtcagcctg acctgcctgg tcaaaggctt ctatcccagc gacatcgccg tggagtggga   1140
gagcaatggg cagccggaga acaactacaa gaccacgcct cccgtgctgg actccgacgg   1200
ctccttcttc ctctacagca agctcaccgt ggacaagagc aggtggcagc aggggaacgt   1260
cttctcatgc tccgtgatgc atgaggctct gcacaaccac tacacgcaga gagcctctc   1320 cctgtctccg ggtaaatga                                                1339
```

<210> SEQ ID NO 73
<211> LENGTH: 365
<212> TYPE: PRT
<213> ORGANISM: Artificial
<220> FEATURE:
<223> OTHER INFORMATION: fusion protein

<400> SEQUENCE: 73

```
Met Glu Thr Asp Thr Leu Leu Leu Trp Val Leu Leu Leu Trp Val Pro
1               5                   10                  15

Gly Ser Thr Gly Cys Gln Pro Ile Ser Ile Pro Leu Cys Thr Asp Ile
            20                  25                  30

Ala Tyr Asn Gln Thr Ile Leu Pro Asn Leu Leu Gly His Thr Asn Gln
        35                  40                  45

Glu Asp Ala Gly Leu Glu Val His Gln Phe Tyr Pro Leu Val Lys Val
    50                  55                  60

Gln Cys Ser Pro Glu Leu Arg Phe Phe Leu Cys Ser Met Tyr Ala Pro
65                  70                  75                  80

Val Cys Thr Val Leu Asp Gln Ala Ile Pro Pro Cys Arg Ser Leu Cys
                85                  90                  95

Glu Arg Ala Arg Gln Gly Cys Glu Ala Leu Met Asn Lys Phe Gly Phe
            100                 105                 110

Gln Trp Pro Glu Arg Leu Arg Cys Glu Asn Phe Pro Val His Gly Ala
        115                 120                 125

Gly Glu Ile Cys Ala Glu Pro Arg Ser Ser Asp Lys Thr His Thr Cys
    130                 135                 140

Pro Pro Cys Pro Ala Pro Glu Ala Glu Gly Ala Pro Ser Val Phe Leu
145                 150                 155                 160

Phe Pro Pro Lys Pro Lys Asp Thr Leu Met Ile Ser Arg Thr Pro Glu
                165                 170                 175

Val Thr Cys Val Val Val Asp Val Ser His Glu Asp Pro Glu Val Lys
            180                 185                 190

Phe Asn Trp Tyr Val Asp Gly Val Glu Val His Asn Ala Lys Thr Lys
```

```
            195                 200                 205
Pro Arg Glu Glu Gln Tyr Asn Ser Thr Tyr Arg Val Val Ser Val Leu
    210                 215                 220

Thr Val Leu His Gln Asp Trp Leu Asn Gly Lys Glu Tyr Lys Cys Ala
225                 230                 235                 240

Val Ser Asn Lys Ala Leu Pro Ala Ser Ile Glu Lys Thr Ile Ser Lys
                245                 250                 255

Ala Lys Gly Gln Pro Arg Glu Pro Gln Val Tyr Thr Leu Pro Pro Ser
            260                 265                 270

Arg Asp Glu Leu Thr Lys Asn Gln Val Ser Leu Thr Cys Leu Val Lys
        275                 280                 285

Gly Phe Tyr Pro Ser Asp Ile Ala Val Glu Trp Glu Ser Asn Gly Gln
        290                 295                 300

Pro Glu Asn Asn Tyr Lys Thr Thr Pro Pro Val Leu Asp Ser Asp Gly
305                 310                 315                 320

Ser Phe Phe Leu Tyr Ser Lys Leu Thr Val Asp Lys Ser Arg Trp Gln
                325                 330                 335

Gln Gly Asn Val Phe Ser Cys Ser Val Met His Glu Ala Leu His Asn
            340                 345                 350

His Tyr Thr Gln Lys Ser Leu Ser Leu Ser Pro Gly Lys
        355                 360                 365
```

PHARMACEUTICAL COMPOSITION FOR TREATING BONE DISEASES WHICH COMPRISES PROTEIN COMPRISING FRIZZLED1, FRIZZLED2 OR FRIZZLED7 EXTRACELLULAR CYSTEINE-RICH DOMAIN

CROSS-REFERENCE TO RELATED APPLICATIONS

This application is a Divisional of U.S. application Ser. No. 13/121,637, filed Jun. 13, 2011 (now abandoned); which is a 371 National Stage of International Application No. PCT/JP2009/066996 filed Sep. 30, 2009; which claims priority based on Japanese Patent Application No. 2008-255804, filed Sep. 30, 2008, and Japanese Patent Application No. 2009-131449 filed May 29, 2009; the contents of each of which are incorporated herein by reference in their entirety.

TECHNICAL FIELD

The present invention relates to a novel application of a therapeutic agent for a bone disease comprising a protein comprising the extracellular cysteine-rich domain of Frizzled 1, Frizzled 2, or Frizzled 7, which is known as a Wnt ligand receptor protein, or a mutant of the domain.

This finding resulted from analysis of properties of a knock-in mouse expressing the Frizzled extracellular cysteine-rich domain and a mouse to which a protein comprising the Frizzled extracellular cysteine-rich domain had been administered.

BACKGROUND ART

A super-aging society has arrived, the number of people with osteoporosis has increased, and bone fractures resulting therefrom have come to constitute a serious issue of concern at a societal level. In particular, patients with femoral neck fractures and vertebral body fractures become bedridden, which causes significant deterioration of the quality of life thereof, and the social, medical, and econimc burdens caused by care and hospital treatment have increased (Tosteson, A. N., et al., Osteoporos Int., 12, 1042-1049, 2001; and Yoh, K., et al., J. Bone Miner. Metab., 23, 167-173, 2005). It has also been discovered in recent years that osteoporosis is significantly associated with mortality in old age (Nguyen, N. D., et al., J. Bone Miner. Res., 22, 1147-1154, 2007; and Muraki, S., et al., J. Bone Miner. Metab., 24, 100-104, 2006). Under such circumstances, prevention and treatment of osteoporosis have become critical objectives to be achieved. Osteoporosis (i.e., a pathological condition where bone mass is reduced while the rate of the amount of the bone matrix to the amount of the mineralized bone matrix is held) is classified as primary osteoporosis or secondary osteoporosis. The former type is a pathological condition heretofore referred to as postmenopausal osteoporosis or senile osteoporosis. The latter type is a pathological condition caused by changes in bone metabolism resulting from other diseases, and such osteoporosis is classified based on the cause thereof, such as osteoporosis caused by endocrine, nutritional/metabolic, inflammatory, immobile, drug-induced, hematologic, congenital, or other diseases. According to the above classification, examples of causes for secondary osteoporosis include: endocrine causes, such as hyperparathyreosis, hyperthyreosis, hypogonadism, Cushing's syndrome, somatotropin deficiency, diabetes, Addison's disease, and calcitonin deficiency; nutritional/metabolic causes, such as chronic degenerative diseases, emaciation, serious liver diseases (primary biliary cirrhosis, in particular), gastric resection, scorbutus, malabsorption syndrome (including celiac disease), hypophosphatemia, chronic renal disease, hypercalciuria, hemochromatosis, amyloidosis, mast cell tumor, ingestion of excess sodium, insufficient calcium intake, and hypervitaminosis D or A; inflammatory causes, such as articular rheumatism, periarticular bone disease (elevated bone resorption induced by proinflammatory cytokines), and sarcoidosis; immobility-related causes, such as systemic, bed rest, paralysis, local, and post-fracture causes; drug-induced causes, such as with the use of steroids (steroids are extensively used for inflammatory diseases as immunosuppressive agents; examples of diseases treated with the use of steroids include collagen diseases, asthma, inflammatory bowel diseases, and in the case of organ transplantation, and bone loss is a serious side effect of such therapy), methotrexate, heparine, warfarin, anticonvulsant agents, lithium, and tamoxifen; blood-disease-induced causes, such as multiple myeloma, lymphoma, leukaemia, hemophilia, and chronic hemolytic diseases; congenital causes, such as dysosteogenesis, Marfan's syndrome, Kleinfelter's syndrome, congenital erythropoetic porphyria, and cystic fibrosis; and other disease-induced causes, such as with chronic obstructive lung diseases, hepatic failure, renal diseases, articular rheumatism, pregnancy, hyperoxemia, and HIV infection (Committee for Creation of Guidelines for Prevention and Treatment of Osteoporosis, Guidelines for Prevention and Treatment of Osteoporosis 2006, Life Science Publishing, Co., Ltd., Japan, 2006).

Among the above-mentioned diseases, bone diseases resulting from osteoarthritis, articular rheumatism, malignant tumors, or renal diseases are specifically regarded as bone diseases that impose serious influences at the societal level, in addition to primary osteoporosis.

Osteoarthritis develops most often in locomotor regions. The number of patients afflicted therewith is said to be 10,000,000 in Japan, and it has been deduced that the number of patients will keep increasing as the aging of society advances. Advanced articular disorders are treated via artificial joint replacement; however, radical treatment of moderate or milder symptoms has not yet been reported (Nampei, A. & Hashimoto, J., The Bone, 22, 3, 109-113, 2008).

Articular rheumatism is a chronic and progressive inflammatory disease characterized mainly by multiple arthritis. Articular synovial proliferation gradually causes infiltration of cartilage or bones in the vicinity thereof, and articular rheumatism often leads to destruction and deformation of joints. It has been reported that treatment with the use of an antirheumatic drug (methotrexate) cannot sufficiently inhibit the progress of joint destruction, and a biological agent targeting a tumor necrosis factor (TNF) α produces significant effects of inhibiting joint destruction. Thus, it is considered to be a revolutionary agent. However, increased incidence, as a side effect, of opportunistic infection, tuberculosis (extrapulmonary tuberculosis), *Pneumocystis* pneumonia, or the like when using such agent is an issue of concern (Soen, S., The Bone, 22, 3, 103-107, 2008).

Major examples of bone diseases involved in malignant tumors include hypercalcemia and bone metastasis related to malignant tumors. Hypercalcemia causes loss of appetite and diuresis, and it causes dehydration and renal failure caused thereby. Bone metastasis is often observed in patients with breast cancer, prostate cancer, or lung cancer, in particular. While bone metastasis is hardly ever fatal by itself, it causes bone ache, pathologic fracture, neuroparalysis, or the like. It thus often significantly deteriorate patients' QOL, and bone metastasis control is a critical objective in clinical settings (Takahashi, S., The Bone, 22, 3, 115-120, 2008). These bone diseases related to malignant tumors are treated with the use of bisphosphonate preparations, although the problem of side effects has been pointed out.

Among bone diseases related to renal diseases, a pathological condition of bone damage caused by renal tissue damage is referred to as renal osteodystrophy. Bone disease experienced by kidney dialysis patients are mainly caused by secondary hyperparathyreosis. Because of the elevated PTH concentration caused by hyperparathyreosis and, for example, insufficient production of bone morphogenetic protein (BMP) 7, renal osteodystrophy advances. Dialysis patients often exhibit lowered reactivity of the bone with the parathyroid hormone (PTH). When the PTH concentration is chronically and significantly elevated, accordingly, fibrous ostitis (high bone turnover) develops. When the PTH concentration is maintained within a standard range, in contrast, bone aplasia (low bone turnover) develops.

When fibrous ostitis advances, collagen fibers are irregularly formed, such fibers are mineralized as non-crystalline calcium phosphate, and woven bone is then formed. This enhances bone formation, although the bone becomes easily fracturable. Basic treatment of fibrous ostitis involves inhibition of parathyroid hormone secretion, which mainly entails calcium ingestion and administration of active vitamin D. When a patient has a chronic kidney disease (CKD) and receives dialysis treatment, in particular, various regulations, such as restrictions on food or water intake, are necessary. When secondary hyperparathyreosis advances, hypercalcemia also becomes an issue of concern. When prescribing active vitamin D, extreme caution, such as via the monitoring of renal functions (i.e., serum creatinine level) and serum calcium level, is always required.

Bone aplasia develops because of prolonged use and excessive administration of active vitamin D preparations or suppression of parathyroid hormone after parathyroidectomy (PTX).

The rate of fractures associated with bone aplasia is higher than that associated with fibrous ostitis, and it induces hypercalcemia or mineralization of blood vessels or other soft tissues. Thus, adequate treatment techniques have been desired. A pathological condition of bone aplasia is low bone turnover in which bone resorption and bone formation are inhibited, and there is no established treatment technique at present (Daugirdas, J. T., et al., *Rinsho Toseki Handbook* (Handbook of Dialysis), Fourth Edition, Medical Sciences International, Ltd., Japan, 2009).

Hyperphosphatemia or hypercalcemia caused by lowered capacity of the bone for phosphorus or calcium intake (low-turnover metabolic bone) or lowered storage capacity (high-turnover metabolic bone) is considered to be a cause of ectopic (vascular) mineralization. Cardiovascular complications account for 40% or more of the deaths of patients with chronic renal failures, and dialysis patients in particular, and arteriosclerosis involving vascular mineralization has drawn attention as a serious pathological condition. Treatment of mineralization of advanced lesions in patients with chronic renal failures remains difficult at present and the prognosis thereof is poor (Fujiu, A. et al., *Rinsho Toseki* (the Japanese Journal of Clinical Dialysis), 24, 43-50, Nihon Medical Center, Japan, 2008). In addition to agents for treating primary osteoporosis, accordingly, development of agents that more effectively act on bone diseases resulting from osteoarthritis, articular rheumatism, malignant tumors, or renal disease and vascular mineralization resulting from bone diseases with reduced side effects has been desired.

It is considered that bone metabolism is regulated by the balance between osteoblast functions and osteoclast functions, and osteoporosis develops when the bone-destroying activity exceeds bone-building activity (Cohen, M. M. Jr., American J. Med. Genetics, Part A, 140A, 2646-2706, 2006). In particular, secretion of the female hormone that assumes the role of protecting bones is lowered in postmenopausal women, a lowered capacity of osteoblasts for bone formation and the elevated bone resorption activity of osteoclasts are consequently observed, and it is highly likely that symptoms of osteoporosis would develop (Kousteni, S., et al., Cell, 104, 719-730, 2001; and Nakamura, T., et al., Cell, 130, 811-823, 2007). In order to overcome such problems, estrogen preparations have been used; however, application thereof has been restricted due to the increased risk of thrombosis and breast cancer caused by the use of such preparations. It is also reported that use of a selective estrogen receptor modulator would increase the risk of deep vein thrombosis (Wada, S., et al., Mebio, 25, 8, 89-95, 2008).

At present, calcitonin, bisphosphonate, and the like are used as agents that inhibit the bone resorption activity of osteoclasts. Calcitonin is known to bind to a calcitonin receptor expressed on the osteoclast surface to inactivate osteoclasts, and it is used for treatment of not only osteoporosis but also hypercalcemia, Paget's disease of bone, and the like in clinical settings. However, no effects thereof on bone fracture inhibition have yet been found, and calcitonin receptor expression is reported to be down-regulated by calcitonin administration (Wada, S., et al., Mebio, 25, 8, 89-95, 2008; and Wada, S. & Yasuda, S., Clin. Calcium, 11, 9, 1169-1175, 2001). Bisphosphonate exhibits potent bone resorption inhibitory activity, and amino-containing bisphosphonates, such as andronate and risedronate, are major therapeutic agents for osteoporosis in Japan. Such bisphosphonate preparations inhibit farnesyl diphosphate synthase, block lipid protein prenylation, and induce inhibition of bone-resorption functions and osteoclast apoptosis (Nakamura, T., The Bone, 22, 3, 147-151, 2008). However, the FDA warned of crises of severe skeletal, articular, or muscular pain in 2008 as problems of bisphosphonate preparations. In addition, side effects, such as jaw bone necrosis, caused by the prolonged use thereof (i.e., for 2 or 3 years or longer) after dental care have been reported (Sanna, G., et al., Ann. Oncol., 16, 1207-1208, 2005). An anti-RANKL antibody has been expected as a novel osteoclastic inhibitor other than those described above. Further, application of the anti-RANKL antibody as an inhibitor of articular destruction in the case of articular rheumatism or as a therapeutic agent for multiple myeloma has been expected, and clinical development thereof is in progress. Based on a report to the effect that the RANKL/RANK pathway is important for the survival and maintenance of dendritic cells (Theill, L. E., et al., Ann. Rev. Immunol., 20, 795-823, 2002) or a report to the effect that lymph node dysplasia is caused in an RANK- or RANKL-deficient mouse (Kong, Y. Y., et al., Nature, 397, 315-323, 1999; and Dougall, W. C., et al., Genes Dev., 13, 2412-2424, 1999), the influence of an anti-RANKL antibody preparation on the immune system has become an issue of concern. In 2008, AMGEN reported that an increased rate of development of some infectious diseases was found through a clinical test of the anti-RANKL antibody preparation (Denosumab). As a result of the clinical test of the anti-RANKL antibody conducted in 2009, development of jaw bone necrosis was found to be a side effect, as in the cases of the bisphosphonate preparations. Treatment via intermittent administration of PTH alone as an osteogenesis accelerator that activates osteoblasts has been conducted (Teriparatide, Eli Lilly; an unapproved drug in Japan), but such agent is not different from other therapeutic agents, such as bisphosphonate preparations, in that activity of increasing cortical bone thickness is not very high compared with activity of increasing cancellous bone mass. Accordingly, the effects thereof for bone fracture prevention are not considered to be very high. In relation to PTH, further, Asahi Kasei Pharma Corp. (Japan) has reported problems, such as side effects such as palpitation, tachycardia, and a lowering in blood pressure, and osteosarcoma observed in a long-term administration test to rats, unapproved continuous use thereof for 1.5 to 2 years or longer in Europe and the United States, and prohibited application thereof to cancer patients. Thus, it is impossible to use PTH for inhibition of cancer bone metastasis, treatment of cancer-induced hypercalcemia (paraneoplastic humoral hypercalcemia or local osteolytic hypercalcemia caused by the parathyroid-hormone-related peptide produced by tumor cells), or other purposes.

Accordingly, development of agents that more effectively work for osteoporosis caused by the lowered capacity of osteoblasts for bone formation or elevated bone resorption activity of osteoclasts in postmenopausal women, hypercalcemia, Paget's disease of bone, inhibition of bone metastasis inhibition of articular destruction associated with articular rheumatism, or multiple myeloma with reduced side effects has been awaited.

In addition thereto, osteohalisteresis and rachitis are known as bone diseases induced by selective inhibition of mineralization, unlike osteoporosis. A bone is formed by mineralization of a matrix layer comprising collagen or the like via hydroxyapatite deposition. Osteohalisteresis is a pathological condition in which such mineralization is blocked and osteoids increase, and it is referred to as rachitis if developed during childhood. Symptoms include bone and joint pains, such as chiropodalgia, arthralgia, lumbago, and backache, which lead to gait impairment and to a state in which bone is easily fractured. In the case of children, developmental disorders, limb deformities such as bow-legs, pigeon breast deformity, or other symptoms are observed. Such symptoms are generally treated with the use of vitamin D, calcium preparations, and phosphorus preparations, in addition to alimentary therapy. If the level of dysfunction caused by a deformity is high, however, surgical operation is the only possible symptomatic treatment. Therefore, development of agents that are more effective on osteohalisteresis or rachitis has been awaited.

As described above, bone is tissue that is always regulated by the balance between osteoblast functions and osteoclast functions and remodeled. In order to achieve tough bone that is more resistant to fracture, accordingly, a mere increase in bone mass may not be sufficient. In the case of hereditary diseases, such as osteopetrosis (Horiuchi A., CLINICIAN, 47, 401-404, 2000), Paget's disease of bone (Daroszewska, A., & Ralston, S. H., Nature Clinical Practice Rheumatology, 2, 270-277, 2006), or Camurati-Engelmann's disease (CED) (Janssens, K., et al., Nature Genetics, 26, 273-275, 2000; and Tang, Y., et al., Nature Medicine, 15, 757-765, 2009), for example, it is known that the balance between bone formation and bone resorption becomes abnormal due to different causes, and bone strength is lowered even though bone mass is increased. Examples of factors that determine bone strength from the viewpoint of mechanisms of materials include form-related factors, such as connectivity of cancellous bones, thickness of cortical bones, porosity, and cross-sectional moment, and qualitative factors, such as mineralization or bone fatigue, in addition to quantitative factors represented by bone density (Mori S., CLINICIAN, 49, 621-626, 2002). Therefore, development of agents useful for improving bone strength, in addition to increasing bone mass, has been awaited for the purpose of treatment of primary osteoporosis and secondary osteoporosis.

In recent years, factors associated with the Wnt/LRP signal control mechanism have drawn attention as targets for drug discovery regarding a bone formation accelerator. Wnt is a secreted glycoprotein that has been lipid-modified by palmitic acid having a molecular weight of about 40,000, and 19 types thereof are considered to be present in mammalian animals. As Wnt receptors, 10 types of seven-transmembrane receptors (i.e., Frizzled receptors) and two types of single-transmembrane receptors (i.e., LRP5/6 receptors) have been reported (Tamai, K., et al., Nature, 407, 530-535, 2000). A region referred to as a cysteine-rich domain (CRD) containing conserved 10 cysteine residues is present in an extracellular region of the Frizzled receptor family molecule to which Wnt is considered to bind. The region from the cysteine residue located closest to the N-terminus to the cysteine residue located closest to the C-terminus of such 10 cysteine residues may be exclusively designated as a CRD (Masiakowski, P. & Yancopoulos, G. D., Curr. Biol. 8, R407, 1998), or a region comprising such 10 cysteine residues and sequences each located closer to the C- or N-terminus may be designated as a CRD (R & D systems). CRDs were reported to have homodimer structures based on crystal structural analysis using a CRD of mouse Frizzled 8 (Dann, C. E., et al., Nature, 412, 86-90, 2001). At least three types of Wnt signaling pathways are considered to exist: a canonical-Wnt signaling pathway; a non-canonical Wnt signaling pathway, which is a PCP (planar cell polarity) pathway mediated by a small G-binding protein; and a $Ca^{2+}$ pathway mediated by a trimeric G protein. Bone-metabolism-related research on the canonical-Wnt signaling pathway is the most advanced, and Wnt is considered to promote bone formation (Rawadi, G. & Roman-Roman, S., Expert Opin. Ther. Targets, 9, 5, 1063-1077, 2005). Therefore, regulation of functions of endogenous factors that inhibit this signaling pathway has been attempted in recent years for the purpose of application thereof to treatment of bone diseases.

Sclerostin was recognized as a BMP antagonist at first; however, it was reported to be a factor that would directly bind to LRP5/6 to inhibit the signaling pathway in research conducted later (Semenov, M., et al., J. B. C., 280, 29, 26770-26775, 2005). A significant increase was observed in bone density in a Sclerostin-knockout mouse (Li, X., et al., J. Bone Miner. Res., 23, 860-869, 2008). At present, a Sclerostin-neutralizing antibody is undergoing phase I trials in Europe and the United States of America (AMG785, Amgen & UCB), and the future development thereof has drawn attention. A DKK1 (Dickkopf-1)-neutralizing antibody that is known as another canonical-Wnt signal inhibitor was prepared, inhibition of lowered bone density was observed in an SCID mouse into which multiple myeloma (MM) cells had been transplanted (Yaccoby, S., Blood., 109, 2106-2111, 2007), and clinical trials using a neutralizing antibody (BHQ880, Novartis) have been conducted.

sFRP (soluble frizzled-related protein) that is considered to be a Wnt decoy receptor and has high amino acid sequence homology to the Frizzled extracellular domain is considered to negatively regulate Wnt signals (Nakanishi, R., et al., J. Bone Miner. Res., 21, 1713-1721, 2006), and an increase in the amount of cancellous bone in the femur of an sFRP1 knockout mouse has been reported (Trevant, B., et al., J. Cell. Physiol. 217, 113-126, 2008). Under such circumstances, research and development related to sFRP 1 inhibitors have proceeded (Wyeth).

Frizzled 7 has been identified as a receptor that binds to a Wnt ligand and transmits signals thereof (Wang, Y., et al., J. B. C., 271, 8, 4468-4476, 1996; and Huang, H-C., & Klein, P. S., Genome Biology, 5, 234, 1-7, 2004). The amino acid sequence of the human Frizzled 7 extracellular cysteine-rich domain (when a region from the cysteine residue located closest to the N-terminus to the cysteine residue located closest to the C-terminus of such 10 conserved cysteine residues is exclusively designated as a CRD) is completely identical to that of the mouse Frizzled 7 extracellular cysteine-rich domain (i.e., there is no difference between species). Involvement thereof with generation and differentiation of individual organisms (Wheeler, G. N., Current Biology, 10, 849-852, 2000) and involvement thereof with liver cell multiplication (Matsumoto, K., et al., Dev. Biol., 319, 2, 234-247, 2008) have been reported.

Expression patterns of such molecules have been reported: an expression pattern localized in the crypt base of the mouse small intestine or large intestine (Gregorieff, A., et al., Gastroenterology, 129, 626-638, 2005); elevated expression levels in various cancer cells (Katoh, M. & Katoh, M., Int. J. Mol. Med., 19, 529-533, 2007); expression in various tissues (the brain, eyeball, heart, kidney, liver, lung, or spermary) other than those of the spleen via expression analysis of adult mouse-derived tissues of (Wang, Y., et al., J. B. C., 271, 8, 4468-4476, 1996); and expression in tissue (the lung or kidney) other than those of the brain and the liver via expression analysis of human fetal tissue and potent expression in the skeletal muscle and relatively potent expression in the heart, weak expression in the brain, the placenta, and the kidney; and no expression in the lung, the liver, the pancreas, the spleen, the thymic gland, the prostate, the testicle, the ovary, the small intestine, or the large intestine via expression analysis of adult human-derived tissue (Sagara, N., et al., B. B. R. C., 252, 117-122, 1998).

An extracellular cysteine-rich domain that is a soluble receptor of the Frizzled receptor is considered to bind to Wnt and inhibit functions thereof. It is reported by an in vitro experimentation system that a fusion product of the Frizzled 7 extracellular cysteine-rich domain (comprising a region from the cysteine residue located closest to the N-terminus to the cysteine residue located closest to the C-terminus of the conserved 10 cysteine residues and sequences each located closer to the C- or N-terminus) and Fc (R & D Systems) inhibits stabilization of cytoplasmic β-catenin by Wnt3a (Kemp, C. R., et al., Dev. Dynanics, 236, 2011-2019, 2007). Since the expression level of Frizzled 7 is elevated in cancer cells, it has drawn attention as a target molecule for tumor treatment (WO 2008/031009; and Merle, P., et al., J. Hepatol., 43, 5, 854-862, 2005). Regarding colon cancer cells into which a vector that expresses a Frizzled 7 extracellular domain has been introduced, for example, growth thereof was inhibited to a greater extent in a xenograft tumor cell transplantation model compared with colon cancer cells into which a control vector had been introduced (Vincan, E., et al., Differentiation, 73, 142-153, 2005). This suggests the possibility that Frizzled 7 would be a target of drug discovery for tumor treatment.

As described above, 10 types of Frizzled family molecules have been reported, and Frizzled 1 and Frizzled 2 have been reported as molecules having particularly high primary sequence homology with Frizzled 7 in the extracellular cysteine-rich domain (when a region from the cysteine residue located closest to the N-terminus to the cysteine residue located closest to the C-terminus of the conserved 10 cysteine residues is exclusively designated as a CRD, Daroszewska, A., & Ralston, S. H., Nature Clinical Practice Rheumatology, 2, 270-277, 2006). The amino acid homologies of Frizzled 7 in the cysteine rich domain (when a region from the cysteine residue located closest to the N-terminus to the cysteine residue located closest to the C-terminus of the conserved 10 cysteine residues is exclusively designated as a CRD) of such molecule to Frizzled 1 and Frizzled 2 are 91% and 93% respectively in humans and mice. That is, such amino acid sequence homology is very high. As with the case of Frizzled 7, Frizzled 1 and Frizzled 2 do not show differences between mouse-derived and human-derived amino acid sequences in the cysteine rich domain (when a region from the cysteine residue located closest to the N-terminus to the cysteine residue located closest to the C-terminus of the conserved 10 cysteine residues is exclusively designated as a CRD); i.e., such sequences are 100% consistent with each other.

As with Frizzled 7, it is reported that both Frizzled 1 and Frizzled 2 interact with Wnt and Frizzled 1 interacts with Wnt3a to protect the hippocampal neuron from being destroyed by amyloid β peptide (Chacon, M. A., et al., J. Cell Physiol., 217, 215-227, 2008). In addition, regarding Frizzled 1 expression patterns, potent expression in the heart, the placenta, the lung, the kidney, the pancreas, the prostate, and the ovary observed via expression analysis of adult human-derived tissue and potent expression in the lung and the kidney observed via expression analysis of fetus-derived tissue have been reported (Sagara, N., et al., B. B. R. C., 252, 117-122, 1998). Since the expression levels of both Frizzled 1 and Frizzled 2 are elevated in the case of colon cancer or breast cancer, the correlation thereof with canceration is suggested, and they have drawn attention as target molecules for tumor treatment (WO 2008/061013; Holcombe, R. F., et al., Mol. Pathol., 55, 220-226, 2002; and Milovanovic, T., et al., Int. J. Oncology, 25, 1337-1342, 2004). Further, it was reported that Frizzled 1 would not cause any changes in the phenotype of the Frizzled 1 gene-disrupted mouse (Deltagen, Inc., "NIH initiative supporting placement of Deltagen, Inc. mice into public repositories" MGI Direct Data Submission 2005 (informatics.jax-.org/javawi2/servlet/
WIFetch?page=alleleDetail&key=40116)). When a protein comprising an extracellular cysteine-rich domain derived from the Frizzled 1, Frizzled 2, or Frizzled 7 receptor is expressed in vivo at high levels or when a protein comprising an extracellular cysteine-rich domain derived from Frizzled 1, Frizzled 2, or Frizzled 7 is administered in vivo, accordingly, it has been very difficult to deduce that such protein would promotively and specifically function so as to increase bone mass and to enhance bone strength.

SUMMARY OF THE INVENTION

Problem to be Solved by the Invention

Since the arrival of a super-aging society, treatment of bone diseases resulting from osteoporosis, osteoarthritis, articular rheumatism, and malignant tumors, and bone diseases associated therewith have become critical issues in the society, and research and development regarding therapeutic agents for bone diseases have been extensively and actively conducted. At present, bisphosphonate is one of the most commonly used agents, and it has high efficacy, although the side effects thereof have become problematic in recent years. Problems to be overcome have been pointed out regarding other agents. Therefore, development of an agent that is more effective for treatment of bone diseases with reduced side effects has been strongly desired.

Means for Solving the Problem

Despite earlier deductions, surprisingly, the present inventors have now found for the first time that, when a protein comprising an extracellular cysteine-rich domain derived from the Frizzled 1, Frizzled 2, or Frizzled 7 receptor is expressed in vivo at high level or when a protein comprising an extracellular cysteine-rich domain derived from Frizzled 1, Frizzled 2, or Frizzled 7 is administered in vivo, such protein would promotively and specifically function so as to increase the bone mass and to enhance bone strength.

The present inventors have now prepared a mouse overexpressing a fusion protein, which comprises Frizzled 1, Frizzled 2, or Frizzled 7 extracellular cysteine-rich domain, and Fc, and discovered based on overexpression of the fusion of a protein, which comprises the Frizzled 7 extracellular cysteine-rich domain, and Fc the following: whitening of the femur, whitening of the sternum, whitening and hardening of the cranium, whitening and hardening of the spondylus, and hardening of the costa; the increased femoral cancellous bone and the increased sternal cancellous bone via observation of H&E stained pathological sections; increased tibial bone density via X-ray photography; increases in the tibial bone volume/tissue volume, the mineral apposition rate, the mineralization surface, and the bone formation rate via bone morphometry; the increased maximum load of femur via bone strength assays; the increased bone volume/tissue volume, increased trabecular thickness, increased trabecular number, decreased trabecular separation, or decreased trabecular spacing in the cancellous bone region of the proximal tibial metaphysis or the distal femoral metaphysis via bone structural analysis; and the increased femoral cancellous bones, the thickened diaphyseal wall, and the increased sternal cancellous bone via observation of H&E stained pathological sections. They also discovered based on overexpression of the fusion of a protein, which comprises the Frizzled 1 extracellular cysteine-rich domain, and Fc: whitening of the femur, whitening of the sternum, whitening and hardening of the cranium, hardening of the spondylus, and hardening of the costa; the increased tibial bone density via X-ray photography; the thickened diaphyseal wall, the increased cancellous bone, and the increased sternal cancellous bone of the femur via observation of H&E stained pathological sections; increases in the increased tibial bone volume/tissue volume, the mineral apposition rate, the mineralization surface, and the bone formation rate via bone morphometry; the increased maximum load of femur via bone strength assays; and the increased bone volume/tissue volume, the increased trabecular thickness, the increased trabecular number, the decreased trabecular separation, and the decreased trabecular spacing in the cancellous bone region at the distal femoral metaphysis via bone structural analysis. They further discovered based on overexpression of the fusion of a protein, which comprises the Frizzled 2 extracellular cysteine-rich domain, and Fc: whitening of the femur, whitening of the sternum, whitening and hardening of the cranium, hardening of the spondylus, and hardening of the costa; the thickened femoral diaphyseal wall via observation of H&E stained pathological sections; increases in the tibial bone volume/tissuel volume, the mineral apposition rate, the mineralization surface, and the bone formation rate via bone morphometry; the increased maximum load of femur via bone strength assays; and the increased bone volume/tissue volume, the increased trabecular thickness, the increased trabecular number, the decreased trabecular separation, and the decreased trabecular spacing in the cancellous bone region at the distal femoral metaphysis via bone structural analysis.

Further, the present inventors have now obtained a fusion protein, which comprises the Frizzled 1, Frizzled 2, or Frizzled 7 extracellular cysteine-rich domain, and Fc, as a recombinant protein. The present inventors have now discovered via administration of the obtained recombinant fusion protein, which comprises the Frizzled 7 extracellular cysteine-rich domain, and Fc to a mouse: whitening of the femur, whitening of the cranium, whitening of the sternum, and a tendency of thickening node; the thickened femoral diaphyseal wall via observation of H&E stained pathological sections; and increased bone volume/tissue volume in the secondary cancellous bone at the tibial metaphysis via bone morphometry. The present inventors have also discovered via administration of the obtained recombinant fusion protein of a protein, which comprises the Frizzled 7 extracellular cysteine-rich domain: whitening of the femur, whitening of the sternum, whitening and hardening of the cranium, hardening of the costa, and hardening of the spondylus, and Fc to an ovariectomized mouse (OVX); the thickened femoral diaphyseal wall via observation of H&E stained pathological sections; the increased cortical bone cross-sectional area of the femur via 2D micro CT; and the increased maximum load of femur via bone strength assays. Further, the present inventors have now administered the obtained recombinant fusion protein of a protein, which comprises a minimum CRD sequence comprising the amino acid sequence from N-terminal side cysteine-1 to C-terminal side cysteine-10 in the Frizzled 7 extracellular cysteine-rich domain to a mouse. As a result, the present inventors have now discovered the increased maximum load of femur via bone strength assays and the increased bone volume/tissue volume, the increased trabecular thickness, the increased trabecular number, the decreased trabecular separation, and the decreased trabecular spacing of the tibia via bone structural analysis. Also, the present inventors have now administered the obtained recombinant fusion protein of a protein, which comprises the Frizzled 1 extracellular cysteine-rich domain, and Fc to a mouse and observed that whitening and epiphyseal hypertrophy of the femur, whitening of the sternum, whitening and hardening of the cranium, and hardening of the costa had occurred.

Based on such findings, it was demonstrated that a therapeutic agent for a bone disease comprising, as an active ingredient, a protein comprising the Frizzled 1, Frizzled 2, or Frizzled 7 extracellular cysteine-rich domain or a mutant thereof can be provided as a novel therapeutic agent for a bone disease resulting from osteoporosis, arthritis, or malignant tumors.

Specifically, the present invention includes the following features.

(1) A pharmaceutical composition for treating a bone disease comprising, as an active ingredient, a protein comprising an extracellular cysteine-rich domain, which is from the Frizzled receptor selected from the group consisting of mammalian animal-derived Frizzled 1, Frizzled 2, and Frizzled 7 and has activity of increasing bone mass, bone density, and/or bone strength, or a mutant of such domain having sequence identity of 85% or higher to the amino acid sequence of such domain and having activity of increasing bone mass, bone density, and/or bone strength, or a vector comprising a nucleic acid encoding the protein.

(2) The composition according to (1), wherein the protein is a fusion protein of the extracellular cysteine-rich domain or a mutant thereof and the mammalian animal-derived immunoglobulin Fc protein or a mutant thereof, and the nucleic acid encoding the protein is a nucleic acid encoding such fusion protein.

(3) The composition according to (1) or (2), wherein the protein is chemically modified.

(4) The composition according to (3), wherein the chemical modification is a binding of one or a plurality of polyethylene glycol molecules.

(5) The composition according to (3), wherein the chemical modification is a binding of a sugar chain.

(6) The composition according to any of (1) to (5), wherein the protein is a fragment of an extracellular region protein of the Frizzled receptor, which fragment comprises the extracellular cysteine-rich domain.

(7) The composition according to any of (1) to (6), wherein the protein is a recombinant protein.

(8) The composition according to any of (1) to (7), wherein the extracellular cysteine-rich domain comprises an amino acid sequence comprising at least the amino acid sequence spanning from the 1st cysteine residue on the N-terminal side to the 10th cysteine residue in the amino acid sequence of the extracellular region protein of the Frizzled receptor.

(9) The composition according to any of (6) to (8), wherein the extracellular region protein comprises the amino acid sequence of SEQ ID NO: 19, 20, 22, 23, or 25.

(10) The composition according to any of (1) to (9), wherein the protein comprising the extracellular cysteine-rich domain comprises a protein comprising the amino acid sequence spanning from the 1st cysteine residue on the N-terminal side to the 10th cystein residue as shown in SEQ ID NO: 21, 24, or 26.

(11) The composition according to any of (1) to (10), wherein the nucleic acid encoding a protein comprising the extracellular cysteine-rich domain comprises a nucleotide sequence as shown in any of SEQ ID NOs: 44 to 49.

(12). The composition according to any of (2) to (11), wherein the Fc protein comprises the amino acid sequence of SEQ ID NO: 4.

(13) The composition according to any of (2) to (11), wherein the nucleic acid encoding the Fc protein comprises the nucleotide sequence of SEQ ID NO: 3.

(14) The composition according to any of (2) to (11), wherein the fusion protein comprises the amino acid sequence as shown in any of SEQ ID NOs: 27 to 31.

(15) The composition according to any of (2) to (11), wherein the nucleic acid encoding the fusion protein comprises the nucleotide sequence as shown in any of SEQ ID NOs: 38 to 43.

(16) The composition according to any of (1) to (15), wherein the mammalian animal is a human.

(17) The composition according to any of (1) to (16), wherein the bone disease is accompanied with lowering of bone mass, bone density, and/or bone strength.

(18) A method for treating a bone disease comprising administering the composition according to any of (1) to (17) to a mammalian animal.

(19) The method according to (18), wherein the mammalian animal is a human.

(20) The method according to (18), wherein the bone disease is accompanied with lowering of bone mass, bone density and/or bone strength.

(21) The method according to any of (18) to (20), wherein the composition is simultaneously or continuously administered in combination with another therapeutic agent for bone disease.

Effects of the Invention

The present invention can increase bone mass, bone density, and/or bone strength. Accordingly, a disease involving lowering of bone mass, bone density, and/or bone strength, such as a bone disease resulting from osteoporosis, osteoarthritis, articular rheumatism, malignant tumors, or other diseases and various bone diseases or disorders associated therewith can be treated without causing side effects.

PREFERRED EMBODIMENTS OF THE INVENTION

Figure 1:
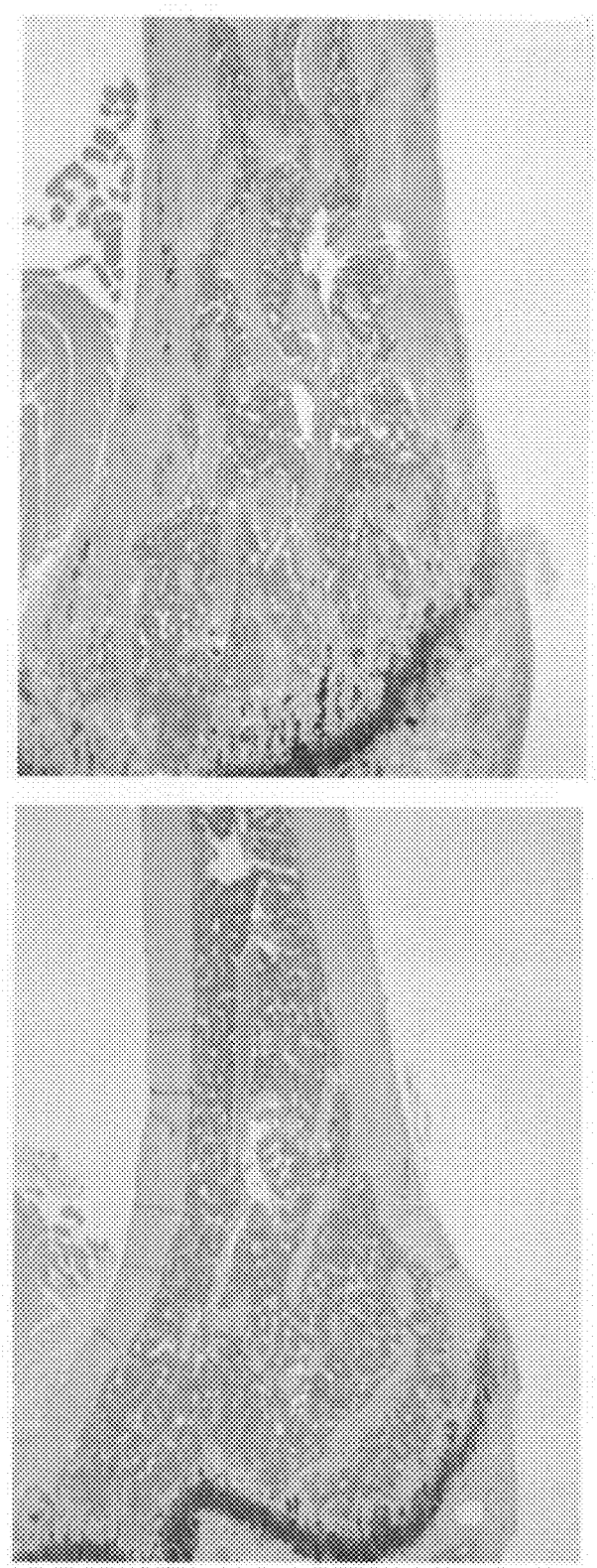
FIG. 1 shows images of H&E stained pathological sections obtained from the femurs of a 16-week-old USmFZD7crd-hFcm KI chimeric mouse (right diagram) and a control mouse (left diagram).

Hereafter, the present invention is described in detail.

As described above, the present invention provides a pharmaceutical composition for treatment of a bone disease comprising, as an active ingredient, a protein which comprises an extracellular cysteine-rich domain derived from the Frizzled receptor selected from the group consisting of mammalian animal-derived Frizzled 1, Frizzled 2, and Frizzled 7 and having activity of increasing bone mass, bone density, and/or bone strength or a mutant thereof having a 85% or higher sequence identity to the amino acid sequence of said domain and having activity of increasing bone mass, bone density, and/or bone strength, or a vector comprising a nucleic acid encoding said protein.

The present invention is based on the finding of that a fragment comprising an extracellular cysteine-rich domain in the extracellular region protein of a Frizzled receptor has a function of increasing the bone mass, bone density, and/or bone strength of a mammalian animal. Specifically, the present inventors have now prepared a mouse expressing the Frizzled extracellular cysteine-rich domain from mouse ES cells by a knock-in technique or administered a recombinant fusion protein of a protein, which comprises the Frizzled extracellular cysteine-rich domain, and Fc to a mouse. As a result, they have now found, for the first time, that the bone mass, bone density, and/or bone strength at a bone site of interest would be increased to the extent that such increase could be visually and sensuously recognized compared with wild-type mice. Further, the present inventors have now discovered that, surprisingly, the effects of the extracellular cysteine-rich domain for increasing the bone mass, bone density, and/or bone strength were bone-specific and such effects were not influential at all or substantially not influential on other tissue or organs; i.e., no side effects were observed. According to the past findings, the extracellular cysteine-rich domain of the Frizzled receptor had been considered to bind to Wnt, which is a ligand of the receptor and associated with bone morphogenesis, and inhibit the functions of the domain, as described in the "Background Art" above. Thus, such domain was not deduced to be involved in bone growth acceleration. The extracellular cysteine-rich domain of Frizzled 7 is reported to be particularly effective for inhibiting proliferation of tumors such as colon cancer and it has drawn attention as the target of drug discovery for cancer treatment.

Thus, the present inventors have now discovered that the extracellular cysteine-rich domain of a Frizzled receptor has novel useful functions of specifically and promotively increasing the bone mass, bone density, and/or bone strength. The pharmaceutical composition of the present invention can be used for treatment of a bone disease aimed at increasing the bone mass, bone density, and/or bone strength at a bone site.

Hereafter, the pharmaceutical composition of the present invention is described in greater detail.

<Extracellular Cysteine-rich Domain of Frizzled Receptor>

The Frizzled receptor of the present invention is mammalian animal-derived Frizzled 1, Frizzled 2, or Frizzled 7. Such receptor has particularly high identity of the extracellular cysteine-rich domain (hereafter, it is occasionally referred to as "CRD") among ten types of Frizzled receptors whose ligands are Wnt. Identity of the amino acid sequences comprising N-terminal side cysteine-1 to C-terminal side cysteine-10 between CRDs of such receptors is 93% between a CRD of Frizzled 7 and a CRD of Frizzled 2 and 91% between a CRD of Frizzled 7 and a CRD of Frizzled 1, in the case of the human- and mouse-derived sequences. The amino acid sequence of such region of a human is identical to that of a mouse and highly conserved across species. Sequence identity between a CRD of any of Frizzled 3 to 6 and 8 to 10 and that of Frizzled 7 is as low as 42% to 56%.

Information regarding the amino acid and nucleotide sequences of Frizzled 1, Frizzled 2, and Frizzled 7 is available from NCBI (U.S.A.).

Frizzled 7 (also referred to as "FZD7") is isolated from, for example, human, mouse, Rhesus monkey, red junglefowl, zebrafish, or *Xenopus*, and sequence information is open to the public. In the present invention, the origin of the Frizzled 7 protein or a nucleic acid encoding the same is not limited, and it is preferably derived from, for example, a mammalian animal, such as a primate including a human and a rodent including mouse. Sequence information of human- or mouse-derived Frizzled 7 is registered under, for example, Accession Number: NM_003507.1 or NP_003498.1 in the case of human Frizzled 7, or Accession Number: NM_008057.1, NP_032083.1, NM_008057.2, NP_032083.2, NM_008057.3, or NP_032083.3 in the case of mouse Frizzled 7, with the GenBank (NCBI, U.S.A.).

The amino acid sequences of the extracellular region proteins of human and mouse Frizzled 7 are as follows.

Amino acid sequence of extracellular region protein of human Frizzled 7 (SEQ ID NO: 19):

QPYHGEKGISVPDHGFCQPISIPLCTDIAYNQTILPNLLGHTNQEDAGLEVHQFYPLVK
VQCSPELRFFLCSMYAPVCTVLDQAIPPCRSLCERARQGCEALMNKFGFQWPERLRC
ENFPVHGAGEICVGQNTSDGSGGPGGGPTAYPTAPYL

Amino acid sequence of the extracellular region protein of mouse Frizzled 7 (SEQ ID NO: 20):

QPYHGEKGISVPDHGFCQPISIPLCTDIAYNQTILPNLLGHTNQEDAGLEVHQFYPLVK
VQCSPELRFFLCSMYAPVCTVLDQAIPPCRSLCERARQGCEALMNKFGFQWPERLRC
ENFPVHGAGEICVGQNTSDGSGGAGGSPTAYPTAPYL

The underlined portion represents a sequence comprising N-terminal side cysteine-1 to C-terminal side cysteine-10, which is the minimal CRD region (SEQ ID NO: 21).

SEQ ID NO: 21:
CQPISIPLCTDIAYNQTILPNLLGHTNQEDAGLEVHQFYPLVKVQCSPE
LRFFLCSMYAPVCTVLDQAIPPCRSLCERARQGCEALMNKFGFQWPERL
RCENFPVHGAGEIC

Frizzled 1 (also referred to as "FZD1") is isolated from, for example, human, mouse, rat, red junglefowl, or Xenopus, and sequence information is open to the public. In the present invention, the origin of the Frizzled 1 protein or a nucleic acid encoding the same is not limited, and it is preferably derived from, for example, a mammalian animal, such as a primate including a human and a rodent including mouse. Sequence information of human- or mouse-derived Frizzled 1 is registered under, for example, Accession Number: NM_003505.1 or NP_003496.1 in the case of human Frizzled 1, or Accession Number: NM_021457.1, NP_067432.1, NM_021457.2, NP_067432.2, or NM_021457.3 in the case of mouse FZD1, with the GenBank.

The amino acid sequences of the extracellular region proteins of human and mouse Frizzled 1 are as follows.

Amino acid sequence of extracellular region protein of human Frizzled 1 (SEQ ID NO: 22):

QAAGQGPGQGPGPGQQPPPPPQQQQSGQQYNGERGISVPDHGYCQPISI
PLCTDIAYNQTIMPNLLGHTNQEDAGLEVHQFYPLVKVQCSAELKFFLC
SMYAPVCTVLEQALPPCRSLCERARQGCEALMNKFGFQWPDTLKCEKFP
VHGAGELCVGQNTSDKGTPTPSLLPEFWTSNPQH

Amino acid sequence of extracellular region protein of mouse Frizzled 1 (SEQ ID NO: 23):

QAAGQVSGPGQQAPPPPQPQQSGQQYNGERGISIPDHGYCQPISIPLCT
DIAYNQTIMPNLLGHTNQEDAGLEVHQFYPLVKVQCSAELKFFLCSMYA
PVCTVLEQALPPCRSLCERARQGCEALMNKFGFQWPDTLKCEKFPVHGA
GELCVGQNTSDKGTPTPSLLPEFWTSNPQH

The underlined portion represents a sequence spanning from the 1st cysteine residue on the N-terminal side to the 10th cystein residue on the C-terminal side, which portion is the minimal CRD region (SEQ ID NO: 24). The amino acid sequence of this region of a human is identical to that of a mouse.

SEQ ID NO: 24:
CQPISIPLCTDIAYNQTIMPNLLGHTNQEDAGLEVHQFYPLVKVQCSAE
LKFFLCSMYAPVCTVLEQALPPCRSLCERARQGCEALMNKFGFQWPDTL
KCEKFPVHGAGELC

Frizzled 2 (also referred to as "FZD2") is isolated from, for example, human, mouse, rat, or Xenopus, and sequence information is open to the public. In the present invention, the origin of the Frizzled 2 protein or a nucleic acid encoding the same is not limited, and it is preferably derived from, for example, a mammalian animal, such as a primate including a human and a rodent including mouse. Sequence information of human- or mouse-derived Frizzled 2 is registered under, for example, Accession Number: NM_001466.1, NM_001466.2, or NP_001457.1 in the case of human Frizzled 2, or Accession Number: NM_020510.1, NM_020510.2, NP_065256.1 in the case of mouse FZD2, with the GenBank.

The amino acid sequences of the extracellular region proteins of human Frizzled 2 is identical to that of mouse Frizzled 2 as shown below.

Amino acid sequences of extracellular region proteins of human and mouse Frizzled 2 (SEQ ID NO: 25):

QFHGEKGISIPDHGFCQPISIPLCTDIAYNQTIMPNLLGHTNQEDAGLE
VHQFYPLVKVQCSPELRFFLCSMYAPVCTVLEQAIPPCRSICERARQGC
EALMNKFGFQWPERLRCEHFPRHGAEQICVGQNHSEDGAPAL

The underlined portion represents a sequence spanning from the 1st cysteine residue on the N-terminal side to the 10th cystein residue on the C-terminal side, which portion is the minimal CRD region (SEQ ID NO: 26).

SEQ ID NO: 26:
CQPISIPLCTDIAYNQTIMPNLLGHTNQEDAGLEVHQFYPLVKVQCSPE

LRFFLCSMYAPVCTVLEQAIPPCRSICERARQGCEALMNKFGFQWPERL

RCEHFPRHGAEQIC

In the present invention, the term "extracellular cysteine-rich domain" refers to a protein which comprises at least an amino acid sequence spanning the 1st cysteine residue on the N-terminal side to the 10th cysteine residue in the extracellular region protein of the Frizzled receptor selected from the group consisting of mammalian animal-derived Frizzled 1, Frizzled 2, and Frizzled 7 and which is capable of increasing the bone mass, bone density and/or bone strength of a mammalian animal. The expression "comprising at least" as used herein means that the extracellular cysteine-rich domain may be composed of a minimum CRD sequence spanning from the 1st cysteine residue on the N-terminal side to the 10th cysteine residue in the extracellular region protein of the Frizzled receptor, or alternatively that any foreign sequence may be added to the N- and/or C-terminus of the minimum CRD sequence, provided that the resulting sequence has an ability to increase the bone mass, bone density, and/or bone strength. The term "foreign sequence" may refer to, for example, a sequence derived from any foreign protein unrelated to the extracellular region protein of the Frizzled receptor, an artificial sequence, or a sequence derived from a portion of the extracellular region protein of a foreign Frizzled receptor other than the minimum CRD sequence.

The extracellular cysteine-rich domain according to the present invention is a protein which comprises an amino acid sequence comprising at least the amino acid sequence spanning from the 1st cysteine residue on the N-terminal side to the 10th cystein residue in the extracellular region protein of the Frizzled receptor selected from the group consisting of mammalian animal-derived Frizzled 1, Frizzled 2, and Frizzled 7 and which is capable of increasing the bone mass, bone density, and/or bone strength of a mammalian animal. The expression "comprising at least" as used herein means that the minimum sequence consists of the amino acid sequence spanning the 1st cystein residue on the N-terminal side to the 10th cysteine residue in the extracellular region protein of the Frizzled receptor, and a sequence derived from the extracellular region protein of the Frizzled receptor of the same species may be adequately extended and comprised at the N-terminus and/or C-terminus of the minimum sequence. Accordingly, the extracellular cysteine-rich domain can comprise any amino acid sequence spanning from the aforementioned minimum CRD sequence to the maximum CRD sequence of the extracellular region protein of the Frizzled receptor.

In the present invention, examples of mammalian animals include, but are not limited to, primates, livestock animals, rodents, ungulates, and pet animals. Preferable mammalian animals are humans and mice. Mice are important since they have the amino acid sequence of the extracellular cysteine-rich domain (CRD); specifically, the minimum CRD sequence spanning from the 1st cystein residue on the N-terminal side to the 10th cystein residue on the C-terminal side is identical to a human-derived sequence.

In the present invention, a preferable CRD is a protein which comprises an amino acid sequence comprising at least the amino acid sequence spanning from the 1st cystein residue on the N-terminal side to the 10th cysteine residue in the extracellular region protein of the Frizzled receptor selected from the group consisting of human- or mouse-derived Frizzled 7, Frizzled 1, and Frizzled 2 (SEQ ID NO: 21, 24, or 26) and which has an ability to increase the bone mass, bone density, and/or bone strength of a mammalian animal.

In the present invention, another preferable CRD is a protein which comprises an amino acid sequence comprising at least the amino acid sequence spanning the 1st cystein residue on the N-terminal side to the 10th cystein residue (as shown in SEQ ID NO: 21, 24, or 26) in the amino acid sequence (as shown in SEQ ID NO: 19, 20, 22, 23, or 25, respectively) of the extracellular region protein of the Frizzled receptor selected from the group consisting of human- or mouse-derived Frizzled 7, Frizzled 1, and Frizzled 2 and which has an ability to increase the bone mass, bone density, and/or bone strength of a mammalian animal.

In the present invention, an increase in "the bone mass, bone density, and/or bone strength" involves at least the increased cancellous bone, the thickened and proliferated diaphysis, or the increased maximum load, for example.

<Mutant of Extracellular Cysteine-rich Domain>

The extracellular cysteine-rich domain of the present invention includes a mutant of the extracellular cysteine-rich domain described in the section of <Extracellular cysteine-rich domain of Frizzled receptor> above. Such mutant may be a naturally-occurring or artificial mutant, which comprises an amino acid sequence comprising a substitution(s), deletion(s), or addition(s) of one or more (preferably one or several) amino acids in the amino acid sequence of the extracellular cysteine-rich domain, or comprises an amino acid sequence having 80% or higher, preferably 85% or higher, and more preferably 90% or higher, such as 93% or higher, 95% or higher, 97% or higher, 98% or higher, or 99% or higher identity with the amino acid sequence of the extracellular cysteine-rich domain, and which has an ability to increase the bone mass, bone density, and/or bone strength.

For example, the mutant comprises an amino acid sequence comprising a substitution(s), deletion(s), or addition(s) of one or more (preferably one or several) amino acids in the amino acid sequence as shown in SEQ ID NO: 21, 24 or 26, 19, 20, 22, 23, or 25, or comprises an amino acid sequence having 80% or higher, preferably 85% or higher, and more preferably 90% or higher, such as 93% or higher, 95% or higher, 97% or higher, 98% or higher, or 99% or higher identity with the amino acid sequence as shown in SEQ ID NO: 21, 24 or 26, 19, 20, 22, 23, or 25, and the mutant has an ability to increase the bone mass, bone density, and/or bone strength.

The term "several" used herein generally refers to an arbitrary integer between 2 and 10, and it is preferably an integer between 2 and 5.

The term "identity" as used herein refers to a degree of coincidence between two amino acid sequences (or nucleotide sequences) that are aligned to maximize the number of identical amino acid residues (or the number of identical nucleotides). Specifically, the identity is represented by a percentage (%) of the number of identical amino acid residues (or the number of identical nucleotides) relative to the total number of amino acid residues (or the total number of nucleotides). When a gap is introduced as in the case of FASTA, the number of gaps is added to the total number of amino acid residues (or the total number of nucleotides).

Proteins having 80% or higher, and preferably 85% or higher sequence identity, can be screened for by accessing, for example, the sequence databases of NCBI (U.S.A.) or EMBL (Europe) and utilizing a sequence homology search program, such as BLAST or FASTA (e.g., Altschul, S. F. et al., 1990, J. Mol. Biol. 15:403-410; Karlin, S. and Altschul S. F., 1990, Proc. Natl. Acad. Sci., U.S.A., 87: 2264-2268). According to BLAST, a sequence is divided into words of a fixed length, similar fragments are screened for in the word unit, such fragments are extended toward the both directions to maximize the similarity, local alignment is performed, and the aligned sequences are bound in the end to perform the final alignment. According to FASTA, continuously coincide sequence fragments are screened for at a high speed, fragments exhibiting high similarity are selectively subjected to local alignment, the fragments are bound to each other in the end while gaps are taken into consideration to perform alignment.

When a mutation is introduced into the extracellular cysteine-rich domain of the present invention, it is preferable that amino acid residues other than 10 cysteine residues in the sequence spanning the 1st cystein residue on the N-terminal side to the 10th cysteine residue on the C-terminal side of the extracellular region protein of the Frizzled receptor be exclusively subjected to a mutation of substitution, deletion, or addition, natural disulfide bonds be not destructed, and a natural conformation be substantially maintained. If a natural disulfide bond(s) in the extracellular cysteine-rich domain is destructed and an inherent conformation is altered, the protein domain may disadvantageously lose or significantly reduce the ability of increasing the bone mass, bone density, and/or bone strength.

A preferable mutagenesis technique is a site-directed mutagenesis utilizing PCR involving the use of primers synthesized based on the known sequence of the extracellular cysteine-rich domain (including a complementary mutant sequence) (e.g., Kunkel et al., Proc. Natl. Acad. Sci., U.S.A., 1985, 82: 488-492; F. M. Ausubel et al., Short Protocols in Molecular Biology, 1995, John Wiley & Sons; J. Sambrook et al., Molecular Cloning: A Laboratory Manual, 2nd ed., 1989, Cold Spring Harbor Laboratory Press). Since mutagenesis kits are commercially available (e.g., Takara Shuzo Co., Ltd.), mutation can be introduced with the use of such kits in accordance with the instructions.

Briefly, the method of Kunkel comprises using a plasmid containing DNA encoding the extracellular cysteine-rich domain as a template, annealing a primer having a phosphorylated 5' terminus with T4 DNA polynucleotide kinase (including a complementary mutant sequence) to the template, synthesizing DNA, ligating the terminuses with the aid of T4 DNA ligase, and purifying DNA containing mutation of interest.

In the present invention, the mutation includes a substitution, a deletion, an addition, an insertion, or combinations thereof.

Substitution may be conservative or non-conservative. Conservative substitution is preferable in order to substantially refrain from altering the conformation of a protein of the extracellular cysteine-rich domain. The term "conservative substitution" refers to substitution across amino acids having similar structural properties (e.g., a branch state or aromaticity), electric properties (e.g., acidic or basic properties), and chemical and physical properties (e.g., polar or hydrophobic properties). Examples of branched amino acids include valine, leucine, and isoleucine. Examples of aromatic amino acids include tyrosine, tryptophan, phenylalanine, and histidine. Examples of acidic amino acids include glutamic acid and aspartic acid. Examples of basic amino acids include lysine, arginine, and histidine. Examples of polar amino acids include serine, threonine, glutamine, asparagine, tyrosine, cysteine, glycine, and proline. Examples of hydrophobic amino acids include alanine, valine, leucine, isoleucine, and methionine.

Deletion involves loss of one or a plurality of amino acid residues. Addition involves binding of one or a plurality of amino acid residues to the protein N- or C-terminus. Insertion involves binding of one or a plurality of amino acid residues to the inside of a protein. Deletion and insertion can be performed, provided that a protein conformation of the extracellular cysteine-rich domain is not substantially changed. Thus, the number of amino acid residues that can be subjected to deletion or insertion is preferably limited to about 1 to 5.

<Protein Comprising an Extracellular Cysteine-rich Domain or a Mutant thereof>

As described above, an active ingredient of the pharmaceutical composition of the present invention is a protein comprising an extracellular cysteine-rich domain derived from the Frizzled receptor selected from the group consisting of mammalian animal-derived Frizzled 1, Frizzled 2, and Frizzled 7 and having activity of increasing bone mass, bone density, and/or bone strength or a mutant thereof having 85% or higher sequence identity to the amino acid sequence of such domain and having activity of increasing bone mass, bone density, and/or bone strength.

The expression "comprise" or "comprising" used herein refers that the extracellular cysteine-rich domain or a mutant thereof may comprise a foreign peptide, polypeptide, or protein bound or fused to the N- or C-terminus of such domain or a mutant thereof via an adequate peptide linker (e.g., 1 to 20 amino acid residues), where needed. Examples of preferable foreign proteins include the mammalian animal-derived immunoglobulin Fc protein and a mutant thereof. Since a rejection reaction may take place upon administration of such foreign protein in an organism, it may be preferable that a protein inherent to a mammalian animal to which such protein is to be administered be used as the foreign protein, in order to avoid such rejection as much as possible.

A preferable Fc protein is a human immunoglobulin Fc protein from the viewpoint of application thereof to a human. Examples of immunoglobulin classes and subclasses include, but are not limited to, IgG, IgD, IgE, IgM, IgA, IgG1, IgG2, IgG2a, IgG2b, IgG2c, IgG3, IgG4, IgA1, and IgA2. Use of a human immunoglobulin class and subclass is preferable if the protein is applied to a human. The Fc protein can improve stability of the extracellular cysteine-rich domain or a mutant thereof in vivo. In such a case, however, biological activity, such as antibody dependent cellular cytotoxicity (ADCC) and/or complement dependent cytotoxicity (CDC), of the Fc protein is preferably lowered in advance in order to avoid the influence of such biological activity in vivo. To this end, it is preferable that a mutation for suppressing, lowering, or losing such biological activity be introduced. Such mutation is amino acid substitution of, for example, 1 to 10, preferably 1 to 5, and more preferably 1 to 3 amino acid residues in the amino acid sequence of the mammalian animal-derived Fc protein. Arbitrary amino acid substitution reduces ADCC and/or CDC activity. A specific example is substitution as described in Example 1 below. A preferable example of the Fe protein is a human IgG1 Fc mutant comprising the amino acid sequence as shown in SEQ ID NO: 4. An Fc protein may bound to an N- or C-terminal site of the extracellular cysteine-rich domain or a mutant thereof, with the C-terminal site being preferable.

Specific examples of the Fc fusion protein include proteins comprising amino acid sequences as shown in SEQ ID NOs: 27 to 31 below. The underlined portion represents a protein comprising the extracellular cysteine-rich domain and the non-underlined portion represents a human IgG1 Fc mutant protein.

SEQ ID NO: 27 (SEQ ID NO: 19 + SEQ ID NO: 4):
QPYHGEKGISVPDHGFCQPISIPLCTDIAYNQTILPNLLGHTNQEDAGL
EVHQFYPLVKVQCSPELRFFLCSMYAPVCTVLDQAIPPCRSLCERARQG
CEALMNKFGFQWPERLRCENFPVHGAGEICVGQNTSDGSGGPGGGPTAY
PTAPYLAEPRSSDKTHTCPPCPAPEAEGAPSVFLFPPKPKDTLMISRTP
EVTCVVVDVSHEDPEVKFNWYVDGVEVHNAKTKPREEQYNSTYRVVSVL
TVLHQDWLNGKEYKCAVSNKALPASIEKTISKAKGQPREPQVYTLPPSR
DELTKNQVSLTCLVKGFYPSDIAVEWESNGQPENNYKTTPPVLDSDGSF
FLYSKLTVDKSRWQQGNVFSCSVMHEALHNHYTQKSLSLSPGK

SEQ ID NO: 28 (SEQ ID NO: 20 + SEQ ID NO: 4):
QPYHGEKGISVPDHGFCQPISIPLCTDIAYNQTILPNLLGHTNQEDAGL
EVHQFYPLVKVQCSPELRFFLCSMYAPVCTVLDQAIPPCRSLCERARQG
CEALMNKFGFQWPERLRCENFPVHGAGEICVGQNTSDGSGGAGGSPTAY
PTAPYLAEPRSSDKTHTCPPCPAPEAEGAPSVFLFPPKPKDTLMISRTP
EVTCVVVDVSHEDPEVKFNWYVDGVEVHNAKTKPREEQYNSTYRVVSVL
TVLHQDWLNGKEYKCAVSNKALPASIEKTISKAKGQPREPQVYTLPPSR
DELTKNQVSLTCLVKGFYPSDIAVEWESNGQPENNYKTTPPVLDSDGSF
FLYSKLTVDKSRWQQGNVFSCSVMHEALHNHYTQKSLSLSPGK

SEQ ID NO: 29 (SEQ ID NO: 22 + SEQ ID NO: 4):
QAAGQGPGQGPGPGQQPPPPQQQQSGQQYNGERGISVPDHGYCQPISI
PLCTDIAYNQTIMPNLLGHTNQEDAGLEVHQFYPLVKVQCSAELKFFLC
SMYAPVCTVLEQALPPCRSLCERARQGCEALMNKFGFQWPDTLKCEKFP
VHGAGELCVGQNTSDKGTPTPSLLPEFWTSNPQHAEPRSSDKTHTCPPC
PAPEAEGAPSVFLFPPKPKDTLMISRTPEVTCVVVDVSHEDPEVKFNWY
VDGVEVHNAKTKPREEQYNSTYRVVSVLTVLHQDWLNGKEYKCAVSNKA
LPASIEKTISKAKGQPREPQVYTLPPSRDELTKNQVSLTCLVKGFYPSD
IAVEWESNGQPENNYKTTPPVLDSDGSFFLYSKLTVDKSRWQQGNVFSC
SVMHEALHNHYTQKSLSLSPGK

SEQ ID NO: 30 (SEQ ID NO: 23 + SEQ ID NO: 4):
QAAGQVSGPGQQAPPPPQPQQSGQQYNGERGISIPDHGYCQPISIPLCT
DIAYNQTIMPNLLGHTNQEDAGLEVHQFYPLVKVQCSAELKFFLCSMYA
PVCTVLEQALPPCRSLCERARQGCEALMNKFGFQWPDTLKCEKFPVHGA
GELCVGQNTSDKGTPTPSLLPEFWTSNPQHAEPRSSDKTHTCPPCPAPE
AEGAPSVFLFPPKPKDTLMISRTPEVTCVVVDVSHEDPEVKFNWYVDGV
EVHNAKTKPREEQYNSTYRVVSVLTVLHQDWLNGKEYKCAVSNKALPAS
IEKTISKAKGQPREPQVYTLPPSRDELTKNQVSLTCLVKGFYPSDIAVE
WESNGQPENNYKTTPPVLDSDGSFFLYSKLTVDKSRWQQGNVFSCSVMH
EALHNHYTQKSLSLSPGK

SEQ ID NO: 31 (SEQ ID NO: 25 + SEQ ID NO: 4):
QFHGEKGISIPDHGFCQPISIPLCTDIAYNQTIMPNLLGHTNQEDAGLE
VHQFYPLVKVQCSPELRFFLCSMYAPVCTVLEQAIPPCRSICERARQGC
EALMNKFGFQWPERLRCEHFPRHGAEQICVGQNHSEDGAPALAEPRSSD
KTHTCPPCPAPEAEGAPSVFLFPPKPKDTLMISRTPEVTCVVVDVSHED
PEVKFNWYVDGVEVHNAKTKPREEQYNSTYRVVSVLTVLHQDWLNGKEY
KCAVSNKALPASIEKTISKAKGQPREPQVYTLPPSRDELTKNQVSLTCL
VKGFYPSDIAVEWESNGQPENNYKTTPPVLDSDGSFFLYSKLTVDKSRW
QQGNVFSCSVMHEALHNHYTQKSLSLSPGK

The extracellular cysteine-rich domain in the amino acid sequence as shown in any of SEQ ID NOs: 27 to 31 is derived from the extracellular region protein of the Frizzled 7, Frizzled 1, or Frizzled 2 receptor, and the amino acid sequence of such domain may include mutation as described in the above <Mutant of extracellular cysteine-rich domain>, provided that it has the capacity for increasing the bone mass, bone density, and/or bone strength.

In the present invention, a protein comprising the extracellular cysteine-rich domain or a mutant thereof is not always required to bind or fuse to a foreign peptide, polypeptide, or protein. Specifically, the protein of the present invention may be a fragment of the extracellular region protein of the Frizzled 1, 2, or 7 receptor comprising the aforementioned extracellular cysteine-rich domain. Such fragment may include a mutation as described in the above <Mutant of extracellular cysteine-rich domain>, provided that the mutant has the capacity for increasing the bone mass, bone density, and/or bone strength.

The protein comprising the extracellular cysteine-rich domain or a mutant thereof according to the present invention can be prepared via a gene recombination technique common in the art. Briefly, such protein preparation comprises preparing DNA encoding the protein of the present invention, constructing an expression vector comprising the DNA, transforming or transfecting prokaryotic or eukaryotic cells with the use of such vector, and recovering a target recombinant protein from the cultured cells. Protein purification can be carried out by employing common protein purification techniques, such as ammonium sulfate precipitation, organic solvent precipitation, dialysis, electrophoresis, chromatofocusing, gel filtration chromatography, ion exchange chromatography, affinity chromatography, and HPLC, in adequate combination.

The DNA and the vector mentioned above are as described in the above <Nucleic acid and vector> and Examples below. Gene recombination techniques described in, for example, F. M. Ausubel et al., Short Protocols in Molecular Biology, 1995 or John Wiley & Sons, J. Sambrook et al., Molecular Cloning: A Laboratory Manual, 2nd ed., 1989, Cold Spring Harbor Laboratory Press can be applied to the present invention.

The protein comprising the extracellular cysteine-rich domain or a mutant thereof according to the present invention may be chemically modified.

Examples of chemical modification techniques include, but are not limited to, glycosylation, pegylation (PEG), acetylation, amidation, and phosphorylation. Particularly preferable chemical modification techniques are glycosylation and pegylation.

The term "pegylation" refers to binding of one or a plurality of polyethylene glycol (PEG) molecules to, for example, an amino acid residue, such as an N-terminal amino group of a protein or a ϵ-amino group of lysine (Lys).

In general, a PEG molecule is bound to a free amino group of an amino acid. An average molecular weight of PEG can be in the range of, but is not limited to, about 3,000 to about 50,000. PEG can be bound to a protein by introducing an active group, such as a carboxyl, formyl (aldehyde), N-hydroxysuccinimide ester, amino, thiol, or maleimide group, to a terminus of PEG and allowing such group to react with a group of a protein, such as an amino, carboxyl, thiol, or hydroxyl group.

The term "glycosylation" refers to binding of a carbohydrate chain (i.e., a sugar chain) to an asparagine, serine, or threonine residue of a protein. In general, glycosylation takes place upon recognition of an Asn-X-Thr/Ser sequence (wherein X represents an amino acid residue other than Pro). When an amino acid sequence of the protein is modified so as to have such sequence, a sugar chain can be introduced into a site that is different from that of a naturally-occurring protein. In general, a nucleic acid encoding a recombinant protein is expressed in an eukaryotic cell (e.g., an yeast, animal, or plant cell) via genetic recombination to cause glycosylation of a recombinant protein. In the present invention, a sugar chain structure is not particularly limited, and it is considered to differ depending on a type of a cell selected for expression. When used for a human, a human-derived cell, an yeast cell capable of synthesizing a human sugar chain, a Chinese hamster ovary (CHO) cell, or the like can be used.

It is preferable that acetylation or amidation be mainly carried out at the protein N- or C-terminus. Such reaction can be carried out with the use of, for example, an alcohol, such as aliphatic alcohol or fatty acid, or a carboxylic acid. The number of carbon atoms in the alkyl moiety is, for example, about 1 to 20; however, conditions in terms of water-solubility and avirulence need to be satisfied.

<Nucleic Acid and Vector>

An example of an active ingredient of the composition of the present invention is a vector comprising a nucleic acid encoding a protein comprising the extracellular cysteine-rich domain or a mutant thereof.

The term "nucleic acid" used herein refers to both DNA and RNA, wherein DNA encompasses genomic DNA and cDNA, and RNA encompasses mRNA.

The extracellular cysteine-rich domain, the mutant thereof, and the protein comprising the same, including the fusion protein with the Fc protein, are as described in the above sections <Extracellular cysteine-rich domain of Frizzled receptor>, <Mutant of extracellular cysteine-rich domain>, and <Protein comprising an extracellular cysteine-rich domain or a mutant thereof, and all descriptions made in such sections are employed herein. Accordingly, the term "nucleic acid" used in the present invention encompasses the nucleic acid encoding a protein comprising the extracellular cysteine-rich domain or a mutant thereof specifically described above.

Specifically, examples of such nucleic acids include nucleic acids encoding amino acid sequences comprising at least CRD minimal sequences comprising amino acid sequences composed of a region from N-terminal side cysteine-1 to C-terminal side cysteine-10 (SEQ ID NOs: 21, 24, and 26) derived from the amino acid sequences comprising the extracellular region protein of mouse Frizzled 7, Frizzled 1, and Frizzled 2 (SEQ ID NOs: 20, 23, and 25) and the extracellular region protein of human Frizzled 7, Frizzled 1, and Frizzled 2 (SEQ ID NOs: 19, 22, and 25).

In view of nucleic acid expression in an eukaryotic cell and extracellular secretion of the expression product, it is preferable that a nucleotide sequence encoding a signal sequence be further included. Examples of signal sequences include a signal sequence derived from a Frizzled receptor protein, a signal sequence derived from human CD33, a signal sequence derived from human serum albumin, and a signal sequence derived from human preprotrypsin.

Examples of nucleotide sequences encoding protein precursors of the extracellular domains of mouse- and human-derived Frizzled 7, Frizzled 1, and Frizzled 2 are provided below. Underlined portions indicate nucleotide sequences encoding signal sequences and non-underlined portions indicate nucleotide sequences encoding mature sequences of extracellular region proteins.

DNA encoding the mouse Frizzled 7 extracellular region protein (SEQ ID NO: 32):

ATGCGGGGCCCCGGCACGGCGGCGTCGCACTCGCCCCTGGGCCTCTGCG

CCCTGGTGCTTGCTCTTCTGTGCGCGCTGCCCACGGACACCCGGGCTCA

GCCATATCACGGCGAGAAAGGCATCTCGGTACCGGACCACGGCTTCTGCG

CAGCCCATCTCCATCCCTTGTGCACGGATATCGCCTACAACCAGACCATC

CTGCCCAACCTGCTGGGCCACACGAACCAAGAGGACGCGGGCCTCGAGGT

GCACCAGTTCTACCCTCTGGTAAAGGTGCAGTGTTCTCCTGAGCTACGCT

TCTTCTTATGCTCTATGTACGCACCCGTGTGCACCGTGCTCGACCAAGCC

ATTCCTCCGTGCCGTTCCTTGTGCGAGCGCGCCCGACAGGGCTGCGAGGC

GCTCATGAACAAGTTCGGCTTCCAGTGGCCAGAGCGGTTGCGCTGCGAGA

ACTTCCCAGTGCACGGTGCCGGCGAGATCTGCGTGGGGCAGAACACGTCC

GACGGCTCCGGGGCGCGGGCGGCAGTCCCACCGCCTACCCTACTGCTCC

CTACCTG

DNA encoding the human Frizzled 7 extracellular region protein (SEQ ID NO: 33):

ATGCGGGACCCCGGCGCGGCCGCTCCGCTTTCGTCCCTGGGCCTCTGTG

CCCTGGTGCTGGCGCTGCTGGGCGCACTGTCCGCGGGCGCCGGGGCGCA

GCCGTACCACGGAGAGAAGGGCATCTCCGTGCCGGACCACGGCTTCTGC

CAGCCCATCTCCATCCCGCTGTGCACGGACATCGCCTACAACCAGACCA

TCCTGCCCAACCTGCTGGGCCACACGAACCAAGAGGACGCGGGCCTCGA

GGTGCACCAGTTCTACCCGCTGGTGAAGGTGCAGTGTTCTCCCGAACTC

CGCTTTTTCTTATGCTCCATGTATGCGCCCGTGTGCACCGTGCTCGATC

AGGCCATCCCGCCGTGTCGTTCTCTGTGCGAGCGCGCCCGCCAGGGCTG

CGAGGCGCTCATGAACAAGTTCGGCTTCCAGTGGCCCGAGCGGCTGCGC

TGCGAGAACTTCCCGGTGCACGGTGCGGGCGAGATCTGCGTGGGCCAGA

ACACGTCGGACGGCTCCGGGGGCCCAGGCGGCGGCCCCACTGCCTACCC

TACCGCGCCCTACCTG

DNA encoding the mouse Frizzled 1 extracellular region protein (SEQ ID NO: 34):

ATGGCTGAGGAGGCGGCGCCTAGCGAGTCCCGGGCCGCCGGCCGGCTGA

GCTTGGAACTTTGTGCCGAAGCACTCCCGGGCCGGCGGGAGGAGGTGGG

GCACGAGGACACGGCCAGCCACCGCCGCCCCGGGCTGATCCCCGGCGT

-continued

TGGGCTAGCGGGCTGCTGCTGCTGCTTTGGTTGCTGGAGGCTCCTCTGC

TTTTGGGGGTCCGAGCGCAGGCGGCGGGCCAGGTATCCGGGCCGGGCCA

GCAAGCCCCGCCGCCGCCCCAGCCCCAGCAGAGCGGGCAGCAGTACAAC

GGCGAACGGGGCATCTCCATCCCGGACCACGGCTACTGCCAGCCCATCT

CCATCCCGCTGTGCACGGACATCGCGTACAACCAGACCATCATGCCCAA

CCTGCTGGGCCACACGAATCAGGAGGACGCCGGTCTGGAGGTGCACCAG

TTCTACCCTCTGGTGAAGGTGCAGTGCTCCGCCGAGCTCAAGTTCTTCC

TGTGCTCCATGTACGCGCCTGTGTGCACCGTACTGGAGCAGGCGCTACC

GCCCTGCCGCTCCCTGTGCGAGCGCGCACGCCAGGGCTGCGAGGCGCTC

ATGAACAAGTTCGGCTTCCAGTGGCCAGACACACTCAAGTGCGAGAAGT

TCCCGGTGCACGGCGCAGGAGAGCTGTGCGTGGGCCAGAACACGTCCGA

CAAAGGCACCCCAACTCCCTCCTTGCTACCAGAGTTCTGGACCAGTAAT

CCGCAGCAC

DNA encoding the human Frizzled 1 extracellular region protein (SEQ ID NO: 35):

ATGGCTGAGGAGGAGGCGCCTAAGAAGTCCCGGGCCGCCGGCGGTGGCG

CGAGCTGGGAACTTTGTGCCGGGGCGCTCTCGGCCCGGCTGGCGGAGGA

GGGCAGCGGGGACGCCGGTGGCCGCCGCCGCCCGCCAGTTGACCCCCGG

CGATTGGCGCGCCAGCTGCTGCTGCTGCTTTGGCTGCTGGAGGCTCCGC

TGCTGCTGGGGGTCCGGGCCCAGGCGGCGGGCCAGGGGCCAGGCCAGGG

GCCCGGGCCGGGGCAGCAACCGCCGCCGCCGCCTCAGCAGCAACAGAGC

GGGCAGCAGTACAACGGCGAGCGGGGCATCTCCGTCCCGGACCACGGCT

ATTGCCAGCCCATCTCCATCCCGCTGTGCACGGACATCGCGTACAACCA

GACCATCATGCCCAACCTGCTGGGCCACACGAACCAGGAGGACGCGGGC

CTGGAGGTGCACCAGTTCTACCCTCTAGTGAAAGTGCAGTGTTCCGCTG

AGCTCAAGTTCTTCCTGTGCTCCATGTACGCGCCCGTGTGCACCGTGCT

AGAGCAGGCGCTGCCGCCCTGCCGCTCCCTGTGCGAGCGCGCGCGCCAG

GGCTGCGAGGCGCTCATGAACAAGTTCGGCTTCCAGTGGCCAGACACGC

TCAAGTGTGAGAAGTTCCCGGTGCACGGCGCCGGCGAGCTGTGCGTGGG

CCAGAACACGTCCGACAAGGGCACCCCGACGCCCTCGCTGCTTCCAGAG

TTCTGGACCAGCAACCCTCAGCAC

DNA encoding the mouse Frizzled 2 extracellular region protein (SEQ ID NO: 36):

ATGCGGGCCCGCAGCGCCCTGCCCCGCAGCGCCCTGCCCCGCCTGCTGC

TGCCACTGCTGCTGCTGCCGGCCGCCGGACCGGCCCAGTTCCACGGGGA

GAAGGGCATCTCCATCCCGGACCACGGCTTCTGCCAGCCCATCTCCATC

CCGCTGTGCACGGACATCGCCTACAACCAGACCATCATGCCCAACCTTC

TTGGCCACACGAACCAGGAAGACGCGGGCCTGGAGGTGCATCAGTTCTA

CCCGCTGGTGAAGGTGCAGTGCTCGCCCGAGCTGCGCTTCTTCCTGTGC

TCCATGTACGCGCCGGTGTGCACAGTGCTGGAGCAGGCCATCCCGCCGT

GCCGCTCCATCTGCGAGCGCGCGCGCCAAGGCTGCGAGGCGCTCATGAA

CAAGTTCGGCTTCCAATGGCCCGAGCGCCTCCGCTGCGAGCATTTCCCG

CGTCACGGCGCGGAGCAGATCTGCGTGGGCCAGAACCACTCGGAGGACG

GAGCTCCTGCGCTA

DNA encoding the human Frizzled 2 extracellular region protein (SEQ ID NO: 37):

ATGCGGCCCCGCAGCGCCCTGCCCCGCCTGCTGCTGCCGCTGCTGCTGC

TGCCCGCCGCCGGGCCGGCCCAGTTCCACGGGGAGAAGGGCATCTCCAT

CCCGGACCACGGCTTCTGCCAGCCCATCTCCATCCCGCTGTGCACGGAC

ATCGCCTACAACCAGACCATCATGCCCAACCTTCTGGGCCACACGAACC

AGGAGGACGCAGGCCTAGAGGTGCACCAGTTCTATCCGCTGGTGAAGGT

GCAGTGCTCGCCCGAACTGCGCTTCTTCCTGTGCTCCATGTACGCACCC

GTGTGCACCGTGCTGGAACAGGCCATCCCGCCGTGCCGCTCTATCTGTG

AGCGCGCGCGCCAGGGCTGCGAAGCCCTCATGAACAAGTTCGGTTTTCA

GTGGCCCGAGCGCCTGCGCTGCGAGCACTTCCCGCGCCACGGCGCCGAG

CAGATCTGCGTCGGCCAGAACCACTCCGAGGACGGAGCTCCCGCGCTA

The term "nucleic acid" used in the present invention encompasses a nucleic acid encoding a fusion protein of a protein comprising the extracellular cysteine-rich domain of the Frizzled receptor or a mutant thereof and the foreign protein defined above. A preferable example of the foreign protein is a mammalian animal-derived immunoglobulin Fc protein, with a human Fc protein being particularly preferable. It is preferable that such foreign protein be introduced so as to reduce or lose biological activity (ADCC and CDC in particular). An example of a nucleotide sequence encoding a mutant human IgG1-derived Fc protein is shown in SEQ ID NO: 3. Further, examples of nucleotide sequences encoding fusion proteins of the mutant human IgG1-derived Fc proteins (underlined portions) and proteins comprising the extracellular cysteine-rich domains of the mouse- or human-derived Frizzled 7, 1, and 2 receptors (non-underlined portions) are shown below.

DNA encoding the fusion protein of the mouse Frizzled 7 extracellular region protein and the mutant human IgG1-derived Fc protein (SEQ ID NO: 38):

CAGCCATATCACGGCGAGAAAGGCATCTCGGTACCGGACCACGGCTTCT

GCCAGCCCATCTCCATCCCGTTGTGCACGGATATCGCCTACAACCAGAC

CATCCTGCCCAACCTGCTGGGCCACACGAACCAAGAGGACGCGGGCCTC

GAGGTGCACCAGTTCTACCCTCTGGTAAAGGTGCAGTGTTCTCCTGAGC

TACGCTTCTTCTTATGCTCTATGTACGCACCCGTGTGCACCGTGCTCGA

CCAAGCCATTCCTCCGTGCCGTTCCTTGTGCGAGCGCGCCCGACAGGGC

TGCGAGGCGCTCATGAACAAGTTCGGCTTCCAGTGGCCAGAGCGGTTGC

GCTGCGAGAACTTCCCAGTGCACGGTGCCGGCGAGATCTGCGTGGGGCA

GAACACGTCCGACGGCTCCGGGGCGCGGGCGGCAGTCCCACCGCCTAC

CCTACTGCTCCCTACCTGGCCGAGCCTAGGTCTTCAGACAAAACTCACA

CATGCCCACCGTGCCCAGCACCTGAAGCCGAGGGGGCCCCGTCAGTCTT

CCTCTTCCCCCCAAAACCCAAGGACACCCTCATGATCTCCCGGACCCCT

GAGGTCACATGCGTGGTGGTGGACGTGAGCCACGAAGACCCTGAGGTCA

AGTTCAACTGGTACGTGGACGGCGTGGAGGTGCATAATGCCAAGACAAA

GCCGCGGGAGGAGCAGTACAACAGCACGTACCGTGTGGTCAGCGTCCTC

ACCGTCCTGCACCAGGACTGGCTGAATGGCAAGGAGTACAAGTGCGCCG

TCTCCAACAAAGCCCTCCCAGCCTCCATCGAGAAAACCATCTCCAAAGC

CAAAGGGCAGCCCCGAGAACCACAGGTGTACACCCTGCCCCCATCCCGG

GATGAGCTGACCAAGAACCAGGTCAGCCTGACCTGCCTGGTCAAAGGCT

TCTATCCCAGCGACATCGCCGTGGAGTGGGAGAGCAATGGGCAGCCGGA

GAACAACTACAAGACCACGCCTCCCGTGCTGGACTCCGACGGCTCCTTC

TTCCTCTACAGCAAGCTCACCGTGGACAAGAGCAGGTGGCAGCAGGGGA

ACGTCTTCTCATGCTCCGTGATGCATGAGGCTCTGCACAACCACTACAC

GCAGAAGAGCCTCTCCCTGTCTCCGGGTAAATGA

DNA encoding the fusion protein of the human Frizzled 7 extracellular region protein and the mutant human IgG1-derived Fc protein (SEQ ID NO: 39):

CAGCCGTACCACGGAGAGAAGGGCATCTCCGTGCCGGACCACGGCTTCT

GCCAGCCCATCTCCATCCCGCTGTGCACGGACATCGCCTACAACCAGAC

CATCCTGCCCAACCTGCTGGGCCACACGAACCAAGAGGACGCGGGCCTC

GAGGTGCACCAGTTCTACCCGCTGGTGAAGGTGCAGTGTTCTCCCGAAC

TCCGCTTTTTCTTATGCTCCATGTATGCGCCCGTGTGCACCGTGCTCGA

TCAGGCCATCCCGCCGTGTCGTTCTCTGTGCGAGCGCGCCCGCCAGGGC

TGCGAGGCGCTCATGAACAAGTTCGGCTTCCAGTGGCCCGAGCGGCTGC

GCTGCGAGAACTTCCCGGTGCACGGTGCGGGCGAGATCTGCGTGGGCCA

GAACACGTCGGACGGCTCCGGGGGCCCAGGCGGCGGCCCCACTGCCTAC

CCTACCGCGCCCTACCTGGCCGAGCCTAGGTCTTCAGACAAAACTCACA

CATGCCCACCGTGCCCAGCACCTGAAGCCGAGGGGGCCCCGTCAGTCTT

CCTCTTCCCCCCAAAACCCAAGGACACCCTCATGATCTCCCGGACCCCT

GAGGTCACATGCGTGGTGGTGGACGTGAGCCACGAAGACCCTGAGGTCA

AGTTCAACTGGTACGTGGACGGCGTGGAGGTGCATAATGCCAAGACAAA

GCCGCGGGAGGAGCAGTACAACAGCACGTACCGTGTGGTCAGCGTCCTC

ACCGTCCTGCACCAGGACTGGCTGAATGGCAAGGAGTACAAGTGCGCCG

TCTCCAACAAAGCCCTCCCAGCCTCCATCGAGAAAACCATCTCCAAAGC

CAAAGGGCAGCCCCGAGAACCACAGGTGTACACCCTGCCCCCATCCCGG

GATGAGCTGACCAAGAACCAGGTCAGCCTGACCTGCCTGGTCAAAGGCT

TCTATCCCAGCGACATCGCCGTGGAGTGGGAGAGCAATGGGCAGCCGGA

GAACAACTACAAGACCACGCCTCCCGTGCTGGACTCCGACGGCTCCTTC

TTCCTCTACAGCAAGCTCACCGTGGACAAGAGCAGGTGGCAGCAGGGGA

ACGTCTTCTCATGCTCCGTGATGCATGAGGCTCTGCACAACCACTACAC

GCAGAAGAGCCTCTCCCTGTCTCCGGGTAAATGA

DNA encoding the fusion protein of the mouse Frizzled 1 extracellular region protein and the mutant human IgG1-derived Fc protein (SEQ ID NO: 40):

CAGGCGGCGGGCCAGGTATCCGGGCCGGGCCAGCAAGCCCCGCCGCCGCC

CCAGCCCCAGCAGAGCGGGCAGCAGTACAACGGCGAACGGGGCATCTCCA

TCCCGGACCACGGCTACTGCCAGCCCATCTCCATCCCGCTGTGCACGGAC

ATCGCGTACAACCAGACCATCATGCCCAACCTGCTGGGCCACACGAATCA

GGAGGACGCCGGTCTGGAGGTGCACCAGTTCTACCCTCTGGTGAAGGTGC

AGTGCTCCGCCGAGCTCAAGTTCTTCCTGTGCTCCATGTACGCGCCTGTG

TGCACCGTACTGGAGCAGGCGCTACCGCCCTGCCGCTCCCTGTGCGAGCG

CGCACGCCAGGGCTGCGAGGCGCTCATGAACAAGTTCGGCTTCCAGTGGC

CAGACACACTCAAGTGCGAGAAGTTCCCGGTGCACGGCGCAGGAGAGCTG

TGCGTGGGCCAGAACACGTCCGACAAAGGCACCCCAACTCCCTCCTTGCT

ACCAGAGTTCTGGACCAGTAATCCGCAGCACGCCGAGCCTAGGTCTTCAG

ACAAAACTCACACATGCCCACCGTGCCCAGCACCTGAAGCCGAGGGGGCC

CCGTCAGTCTTCCTCTTCCCCCCAAAACCCAAGGACACCCTCATGATCTC

CCGGACCCCTGAGGTCACATGCGTGGTGGTGGACGTGAGCCACGAAGACC

CTGAGGTCAAGTTCAACTGGTACGTGGACGGCGTGGAGGTGCATAATGCC

AAGACAAAGCCGCGGGAGGAGCAGTACAACAGCACGTACCGTGTGGTCAG

CGTCCTCACCGTCCTGCACCAGGACTGGCTGAATGGCAAGGAGTACAAGT

GCGCCGTCTCCAACAAAGCCCTCCCAGCCTCCATCGAGAAAACCATCTCC

AAAGCCAAAGGGCAGCCCCGAGAACCACAGGTGTACACCCTGCCCCCATC

CCGGGATGAGCTGACCAAGAACCAGGTCAGCCTGACCTGCCTGGTCAAAG

GCTTCTATCCCAGCGACATCGCCGTGGAGTGGGAGAGCAATGGGCAGCCG

GAGAACAACTACAAGACCACGCCTCCCGTGCTGGACTCCGACGGCTCCTT

CTTCCTCTACAGCAAGCTCACCGTGGACAAGAGCAGGTGGCAGCAGGGGA

ACGTCTTCTCATGCTCCGTGATGCATGAGGCTCTGCACAACCACTACACG

CAGAAGAGCCTCTCCCTGTCTCCGGGTAAATGA

DNA encoding the fusion protein of the human Frizzled 1 extracellular region protein and the mutant human IgG1-derived Fc protein (SEQ ID NO: 41):

CAGGCGGCGGGCCAGGGGCAGGCCAGGGGCCCGGGCCGGGGCAGCAACC

GCCGCCGCCGCCTCAGCAGCAACAGAGCGGGCAGCAGTACAACGGCGAGC

GGGGCATCTCCGTCCCGGACCACGGCTATTGCCAGCCCATCTCCATCCCG

CTGTGCACGGACATCGCGTACAACCAGACCATCATGCCCAACCTGCTGGG

CCACACGAACCAGGAGGACGCGGGCCTGGAGGTGCACCAGTTCTACCCTC

TAGTGAAAGTGCAGTGTTCCGCTGAGCTCAAGTTCTTCCTGTGCTCCATG

TACGCGCCCGTGTGCACCGTGCTAGAGCAGGCGCTGCCGCCCTGCCGCTC

CCTGTGCGAGCGCGCGCGCCAGGGCTGCGAGGCGCTCATGAACAAGTTCG

GCTTCCAGTGGCCAGACACGCTCAAGTGTGAGAAGTTCCCGGTGCACGGC

```
GCCGGCGAGCTGTGCGTGGGCCAGAACACGTCCGACAAGGGCACCCCGAC

GCCCTCGCTGCTTCCAGAGTTCTGGACCAGCAACCCTCAGCACGCCGAGC

CTAGGTCTTCAGACAAAACTCACACATGCCCACCGTGCCCAGCACCTGAA

GCCGAGGGGCCCCGTCAGTCTTCCTCTTCCCCCCAAAACCCAAGGACAC

CCTCATGATCTCCCGGACCCCTGAGGTCACATGCGTGGTGGTGGACGTGA

GCCACGAAGACCCTGAGGTCAAGTTCAACTGGTACGTGGACGGCGTGGAG

GTGCATAATGCCAAGACAAAGCCGCGGGAGGAGCAGTACAACAGCACGTA

CCGTGTGGTCAGCGTCCTCACCGTCCTGCACCAGGACTGGCTGAATGGCA

AGGAGTACAAGTGCGCCGTCTCCAACAAAGCCCTCCCAGCCTCCATCGAG

AAAACCATCTCCAAAGCCAAAGGGCAGCCCCGAGAACCACAGGTGTACAC

CCTGCCCCCATCCCGGGATGAGCTGACCAAGAACCAGGTCAGCCTGACCT

GCCTGGTCAAAGGCTTCTATCCCAGCGACATCGCCGTGGAGTGGGAGAGC

AATGGGCAGCCGGAGAACAACTACAAGACCACGCCTCCCGTGCTGGACTC

CGACGGCTCCTTCTTCCTCTACAGCAAGCTCACCGTGGACAAGAGCAGGT

GGCAGCAGGGGAACGTCTTCTCATGCTCCGTGATGCATGAGGCTCTGCAC

AACCACTACACGCAGAAGAGCCTCTCCCTGTCTCCGGGTAAATGA
```

DNA encoding the fusion protein of the mouse Frizzled 2 extracellular region protein and the mutant human IgG1-derived Fc protein (SEQ ID NO: 42):

```
CAGTTCCACGGGGAGAAGGGCATCTCCATCCCGGACCACGGCTTCTGCCA

GCCCATCTCCATCCCGCTGTGCACGGACATCGCCTACAACCAGACCATCA

TGCCCAACCTTCTTGGCCACACGAACCAGGAAGACGCGGGCCTGGAGGTG

CATCAGTTCTACCCGCTGGTGAAGGTGCAGTGCTCGCCCGAGCTGCGCTT

CTTCCTGTGCTCCATGTACGCGCCGGTGTGCACAGTGCTGGAGCAGGCCA

TCCCGCCGTGCCGCTCCATCTGCGAGCGCGCGCGCCAAGGCTGCGAGGCG

CTCATGAACAAGTTCGGCTTCCAATGGCCCGAGCGCCTCCGCTGCGAGCA

TTTCCCGCGTCACGGCGCGGAGCAGATCTGCGTGGGCCAGAACCACTCGG

AGGACGGAGCTCCTGCGCTAGCCGAGCCTAGGTCTTCAGACAAAACTCAC

ACATGCCCACCGTGCCCAGCACCTGAAGCCGAGGGGCCCCGTCAGTCTT

CCTCTTCCCCCCAAAACCCAAGGACACCCTCATGATCTCCCGGACCCCTG

AGGTCACATGCGTGGTGGTGGACGTGAGCCACGAAGACCCTGAGGTCAAG

TTCAACTGGTACGTGGACGGCGTGGAGGTGCATAATGCCAAGACAAAGCC

GCGGGAGGAGCAGTACAACAGCACGTACCGTGTGGTCAGCGTCCTCACCG

TCCTGCACCAGGACTGGCTGAATGGCAAGGAGTACAAGTGCGCCGTCTCC

AACAAAGCCCTCCCAGCCTCCATCGAGAAAACCATCTCCAAAGCCAAAGG

GCAGCCCCGAGAACCACAGGTGTACACCCTGCCCCCATCCCGGGATGAGC

TGACCAAGAACCAGGTCAGCCTGACCTGCCTGGTCAAAGGCTTCTATCCC

AGCGACATCGCCGTGGAGTGGGAGAGCAATGGGCAGCCGGAGAACAACTA

CAAGACCACGCCTCCCGTGCTGGACTCCGACGGCTCCTTCTTCCTCTACA

GCAAGCTCACCGTGGACAAGAGCAGGTGGCAGCAGGGGAACGTCTTCTCA

TGCTCCGTGATGCATGAGGCTCTGCACAACCACTACACGCAGAAGAGCCT

CTCCCTGTCTCCGGGTAAATGA
```

DNA encoding the fusion protein of the human Frizzled 2 extracellular region protein and the mutant human IgG1-derived Fc protein (SEQ ID NO: 43):

```
CAGTTCCACGGGGAGAAGGGCATCTCCATCCCGGACCACGGCTTCTGCCA

GCCCATCTCCATCCCGCTGTGCACGGACATCGCCTACAACCAGACCATCA

TGCCCAACCTTCTGGGCCACACGAACCAGGAGGACGCAGGCCTAGAGGTG

CACCAGTTCTATCCGCTGGTGAAGGTGCAGTGCTCGCCCGAACTGCGCTT

CTTCCTGTGCTCCATGTACGCACCCGTGTGCACCGTGCTGGAACAGGCCA

TCCCGCCGTGCCGCTCTATCTGTGAGCGCGCGCGCCAGGGCTGCGAAGCC

CTCATGAACAAGTTCGGTTTTCAGTGGCCCGAGCGCCTGCGCTGCGAGCA

CTTCCCCGCGCACGGCGCCGAGCAGATCTGCGTCGGCCAGAACCACTCCG

AGGACGGAGCTCCCGCGCTAGCCGAGCCTAGGTCTTCAGACAAAACTCAC

ACATGCCCACCGTGCCCAGCACCTGAAGCCGAGGGGCCCCGTCAGTCTT

CCTCTTCCCCCCAAAACCCAAGGACACCCTCATGATCTCCCGGACCCCTG

AGGTCACATGCGTGGTGGTGGACGTGAGCCACGAAGACCCTGAGGTCAAG

TTCAACTGGTACGTGGACGGCGTGGAGGTGCATAATGCCAAGACAAAGCC

GCGGGAGGAGCAGTACAACAGCACGTACCGTGTGGTCAGCGTCCTCACCG

TCCTGCACCAGGACTGGCTGAATGGCAAGGAGTACAAGTGCGCCGTCTCC

AACAAAGCCCTCCCAGCCTCCATCGAGAAAACCATCTCCAAAGCCAAAGG

GCAGCCCCGAGAACCACAGGTGTACACCCTGCCCCCATCCCGGGATGAGC

TGACCAAGAACCAGGTCAGCCTGACCTGCCTGGTCAAAGGCTTCTATCCC

AGCGACATCGCCGTGGAGTGGGAGAGCAATGGGCAGCCGGAGAACAACTA

CAAGACCACGCCTCCCGTGCTGGACTCCGACGGCTCCTTCTTCCTCTACA

GCAAGCTCACCGTGGACAAGAGCAGGTGGCAGCAGGGGAACGTCTTCTCA

TGCTCCGTGATGCATGAGGCTCTGCACAACCACTACACGCAGAAGAGCCT

CTCCCTGTCTCCGGGTAAATGA
```

Examples of nucleotide sequences encoding amino acid sequences of the cysteine rich domains (CRDs) spanning from the 1st cysteine residue on the N-terminal side to the 10th cysteine residue of the mouse- and human-derived Frizzled 7, Frizzled 1, and Frizzled 2 extracellular region proteins are shown below.

```
SEQ ID NO: 44: mouse Frizzled 7 CRD
TGCCAGCCCATCTCCATCCCGTTGTGCACGGATATCGCCTACAACCAGAC

CATCCTGCCCAACCTGCTGGGCCACACGAACCAAGAGGACGCGGGCCTCG

AGGTGCACCAGTTCTACCCTCTGGTAAAGGTGCAGTGTTCTCCTGAGCTA

CGCTTCTTCTTATGCTCTATGTACGCACCCGTGTGCACCGTGCTCGACCA

AGCCATTCCTCCGTGCCGTTCCTTGTGCGAGCGCGCCCGACAGGGCTGCG

AGGCGCTCATGAACAAGTTCGGCTTCCAGTGGCCAGAGCGGTTGCGCTGC

GAGAACTTCCCAGTGCACGGTGCCGGCGAGATCTGC
```

-continued

SEQ ID NO: 45: human Frizzled 7 CRD
TGCCAGCCCATCTCCATCCCGCTGTGCACGGACATCGCCTACAACCAGAC

CATCCTGCCCAACCTGCTGGGCCACACGAACCAAGAGGACGCGGGCCTCG

AGGTGCACCAGTTCTACCCGCTGGTGAAGGTGCAGTGTTCTCCCGAACTC

CGCTTTTTCTTATGCTCCATGTATGCGCCCGTGTGCACCGTGCTCGATCA

GGCCATCCCGCCGTGTCGTTCTCTGTGCGAGCGCGCCCGCCAGGGCTGCG

AGGCGCTCATGAACAAGTTCGGCTTCCAGTGGCCCGAGCGGCTGCGCTGC

GAGAACTTCCCGGTGCACGGTGCGGGCGAGATCTGC

SEQ ID NO: 46: mouse Frizzled 1 CRD
TGCCAGCCCATCTCCATCCCGCTGTGCACGGACATCGCGTACAACCAGAC

CATCATGCCCAACCTGCTGGGCCACACGAATCAGGAGGACGCCGGTCTGG

AGGTGCACCAGTTCTACCCTCTGGTGAAGGTGCAGTGCTCCGCCGAGCTC

AAGTTCTTCCTGTGCTCCATGTACGCGCCTGTGTGCACCGTACTGGAGCA

GGCGCTACCGCCCTGCCGCTCCCTGTGCGAGCGCGCACGCCAGGGCTGCG

AGGCGCTCATGAACAAGTTCGGCTTCCAGTGGCCAGACACACTCAAGTGC

GAGAAGTTCCCGGTGCACGGCGCAGGAGAGCTGTGC

SEQ ID NO: 47: human Frizzled 1 CRD
TGCCAGCCCATCTCCATCCCGCTGTGCACGGACATCGCGTACAACCAGAC

CATCATGCCCAACCTGCTGGGCCACACGAACCAGGAGGACGCGGGCCTGG

AGGTGCACCAGTTCTACCCTCTAGTGAAAGTGCAGTGTTCCGCTGAGCTC

AAGTTCTTCCTGTGCTCCATGTACGCGCCCGTGTGCACCGTGCTAGAGCA

GGCGCTGCCGCCCTGCCGCTCCCTGTGCGAGCGCGCGCGCCAGGGCTGCG

AGGCGCTCATGAACAAGTTCGGCTTCCAGTGGCCAGACACGCTCAAGTGT

GAGAAGTTCCCGGTGCACGGCGCCGGCGAGCTGTGC

SEQ ID NO: 48: mouse Frizzled 2 CRD
TGCCAGCCCATCTCCATCCCGCTGTGCACGGACATCGCCTACAACCAGAC

CATCATGCCCAACCTTCTTGGCCACACGAACCAGGAAGACGCGGGCCTGG

AGGTGCATCAGTTCTACCCGCTGGTGAAGGTGCAGTGCTCGCCCGAGCTG

CGCTTCTTCCTGTGCTCCATGTACGCGCCGGTGTGCACAGTGCTGGAGCA

GGCCATCCCGCCGTGCCGCTCCATCTGCGAGCGCGCGCGCCAAGGCTGCG

AGGCGCTCATGAACAAGTTCGGCTTCCAATGGCCCGAGCGCCTCCGCTGC

GAGCATTTCCCGCGTCACGGCGCGGAGCAGATCTGC

SEQ ID NO: 49: human Frizzled 2 CRD
TGCCAGCCCATCTCCATCCCGCTGTGCACGGACATCGCCTACAACCAGAC

CATCATGCCCAACCTTCTGGGCCACACGAACCAGGAGGACGCAGGCCTAG

AGGTGCACCAGTTCTATCCGCTGGTGAAGGTGCAGTGCTCGCCCGAACTG

CGCTTCTTCCTGTGCTCCATGTACGCACCCGTGTGCACCGTGCTGGAACA

GGCCATCCCGCCGTGCCGCTCTATCTGTGAGCGCGCGCGCCAGGGCTGCG

AAGCCCTCATGAACAAGTTCGGTTTTCAGTGGCCCGAGCGCCTGCGCTGC

GAGCACTTCCCGCGCCACGGCGCCGAGCAGATCTGC

Examples of the nucleotide sequences encoding the fusion proteins described above further include nucleotide sequences encoding signal sequences. Examples of signal sequences include human protein-derived signal sequences, such as human Frizzled 1, 2, and 7-derived signal sequences, human CD33-derived signal sequences, human serum albumin-derived signal sequences, and human preprotrypsin-derived signal sequences.

Homologs of nucleic acids encoding the proteins can be obtained from cDNA libraries prepared from cells or tissues that are known to express genes derived from mammalian animals other than humans and mice via well-known techniques involving the use of primers or probes prepared based on cDNAs synthesized from mRNAs encoding the human- and mouse-derived Frizzled 7, 1, and 2 genes. Examples of such techniques include PCR and hybridization (e.g., Southern or Northern hybridization).

PCR stands for a polymerase chain reaction, which involves about 25 to 40 cycles of a reaction cycle comprising a denaturing process for dessociating double-stranded DNA into single-stranded DNA (about 94° C. to 96° C. for about 30 seconds to 1 minute), an annealing process for binding a primer to template single-stranded DNA (about 55° C. to 68° C. for about 30 seconds to 1 minute), and an extension process for extending a DNA strand (about 72° C. for about 30 seconds to 1 minute). Also, a pre-heating process can be carried out at about 94° C. to 95° C. for about 5 to 12 minutes prior to the denaturing process and another extension reaction can be carried out at 72° C. for about 7 to 15 minutes after the final cycle of the extension process. PCR is carried out using a commercially available thermal cycler in a PCR buffer containing, for example, thermostable DNA polymerase (e.g., AmpliTaq Gold® (Applied Biosystems)), $MgCl_2$, and dNTP (e.g., dATP, dGTP, dCTP, or dTTP) in the presence of sense and antisense primers (size: about 17 to 30 bases, preferably 20 to 25 bases) and template DNA. Amplified DNA can be separated and purified via agarose gel electrophoresis (ethidium bromide staining).

Hybridization is a technique comprising forming a double strand with an about 20 to 100 bases or longer label probe and detecting a target nucleic acid. In order to enhance selectivity, hybridization can be generally carried out under stringent conditions. Under stringent conditions, for example, hybridization is carried out in the presence of about 1 to 5×SSC at room temperature to about 40° C., and washing is then carried out in the presence of about 0.1 to 1×SSC and 0.1% SDS at about 45° C. to 65° C. The term "1×SSC" used herein refers to a solution comprising 150 mM NaCl and 15 mM Na-citrate (pH 7.0). Under such conditions, nucleic acids having sequence identity of 80% or higher, and preferably 85% or higher, can be detected.

The nucleic acid is inserted into a vector, and the resulting vector is used for the production of a protein as an active ingredient of the pharmaceutical composition of the present invention, or such vector is formulated into and used for a pharmaceutical composition.

Examples of vectors include plasmid, phage, and virus vectors. Examples of plasmid vectors include, but are not limited to, E. coli-derived plasmid (e.g., pRSET, pTZ19R, pBR322, pBR325, pUC118, and pUC119), Bacillus subtilis-derived plasmid (e.g., pUB110 and pTPS), yeast-derived plasmid (e.g., YEp13, YEp24, and YCp50), and Ti plasmid vectors. An example of a phage vector is a λ phage vector. Examples of virus vectors include animal virus vectors, such as retrovirus, vaccinia virus, lentivirus, adenovirus, and adeno-associated virus vectors, and insect virus vectors, such as a baculovirus vector.

A vector may comprise a polylinker or multicloning site to incorporate target DNA, and it can comprise several control elements to express target DNA. Examples of control elements include promoters, enhancers, poly A addition signals, replication origins, selection markers, ribosome binding sequences, and terminators.

Examples of selection markers include drug-resistant genes (e.g., neomycin-resistant genes, ampicillin-resistant genes, kanamycin-resistant genes, and puromycin-resistant genes) and auxotrophic complementary genes (e.g., dihydrofolate reductase (DHFR) genes, HIS3 genes, LEU2 genes, and URA3 genes).

Promoters occasionally vary depending on host cells.

Examples of host cells include, but are not limited to: bacteria of the genus *Escherichia* such as *E. coli*, the genus *Bacillus* such as *Bacillus subtilis*, and the genus *Pseudomonas* such as *Pseudomonas putida*; yeast of the genus *Saccharomyces* such as *Saccharomyces cerevisae* and *Schizosaccharomydces pombe*, the genus *Candida*, and the genus *Pichia*; animal cells, such as CHO, COS, HEK293, NIH3T3, and NS0; insect cells, such as Sf9 and Sf21; and plant cells.

When bacterial host cells such as *E. coli* cells are used, examples of promoters include trp promoters, lac promoters, and $P_L$ or $P_R$ promoters.

When yeast hosts are used, examples of promoters include gal1 promoters, gal10 promoters, heat shock protein promoters, MFα1 promoters, PHO5 promoters, PGK promoters, GAP promoters, ADH promoters, and AOX1 promoters.

When animal host cells are used, examples of promoters include SRα promoters, SV40 promoters, LTR promoters, CMV promoters, human CMV early gene promoters, adenovirus late promoters, vaccinia virus 7.5K promoters, metallothionein promoters, and polyhedral promoters.

When plant host cells are used, examples of promoters include CaMV promoters and TMV promoters.

Examples of transformation or transfection techniques include electroporation, the spheroplast method, the lithium acetate method, the calcium phosphate method, the *agrobacterium* method, the virus infection method, the liposome method, microinjection, the gene gun method, and lipofection method.

The transformed host cells are cultured under the conditions that are suitable for types of bacteria, yeast, animal cells, or plant cells, and target proteins are recovered from the cells or the culture solution.

Microorganisms are cultured with the use of a medium containing carbon sources, nitrogen sources, inorganic salts, and the like assimilable by microorganisms. Examples of carbon sources that can be used include carbohydrates, such as glucose, fructose, sucrose, and starch, organic acids, such as acetic acid and propionic acid, and alcohols, such as ethanol and propanol. Examples of nitrogen sources that can be used include ammonium salts of inorganic acids or organic acids, such as ammonia, ammonium chloride, ammonium sulfate, ammonium acetate, and ammonium phosphate, peptone, meat extract, and corn steep liquor. Examples of inorganic substances that can be used include monopotassium phosphate, dipotassium phosphate, magnesium phosphate, magnesium sulfate, sodium chloride, ferrous sulfate, manganese sulfate, copper sulfate, and calcium carbonate.

Animal cell culture involves the use of a medium prepared by adding fetal calf serum (FCS) or the like to a basal medium such as DMEM or RPMI 1640 medium.

As described above, target proteins can be recovered via common protein purification techniques, such as ammonium sulfate precipitation, organic solvent precipitation, dialysis, electrophoresis, chromatofocusing, gel filtration chromatography, ion exchange chromatography, affinity chromatography, or HPLC.

When a vector is used for a therapeutic purpose, a vector that is not incorporated into the subject's genome and is a virus or non-virus vector capable of infecting cells but is unreplicable is preferable. Examples of such vector include an adeno-associated virus vector and an adenovirus vector. Such vector can contain a promoter, an enhancer, a polyadenylation site, a selection marker, and a reporter gene. Examples of virus vectors include vectors described in J. Virol. 67:5911-5921, 1993, Human Gene Therapy 5: 717-729, 1994, Gene Therapy 1: 51-58, 1994, Human Gene Therapy 5: 793-801, 1994, and Gene Therapy 1:165-169, 1994 and modified vectors thereof. Further, examples of non-virus vectors include human artificial chromosome vectors that are composed of a chromosome fragment comprising human chromosome-derived centromere and telomere. Examples of human chromosome fragments include, but are not particularly limited to, a human chromosome 14 fragment and a human chromosome 21 fragment (e.g., JP Patent Publication (saihyo) No. 2004-031385 A and JP Patent Publication (kokai) No. 2007-295860 A). The nucleic acid defined above is inserted into the vector and the resulting vector is administered to the bone of the subject. Alternatively, the vector is introduced into the bone tissue or cell sampled from the subject and the resultant is then returned to the bone of the subject. Thus, the vector can be administered to the subject.

<Pharmaceutical Composition>

The present invention further provides a composition for treating a bone disease comprising, as an active ingredient, a protein comprising the extracellular cysteine-rich domain of the Frizzled 1, Frizzled 2, or Frizzled 7 receptor or a mutant thereof, or a vector comprising a nucleic acid encoding the protein.

The present invention also provides a method for treating a bone disease comprising administering such composition to a mammalian animal.

In the present invention, the bone disease refers to a disease that involves lowering of bone mass, bone density, and/or bone strength. Examples of the bone disease include osteoporosis, osteoarthritis, articular rheumatism, malignant tumors [e.g., osteoclastoma, osteosarcoma, and multiple myeloma (wherein the following is known with respect to multiple myeloma: Bone pain resulting from multiple myeloma often occurs in the spinal cord and in the costa and it is occasionally worsened by exercise. If the pain is persistent at the same region, pathologic fracture may have occurred. When a lesion exists on the spine, spinal cord compression may occur. In the case of multiple myeloma, IL-6 is released by the multiplied tumor cells. IL-6 is also known as a factor that activates osteoclasts (OAF: osteoclast activating factor), and osteoclasts activated by IL-6 absorb and destroy the bone. If the bone invaded with multiple myeloma is radiographed, accordingly, the bone seems to have holes (i.e., "punched-out" resorptive lesions). Also, bone destruction leads to an elevated blood calcium level, which causes hypercalcemia and various symptoms resulting therefrom)], bone diseases resulting from hypercalcemia, Paget's disease of bone, osteopetrosis, Camurati-engelmann's disease, arthropathy, primary hyperthyreosis, osteopenia, osteoporosis, osteohalisteresis, rachitis, traumatic bone fracture, or fatigue bone fracture, and various bone diseases or disorders associated therewith. Osteoporosis encompasses primary osteoporosis and secondary osteoporosis. Examples of primary osteoporosis include postmenopausal osteoporosis and senile osteoporosis, and examples of causal diseases of secondary osteoporosis include endocrine diseases (e.g., hyperparathyreosis, hyperthyreosis, hypogonadism, Cushing's syndrome, somatotropin deficiency, diabetes, Addison's disease, and calcitonin deficiency), nutritional/metabolic diseases [e.g., chronic degenerative diseases, emaciation, serious liver diseases (primary biliary cirrhosis, in particular), gastric resection, scorbutus, malabsorption syndrome (including celiac disease), hypophosphatemia, chronic renal disease, hypercalciuria, hemochromatosis, amyloidosis, mast cell tumor, ingestion of excess sodium, insufficient calcium intake, and hypervitaminosis D and A], inflammatory diseases [e.g., articular rheumatism, periarticular bone disease (elevated bone resorption induced by proinflammatory cytokines), and sarcoidosis], immobile diseases (e.g., systemic, bed rest, paralytic, local, or post-fracture diseases), drug-induced diseases [e.g., steroid, which is extensively used for inflammatory diseases as immunosuppressive agents, examples of diseases treated with steroid include a collagen disease, asthma, inflammatory bowel diseases, and organ transplantation. Bone loss is a serious side effect of such treatment techniques), methotrexate, heparin, warfarin, anticonvulsant agent, lithium, and tamoxifen], blood diseases [e.g., multiple myeloma, lymphoma, leukaemia, hemophilia, and chronic hemolytic disease], congenital diseases (e.g., dysosteogenesis, Marfan's syndrome, Kleinfelter's syndrome, congenital erythropoetic porphyria, and cystic fibrosis), and diseases resulting from other diseases [e.g., a chronic obstructive lung disease, hepatic failure, renal disease, articular rheumatism, pregnancy, hyperoxemia, and HIV infection].

According to the present invention, the term "bone disease" also refers to a bone disease caused via selective inhibition of a mineralization process, and an example thereof is rachitis.

When the composition of the present invention is administered to a mammalian animal with a bone disease, preferably a mammalian animal with a disease involving lowering of bone mass, bone density, and/or bone strength, the composition specifically acts on the bone site to increase bone mass, bone density, and/or bone strength, which at least enables increase in the cancellous bone and thickening and proliferation of the diaphysis. Since the composition of the present invention is bone-specific, advantageously, it would develop no or substantially no side effects in other tissue.

The dosage form of the composition of the present invention (i.e., a pharmaceutical preparation) is not limited, and it can be an oral or parenteral preparation. Also, the preparation may comprise other therapeutic agents for bone diseases, in addition to the active ingredients of the present invention. Examples of such therapeutic agents include, but are not limited to, calcium preparations (e.g., calcium L-aspartate, calcium gluconate, and calcium lactate), active vitamin $D_3$ preparations (e.g., alfacalcidol and calcitriol), female hormone preparations (e.g., estriol and conjugated estrogen), calcitonin preparations (e.g., salmon calcitonin and elcatonin), vitamin K preparations (e.g., menatetrenone), bisphosphonate preparations (e.g., disodium etidronate, alendronate sodium hydrate, and sodium risedronate hydrate), selective estrogen receptor modulators (e.g, raloxifene hydrochloride), ipriflavone, and an anti-RANKL antibody.

The other therapeutic agents can be administered in combination with the composition of the present invention simultaneously or continuously to a mammalian animal in accordance with the therapeutic regimen made by the primary doctor. The term "continuously" used herein refers that the other therapeutic agent may be administered after the composition of the present invention is administered or the composition of the present invention may be administered after the other therapeutic agent is administered. That is, the timings of administration for such agents are separated. The term "simultaneously" refers that the composition of the present invention is administered simultaneously with the other therapeutic agent. In such a case, the other therapeutic agent may be incorporated into the composition of the present invention to constitute a single preparation.

A preferable form is a parenteral preparation and examples thereof include, but are not limited to, a preparation for intravenous administration, a preparation for intramuscular administration, a preparation for intraperitoneal administration, a preparation for subcutaneous administration, and a preparation for local administration. Local administration includes direct administration to an injured, fractured, or damaged bone, such as the lesion, including the cranial bone, the femur, the sternum, the spondylus, and the costa. For example, the preparation may be administered in the form of a preparation for transplantation prepared by incorporating an active ingredient into an artificial bone component, such as hydroxyapatite. Examples of preparations for parenteral administrations include injection preparations, drops, suppositories, percutaneous absorbent preparations, liposomes, and nanoparticle-encapsulated preparations.

Examples of oral preparations include tablets, pills, granules, capsules, powders, solutions, suspensions, controlled-release preparations, and enteric coated preparations.

When the protein of the present invention is an active ingredient, the composition can contain pharmaceutically acceptable excipients, carriers such as diluents, and additives.

Examples of carriers include physiological saline, glycerol, ethanol, almond oil, vegetable oil, sucrose, starch, and lactose.

Examples of additives include binders (e.g., pregelatinized corn starch, hydroxypropyl methylcellulose, and polyvinyl pyrrolidone), lubricants (e.g., magnesium stearate, talc, and silica), dispersants (e.g., polyvinyl pyrrolidone and corn starch), suspensions (e.g., talc and gum Arabic), emulsifiers (e.g., lecithin and gum Arabic), disintegrators (e.g., potato starch, sodium starch glycolate, and crospovidone), buffers (e.g., phosphate, acetate, citrate, and Tris salt), antioxidants (e.g., ascorbic acid and tocopherol), preservatives (e.g., sorbic acid, methyl p-hydroxybenzoate, and propyl p-hydroxybenzoate), isotonic agents (e.g., sodium chloride), and stabilizers (e.g., glycerol).

Enteric preparations can include, for example, a polymer(s) such as hydroxypropyl methylcellulose phthalate, a copolymer of methacrylic acid-methyl methacrylate, a copolymer of methacrylic acid-ethyl acrylate, and hydroxypropyl acetate succinate.

The dose of the pharmaceutical preparation should be adequately determined in accordance with the age, sex, body weight, and symptoms of the patient, the administration route, and other conditions. For example, it is from about 0.1 µg/kg to 100 mg/kg per day per adult, and preferably from about 1 µg/kg to 10 mg/kg, although the dose is not limited to such range. The pharmaceutical preparation may be administered daily during treatment, and it may be administered at intervals of several days, two weeks, or one month.

Another active ingredient of the present invention is a vector comprising a nucleic acid encoding an extracellular cysteine-rich domain of the Frizzled 7, Frizzled 1, or Frizzled 2 receptor or a mutant thereof.

The vector can be administered in the same manner as in the case of a technique or procedure employed for gene therapy. The vector may be directly administered to a subject (i.e., by the in vivo method). Alternatively, the vector may be introduced into a cell sampled from a subject, a transformed cell expressing the target Frizzled extracellular cysteine-rich domain may be selected, and the selected cell may then be administered to a subject (i.e., by the ex vivo method). Examples of gene delivery means that can be employed for administering a vector to a target tissue or cell include a colloidal dispersion system, a liposome-induced system, and an artificial viral envelope. Examples of delivery means that can be employed include a macromolecule complex, nanocapsules, microspheres, beads, oil-in-water emulsions, micells, mixed micells, and liposomes. Direct vector administration can be carried out via, for example, intravenous injection (including drops), intramuscular injection, intraperitoneal injection, or subcutaneous injection. A vector can be introduced into a cell (i.e., transformation) via a general gene introduction technique, such as the calcium phosphate method, the DEAE-dextran method, electroporation, or lipofection. The amount of the vector or transformant used varies depending on the administration route, the administration frequency, and a subject type. Such amount can be adequately determined in accordance with a technique common in the art.

<Preparation of Frizzled Extracellular Cysteine-rich Domain Knock-in Mouse>

The present invention was discovered through a B-cell-specific expression knock-in chimeric mouse used for analyzing the in vivo functions of the extracellular cysteine-rich domain of the Frizzled 7, Frizzled 1, or Frizzled 2 receptor and a method for producing the same.

In the present invention, a knock-in chimeric mouse expressing a Frizzled 7, Frizzled 1, or Frizzled 2 extracellular cysteine-rich domain, preferably a knock-in chimeric mouse expressing a fusion protein of a Frizzled 7, Frizzled 1, or Frizzled 2 extracellular cysteine-rich domain and Fc, can be prepared in accordance with an established technique (for example, WO 2006/78072). In order to realize more efficient secretion and expression in mouse B cells, for example, a secretory signal sequence of Frizzled 7, Frizzled 1, or Frizzled 2 is substituted with the secretory signal sequence of the mouse Igκ gene. In this case: when knocking-in of the human Frizzled 7 extracellular cysteine-rich domain or the fusion protein of human Frizzled 7 extracellular cysteine-rich domain and Fc is intended, the substitution of the region from the N-terminus to alanine-32 of the human Frizzled 7 extracellular cysteine-rich domain protein (SEQ ID NO: 8) is preferable; when knocking-in of the mouse Frizzled 7 extracellular cysteine-rich domain is intended, the substitution of the region from the N-terminus to alanine-32 of the mouse Frizzled 7 extracellular cysteine-rich domain protein (SEQ ID NO: 2) is preferable; when knocking-in of the human Frizzled 1 extracellular cysteine-rich domain or the fusion protein of the human Frizzled 1 extracellular cysteine-rich domain and Fc is intended, the substitution of the region from the N-terminus to alanine-72 of the human Frizzled 1 extracellular cysteine-rich domain protein (SEQ ID NO: 16) is preferable; when knocking-in of the mouse Frizzled 1 extracellular cysteine-rich domain is intended, the substitution of the region from the N-terminus to alanine-71 of the mouse Frizzled 1 extracellular cysteine-rich domain protein (SEQ ID NO: 12) is preferable; and when knocking-in of the human or mouse Frizzled 2 extracellular cysteine-rich domain or the fusion protein of the human or mouse Frizzled 2 extracellular cysteine-rich domain and Fc is intended, the substitution of the region from the N-terminus to alanine-28 of the mouse Frizzled 2 extracellular cysteine-rich domain protein (SEQ ID NO: 59) is preferable. Since the amino acid sequences of the cysteine rich domains of human and mouse Frizzled 2 are identical to each other, either a human- or mouse-derived amino acid sequence may be used. When a fusion protein with Fc is to be expressed, use of an Fc mutant (hFcm) prepared by varying part of human IgG1-derived Fc into an ADCC and CDC activity-lowered form is preferable.

A knock-in chimeric mouse expressing a human or mouse Frizzled 7, Frizzled 1, or Frizzled 2 extracellular cysteine-rich domain or a fusion protein of a human or mouse Frizzled 7, Frizzled 1, or Frizzled 2 extracellular cysteine-rich domain and hFcm, and a control chimeric mouse prepared with the use of ES cells into which a foreign cDNA expression unit has not been inserted or only the hFcm expression unit has been exclusively inserted can be subjected to, for example, pathologic analysis of tissue, immunohistochemical analysis, biochemical examination of serum samples, or assay of blood cell components to identify changes resulting from the expression of the Frizzled 7, Frizzled 1, or Frizzled 2 extracellular cysteine-rich domain. In Examples 2 and 13 below, whitening of the femur, whitening of the sternum, whitening and hardening of the cranium, whitening and hardening of the spondylus, and hardening of the costa were more significantly observed in Example 2 (2-1) as phenotypes specific for a knock-in chimeric mouse expressing a mouse Frizzled 7 extracellular cysteine-rich domain compared with the control chimeric mouse. The increased femoral cancellous bone and the increased sternal cancellous bone were observed via observation of hematoxylin-eosin (H&E)-stained pathological sections in Example 2 (2-2). The increased tibial bone density was observed via X-ray photography of the tibia in Example 2 (2-3). The increased tibial bone volume/tissue volume was observed in Example 13 (13-2-2). The increased mineral apposition rate, the increased mineralization surface, and the increased bone formation rate of the tibia were observed in Example 13 (13-2-4). The increased maximum load of femur was observed in Example 13 (13-3). The increased bone volume/tissue volume, the increased trabecular thickness, the increased trabecular number, the decreased trabecular separation, and the decreased trabecular spacing in the cancellous bone region of the proximal tibial metaphysis were observed in Example 13 (13-4). In Example 14 below, whitening of the femur, whitening of the sternum, whitening and hardening of the cranium, and hardening of the costa were more significantly observed in Example 14 (14-2) and (14-5) as phenotypes specific for a knock-in chimeric mouse expressing a human Frizzled 7 extracellular cysteine-rich domain compared with the control chimeric mouse. The increased maximum load of femur was observed in Example 14 (14-3). The increased bone volume/tissue volume, the increased trabecular thickness, the increased trabecular number, the decreased trabecular separation, and the decreased trabecular spacing in the cancellous bone region of the distal femoral metaphysis were observed in Example 14 (14-4). In Example 14 (14-6), the increased femoral cancellous bone, the thickened femoral diaphyseal wall, and the increased sternal cancellous bone were observed via observation of H&E stained pathological sections. In Examples 5 and 16 below, whitening of the femur, whitening of the sternum, whitening and hardening of the cranium, hardening of the spondylus, and hardening of the costa were observed in Example 5 (5-1) as phenotypes specific for a knock-in chimeric mouse expressing a Frizzled 1 extracellular cysteine-rich domain. The increased tibial bone density was observed via X-ray photography of the tibia in Example 5 (5-2). The thickened femoral diaphyseal wall, the increased femoral cancellous bone, and the increased sternal cancellous bone were observed via observation of H&E stained pathological sections in Example 5 (5-4). The increased tibial bone volume/tissue volume was observed in Example 16 (16-2-2). The increases in a mineral apposition rate, a mineralization surface, and a bone formation rate of the tibia were observed in Example 16 (16-2-4). The increased maximum load of femur was observed in Example 16 (16-3). The increased bone volume/tissue volume, the increased trabecular thickness, the increased trabecular number, the decreased trabecular separation, and the decreased trabecular spacing in the cancellous bone region of the distal femoral metaphysis were observed in Example 16 (16-4). In Examples 10 and 19 below, whitening of the femur, whitening of the sternum, whitening and hardening of the cranium, hardening of the spondylus, and hardening of the costa were observed in Example 10 (10-1) as phenotypes specific for a knock-in chimeric mouse expressing a Frizzled 2 extracellular cysteine-rich domain. The thickened femoral diaphyseal wall was observed via observation of H&E stained pathological sections in Example 10 (10-2). The increased tibial bone volume/tissue volume was observed in Example 19 (19-4-2). The increased mineral apposition rate, the increased mineralization surface, and the increased bone formation rate of the tibia were observed in Example 19 (19-4-4). The decreased osteoclast number and the decreased osteoclast surface were observed in Example 19-4-5. The increased maximum load of femur was observed in Example 19 (19-5). The increased bone volume/tissue volume, the increased trabecular thickness, the increased trabecular number, the decreased trabecular separation, and the decreased trabecular spacing in the cancellous bone region of the distal femoral metaphysis were observed in Example 19 (19-6).

A knock-in chimeric mouse expressing a Frizzled 7, Frizzled 1, or Frizzled 2 extracellular cysteine-rich domain or a fusion protein of the Frizzled 7, Frizzled 1, or Frizzled 2 extracellular cysteine-rich domain and hFcm can be prepared in accordance with an established method (for example, WO 2006/78072). Whether or not the nucleic acid inserted in the knock-in ES cell-derived cells (i.e., the Frizzled 7, Frizzled 1, or Frizzled 2 extracellular cysteine-rich domain or a fusion protein of the Frizzled 7, Frizzled 1, or Frizzled 2 extracellular cysteine-rich domain and hFcm) is expressed can be detected via, for example, RT-PCR involving the use of RNA derived from the cell of interest, Northern blotting, enzyme-linked immunosorbent assay (ELISA) using an antibody against the Frizzled 7, Frizzled 1, or Frizzled 2 extracellular cysteine-rich domain or hFcm, or Western blotting.

Hereafter, the present invention is described in greater detail with reference to the examples, although the technical scope of the present invention is not limited thereto. Frizzled 7, Frizzled 1, or Frizzled 2 is denoted by FZD7, FZD1, or FZD2, respectively.

EXAMPLES

Example 1

Preparation of USmFZD7crd-hFcm KI Chimeric Mouse

In accordance with the method described in the examples of WO 2006/78072, a pUSmFZD7crd-hFcm KI vector was prepared from mouse FZD7-cDNA (a 1,719-bp sequence comprising a region from an initiation codon to a termination codon, SEQ ID NO: 1) and human IgG1 Fc mutant-cDNA (a 702-bp sequence comprising a region from a linker sequence to a termination codon inserted to bind to the FZD7 extracellular cysteine-rich domain, SEQ ID NO: 3).

The mouse FZD7 signal sequence, a CRD (the cystein-rich-domain), and a region located downstream of a CRD comprising the 7-transmembrane domain in SEQ ID NO: 1 are marked by a single underline, a solid box, and a double underline, respectively, based on the information regarding the GenBank Accession Numbers: NM_008057.2 and NP_032083.2.

```
SEQ ID NO: 1:
ATGCGGGGCCCCGGCACGGCGGCGTCGCACTCGCCCCTGGGCCTCTGCGCCCTGGTGCTTGCTCTTCTGTGCGCGCT

GCCCACGGACACCCGGGCT

CAGCCATATCACGGCGAGAAAGGCATCTCGGTACCGGACCACGGCTTCTGCCAGCCCATCTCCATCCCGTTGTGCAC

GGATATCGCCTACAACCAGACCATCCTGCCCAACCTGCTGGGCCACACGAACCAAGAGGACGCGGGCCTCGAGGTGC

ACCAGTTCTACCCTCTGGTAAAGGTGCAGTGTTCTCCTGAGCTACGCTTCTTCTTATGCTCTATGTACGCACCCGTG

TGCACCGTGCTCGACCAAGCCATTCCTCCGTGCCGTTCCTTGTGCGAGCGCGCCCGACAGGGCTGCGAGGCGCTCAT

GAACAAGTTCGGCTTCCAGTGGCCAGAGCGGTTGCGCTGCGAGAACTTCCCAGTGCACGGTGCCGGCGAGATCTGCG

TGGGGCAGAACACGTCCGACGGCTCCGGGGGCGCGGGCGGCAGTCCCACCGCCTACCCTACTGCTCCCTACCTG

CCAGACCCACCTTTCACTGCGATGTCCCCCTCAGATGGCAGAGGCCGCTTGTCTTTCCCCTTCTCGTGTCCGCGCCA

GCTCAAGGTGCCCCCCTACCTGGGCTACCGCTTCCTAGGTGAGCGTGACTGCGGTGCCCCGTGTGAGCCGGCCGTG

CTAACGGCCTCATGTACTTTAAAGAAGAGGAGAGACGGTTCGCCCGCCTCTGGGTGGGTGTGTGGTCAGTGCTGTGC

TGCGCCTCGACGCTCTTCACGGTGCTCACCTACCTAGTGGACATGCGTCGCTTCAGCTATCCAGAGCGACCCATCAT

CTTCCTGTCGGGTTGCTACTTCATGGTGGCAGTGGCGCACGTGGCAGGCTTCCTGCTAGAGGACCGTGCCGTGTGCG

TGGAGCGCTTCTCGGACGATGGCTACCGCACGGTGGCGCAGGGCACCAAGAAGGAGGGCTGCACCATCCFCTTCATG
```

-continued

```
GTGCTTTACTTCTICGGTATGGCCAGCTCCATCTGGTGGGTCATTCTGTCCCTCACTTGGTTCCTGGCAGCTGGCAT

GAAGTGGGGCCACGAGGCCATCGAGGCCAACTCGCAGTACTTTCATCTGGCCGCGTGGGCTGTGCCAGCGGTCAAGA

CAATCACCATTTTGGCCATGGGCCAGGTGGATGGTGACCTACTCAGTGGAGTGTGCTACGTGGGCCTGICTAGTGTG

GATGCATTGCGGGGCTTCGTGCTGGCGCCCTTGITCGTCTACCTCTTCATCGGGACGTCCTTCCTGTTGGCCGGCTT

TGTGTCTCTCTTTCGCATCCGCACCATCATGAAGCACGACGGCACCAAGACAGAGAAGCTGGAGAAGCTGATGGTGC

GCATCGGCGTCTICAGCGTGCTCTACACGGTGCCGGCCACCATCGTGTTGGCCTGCTACTTTTATGAGCAGGCCITC

CGAGAGCACTGGGAACGCACCTGGCTCCTGCAGACTTGCAAGAGCTACGCTGTGCCCTGCCCTCCGGGCCACTTCTC

TCCCATGAGCCCCGACTTTACAGTCTTCATGATCAAGTACCTGATGACCATGATCGTGGGCATCACTACGGGCTTCT

GGATCTGGTCGGGCAAGACCCTGCAGTCATGGCGTCGCTTCTACCACAGACTCAGCCACAGCAGCAAGGGGGAAACT

GCGGTATGA
```

The amino acid sequence encoded by SEQ ID NO: 1 (572 amino acids, SEQ ID NO: 2) is shown below.

region (amino acid sequences before and after mutation, K→A, P→S) mutated to have a decreased CDC activity are

```
SEQ ID NO: 2:
MRGPGTAASHSPLGLCALVLALLCALPTDTRA

QPYHGEKGISVPDHGFCQPISIPLCTDIAYNQTILPNLLGHTNQEDAGLEVHQFYPLVKVQCSPELRFFLCSMYAPV

CTVLDQAIPPCRSLCERARQGCEALMNKFGFQWPERLRCENFPVHGAGEICVGQNTSDGSGGAGGSPTAYPTAPYL

PDPPFTAMSPSDGRGRLSFPFSCPRQLKVPPYLGYRFLGERDCGAPCEPGRANGLMYFKEEERRFARLWVGVWSVLC

CASTLFTVLTYLVDMRRFSYPERPTIFLSGCYFMVAVAHVAGFLLEDRAVCVERFSDDGYRTVAQGTKKEGCTILFM

VLYFFGMASSIWWVILSLTWFLAAGEIVGHEATEANSQYFHLAAWAVPAVKTITILAMGQVDGDLLSGVCYVGLSSV

DALRGFVLAPLFVYLFIGTSFLLAGFVSLFRIRTIMKHDGTKTEKLEKLNEVRIGVFSVLYTVPATIVLACYFYEQAF

REETWERTWLLQTCKSYAVPCPPGHFSPMSPDFTVFMIKYLMTMIVGITTGFEWSGKTLQSWRRFYHRLSHSSKGET

AV
```

SEQ ID NOs: 3 and 4 show the cDNA sequence and the amino acid sequence of the human IgG1-derived Fc mutant (hFcm). A cDNA region and the amino acid sequence region (amino acids from the N-terminus before and after mutation, L→A, L→E, G→A) with lowered ADCC activity mutated based on known information (Tawara, T., et al., J. Immunology, 180, 2294-2298, 2008; Gross, J. A., et al., Immunity, 15, 289-302, 2001; and WO 02/094852) in the original human IgG1-derived Fc region are marked by a double underline, a cDNA region and an amino acid sequence region (amino acid sequences before and after mutation, K→A, P→S) mutated to have a decreased CDC activity are marked by a solid box, and a linker sequence (including the SfoI recognition sequence) added to the 5' terminus of the original human IgG1-derived Fc sequence so as to bind to the C terminal amino acid in the FZD7 extracellular cysteine-rich domain is marked by a single underline. In addition to the above method, the 116th residue from the N-terminus of the sequence as shown in SEQ ID NO: 4 can be mutated from A to S in order to decrease the CDC activity, based on known information (Gross, J. A., et al., Immunity, 15, 289-302, 2001).

```
SEQ ID NO: 3:
GCCGAGCCTAGGTCTTCAGACAAAACTCACACATGCCCACCGTGCCCAGCACCTGAAGCCGAGGGGGCCCCGTCAGT

CTTCCTCTTCCCCCCAAAACCCAAGGACACCCTCATGATCTCCCGGACCCCTGAGGTCACATGCGTGGTGGTGGACG

TGAGCCACGAAGACCCTGAGGTCAAGTTCAACTGGTACGTGGACGGCGTGGAGGTGCATAATGCCAAGACAAAGCCG

CGGGAGGAGCAGTACAACAGCACGTACCGTGTGGTCAGCGTCCTCACCGTCCTGCACCAGGACTGGCTGAATGGCAA

GGAGTACAAGTGCGCCGTCTCCAACAAAGCCCTCCCAGCCTCCATCGAGAAAACCATCTCCAAAGCCAAAGGGCAG

CCCCGAGAACCACAGGTGTACACCCTGCCCCCATCCCGGGATGAGCTGACCAAGAACCAGGTCAGCCTGACCTGCCT

GGTCAAAGGCTTCTATCCCAGCGACATCGCCGTGGAGTGGGAGAGCAATGGGCAGCCGGAGAACAACTACAAGACCA
```

```
CGCCTCCCGTGCTGGACTCCGACGGCTCCTTCTTCCTCTACAGCAAGCTCACCGTGGACAAGAGCAGGTGGCAGCAG

GGGAACGTCTTCTCATGCTCCGTGATGCATGAGGCTCTGCACAACCACTACACGCAGAAGAGCCTCTCCCTGTCTCC

GGGTAAATGA
```

The amino acid sequence encoded by SEQ ID NO: 3 (233 amino acids, SEQ ID NO: 4) is shown below.

```
SEQ ID NO: 4:
AEPRSSDKTHTCPPCPAPEAEGAPSVFLFPPKPKDTLMISRTPEVTCVVVDVSHEDPEVKFNWYVDGVEVHNAKTKP

REEQYNSTYRVVSVLTVLHQDWLNGKEYKCAVSNKALPASIEKTISKAKGQPREPQVYTLPPSRDELTKNQVSLTC

LVKGFYPSDIAVEWESNGQPENNYKTTPPVLDSDGSFFLYSKLTVDKSRWQQGNVFSCSVMHEALHNHYTQKSLSLS

PGK
```

A polynucleotide sequence comprising a region from the initiation codon to the termination codon of the pUSmFZD7crd-hFcm KI vector expression unit (SEQ ID NO: 5; a 1,462-bp sequence comprising a mouse Igκ signal sequence containing an intron region substituted with the mouse FZD7 signal sequence (a region marked by a single underline) and a mouse FZD7crd-hFcm sequence downstream thereof. A region marked by a solid box represents a mouse Frizzled 7 extracellular cysteine-rich domain, a region marked by a double underline represents hFcm, and the amino acid sequence encoded by the cDNA (SEQ ID NO: 6; a sequence composed of 406 amino acids; a region marked by a single underline represents a mouse Igκ signal sequence, a region marked by a solid box represents a mouse Frizzled 7 extracellular cysteine-rich domain, and a region marked by a double underline represents hFcm) are shown below. As information regarding the mouse Igκ signal sequence containing an intron region, the genomic sequence located upstream of MUSIGKVR1 obtained from the GenBank (Accession Number: K02159) was obtained from the UCSC mouse genome database.

```
SEQ ID NO: 5:
ATGGAGACAGACACACTCCTGTTATGGGTACTGCTGCTCTGGGTTCCAGGTGAGAGTGCAGAGAAGTGTTGGATGCA

ACCTCTGTGGCCATTATGATACTCCATGCCTCTCTGTTCTTGATCACTATAATTAGGGCATTTGTCACTGGTTTTAA

GTTTCCCCAGTCCCCTGAATTTTCCATTTTCTCAGAGTGATGTCCAAAATTATTCTTAAAAATTTAAATAAAAAGGT

CCTCTGCTGTGAAGGCTTTTATACATATATAACAATAATCTTTGTGTTTATCATTCCAGGTTCCACTGGC

CAGCCATATCACGGCGAGAAAGGCATCTCGGTACCGGACCACGGCTTCTGCCAGCCCATCTCCATCCCGTTGTGCAC

GGATATCGCCTACAACCAGACCATCCTGCCCAACCTGCTGGGCCACACGAACCAAGAGGACGCGGGCCTCGAGGTGC

ACCAGTTCTACCCTCTGGTAAAGGTGCAGTGTTCTCCTGAGCTACGCTTCTTCTTATGCTCTATGTACGCACCCGTG

TGCACCGTGCTCGACCAAGCCATTCCTCCGTGCCGTTCCTTGTGCGAGCGCGCCCGACAGGGCTGCGAGGCGCTCAT

GAACAAGTTCGGCTTCCAGTGGCCAGAGCGGTTGCGCTGCGAGAACTTCCCAGTGCACGGTGCCGGCGAGATCTGCG

TGGGGCAGAACACGTCCGACGGCTCCGGGGCGCGGGCGGCAGTCCCACCGCCTACCCTACTGCTCCCTACCTG

GCCGAGCCTAGGTCTTCAGACAAAACTCACACATGCCCACCGTGCCCAGCACCTGAAGCCGAGGGGCCCCGTCAGT

CTTCCTCTTCCCCCCAAAACCCAAGGACACCCTCATGATCTCCCGGACCCCTGAGGTCACATGCGTGGTGGTGGACG

TGAGCCACGAAGACCCTGAGGTCAAGTTCAACTGGTACGTGGACGGCGTGGAGGTGCATAATGCCAAGACAAAGCCG

CGGGAGGAGCAGTACAACAGCACGTACCGTGTGGTCAGCGTCCTCACCGTCCTGCACCAGGACTGGCTGAATGGCAA

GGAGTACAAGTGCGCCGTCTCCAACAAAGCCCTCCCAGCCTCCATCGAGAAAACCATCTCCAAAGCCAAAGGGCAGC

CCCGAGAACCACAGGTGTACACCCTGCCCCCATCCCGGGATGAGCTGACCAAGAACCAGGTCAGCCTGACCTGCCTG

GTCAAAGGCTTCTATCCCAGCGACATCGCCGTGGAGTGGGAGAGCAATGGGCAGCCGGAGAACAACTACAAGACCAC

GCCTCCCGTGCTGGACTCCGACGGCTCCTTCTTCCTCTACAGCAAGCTCACCGTGGACAAGAGCAGGTGGCAGCAGG

GGAACGTCTTCTCATGCTCCGTGATGCATGAGGCTCTGCACAACCACTACACGCAGAAGAGCCTCTCCCTGTCTCCG

GGTAAATGA
```

-continued

SEQ ID NO: 6:
METDTLLLWVLLLWVPGSTG

```
QPYHGEKGISVPDHGFCQPISIPLCTDIAYNQTILPNLLGHTNQEDAGLEVHQFYPLVKVQCSPELRFFLCSMYAPV
```

```
CTVLDQAIPPCRSLCERARQGCEALMNKFGFQWPERLRCENFPVHGAGEICVGQNTSDGSGGAGGSPTAYPTAPYL
```

AEPRSSDKTHTCPPCPAPEAEGAPSVFLFPPKPKDTLMISRTPEVICVVVDVSHEDPEVKFNWYVDGVEMAKTKP

REEQYNSTYRVVSVLTVLHQDWLNGKEYKCAVSNKALPASIEKTISKAKGQPREPQVYMPPSRDELTKNQVSLTCL

VKGFYPSDIAVEWESNGQPENNYKTIPPVLDSDGSFFLYSKLTVDKSRWQQGNVFSCSVNIHEALHNHYTQKSLSLSP

GK

With the use of the pUSmFZD7crd-hFcm KI vector, the USmFZD7crd-hFcm KI chimeric mice expressing a fusion protein of the mouse Frizzled 7 extracellular cysteine-rich domain and human Fcm in a B-cell-specific manner were prepared in accordance with the method described in the examples of WO 2006/78072.

Control chimeric mice used in Examples 2, 13, 14, 16, 17, and 19 below were prepared in accordance with the method described in the examples of WO 2006/78072.

Example 2

Analysis of USmFZD7crd-hFcm KI Chimeric Mouse 2-1. Necropsy Finding

The chimeric mice prepared in Example 1 were subjected to necropsy at age of 16 weeks, and the spleen, the liver, the kidney, the adrenal gland, the stomach, the small intestine, the appendix, the large intestine, the pancreas, the mesenteric lymph node, the female/male reproductive organ, the thymic gland, the lung, the heart, the brain, the muscle, the skin, the femur, the sternum, the cranium, the spondylus, and the costa were observed. As a result, whitening of the femur, whitening of the sternum, whitening and hardening of the cranium, whitening and hardening of the spondylus, and hardening of the costa were more significantly observed as characteristic changes in the USmFZD7crd-hFcm KI chimeric mice compared with the control mice. In addition, spleen enlargement was observed in approximately a half of the USmFZD7crd-hFcm KI chimeric mice. The number of mice exhibiting changes is described below.

2-1-1. Femur

Whitening was observed more significant in all the 20 USmFZD7crd-hFcm KI chimeric mice subjected to necropsy compared with 29 control mice.

2-1-2. Sternum

Whitening was observed more significant in all the 20 USmFZD7crd-hFcm KI chimeric mice subjected to necropsy compared with 29 control mice.

2-1-3. Cranium

Whitening was observed more significant in 16 mice and hardening was observed more significant in 18 mice among all the 20 USmFZD7crd-hFcm KI chimeric mice subjected to necropsy compared with 29 control mice.

2-1-4. Spondylus

Whitening was observed more significant in a mouse and hardening was observed more significant in 10 mice among all the 20 USmFZD7crd-hFcm KI chimeric mice subjected to necropsy compared with 29 control mice.

2-1-5. Costa

Hardening was observed more significant in 7 mice among all the 20 USmFZD7crd-hFcm KI chimeric mice subjected to necropsy compared with 29 control mice.

2-1-6. Spleen

Enlargement was observed more significant in 11 mice among all the 20 USmFZD7crd-hFcm KI chimeric mice subjected to necropsy compared with control mice. Similar changes were observed in 4 of 29 control mice.

Thus, whitening of the femur, whitening of the sternum, whitening and hardening of the cranium, whitening and hardening of the spondylus, and hardening of the costa may have been induced by overexpression of the mouse FZD7 extracellular cysteine-rich domain-human Fc mutant fusion constructs.

2-2. Pathological Finding

Figure 2:
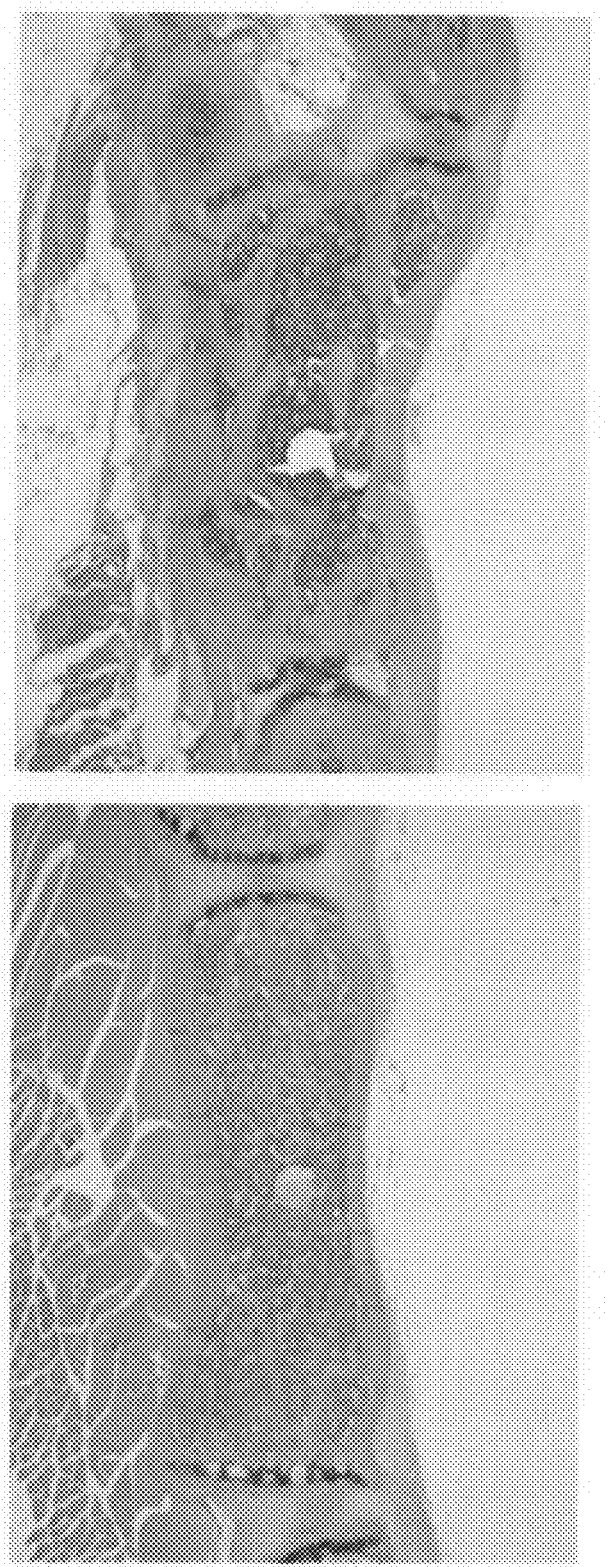
FIG. 2 shows images of H&E stained pathological sections obtained from the sternums of a 16-week-old USmFZD7crd-hFcm KI chimeric mouse (right diagram) and a control mouse (left diagram).

H&E stained pathological sections of the liver, the kidney, the heart, the lung, the spleen, the thymic gland, the mesenteric lymph node, the pancreas, the brain, the adrenal gland, the spermary (in the case of male mice), the ovary (in the case of female mice), the femur, the sternum, the stomach, the duodenum, the jejunum, the ileum, the appendix, the colon, the spinal cord, the aorta, the skeletal muscle, and the skin obtained from seven 16-week-old control chimeric mice and twenty USmFZD7crd-hFcm KI chimeric mice were observed. As a result, increased femoral cancellous bone and the increased sternal cancellous bone were observed in all the USmFZD7crd-hFcm KI chimeric mice (FIG. 1 and FIG. 2). Only one control mouse was observed to exhibit similar changes as described above. There were no significant changes in organs and tissues other than bones compared with control mice.

The above results demonstrate that the increased femoral cancellous bone and the increased sternal cancellous bone may have been induced by overexpression of the mouse FZD7 extracellular cysteine-rich domain-human Fc mutant fusion constructs.

2-3. Analysis of X-Ray Photographs of Tibia

Figure 3:
FIG. 3 shows a X-ray photograph of the tibiae of a 16-week-old female (♀) USmFZD7crd-hFcm KI chimeric mouse (lower portion) and a female (♀) control mouse (upper portion).
Figure 4:
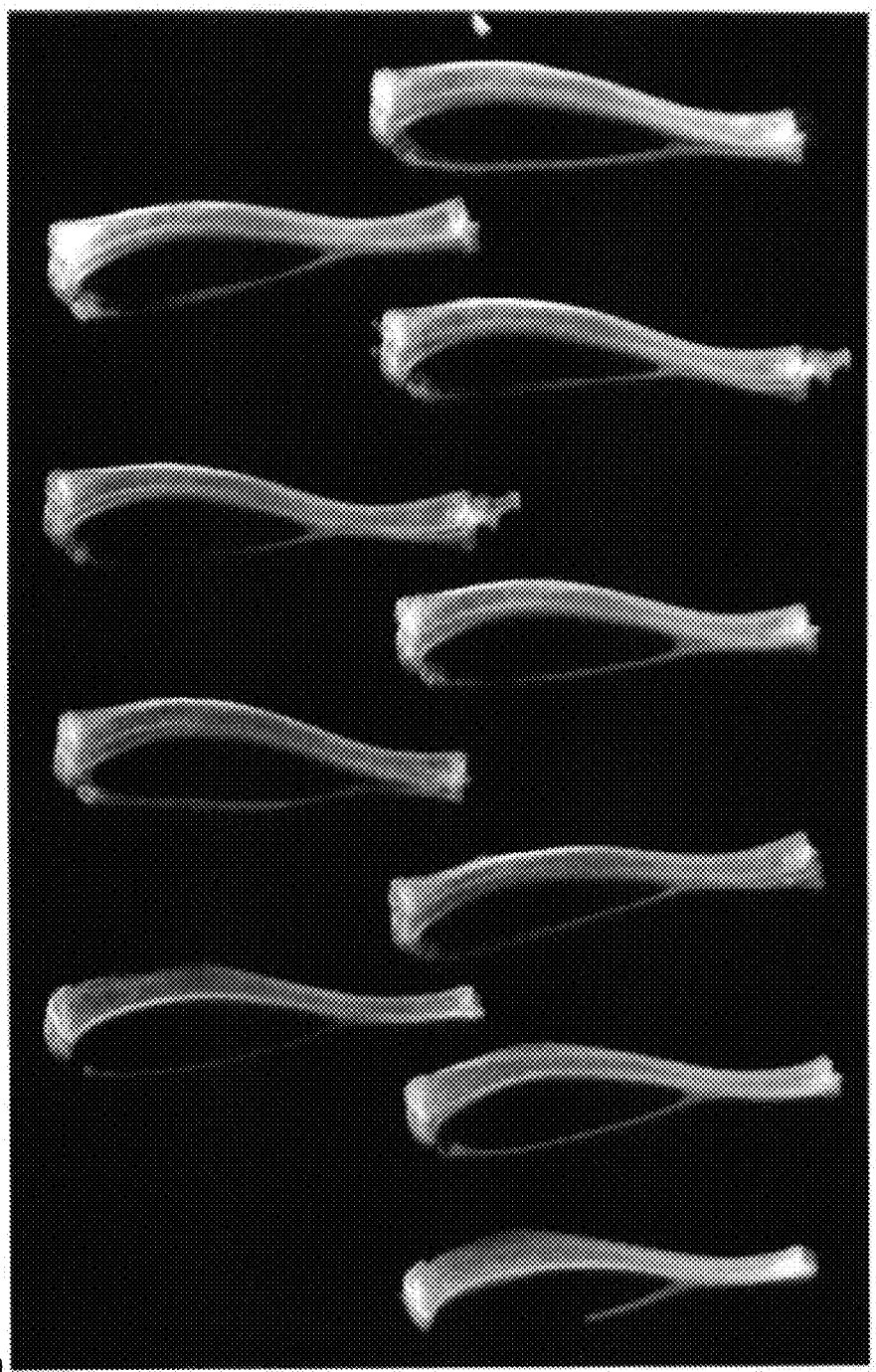
FIG. 4 shows a X-ray photograph of the tibiae of a 16-week-old male (♂) USmFZD7crd-hFcm KI chimeric mouse (lower portion) and a male (♂) control mouse (upper portion).

X-ray photographs (μFX-1000, FUJIFILM) of the tibiae obtained from 16-week-old control chimeric mice (5 female mice and 4 male mice) and the USmFZD7crd-hFcm KI chimeric mice (7 female mice and 6 male mice) were prepared (FIG. 3 and FIG. 4).

In the obtained X-ray photographs of the tibiae, whitening was more advanced in both female and male USmFZD7crd-hFcm KI chimeric mice compared with the control mice.

The above results demonstrate that whitening of the tibia may have been induced by overexpression of the mouse FZD7 extracellular cysteine-rich domain-human Fc mutant fusion constructs.

2-4. Blood Cell Analysis

Fourteen 8-week-old USmFZD7crd-hFcm KI female chimeric mice and six 8-week-old USmFZD7crd-hFcm KI male chimeric mice, fifteen 8-week-old female control mice and nine 8-week-old male control mice, fourteen 15-week-old USmFZD7crd-hFcm KI female chimeric mice and six 15-week-old USmFZD7crd-hFcm KI male chimeric mice, and fourteen 15-week-old female control mice and eleven 15-week-old male control mice were subjected to orbital blood sampling using a glass capillary under ether anesthesia, and the obtained blood samples were subjected to blood component analysis using ADVIA120 (Bayer Medical Ltd.) (blood components: erythrocyte counts, hemoglobin, hematocrit, MCH, MCHC, reticulocyte counts, leukocyte counts, blood platelet counts, lymphocyte counts, neutrophil counts, monocyte counts, eosinophil counts, and basophil counts). As a result, values obtained with the use of the USmFZD7crd-hFcm KI chimeric mice did not show significant changes compared with the control mice at ages of 8 weeks and 15 weeks.

2-5. Biochemical Analysis of Serum

Fourteen USmFZD7crd-hFcm KI female chimeric mice, 6 USmFZD7crd-hFcm KI male chimeric mice, sixteen female control mice, and fourteen male control mice were exsanguinated under ether anesthesia at age of 16 weeks to prepare serum samples. With the use of Hitachi 7180 (Hitachi Science Systems Ltd.), serum samples were subjected to biochemical analysis (LDH activity, GOT activity, GPT activity, CK activity, ALP activity, AMY activity, LAP activity, LIP activity, T-CHO concentration, F-CHO concentration, LDL-CHO concentration, HDL-CHO concentration, TG concentration, PL concentration, GLU concentration, GA %, UA concentration, BUN concentration, CREA concentration, T-BIL concentration, D-BIL concentration, TP concentration, ALB concentration, A/G ratio, IP concentration, Ca concentration, Mg concentration, Na concentration, K concentration, Cl concentration, Fe concentration, UIBC concentration, and TIBC concentration). As a result, the values obtained with the use of the USmFZD7crd-hFcm KI chimeric mice were not significantly different from those of the control mice.

2-6. Confirmation of Expression of the Fusion Protein of Mouse FZD7 Extracellular Cysteine-rich Domain and Human Fc Mutant in USmFZD7crd-hFcm KI Chimeric Mice 2-6-1. ELISA Assay of the Fusion Protein of Mouse FZD7 Extracellular Cysteine-rich Domain and Human Fc Mutant Using Serum Obtained from USmFZD7crd-hFcm KI Chimeric Mice The fusion protein of the mouse FZD7 extracellular cysteine-rich domain and the human Fc mutant existing in the blood sera of 16-week-old USmFZD7crd-hFcm KI chimeric mice (14 female mice and 6 male mice) was detected via ELISA.

In order to assay the concentration of the fusion protein of the FZD7 extracellular cysteine-rich domain and the human Fc mutant in the serum via ELISA, a test sample or a control sample (Recombinant Mouse Frizzled-7/Fc Chimera, R & D Systems, Product Number: 198-FZ) was applied to a 96-well plate (Maxi Soap, Corning) on which anti-Human IgG (γ-Chain Specific, SIGMA, Product Number: I3382) has been immobilized, incubation was carried out at room temperature for 30 minutes, the plate was washed three times with T-PBS(−), peroxidase-labelled antibodies (anti-Human IgG (Fc fragment) peroxidase conjugates developed in goat, Product Number: A0170, SIGMA) were added, and incubation was then carried out at room temperature for 30 minutes. Thereafter, the plate was washed four times with T-PBS(−), a color was developed using a Sumilon peroxidase color-developing kit (Product Number: ML-1120T, Sumitomo Bakelite Co. Ltd.), and the absorbance at 450 nm was assayed to determine the concentration in the serum.

As a result, the average concentration among 14 female mice was 201.7 µg/ml, that among 6 male mice was 168.4 µg/ml, and the concentrations assayed with the use of the serum samples obtained from 5 female control mice and a male control mouse were lower than the detection limit.

The above results suggest that the fusion protein of the mouse FZD7 extracellular cysteine-rich domain and the human Fc mutant is expressed in vivo and circulated in the blood.

Figure 5:
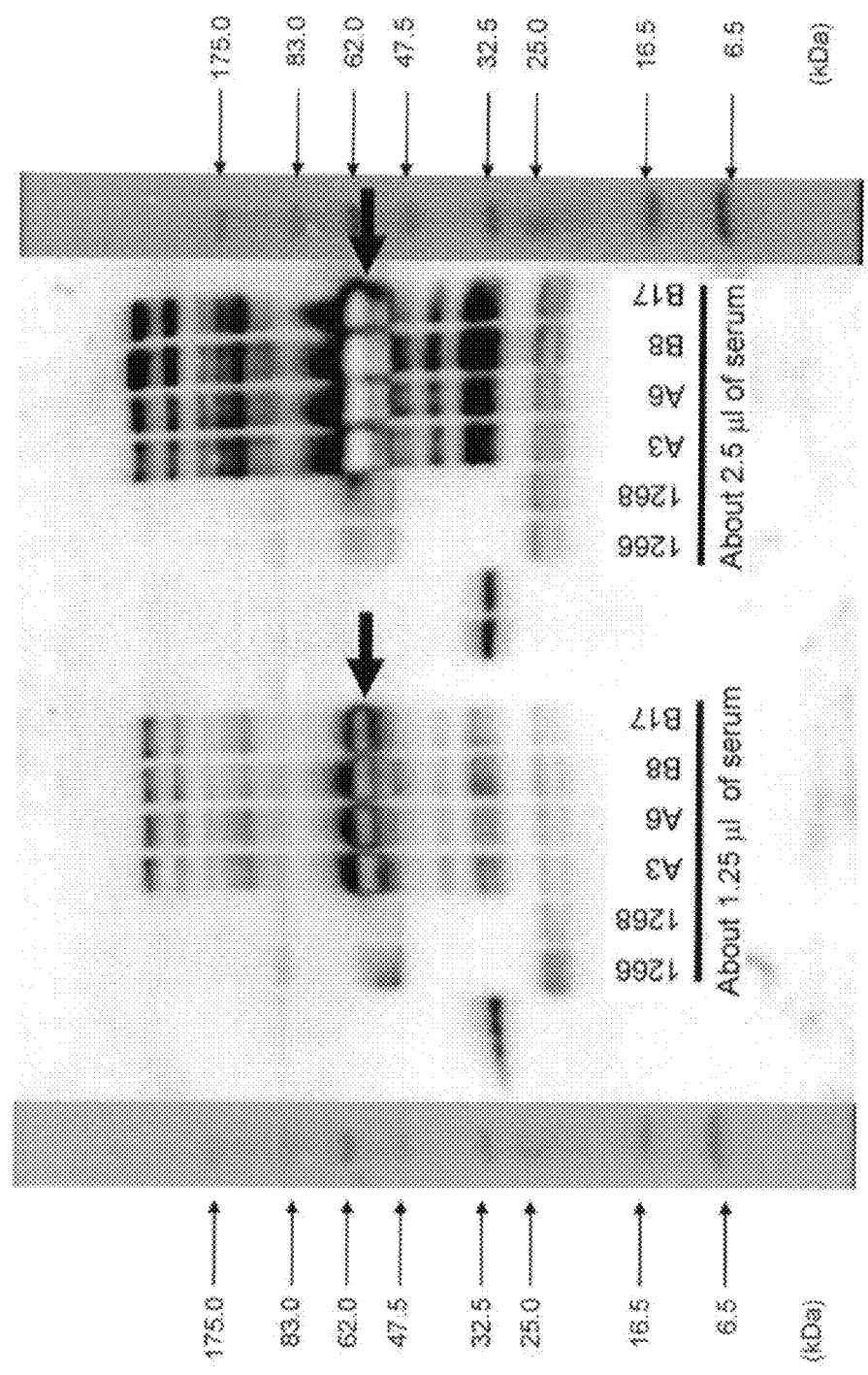
FIG. 5 shows an image showing the results of Western analysis using the serum obtained from the 16-week-old USmFZD7crd-hFcm KI chimeric mouse: wherein 1266 and 1268 represent serum samples obtained from the control chimeric mouse; A3, A6, B8, and B 17 represent serum samples obtained from the USmFZD7crd-hFcm KI chimeric mouse; and an arrow indicates a position of a main band specific to the serum sample obtained from the USmFZD7crd-hFcm KI chimeric mouse.

2-6-2. Western Analysis Using Serum Obtained from USmFZD7crd-hFcm KI Chimeric Mice Serum samples obtained from 16-week-old USmFZD7crd-hFcm KI chimeric mice and control chimeric mice were subjected to Western analysis using human IgG-recognizing rabbit polyclonal antibodies. As samples used for Western analysis, 50 µl of serum samples were applied to Protein G columns (resin volume: about 100 µl, GE Healthcare) in advance, nonspecific adsorbates were removed, and 1.25 µl of serum samples and 2.5 µl equivalent of resin were used as samples to be analyzed. As a result, a main band specific for the USmFZD7crd-hFcm KI chimeric mice was detected at around 60 kDa under reducing conditions (FIG. 5). The molecular weight determined via this analysis was larger than that deduced based only on the amino acid sequence (42.8 kDa under reducing conditions); however, the fusion protein of interest comprised 3 each of N-linked and O-linked glycosylation prediction sites, which indicates an increased molecular weight via glycosylation.

The above results suggest that the USmFZD7crd-hFcm KI chimeric mice prepared in this experiment express a fusion protein of the mouse FZD7 extracellular cysteine-rich domain and the human Fc mutant.

Example 3

Preparation of UShFZD7crd-hFcm KI Chimeric Mouse

A pUShFZD7crd-hFcm KI vector was prepared from human FZD7-cDNA (SEQ ID NO: 7) and human IgG1 Fc mutant-cDNA (SEQ ID NO: 3) in accordance with the method described in Example 1.

The human FZD7 signal sequence, CRD, and a region located downstream of a CRD comprising the 7-transmembrane domain in SEQ ID NO: 7 are marked by a single underline, a solid box, and a double underline, respectively, based on the information regarding the GenBank Accession Numbers: NM_003507.1 and NP_003498.1.

SEQ ID NO: 7:
<u>ATGCGGGACCCCGGCGCGGCCGCTCCGCTTTCGTCCCTGGGCCTCTGTGCCCTGGTGCTGGCGCTGCTGGGCGCACT</u>

<u>GTCCGCGGGCGCCGGGGCG</u>

```
CAGCCATATCACGGCGAGAAAGGCATCTCGGTACCGGACCACGGCTTCTGCCAGCCCATCTCCATCCCGTTGTGCAC

GGATATCGCCTACAACCAGACCATCCTGCCCAACCTGCTGGGCCACACGAACCAAGAGGACGCGGGCCTCGAGGTGC

ACCAGTTCTACCCTCTGGTAAAGGTGCAGTGTTCTCCTGAGCTACGCTTCTTCTTATGCTCTATGTACGCACCCGTG

TGCACCGTGCTCGACCAAGCCATTCCTCCGTGCCGTTCCTTGTGCGAGCGCGCCCGACAGGGCTGCGAGGCGCTCAT

GAACAAGTTCGGCTTCCAGTGGCCAGAGCGGTTGCGCTGCGAGAACTTCCCAGTGCACGGTGCCGGCGAGATCTGCG

TGGGGCAGAACACGTCCGACGGCTCCGGGGGCGCGGGCGGCAGTCCCACCGCCTACCCTACTGCTCCCTACCTG
```

CCGGACCTGCCCTTCACCGCGCTGCCCCCGGGGGCCTCAGATGGCAGGGGGCGTCCCGCCTTCCCCTTCTCATGCCC

CCGTCAGCTCAAGGTGCCCCCGTACCTGGGCTACCGCTTCCTGGGTGAGCGCGATTGTGGCGCCCCGTGCGAACCGG

GCCGTGCCAACGGCCTGATGTACITTAAGGAGGAGGAGAGGCGCTTCGCCCGCCTCTGGGTGGGCGTGTGGTCCGTG

CTGTGCTGCGCCTCGACGCTCTTTACCGTTCTCACCTACCTGGTGGACATGCGGCGCTTCAGCTACCCAGAGCGGCC

CATCATCTTCCTGTCGGGCTGCTACTTCATGGTGGCCGTGGCGCACGTGGCCGGCTTCCTTCTAGAGGACCGCGCCG

TGTGCGTGGAGCGCTTCTCGGACGATGGCTACCGCACGGTGGCGCAGGGCACCAAGAAGGAGGGCTGCACCATCCTC

TTCATGGTGCTCTACTTCTTCGGCATGGCCAGCTCCATCTGGTGGGTCATTCTGTCTCTCACTIGGTTCCTGGCGGC

CGGCATGAAGTGGGGCCACGAGGCCATCGAGGCCAACTCGCAGTACTTCCACCTGGCCGTGGGCCGTGCCCGCCG

TCAAGACCATCACTATCCTGGCCATGGGCCAGGTAGACGGGGACCTGCTGAGCGGGGTGTGCTACGTTGGCCTCTCC

AGTGTGGACGCGCTGCGGGGCTTCGTGCTGGCGCCTCTGTTCGTCTACCTCTTCATAGGCACGTCCTTCTTGCTGGC

CGGCTTCGTGTCCCTCTTCCGTATCCGCACCATCATGAAACACGACGGCACCAAGACCGAGAAGCTGGAGAAGCTCA

TGGTGCGCATCGGCGTCTTCAGCGTGCTCTACACAGTGCCCGCCACCATCGTCCTGGCCTGCTACTTCTACGAGCAG

GCCTTCCGCGAGCACTGGGAGCGCACCTGGCTCCTGCAGACGTGCAAGAGCTATGCCGTGCCCTGCCCGCCCGGCCA

CTTCCCGCCCATGAGCCCCGACTTCACCGTCTTCATGATCAAGTACCTGATGACCATGATCGTCGGCATCACCACTG

GCTTCTGGATCTGGTCGGGCAAGACCCTGCAGTCGTGGCGCCGCTTCTACCACAGACTTAGCCACAGCAGCAAGGGG

GAGACTGCGGTATGA

The amino acid sequence encoded by SEQ ID NO: 7 (574 amino acids, SEQ ID NO: 8) is shown below.

rich domain and the region marked by a double underline represents hFcm) and the amino acid sequence encoded by

SEQ ID NO: 8:
MRDPGAAAPLSSLGLCALVLALLGALSAGAGA

```
QPYHGEKGISVPDHGFCQPISIPLCTDIAYNQTILPNLLGHTNQEDAGLEVHQFYPLVKVQCSPELRFFLCSMYAPV

CTVLDQAIPPCRSLCERARQGCEALMNKFGFQWPERLRCENFPVHGAGEICVGQNTSDGSGGPGGGPTAYPTAPYL
```

PDLPFTALPPGASDGRGRPAFPFSCPRQLKVPPYLGYRFLGERDCGAPCEPGRANGLMYFKEEERRFARLINVGVWSV

LCCASTLFTVLTYLVDMRRFSYPERPIIFLSGCYFMVAVAHVAGFLLEDRAVCVERFSDDGYRTVAQGTKKEGCTIL

FMVLYFFGMASSIWWVILSLTWFLAAGMKWGHEAIEANSQYFHLAAWAVPAVKTITILAMGQVDGDLLSGVCYVGLS

SVDALRGFVLAPLFVYLFIGTSFLLAGFVSLFRIRTIMICHDGTKTEKLEKLMVRIGVFSVLYTYPATIVLACYFYEQ

AFREHWERTVILQICKSYAVPCPPGHFPPMSPDFTVFMIKYLMTMIVGITTGFEWSGKTLQSWRRFYHRLSESKG

ETAV

A polynucleotide sequence comprising a region from the initiation codon to the termination codon of the pUShFZD7crd-hFcm KI vector expression unit (SEQ ID NO: 9; a 1,462-bp sequence comprising a mouse Igκ signal sequence containing an intron region (a region marked by a single underline) substituted with the human FZD7 signal sequence and the human FZD7crd-hFcm sequence located downstream thereof; wherein the region marked by a solid box represents the human Frizzled 7 extracellular cysteine-rich domain, and the region marked by a double underline represents hFcm) are shown below. Information regarding the mouse Igκ signal sequence containing an intron region was obtained from the UCSC mouse the cDNA (SEQ ID NO: 10; a sequence comprising 406 amino acids; wherein the region marked by a single underline represents the mouse Igκ signal sequence, the region marked by a solid box represents the human Frizzled 7 extracellular cysteine-rich domain, and the region marked by a double underline represents hFcm) are shown below. Information regarding the mouse Igκ signal sequence containing an intron region was obtained from the UCSC mouse genome database as the genome sequence located upstream of MUSIGKVR1 obtained from the GenBank (Accession Number: K02159).

The UShFZD7crd-hFcm KI chimeric mice expressing a fusion protein of the human Frizzled 7 extracellular cysteine-rich domain and human Fcm in a B-cell-specific manner SEQ ID NO: 9:
ATGGAGACAGACACACTCCTGTTATGGGTACTGCTGCTCTGGGTTCCAGGTGAGAGTGCAGAGAAGTGTTGGATGCA

ACCTCTGTGGCCATTATGATACTCCATGCCTCTCTGTTCTTGATCACTATAATTAGGGCATTTGTCACTGGTTTTAA

GTTTCCCCAGTCCCCTGAATTTTCCATTTTCTCAGAGTGATGTCCAAAATTATTCTTAAAAATTTAAATAAAAAGGT

CCTCTGCTGTGAAGGCTTTTATACATATATAACAATAATCTTTGTGTTTATCATTCCAGGTTCCACTGGC

CAGCCGTACCACGGAGAGAAGGGCATCTCCGTGCCGGACCACGGCTTCTGCCAGCCCATCTCCATCCCGCTGTGCAC

GGACATCGCCTACAACCAGACCATCCTGCCCAACCTGCTGGGCCACACGAACCAAGAGGACGCGGGCCTCGAGGTGC

ACCAGTTCTACCCGCTGGTGAAGGTGCAGTGTTCTCCCGAACTCCGCTTTTTCTTATGCTCCATGTATGCGCCCGTG

TGCACCGTGCTCGATCAGGCCATCCCGCCGTGTCGTTCTCTGTGCGAGCGCGCCCGCCAGGGCTGCGAGGCGCTCAT

GAACAAGTTCGGCTTCCAGTGGCCCGAGCGGCTGCGCTGCGAGAACTTCCCGGTGCACGGTGCGGGCGAGATCTGCG

TGGGCCAGAACACGTCGGACGGCTCCGGGGGCCCAGGCGGCGGCCCCACTGCCTACCCTACCGCGCCCTACCTG

GCCGAGCCTAGGTCTTCAGACAAAACTCACACATGCCCACCGTGCCCAGCACCTGAAGCCGAGGGGGCCCCGTCAGT

CTTCCTCTTCCCCCCAAAACCCAAGGACACCCTCATGATCTCCCGGACCCCTGAGGTCACATGCGTGGTGGTGGACG

TGAGCCACGAAGACCCTGAGGTCAAGTTCAACTGGTACGTGGACGGCGTGGAGGTGCATAATGCCAAGACAAAGCCG

CGGGAGGAGCAGTACAACAGCACGTACCGTGTGGTCAGCGTCCTCACCGTCCTGCACCAGGACTGGCTGAATGGCAA

GGAGTACAAGTGCGCCGTCTCCAACAAAGCCCTCCCAGCCTCCATCGAGAAAACCATCTCCAAAGCCAAAGGGCAGC

CCCGAGAACCACAGGIGTACACCCTGCCCCCATCCCGGGATGAGCTGACCAAGAACCAGGTCAGCCTGACCTGCCTG

GTCAAAGGCTTCTATCCCAGCGACATCGCCGTGGAGTGGGAGAGCAATGGGCAGCCGGAGAACAACTACAAGACCAC

GCCTCCCGTGCTGGACTCCGACGGCTCCTTCTTCCTCTACAGCAAGCTCACCGTGGACAAGAGCAGGTGGCAGCAGG

GGAACGTCTTCTCATGGFCCGTGATGCATGAGGCTCTGCACAACCACTACACGCAGAAGAGCCTCTCCCTGTCTCCG

GGTAAATGA

SEQ ID NO: 10:
METDTLLLWVLLLWVPGSTG

QPYHGEKGISVPDHGFCQPISIPLCTDIAYNQTILPNLLGHTNQEDAGLEVHQFYPLVKVQCSPELRFFLCSMYAPV

CTVLDQAIPPCRSLCERARQGCEALMNKFGFQWPERLRCENFPVHGAGEICVGQNTSDGSGPGGGPTAYPTAPYL

AEPRSSDKTHTCPPCPAPEAEGAPSVFLFPPKPKDTLMISRTPEVTCVVVDVSHEDPEVKFNWYVDGVEVHNAKTKP

REEQYNSTYRVVSVLTVLHQDWLNGKEYKCAVSNKALPASIEKTISKAKGQPREPQVYTLPPSRDELTKNQVSLTCL

VKGFYPSDIAVEWESNGUENNYKTTPPVLDSDGSFFLYSKLTVDKSRWQQGNVFSCSVMHEALIINHYTQKSLSISP

GK are prepared with the use of the pUShFZD7crd-hFcm KI vector in accordance with the method described in the examples of WO 2006/78072.

Control chimeric mice into which no foreign cDNA expression unit has been inserted are prepared in accordance with the method described in the examples of WO 2006/78072.

Example 4

Preparation of USmFZD1crd-hFcm KI Chimeric Mouse

A pUSmFZD1crd-hFcm KI vector was prepared from mouse FZD1-cDNA (a 1,929-bp sequence comprising a region from an initiation codon to a termination codon; SEQ ID NO: 11) and human IgG1 Fc mutant-cDNA (SEQ ID NO: 3) in accordance with the method described in Example 1.

The mouse FZD1 signal sequence, a CRD (the cystein-rich-domain), and a region located downstream of a CRD comprising the 7-transmembrane domain in SEQ ID NO: 11 are marked by a single underline, a solid box, and a double underline, respectively, based on the information regarding the GenBank Accession Numbers: NM_021457.2 and NP_067432.2.

```
SEQ ID NO: 11:
ATGGCTGAGGAGGCGGCGCCTAGCGAGTCCCGGGCCGCCGGCCGGCTGAGCTTGGAACTTTGTGCCGAAGCACTCCC

GGGCCGGCGGGAGGAGGTGGGGCACGAGGACACGGCCAGCCACCGCCGCCCCCGGGCTGATCCCCGGCGTTGGGCTA

GCGGGCTGCTGCTGCTGCTTTGGTTGCTGGAGGCTCCTCTGCTTTTGGGGGTCCGAGCG

CAGGCGGCGGGCCAGGTATCCGGGCCGGGCCAGCAAGCCCCGCCGCCGCCCCAGCCCCAGCAGAGCGGGCAGCAGTA

CAACGGCGAACGGGGCATCTCCATCCCGGACCACGGCTACTGCCAGCCCATCTCCATCCCGCTGTGCACGGACATCG

CGTACAACCAGACCATCATGCCCAACCTGCTGGGCCACACGAATCAGGAGGACGCCGGTCTGGAGGTGCACCAGTTC

TACCCTCTGGTGAAGGTGCAGTGCTCCGCCGAGCTCAAGTTCTTCCTGTGCTCCATGTACGCGCCTGTGTGCACCGT

ACTGGAGCAGGCGCTACCGCCCTGCCGCTCCCTGTGCGAGCGCGCACGCCAGGGCTGCGAGGCGCTCATGAACAAGT

TCGGCTTCCAGTGGCCAGACACACTCAAGTGCGAGAAGTTCCCGGTGCACGGCGCAGGAGAGCTGTGCGTGGGCCAG

AACACGTCCGACAAAGGCACCCCAACTCCCTCCTTGCTACCAGAGTTCTGGACCAGTAATCCGCAGCAC

GGCGGCGGTGGTTACCGCGGCGGCTACCCGGGGGGTGCCGGGACGGTGGAGCGGGGAAAGTTCTCCTGCCCGCGCGC

CCTCAGGGTGCCCTCCTACCTCAACTACCACTTTCTGGGGGAGAAGGACTGCGGCGCACCCTGCGAACCCACCAAGG

TTTACGGGCTCATGTACTTCGGGCCAGAGGAGCTGCGCTTCTCGCGCACCTGGATAGGCATCTGGTCCGTGCTGTGC

TGCGCCTCCACGCTCTTCACGGTGCTCACGTACCTAGTGGACATGCGGCGCTTCAGCTACCCGGAACGGCCCATCAT

TTTCCTGTCCGGCTGTTACACAGCGGTGGCGGTGGCCTACATCGCTGGCTTTCTGTTGGAGGACCGGGTGGTGTGCA

ACGACAAGTTTGCAGAGGACGGGGCGCGCACGGTGGCGCAGGGCACTAAGAAAGAAGGCTGCACTATACTCTTTATG

ATGCTCTACTTCTTCAGCATGGCCAGCTCCATCTGGTGGGTGATCCTGTCCCTCACCTGGTTCCTGGCAGCCGGCAT

GAAGTGGGGCCACGAAGCCATCGAGGCCAACTCACAGTATTTCCATTTAGCCGCCTGGGCTGTGCCAGCCATCAAAA

CTATAACCATCTTGGCGTTGGGCCAGGTGGATGGCGACGTACTGAGCGGAGTGTGTTTTGTGGGGCTCAACAACGTG

GACGCACTGCGTGGCTTTGTGCTGGCGCCTCTCTTCGTTTATCTGTTCATTGGCACTTCTTTCCTGCTGGCCGGTTT

CGTGTCACTCTTCCGCATCCGCACCATCATGAAGCATGACGGCACCAAGACAGAGAAGCTGGAGAAGCTCATGGTGC

GCATCGGAGTCTTCAGTGTCCTCTACACTGTGCCGGCCACCATCGTCATCGCCTGCTACTTCTATGAACAGGCCTTT

CGGGACCAGTGGGAGCGCAGCTGGGTGGCCCAGAGCTGCAAGAGTTATGCCATCCCTTGCCCTCACCTCCAGGGAGG

TGGAGGAGTCCCACCACACCCGCCCATGAGCCCAGACTTTACAGTCTTCATGATCAAGTATCTCATGACGCTGATTG

TGGGCATCACATCGGGCTTCTGGATCTGGTCCGGCAAGACACTGAATTCCTGGAGGAAGTTCTACACGAGGCTTACC

AACAGCAAACAGGGGGAGACTACCGTCTGA
```

The amino acid sequence encoded by SEQ ID NO: 11 (642 amino acids, SEQ ID NO: 12) is shown below.

represents hFcm) and the amino acid sequence encoded by the cDNA (SEQ ID NO: 14; 430 amino acids; wherein the region marked by a single underline represents the mouse Igκ signal sequence, the region marked by a solid box represents the mouse Frizzled 1 extracellular cysteine-rich domain, and the region marked by a double underline represents hFcm) are shown below. Information regarding the mouse Igκ signal sequence containing an intron region was obtained from the UCSC mouse genome database as the genome sequence located upstream of MUSIGKVR1 obtained from the GenBank (Accession Number: K02159).

```
SEQ ID NO: 12:
MAEEAAPSESRAAGRLSLELCAEALPGRREEVGHEDTASHRRPRADPRRWASGLLLLLWLLEAPLLLGVRA

QAAGQVSGPGQQAPPPPQPQQSGQQYNGERGISIPDHGYCQPISIPLCTDIAYNQTIMPNLLGHTNQEDAGLEVHQF

YPLKVQCSAELKFFLCSMYAPVCTVLEQALPPCRSLCERARQGCEALMNKFGFQWPDTLKCEKFPVHGAGELCVGQ

NTSDKGTPTPSLLPEFWTSNPQH

GGGGYRGGYPGGAGTVERGICFSCPRALRVPSYLNYHFLGEKDCGAPCEPTKVYGLMYFGPEELRFSRTIVIGIWSVLC

CASTLFTVLTYLVDMRRFSYPERPIIFLSGCYTAVAVAYIAGFLLEDRVVCNDKFAEDGARTVAQGTKKEGCTILFM

MLYFFSMASSIWWVILSLTWFLAAGNIKKHEAIRANSQYFHLAAWAVPAIKTITILALGQVDGDVLSGVCFVGLNNV

DALRGFVLAPLFVYLFIGTSFLLAGFVSLFRIRTIEHDGTKTEICLEKLMVRIGVFSVLYTVPATIVIACYFYEQAF

RDQWERSWVAQSCKSYAIPCPHLQGGGGVPPHPPMSPDFTVFMIKYLMTLIVGITSGFEWSGKTLNSWRKFYTRLT

NSKQGETTV
```

A polynucleotide sequence comprising a region from the initiation codon to the termination codon of the pUSmFZD1crd-hFcm KI vector expression unit (SEQ ID NO: 13; a 1,534-bp sequence comprising a mouse Igκ signal sequence containing an intron region (a region marked by a single underline) substituted with the mouse FZD1 signal sequence and the mouse FZD1crd-hFcm sequence located downstream thereof; wherein the region marked by a solid box represents the mouse Frizzled 1 extracellular cysteine-rich domain and the region marked by a double underline

```
SEQ ID NO: 13:
ATGGAGACAGACACACTCCTGTTATGGGTACTGCTGCTCTGGGTTCCAGGTGAGAGTGCAGAGAAGTGTTGGATGCA

ACCTCTGTGGCCATTATGATACTCCATGCCTCTCTGTTCTTGATCACTATAATTAGGGCATTTGTCACTGGTTTTAA

GTTTCCCCAGTCCCCTGAATTTTCCATTTTCTCAGAGTGATGTCCAAAATTATTCTTAAAAATTTAAATAAAAAGGT

CCTCTGCTGTGAAGGCTTTTATACATATATAACAATAATCTTTGTGTTTATCATTCCAGGTTCCACTGGC

CAGGCGGCGGGCCAGGTATCCGGGCCGGGCCAGCAAGCCCCGCCGCCGCCCCAGCCCCAGCAGAGCGGGCAGCAGTA

CAACGGCGAACGGGGCATCTCCATCCCGGACCACGGCTACTGCCAGCCCATCTCCATCCCGCTGTGCACGGACATCG

CGTACAACCAGACCATCATGCCCAACCTGCTGGGCCACACGAATCAGGAGGACGCCGGTCTGGAGGTGCACCAGTTC

TACCCTCTGGTGAAGGTGCAGTGCTCCGCCGAGCTCAAGTTCTTCCTGTGCTCCATGTACGCGCCTGTGTGCACCGT

ACTGGAGCAGGCGCTACCGCCCTGCCGCTCCCTGTGCGAGCGCGCACGCCAGGGCTGCGAGGCGCTCATGAACAAGT

TCGGCTTCCAGTGGCCAGACACACTCAAGTGCGAGAAGTTCCCGGTGCACGGCGCAGGAGAGCTGTGCGTGGGCCAG

AACACGTCCGACAAAGGCACCCCAACTCCCTCCTTGCTACCAGAGTTCTGGACCAGTAATCCGCAGCAC

GCCGAGCCTAGGTCTTCAGACAAAACTCACACATGCCCACCGTGCCCAGCACCTGAAGCCGAGGGGCCCCGTCAGT

CTTCCTCTTCCCCCCAAAACCCAAGGACACCCTCATGATCTCCCGGACCCCTGAGGTCACATGCGTGGTGGTGGACG

TGAGCCACGAAGACCCTGAGGTCAAGTTCAACTGGTACGTGGACGGCGTGGAGGTGCATAATGCCAAGACAAAGCCG

CGGGAGGAGCAGTACAACAGCACGTACCGTGTGGTCAGCGTCCTCACCGTCCTGCACCAGGACTGGCTGAATGGCAA

GGAGTACAAGTGCGCCGTCTCCAACAAAGCCCTCCCAGCCTCCATCGAGAAAACCATCTCCAAAGCCAAAGGGCAGC

CCCGAGAACCACAGGTGTACACCCTGCCCCCATCCCGGGATGAGCTGACCAAGAACCAGGTCAGCCTGACCTGCCTG

GTCAAAGGCTTCTATCCCAGCGACATCGCCGTGGAGTGGGAGAGCAATGGGCAGCCGGAGAACAACTACAAGACCAC

GCCTCCCGTGCTGGACTCCGACGGCTCCTTCTTCCTCTACAGCAAGCTCACCGTGGACAAGAGCAGGTGGCAGCAGG
```

-continued

GGAACGTCTTCTCATGCTCCGTGATGCATGAGGCTCTGCACAACCACTACACGCAGAAGAGCCTCTCCCTGTCTCCG

GGTAAATGA

SEQ ID NO: 14:
METDTLLLWVLLLWVPGSTG

QAAGQVSGPGQQAPPPPQPQQSGQQYNGERGISIPDHGYCQPISIPLCTDIAYNQTIMPNLLGHTNQEDAGLEVHQF

YPLKVQCSAELKFFLCSMYAPVCTVLEQALPPCRSLCERARQGCEALMNKFGFQWPDTLKCEKFPVHGAGELCVGQ

NTSDKGTPTPSLLPEFWTSNPQH

AEPESSDKTHTCPPCPAPEAEGAPSVFLFPPKPKDTLMISRTPEVTCVVVDVSHEDPEVKFHWYVDGVEVIINAKTKP

REEQEYNSTYRVVSVLTVLHQDVINGKEYKCAVSNKALPASIEKTISKAKGQPREPQVYTLPPSRDELTKNQVSLTCL

VKGFYPSDIAVEWESNGQPENNYKTTPPVLDSDGSFFLYSKLTVDKSRWQQGNVFSCSVMHEALHNHYTQKSLSLSP

GK

The USmFZD1crd-hFcm KI chimeric mice expressing a fusion protein of the mouse Frizzled 1 extracellular cysteine-rich domain and human Fcm in a B-cell-specific manner are prepared with the use of the pUSmFZD1crd-hFcm KI vector in accordance with the method described in the examples of WO 2006/78072.

Further, control chimeric mice used in Example 5 below were prepared in accordance with the method described in the examples of WO 2006/78072.

Example 5

Analysis of USmFZD1crd-hFcm KI Chimeric Mouse 5-1. Necropsy Finding

The chimeric mice prepared in Example 4 were subjected to necropsy at age of 16 weeks, and the spleen, the liver, the kidney, the adrenal gland, the stomach, the small intestine, the appendix, the large intestine, the pancreas, the mesenteric lymph node, the female/male reproductive organ, the thymic gland, the lung, the heart, the brain, the muscle, the skin, the femur, the sternum, the cranium, the spondylus, and the costa were observed. As a result, whitening of the femur, whitening of the sternum, whitening and hardening of the cranium, hardening of the spondylus, and hardening of the costa were observed as characteristic changes in the USmFZD1crd-hFcm KI chimeric mice compared with the control mice. The number of mice exhibiting changes is described below.

5-1-1. Femur

Whitening was observed more significant in 10 of the 20 USmFZD1crd-hFcm KI chimeric mice subjected to necropsy compared with 10 control mice.

5-1-2. Sternum

Whitening was observed more significant in 18 mice among the 20 USmFZD1crd-hFcm KI chimeric mice subjected to necropsy compared with 10 control mice.

5-1-3. Cranium

Whitening was observed more significant in 19 mice and hardening was observed more significant in 13 mice among the 20 USmFZD1crd-hFcm KI chimeric mice subjected to necropsy compared with 10 control mice.

5-1-4. Spondylus

Hardening was observed more significant in 10 mice among the 20 USmFZD1crd-hFcm KI chimeric mice subjected to necropsy compared with 10 control mice.

5-1-5. Costa

Hardening was observed more significant in 7 mice among the 20 USmFZD1crd-hFcm KI chimeric mice subjected to necropsy compared with 10 control mice.

The above results demonstrate that whitening of the femur, whitening of the sternum, whitening and hardening of the cranium, hardening of the spondylus, and hardening of the costa may have been induced by overexpression of the mouse FZD1 extracellular cysteine-rich domain-human Fc mutant fusion constructs.

5-2. Analysis of X-ray Photograph of Tibia

Figure 6:
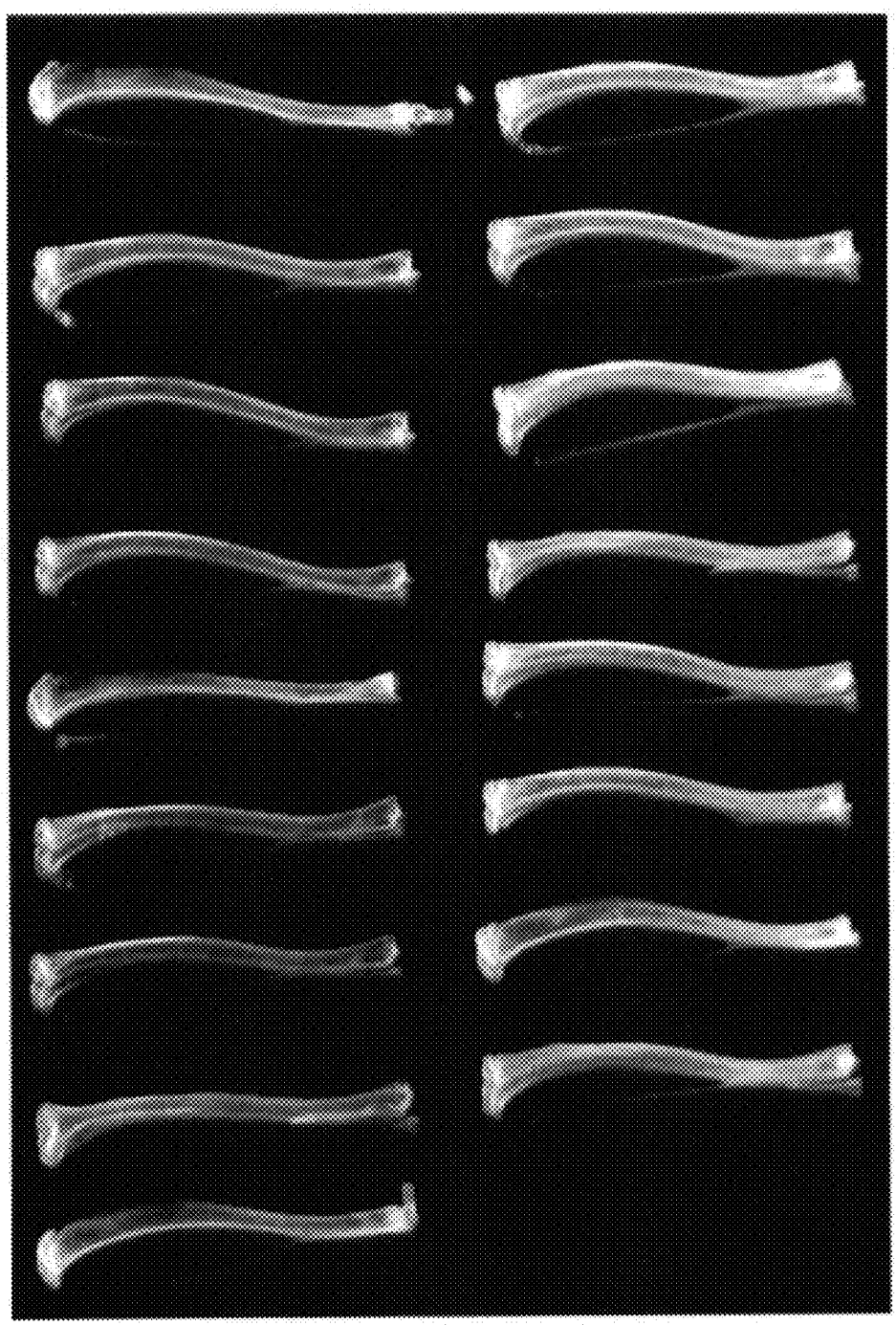
FIG. 6 shows a X-ray photograph of the tibiae of the 16-week-old female (♀) USmFZD1crd-hFcm KI chimeric mouse (lower portion) and the female (♀) control mouse (upper portion).
Figure 7:
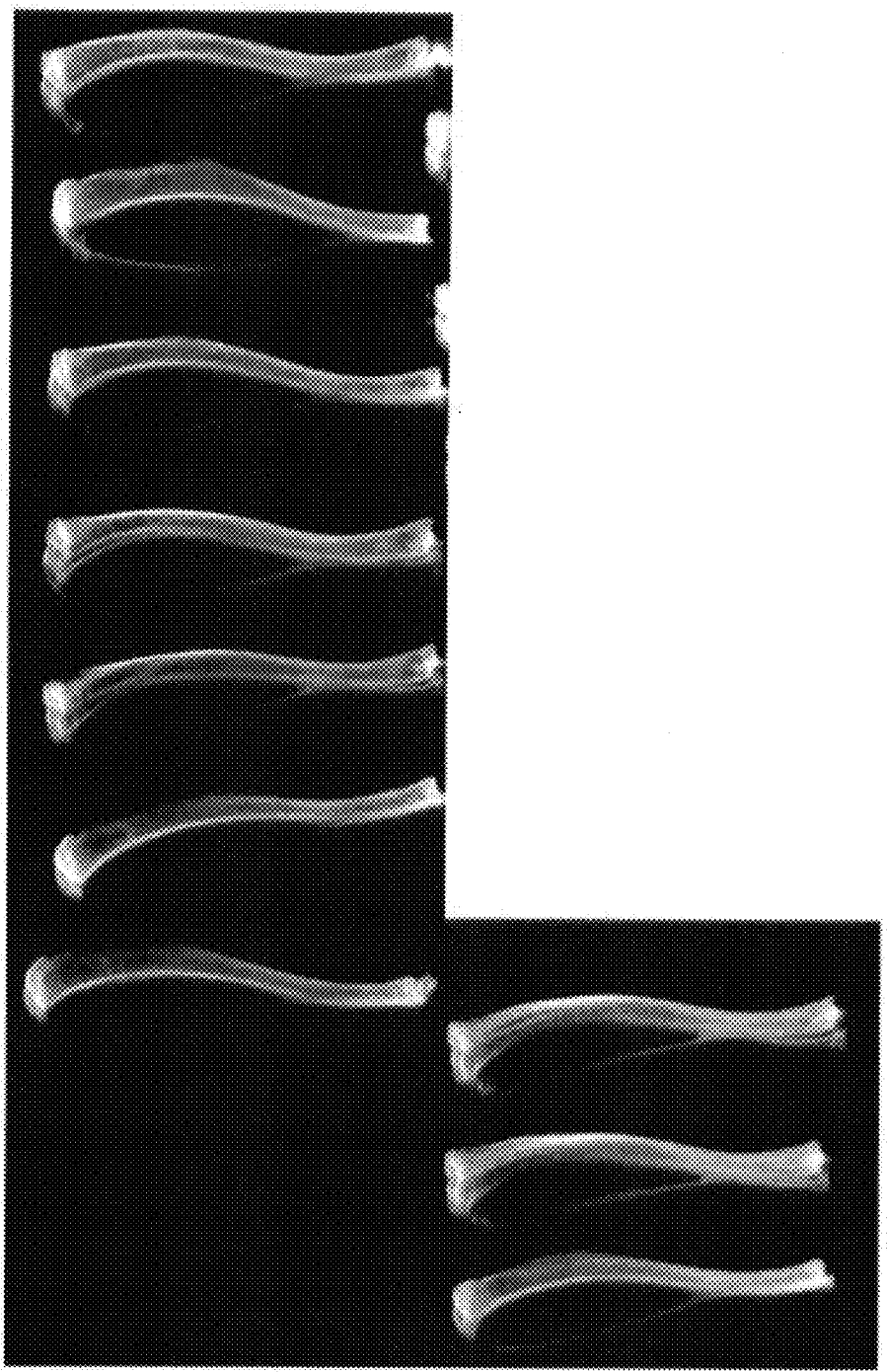
FIG. 7 shows a X-ray photograph of the tibiae of the 16-week-old male (♂) USmFZD1crd-hFcm KI chimeric mouse (lower portion) and the male (♂) control mouse (upper portion).

X-ray photographs (µFX-1000, FUJIFILM) of tibiae obtained from the 16-week-old control chimeric mice (9 female mice and 7 male mice) and the USmFZD1crd-hFcm KI chimeric mice (8 female mice and 3 male mice) were obtained (FIGS. 6 and 7).

In the obtained X-ray photographs of tibiae, whitening was more advanced in both female and male USmFZD1crd-hFcm KI chimeric mice compared with control mice.

The above results demonstrate that whitening of the tibia may have been induced by overexpression of mouse FZD1 extracellular cysteine-rich domain-human Fc mutant fusion constructs.

5-3. Blood Cell Analysis

Seventeen 8-week-old USmFZD1crd-hFcm KI female chimeric mice, three 8-week-old USmFZD1crd-hFcm KI male chimeric mice, twenty one 8-week-old female control mice and four 8-week-old male control mice, seventeen 15-week-old USmFZD1crd-hFcm KI female chimeric mice and three 15-week-old USmFZD1crd-hFcm KI male chimeric mice, and seventeen 15-week-old female control mice and four 15-week-old male control mice were subjected to orbital blood sampling using a glass capillary under ether anesthesia to analyze the blood cell components with the use of ADVIA120 (Bayer Medical Ltd.) (blood cell components; erythrocyte counts, hemoglobin, hematocrit, MCH, MCHC, reticulocyte counts, leukocyte counts, blood platelet counts, lymphocyte counts, neutrophil counts, monocyte counts, eosinophil counts, and basophil counts). As a result, the values obtained with the use of the USmFZD1crd-hFcm KI chimeric mice were not significantly different from those of the control mice at ages of 8 and 15 weeks.

5-4. Pathological Finding

Figure 8:
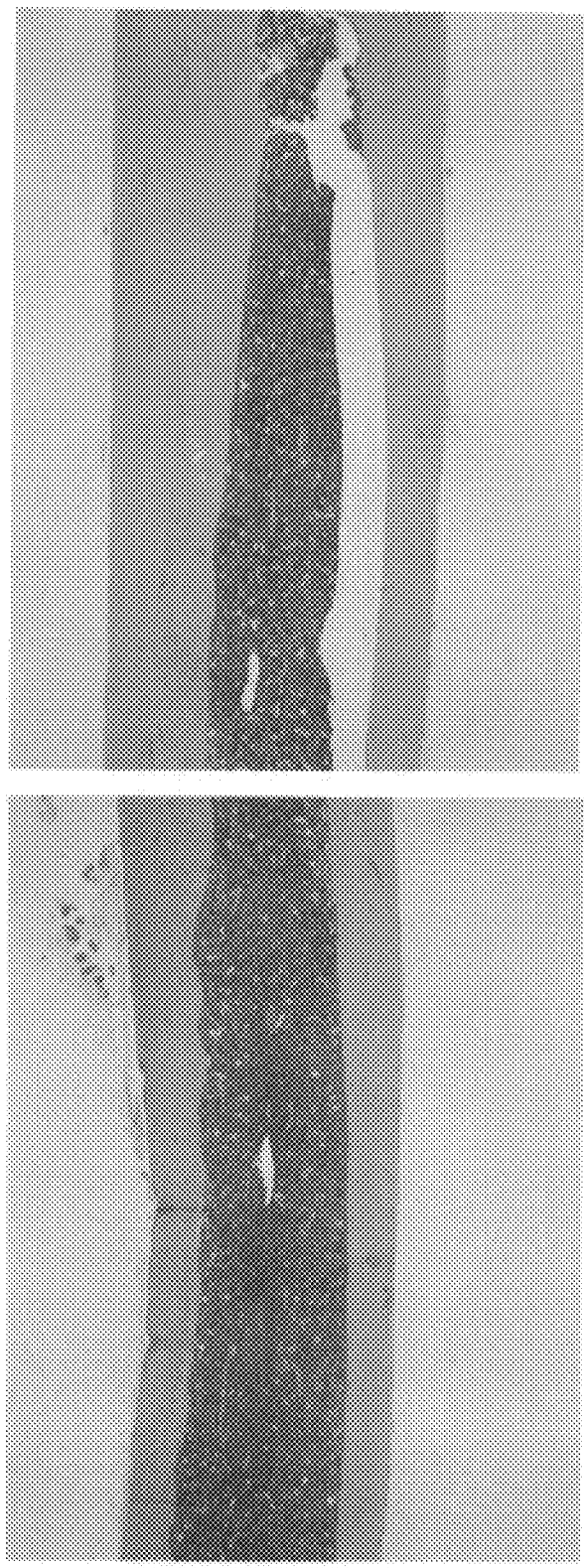
FIG. 8 shows images of H&E stained pathological sections obtained from the femoral diaphyses of the 16-week-old USmFZD1crd-hFcm KI chimeric mouse (right diagram) and the control mouse (left diagram).
Figure 10:
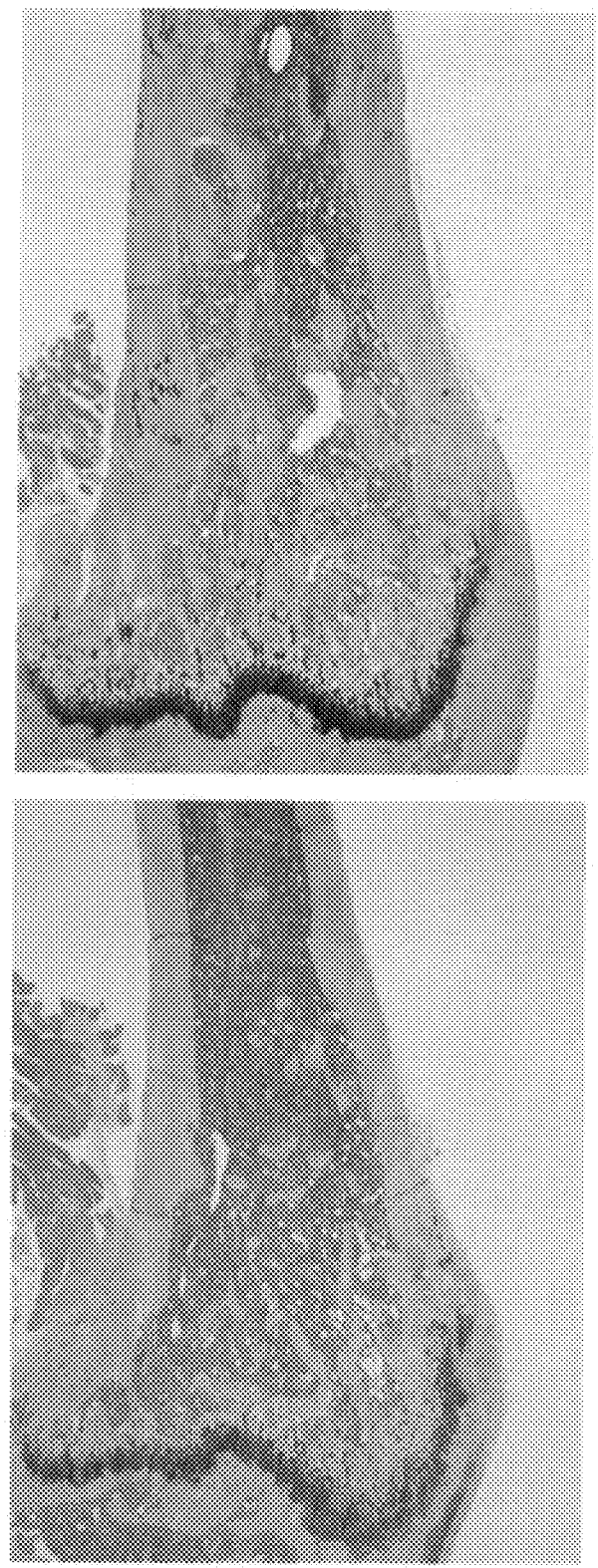
FIG. 10 shows images of H&E stained pathological sections of the proximal femoral growth plates of the 16-week-old USmFZD1crd-hFcm KI chimeric mouse (right diagram) and the control mouse (left diagram).
Figure 11:
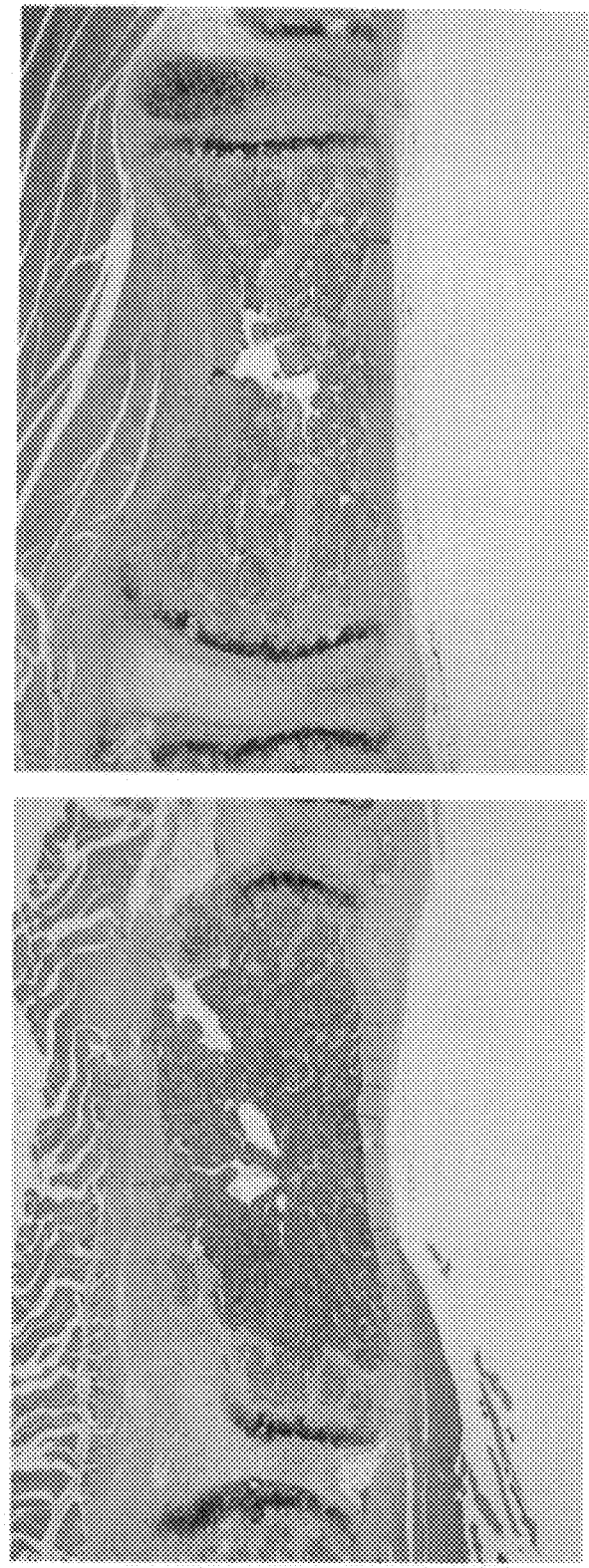
FIG. 11 shows images of H&E stained pathological sections of the sternums of the 16-week-old USmFZD1crd-hFcm KI chimeric mouse (right diagram) and the control mouse (left diagram).

H&E stained pathological sections of the liver, the kidney, the heart, the lung, the spleen, the thymic gland, the mesenteric lymph node, the pancreas, the brain, the adrenal gland, the spermary (in the case of male mice), the ovary (in the case of female mice), the femur, the sternum, the stomach, the duodenum, the jejunum, the ileum, the appendix, the colon, the spinal cord, the aorta, the skeletal muscle, and the skin obtained from nine 16-week-old control chimeric mice and twenty USmFZD1crd-hFcm KI chimeric mice were observed. As a result, the thickened femoral diaphyseal wall (FIGS. 8 and 9, Table 1), the increased cancellous bone (FIG. 10), and the increased sternal cancellous bone (FIG. 11) were observed as characteristic changes in the USmFZD1crd-hFcm KI chimeric mice compared with the control mouse. The number of mice exhibiting changes is described below.

of 16-week-old USmFZD1crd-hFcm KI chimeric mice (17 female mice and 3 male mice) were detected via ELISA.

In order to assay the concentration of the fusion protein of the FZD1 extracellular cysteine-rich domain and the human Fc mutant in the serum via ELISA, a test sample or a control sample (Recombinant Mouse Frizzled-7/Fc Chimera, R & D Systems, Product Number: 198-FZ; notes: this assay system is a sandwich ELISA system involving the use of an antibody recognizing an Fc region, and use of the mouse Frizzled-7/Fc chimera as a control sample is not considered problematic if expression could be confirmed) was applied to a 96-well plate (Maxi Soap, Corning) on which anti-Human IgG (γ-Chain Specific, SIGMA, Product Number:

TABLE 1

| Genes | Mouse No.. | Minimum diaphyseal wall thickness at site 30% away from proximal end (mm) | Average (mm) | Maximum diaphyseal wall thickness at site 50% away from proximal end (mm) | Average (mm) | Minimum diaphyseal wall thickness at site 50% away from proximal end (mm) | Average (mm) | Minimum diaphyseal wall thickness at site 80% away from proximal end (mm) | Average (mm) | Increased cancellous bone |
|---|---|---|---|---|---|---|---|---|---|---|
| Control | TAe1380 | 0.24 | 0.25 | 0.25 | 0.31 | 0.17 | 0.18 | 0.15 | 0.15 | – |
|  | TAe1383 | 0.25 |  | 0.37 |  | 0.19 |  | 0.15 |  | – |
| mFZD1crd-hFcm | USN-103FcA2 | 0.26 | 0.25 | 0.36 | 0.42 | 0.2 | 0.20 | 0.13 | 0.13 | – |
|  | USN-103FcA3 | 0.28 |  | 0.45 |  | 0.24 |  | 0.16 |  | ± |
|  | USN-103FcA4 | 0.24 |  | 0.33 |  | 0.2 |  | 0.09 |  | – |
|  | USN-103FcB11 | 0.22 |  | 0.46 |  | 0.18 |  | 0.13 |  | ++ |
|  | USN-103FcB14 | 0.24 |  | 0.4 |  | 0.21 |  | 0.14 |  | + |
|  | USN-103FcB16 | 0.24 |  | 0.46 |  | 0.18 |  | 0.16 |  | + |
|  | USN-103FcB19 | 0.25 |  | 0.5 |  | 0.22 |  | 0.07 |  | + |

Measurement of femoral diaphyseal wall thickness and finding on cancellous bone of 16-week-old USmFZD1crd-hFcm KI chimeric mice and control mice (cross-section)

5-4-1. Femur

Figure 9:
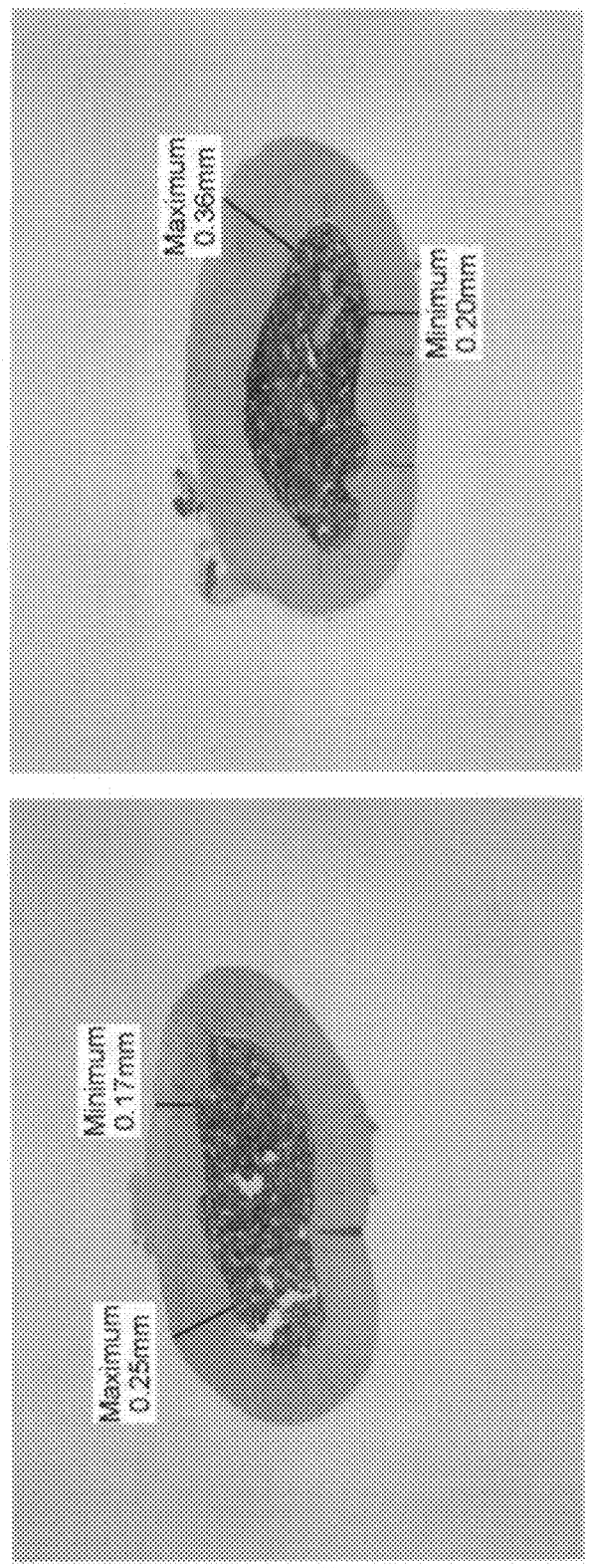
FIG. 9 shows images of H&E stained pathological sections obtained from the femurs (at a site 50% away from the proximal end) of the 16-week-old USmFZD1crd-hFcm KI chimeric mouse (right diagram) and the control mouse (left diagram).

In comparison with 9 control mice, the thickened diaphyseal wall was observed in 11 mice and the increased cancellous bone was observed in 15 mice among the 20 USmFZD1crd-hFcm KI chimeric mice subjected to necropsy. Further, transected sections obtained from 3 femoral sites (i.e., sites 30%, 50%, and 80% away from the proximal end) were subjected to measurement of the diaphyseal wall thickness using samples obtained from 7 USmFZD1crd-hFcm KI chimeric mice and 2 control mice. As a result, the maximum wall thickness of the site 50% away from the proximal end thereof was found to be larger than that of control mice (FIG. 9, Table 1). Also, an increase was observed in the cancellous bone at the site 80% away from the end in 5 of the 7 mice (Table 1).

5-4-2. Sternum

An increase in the cancellous bone was observed more significant in 14 mice among the 20 USmFZD1crd-hFcm KI chimeric mice subjected to necropsy compared with 9 control mice.

No significant changes were observed in organs or tissues other than bones compared with control mice.

The above results demonstrate that the thickened femoral diaphyseal wall, the increased cancellous bone, and the increased sternal cancellous bone may have been induced by overexpression of the mouse FZD1 extracellular cysteine-rich domain-human Fc mutant fusion constructs.

5-5. ELISA Assay Using Serum Sample Aimed at Confirmation of Expression of Fusion Protein of Mouse FZD1 Extracellular Cysteine-rich Domain and Human Fc Mutant in USmFZD1crd-hFcm KI Chimeric Mouse Fusions of the mouse FZD1 extracellular cysteine-rich domain and the human Fc mutant existing in the blood sera I3382) has been immobilized, incubation was carried out at room temperature for 30 minutes, the plate was washed three times with T-PBS(−), peroxidase-labelled antibodies (anti-Human IgG (Fc fragment) peroxidase conjugates developed in goat, Product Number: A0170, SIGMA) were added, and incubation was then carried out at room temperature for 30 minutes. Thereafter, the plate was washed four times with T-PBS(−), a color was developed using a Sumilon peroxidase color-developing kit (Product Number: ML-1120T, Sumitomo Bakelite Co. Ltd.), and the absorbance at 450 nm was assayed to determine the concentration in the serum.

As a result, the average concentration among 17 female mice was 298.4 μg/ml, that among 3 male mice was 308.8 μg/ml (both values are references), and the concentrations assayed with the use of the serum samples obtained from 5 female control mice and a male control mouse were lower than the detection limit.

The above results suggest that the fusion protein of the mouse FZD1 extracellular cysteine-rich domain and the human Fc mutant is expressed in vivo and circulated in the blood.

Example 6

Preparation of UShFZD1crd-hFcm KI Chimeric Mouse

A pUShFZD7crd-hFcm KI vector was prepared from human FZD1-cDNA (SEQ ID NO: 15) and human IgG1 Fc mutant-cDNA (SEQ ID NO: 3) in accordance with the method described in Example 1.

The human FZD1 signal sequence, a CRD (the cystein-rich-domain), and a region located downstream of a CRD comprising the 7-transmembrane domain in SEQ ID NO: 15 are marked by a single underline, a solid box, and a double underline, respectively, based on the information regarding the GenBank Accession Numbers: NM_003505.1 and NP_003496.1.

```
SEQ ID NO: 15:
ATGGCTGAGGAGGAGGCGCCTAAGAAGTCCCGGGCCGCCGGCGGTGGCGCGAGCTGGGAACTTTGTGCCGGGGCGCT

CTCGGCCCGGCTGGCGGAGGAGGGCAGCGGGGACGCCGGTGGCCGCCGCCGCCCGCCAGTTGACCCCCGGCGATTGG

CGCGCCAGCTGCTGCTGCTGCTTTGGCTGCTGGAGGCTCCGCTGCTGCTGGGGGTCCGGGCC
```

```
CAGGCGGCGGGCCAGGGGCCAGGCCAGGGGCCCGGGCCGGGGCAGCAACCGCCGCCGCCGCCTCAGCAGCAACAGAG

CGGGCAGCAGTACAACGGCGAGCGGGGCATCTCCGTCCCGGACCACGGCTATTGCCAGCCCATCTCCATCCCGCTGT

GCACGGACATCGCGTACAACCAGACCATCATGCCCAACCTGCTGGGCCACACGAACCAGGAGGACGCGGGCCTGGAG

GTGCACCAGTTCTACCCTCTAGTGAAAGTGCAGTGTTCCGCTGAGCTCAAGTTCTTCCTGTGCTCCATGTACGCGCC

CGTGTGCACCGTGCTAGAGCAGGCGCTGCCGCCCTGCCGCTCCCTGTGCGAGCGCGCGCGCCAGGGCTGCGAGGCGC

TCATGAACAAGTTCGGCTTCCAGTGGCCAGACACGCTCAAGTGTGAGAAGTTCCCGGTGCACGGCGCCGGCGAGCTG

TGCGTGGGCCAGAACACGTCCGACAAGGGCACCCCGACGCCCTCGCTGCTTCCAGAGTTCTGGACCAGCAACCCTCA
```

```
GCAC
```

```
GGCGGCGGAGGGCACCGTGGCGGCTTCCCGGGGGGCGCCGGCGCGTCGGAGCGAGGCAAGTTCTCCTGCCCGCGCGC

CCTCAAGGTGCCCTCCTACCTCAACTACCACTTCCTGGGGGAGAAGGACTGCGGCGCACCTTGTGAGCCGACCAAGG

TGTATGGGCTCATGTACTTCGGGCCCGAGGAGCTGCGCTTCTCGCGCACCTGGATTGGCATTTGGTCAGTGCTGTGC

TGCGCCTCCACGCTCTTCACGGTGCTTACGTACCTGGTGGACATGCGGCGCTTCAGCTACCGGAGCGGCCCATCAT

CTTCTTGTCCGGCTGTTACACGGCCGTGGCCGTGGCCTACATCGCCGGCTTCCTCCTGGAAGACCGAGTGGTGTGTA

ATGACAAGTTCGCCGAGGACGGGGCACGCACTGTGGCGCAGGGCACCAAGAAGGAGGGCTGCACCATCCTCTTCATG

ATGCTCTACTTCTTCAGCATGGCCAGCTCCATCTGGTGGGTGATCCTGTCGCTCACCTGGTTCCTGGCGGCTGGCAT

GAAGTGGGGCCACGAGGCCATCGAAGCCAACTCACAGTATTTTCACCTGGCCGCCTGGGCTGTGCCGGCCATCAAGA

CCATCACCATCCTGGCGCTGGCCAGGTGGACGGCGATGTGCTGAGCGGAGTGTGCTTCGTGGGCTTAACAACGTG

GACGCGCTGCGTGGCTTCGTGCTGGCGCCCCTCTTCGTGTACCTGTTTATCGGCACGTCCTTTCTGCTGGCCGGCTT

TGTGTCGCTCTTCCGCATCCGCACCATCATGAAGCACGATGGCACCAAGACCGAGAAGCTGGAGAAGCTCATGGTGC

GCATTGGCGTCTTCAGCGTGCTGTACACTGTGCCAGCCACCATCGTCATCGCCTGCTACTTCTACGAGCAGGCCTTC

CGGGACCAGTGGGAACGCAGGTGGGTGGCCCAGAGCTGCAAGAGCTACGCTATCCCCTGCCCTCACCTCCAGGCGGG

CGGAGGCGCCCCGCCGCACCCGCCCATGAGCCCGGACTTCACGGTCTTCATGATTAAGTACCTTATGACGCTGATCG

TGGGCATCACGTCGGGCTTCTGGATCTGGTCCGGCAAGACCCTCAACTCCTGGAGGAAGTTCTACACGAGGCTCACC

AACAGCAAACAAGGGGAGACTACAGTCTGA
```

The amino acid sequence encoded by SEQ ID NO: 15 (574 amino acids, SEQ ID NO: 16) is shown below.

```
SEQ ID NO: 16:
MAEEEAPKKSRAAGGGASWELCAGALSARLAEEGSGDAGGRRRPPVDPRRLARQLLLLLWLLEAPLLLGVRA
```

```
QAAGQGPGQGPGPGQQPPPPPQQQQSGQQYNGERGISVPDHGYCQPISIPLCTDIAYNQTIMPNLLGHTNQEDAGLE

VHQFYPLVKVQCSAELKFFLCSMYAPVCTVLEQALPPCRSLCERARQGCEALMNKFGFQWPDTLKCEKFPVHGAGEL
```

```
CVGQNTSDKGTPTPSLLPEFWTSNPQH
```

```
GGGGHRGGFPGGAGASERGKFSCPRALKVPSYLNYHFLGEKDCGAPCEPTKVYGLMYFGPEELRFSRTWIGIWSVLC
```

-continued

CASTLFTVLTYLVDMRRFSYPERPIIFLSGCYTAVAVAYIAGFLLEDRVVCNDKFAEDGARTVAQGTKKEGCTILFM

MLYFFSMASSIWWVILSLTWFLAAGMKWGHEATEANSQYFHLAAWAVPAIKTITILALGQVDGDVLSGVCFVGLNNV

DALRGFVLAPLFVYLFIGTSFLLAGFVSLFRIRTIKKHDGTKTEKLEKLMVRIGVFSVLYTYPATIVIACYFYEQAF

RDQWERSWVAQSCKSYAIPCPHLQAGGGAPPHPPMSPDFTVFMIKYLMTLIVGITSGFWIWSGKTLNSWRKFYTRLT

NSKQGETTV

A polynucleotide sequence comprising a region from the initiation codon to the termination codon of the pUShFZD1crd-hFcm KI vector expression unit (SEQ ID NO: 17; a 1,546-bp sequence comprising a mouse Igκ signal sequence containing an intron region (a region marked by a single underline) substituted with the human FZD1 signal sequence and the human FZD1crd-hFcm sequence located downstream thereof; wherein the region marked by a solid box represents the human Frizzled 1 extracellular cysteine-rich domain and the region marked by a double underline represents hFcm) and the amino acid sequence encoded by the cDNA (SEQ ID NO: 18; a sequence comprising 434 amino acids; wherein the region marked by a single underline represents the mouse Igκ signal sequence, the region marked by a solid box represents the human Frizzled 1 extracellular cysteine-rich domain, and the region marked by a double underline represents hFcm) are shown below. Information regarding the mouse Igκ signal sequence containing an intron region was obtained from the UCSC mouse genome database as the genome sequence located upstream of MUSIGKVR1 obtained from the GenBank (Accession Number: K02159).

SEQ ID NO: 17:
ATGGAGACAGACACACTCCTGTTATGGGTACTGCTGCTCTGGGTTCCAGGTGAGAGTGCAGAGAAGTGTTGGATGCA

ACCTCTGTGGCCATTATGATACTCCATGCCTCTCTGTTCTTGATCACTATAATTAGGGCATTTGTCACTGGTTTTAA

GTTTCCCCAGTCCCCTGAATTTTCCATTTTCTCAGAGTGATGTCCAAAATTATTCTTAAAAATTTAAATAAAAAGGT

CCTCTGCTGTGAAGGCTTTTATACATATATAACAATAATCTTTGTGTTTATCATTCCAGGTTCCACTGGC

| CAGGCGGCGGGCCAGGGGCCAGGCCAGGGGCCCGGGCCGGGGCAGCAACCGCCGCCGCCGCCTCAGCAGCAACAGAG |

| CGGGCAGCAGTACAACGGCGAGCGGGGCATCTCCGTCCCGGACCACGGCTATTGCCAGCCCATCTCCATCCCGCTGT |

| GCACGGACATCGCGTACAACCAGACCATCATGCCCAACCTGCTGGGCCACACGAACCAGGAGGACGCGGGCCTGGAG |

| GTGCACCAGTTCTACCCTCTAGTGAAAGTGCAGTGTTCCGCTGAGCTCAAGTTCTTCCTGTGCTCCATGTACGCGCC |

| CGTGTGCACCGTGCTAGAGCAGGCGCTGCCGCCCTGCCGCTCCCTGTGCGAGCGCGCGCGCCAGGGCTGCGAGGCGC |

| TCATGAACAAGTTCGGCTTCCAGTGGCCAGACACGCTCAAGTGTGAGAAGTTCCCGGTGCACGGCGCCGGCGAGCTG |

| TGCGTGGGCCAGAACACGTCCGACAAGGGCACCCCGACGCCCTCGCTGCTTCCAGAGTTCTGGACCAGCAACCCTCA |

| GCAC |

GCCGAGCCTAGGTCTTCAGACAAAACTCACACATGCCCACCGTGCCCAGCACCTGAAGCCGAGGGGCCCCGTCAGT

CTTCCTCTTCCCCCCAAAACCCAAGGACACCCTCATGATCTCCCGGACCCCTGAGGTCACATGCGTGGTGGTGGACG

TGAGCCACGAAGACCCTGAGGTCAAGTTCAACTGGTACGTGGACGGCGTGGAGGTGCATAATGCCAAGACAAAGCCG

CGGGAGGAGCAGTACAACAGCACGTACCGTGTGGTCAGCGTCCTCACCGTCCTGCACCAGGACTGGCTGAATGGCAA

GGAGTACAAGTGCGCCGTCTCCAACAAAGCCCTCCCAGCCTCCATCGAGAAAACCATCTCCAAAGCCAAAGGGCAGC

CCCGAGAACCACAGGTGTACACCCTGCCCCCATCCCGGGATGAGCTGACCAAGAACCAGGTCAGCCTGACCTGCCTG

GTCAAAGGCTTCTATCCCAGCGACATCGCCGTGGAGTGGGAGAGCAATGGGCAGCCGGAGAACAACTACAAGACCAC

GCCTCCCGTGCTGGACTCCGACGGCTCCTTCTTCCTCTACAGCAAGCTCACCGTGGACAAGAGCAGGTGGCAGCAGG

GGAACGTCTTCTCATGCTCCGTGATGCATGAGGCTCTGCACAACCACTACACGCAGAAGAGCCTCTCCCTGTCTCCG

GGTAAATGA

SEQ ID NO: 18:
METDTLLLWVLLLWVPGSTG

QAAGQGPGQGPGPGQQPPPPPQQQQSGQQYNGERGISVPDHGYCQPISIPLCTDIAYNQTIMPNLLGHTNQEDAGLE

VHQFYPLVKVQCSAELKFFLCSMYAPVCTVLEQALPPCRSLCERARQGCEALMNKFGFQWPDTLKCEKFPVHGAGEL

CVGQNTSDKGTPTPSLLPEFWTSNPQH

AEPESSDKETCPPCPAPEAEGAPSVFLFPPKPKDTLMISRTPEVTCVVVDVSHEDPEVKFNWYVDGVEVIINAKTKP

REEQYNSTYRVVSVLTVLHQDIVLNGKEYKCAVSNKALPASIEKTISKAKGQPREPQVYTLPPSRDELTKNQVSLTCL

VKGFYPSDIAVEWESNGQPENNYECTTPPVLDSDGSFFLYSKLTVDKSRWQQGNVFSCSVMEALIMYTQKSLSLSP

GK

The UShFZD1crd-hFcm KI chimeric mice expressing a fusion protein of the human Frizzled 1 extracellular cysteine-rich domain and human Fcm in a B-cell-specific manner are prepared with the use of the pUShFZD1crd-hFcm KI vector in accordance with the method described in the examples of WO 2006/78072.

Control chimeric mice into which no foreign cDNA expression unit has been inserted are prepared in accordance with the method described in the examples of WO 2006/78072.

Example 7

Expression and Preparation of mFZD7crd-hFcm Recombinant 7-1. Construction of mFZD7crd-hFcm Recombinant Expression Vector
7-1-1. Construction of pLN1V5 Vector Sense oligo DNA (V5S) having the BamHI, NheI, and SalI sites at the 5' terminus and the XhoI site at the 3' terminus (a V5 tag and a stop codon) and corresponding antisense oligo DNA (V5AS) were synthesized.

V5S:
(SEQ ID NO: 50)
GATCCGCTAGCGTCGACGGTAAGCCTATCCCTAACCCTCTCCTCGGTCTC
GATTCTACGTGAC

V5AS:
(SEQ ID NO: 51)
TCGAGTCACGTAGAATCGAGACCGAGGAGAGGGTTAGGGATAGGCTTACC
GTCGACGCTAGCG

Oligo DNA synthesized above was introduced into the BamHI-XhoI site on the pLN1 vector described in the report of Kakeda et al. (Gene Ther., 12, 852-856, 2005) to construct the pLN1V5 vector.

7-1-2. Synthesis of mFZD7crd-hFcm DNA Fragment

088Fc_BHIkozakFw:
(SEQ ID NO: 52)
TAAAGGATCCCGGCCACCATGCGGGGCCCCGGCACGGCGG

088Fc_mFZD7G1SA_3 primer:
(SEQ ID NO: 53)
GTCTGAAGACCTAGGCTCGGCCAGGTAGGGAGCAGTAGGG G1SA_5primer:
(SEQ ID NO: 54)
GCCGAGCCTAGGTCTTCAGAC SalIG1SARev:
(SEQ ID NO: 55)
TAAAGTCGACTCATTTACCCGGAGACAGGG A reaction solution was prepared using Prime STAR HS DNA Polymerase (Takara Bio Inc., Japan) in accordance with the instructions, 10 pmol each primers shown in SEQ ID NOs: 52 and 53 and mouse FZD7 cDNA (SEQ ID NO: 1) as a template were added to 50 µl of the reaction solution, the resultant was incubated at 98° C. for 1 minute, an amplification cycle of 98° C. for 10 seconds, 57° C. for 5 seconds, and 72° C. for 2 minutes was repeated 20 times, and the resulting 594-bp amplified fragment was separated and recovered with 0.8% gel. The amplified fragment (BamHI mFZD7crd hFcm) was recovered from the gel using the QIAquick Gel Extraction Kit (Qiagen, Japan) in accordance with the instructions.

Similarly, a reaction solution was prepared using Prime STAR HS DNA Polymerase (Takara Bio Inc., Japan) in accordance with the instructions, 10 pmol each primers shown in SEQ ID NOs: 54 and 55 and hFcm cDNA (SEQ ID NO: 3) as a template were added to 50 µl of the reaction solution, the resultant was incubated at 98° C. for 1 minute, an amplification cycle of 98° C. for 10 seconds, 57° C. for 5 seconds, and 72° C. for 2 minutes was repeated 20 times, and the resulting 712-bp amplified fragment was separated and recovered with 0.8% gel. The amplified fragment (hFcm SalI) was recovered from the gel using the QIAquick Gel Extraction Kit (Qiagen, Japan) in accordance with the instructions.

The amplified DNA fragments obtained via the two above PCR procedures (i.e., BamHI mFZD7 hFcm and hFcm SalI) were added to the PrimeSTAR buffer to bring the total amount to 100 µl, the solution was heated at 100° C. for 10 minutes, and the temperature was reduced to room temperature, followed by annealing of the hFcm region. Thereafter, 10 pmol each primers shown in SEQ ID NOs: 52 and 55 were added, an extension reaction was carried out at 72° C. for 5 minutes, an amplification cycle of 98° C. for 10 seconds, 57° C. for 5 seconds, and 72° C. for 2 minutes was repeated 20 times, incubation was carried out at 72° C. for 2 minutes in the end, and the resulting 1,285-bp amplified fragment was separated and recovered with 0.8% gel. The amplified fragment was recovered from the gel using the QIAquick Gel Extraction Kit (Qiagen, Japan) in accordance with the instructions.

7-1-3. Construction of mFZD7crd-hFcm Recombinant Expression Vector

Figure 12:
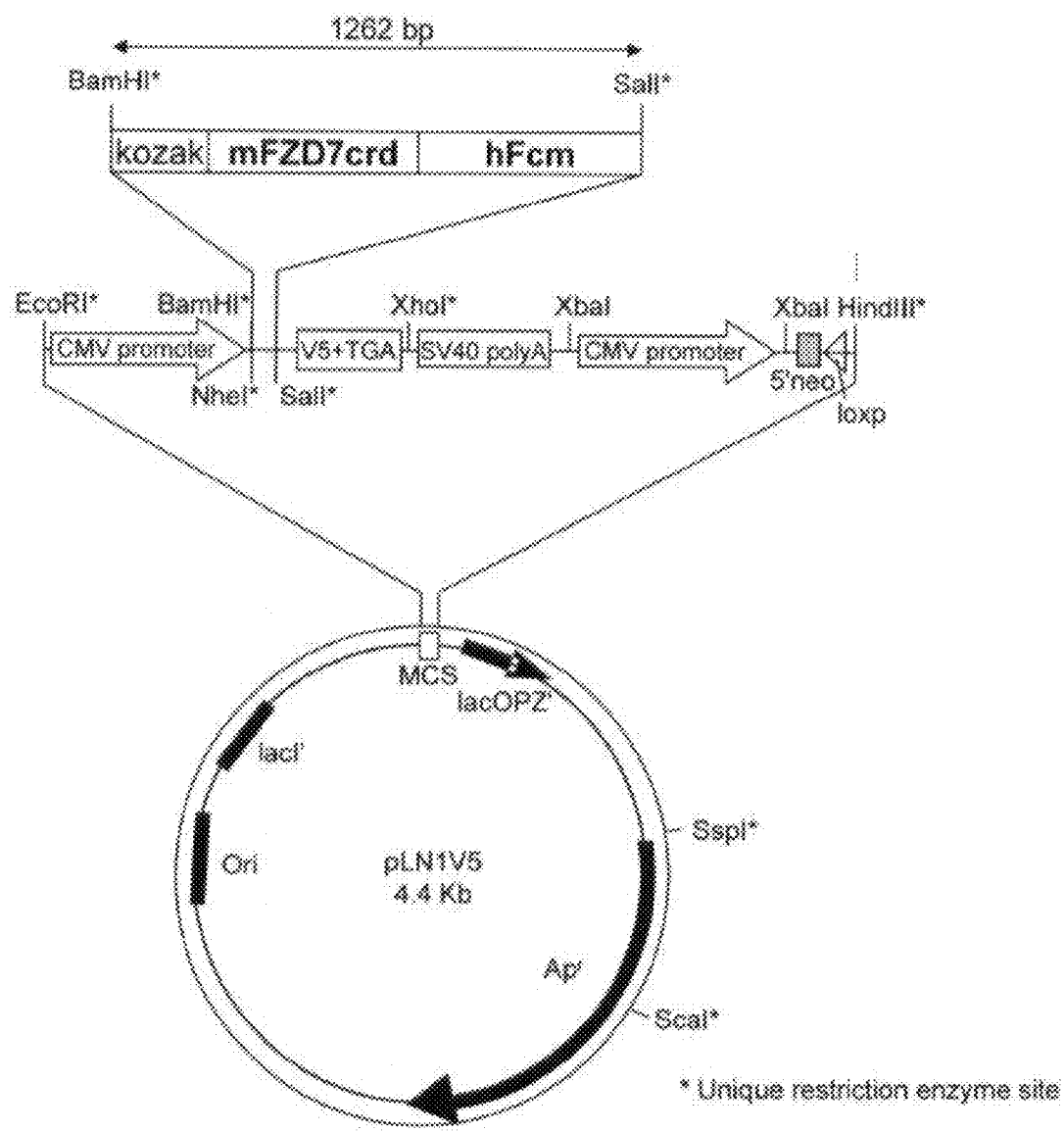
FIG. 12 shows a recombinant mFZD7crd-hFcm expression vector.

The PCR-amplified fragment recovered in Example 7-1-2 was digested with the BamHI and SalI restriction enzymes (Roche Diagnostics, K. K., Japan), and the resultant was separated and recovered with 0.8% agarose gel. The enzyme-treated fragment was recovered from the gel using the QIAquick Gel Extraction Extraction Kit (Qiagen, Japan) in accordance with the instructions. The obtained enzyme-treated fragment was introduced into the BamHI•SalI site of the pLN1V5 vector prepared in Example 7-1-1 to construct the mFZD7crd-hFcm recombinant expression vector (FIG. 12).

A polynucleotide sequence (1,257 bp, SEQ ID NO: 56) comprising a region from the initiation codon to the termination codon of mFZD7crd-hFcm recombinant cDNA and the amino acid sequence (418 amino acids, SEQ ID NO: 57) comprising a signal sequence of mFZD7-hFcm encoded by the cDNA are shown below. In SEQ ID NOs: 56 and 57, an underlined portion represents the mouse FZD7 signal sequence.

```
SEQ ID NO: 56:
ATGCGGGGCCCCGGCACGGCGGCGTCGCACTCGCCCTGGGCCTCTGCGC

CCTGGTGCTTGCTCTTCTGTGCGCGCTGCCCACGGACACCCGGGCTCAGC

CATATCACGGCGAGAAAGGCATCTCGGTACCGGACCACGGCTTCTGCCAG

CCCATCTCCATCCCGTTGTGCACGGATATCGCCTACAACCAGACCATCCT

GCCCAACCTGCTGGGCCACACGAACCAAGAGGACGCGGGCCTCGAGGTGC

ACCAGTTCTACCCTCTGGTAAAGGTGCAGTGTTCTCCTGAGCTACGCTTC

TTCTTATGCTCTATGTACGCACCCGTGTGCACCGTGCTCGACCAAGCCAT

TCCTCCGTGCCGTTCCTTGTGCGAGCGCGCCCGACAGGGCTGCGAGGCGC

TCATGAACAAGTTCGGCTTCCAGTGGCCAGAGCGGTTGCGCTGCGAGAAC

TTCCCAGTGCACGGTGCCGGCGAGATCTGCGTGGGGCAGAACACGTCCGA

CGGCTCCGGGGCGCGGGCGGCAGTCCCACCGCCTACCCTACTGCTCCCT

ACCTGGCCGAGCCTAGGTCTTCAGACAAAACTCACACATGCCCACCGTGC

CCAGCACCTGAAGCCGAGGGGGCCCCGTCAGTCTTCCTCTTCCCCCCAAA

ACCCAAGGACACCCTCATGATCTCCCGGACCCCTGAGGTCACATGCGTGG

TGGTGGACGTGAGCCACGAAGACCCTGAGGTCAAGTTCAACTGGTACGTG

GACGGCGTGGAGGTGCATAATGCCAAGACAAAGCCGCGGGAGGAGCAGTA

CAACAGCACGTACCGTGTGGTCAGCGTCCTCACCGTCCTGCACCAGGACT

GGCTGAATGGCAAGGAGTACAAGTGCGCCGTCTCCAACAAAGCCCTCCCA

GCCTCCATCGAGAAAACCATCTCCAAAGCCAAAGGGCAGCCCCGAGAACC

ACAGGTGTACACCCTGCCCCCATCCCGGGATGAGCTGACCAAGAACCAGG

TCAGCCTGACCTGCCTGGTCAAAGGCTTCTATCCCAGCGACATCGCCGTG

GAGTGGGAGAGCAATGGGCAGCCGGAGAACAACTACAAGACCACGCCTCC

CGTGCTGGACTCCGACGGCTCCTTCTTCCTCTACAGCAAGCTCACCGTGG

ACAAGAGCAGGTGGCAGCAGGGGAACGTCTTCTCATGCTCCGTGATGCAT

GAGGCTCTGCACAACCACTACACGCAGAAGAGCCTCTCCCTGTCTCCGGG

TAAATGA

SEQ ID NO: 57:
MRGPGTAASHSPLGLCALVLALLCALPTDTRAQPYHGEKGISVPDHGFCQ

PISIPLCTDIAYNQTILPNLLGHTNQEDAGLEVHQFYPLVKVQCSPELRF

FLCSMYAPVCTVLDQAIPPCRSLCERARQGCEALMNKFGFQWPERLRCEN

FPVHGAGEICVGQNTSDGSGGAGGSPTAYPTAPYLAEPRSSDKTHTCPPC

PAPEAEGAPSVFLFPPKPKDTLMISRTPEVTCVVVDVSHEDPEVKFNWYV

DGVEVHNAKTKPREEQYNSTYRVVSVLTVLHQDWLNGKEYKCAVSNKALP

ASIEKTISKAKGQPREPQVYTLPPSRDELTKNQVSLTCLVKGFYPSDIAV

EWESNGQPENNYKTTPPVLDSDGSFFLYSKLTVDKSRWQQGNVFSCSVMH

EALHNHYTQKSLSLSPGK
```

7-2. Transient Expression of mFZD7crd-hFcm Using mFZD7crd-hFcm Recombinant Expression Vector 7-2-1. Preparation of Expression Vector Used for Gene Introduction The mFZD7crd-hFcm recombinant expression vector obtained in Example 7-1-3 was introduced into E. coli DH5α, and DNA was prepared from the transformant using a plasmid purification kit (Qiagen plasmid Maxi kit, Qiagen, Japan).

7-2-2. Introduction of Vector into Cultured Cell and Secretory Expression

FreeStyle 293F cells (Invitrogen Japan K. K.) are cultured in FreeStyle 293 expression medium (Invitrogen Japan K. K.) at 37° C. in the presence of 5% $CO_2$ at 125 rpm to reach a cell density of $2\times10^5$ to $3\times10^6$ cells/ml. When culture was conducted using 1 liter of medium, a solution comprising 35 ml of the Opti-MEM I reduced serum medium (Invitrogen Japan K. K.) added to 1 mg of the expression vector and a solution comprising 33.7 ml of the Opti-MEM I reduced serum medium added to 1.3 ml of the 293 fectin transfection reagent (Invitrogen Japan K. K.) were prepared, and the resulting solutions were incubated at room temperature for 5 minutes. These solutions were mixed with each other after incubation, and the resultant was incubated at room temperature for an additional about 30 minutes. Thereafter, the expression vector treated in the manner described above was added to a medium containing $1\times10^9$ cells/l of FreeStyle 293F cells, and culture was conducted for 3 days.

7-3. Purification and Preparation of mFZD7crd-hFcm Recombinant 7-3-1. Pretreatment of Culture Supernatant The supernatant of the culture solution obtained in Example 7-2-2 was recovered, filtered through a 0.22 μm filter (0.22 μm GP Express Membrane 500 ml, Millipore, Japan), and then cooled to 4° C.

7-3-2. Antibody Affinity Chromatography

The acidic buffer used is 1 liter of a solution comprising 3.895 g of citrate monohydrate (Nakalai Tesque, Inc., Japan), 0.38 g of trisodium citrate (Wako Pure Chemical Industries, Ltd., Japan), and 2.92 g of sodium chloride (Junsei Chemical Co., Ltd., Japan) dissolved in water. The neutralizing buffer used is 1 liter of a solution comprising 13.1 g of sodium dihydrogen phosphate dihydrate (Kanto Chemical Co., Inc., Japan) and 41.5 g of disodium hydrogen phosphate dodecahydrate (Wako Pure Chemical Industries, Ltd., Japan) dissolved in water.

The pretreated culture supernatant (1 liter) was applied to a PBS-equilibrated protein G column (Hi Trap Protein G HP, 5 ml, GEHealthcare Bio-Sciences Corp., Japan). Thereafter, the column was washed with 25 ml or more PBS, then with 25 ml or more buffer prepared by adding NaCl to PBS to bring the NaCl concentration to 1.85 M, and with 30 ml of PBS again. After the completion of the washing procedure, 25 ml of acidic buffer was added to the column, and the target protein was recovered. The target protein was neutralized with a neutralizing buffer immediately after it was recovered. AKTAexplorer 10s (GE Healthcare Bio-Sciences Corp, Japan) was used in the separation and purification procedure. Endotoxin was removed before use.

7-3-3. Preparation of Purified Authentic Sample

The purified authentic sample obtained in Example 7-3-2 was concentrated using an ultrafilter membrane VIVAS-PIN20 10,000 MWCO PES (Sartorius Stedim Japan K. K., Japan). Thereafter, the buffer in the sample was substituted with PBS using NAP-25 Columns (GE Healthcare Bio-Sciences Corp, Japan). After the completion of the concentration and substitution procedure, the resultant was filtered through a 0.22 μm filter (Millex GV, Millipore, Japan).

A protein concentration was determined by measuring the specific absorbance at 280 nm (A280 nm) (E1%, 1 cm=10.3).

Example 8

Analysis of Mouse to which mFZD7crd-hFcm Recombinant has been Administered 8-1. Administration to Mouse The mFZD7crd-hFcm recombinant was administered to mice in order to evaluate physiological effects thereof on bone tissue.

Since the mFZD7crd-hFcm recombinant is a protein comprising the human antibody Fc region, the possibility of suppression of activity of the mFZD7crd-hFcm recombinant upon production of the neutralizing antibody in the body resulting from administration was considered. Thus, fully human antibody-producing mice (JP Patent No. 3523245) were used for the administration experiment in order to reduce a risk for the production of neutralizing antibodies. The mice were introduced and naturalized at age of 3 weeks, 1 μl of the blood was sampled from the caudal vein at age of 4 weeks, the blood was dispensed in a 96-well plate (Nunc ImmunoplateII 96 Maxi Soap 442404, Thermo Fisher Scientific K. K., Japan) on which the anti-human IgG (γ-chain specific) goat antibodies (Product Number: I3382, Sigma-Aldrich Japan K. K.) were immobilized, human IgG in the blood was solid-phased, and human antibody production in the mouse blood was assayed via ELISA involving the use of anti-human IgG (Fc fragment) peroxidase labelled goat antibodies (Product Number: A0170, Sigma-Aldrich Japan K. K.) as detection antibodies and developing a color using a Sumilon peroxidase color-developing kit T (Product Number: ML-1120T, Sumitomo Bakelite Co. Ltd., Japan). Mice in which human antibody production was observed in the blood were divided into groups based on body weights at age of 6 weeks on the previous day of the initiation of administration (i.e., day 1).

The mFZD7crd-hFcm recombinant was diluted with PBS to adjust a protein concentration to 5 mg/ml, and the resultant was administered into the caudal veins of mice of the mFZD7crd-hFcm recombinant test group in amounts of 200 μl per mouse once every 10 days (seven times in total). As a control group for comparison of changes in bone tissue, a non-treatment group was designated. The day of the initial administration was designated as day 0, the recombinant was administered to the caudal vein every 10 days up to day 60 (seven times in total), and mice were subjected to necropsy on day 68.

8-2. Pathological Finding

Tissues were sampled from the right femur, sternum, and the like at necropsy, the tissue samples were soaked and fixed in a 10% neutral buffered formalin solution (Wako Pure Chemical Industries, Ltd., Japan), the tissue samples were demineralized, H&E samples were prepared, and the maximum diaphyseal wall thickness at a site 50% away from the proximal end of the femur was measured.

The diaphyseal wall thickness of the samples obtained from 5 control mice and 4 mice to which the mFZD7crd-hFcm recombinants had been administered were measured at necropsy. As a result, the maximum diaphyseal wall thickness at a site 50% away from the proximal end of mice of the test group was higher than that of the control group (Table 2).

TABLE 2

| Groups | Animal No. | Maximum diaphyseal wall thickness at site 50% away from proximal end (mm) | Average (mm) |
|---|---|---|---|
| Control | INT52 | 0.32 | 0.35 |
|  | INT53 | 0.42 |  |
|  | INT54 | 0.39 |  |
|  | INT55 | 0.33 |  |
|  | INT56 | 0.28 |  |
| mFZD7crd-hFcm | mF7FcA7 | 0.32 | 0.44 |
|  | mF7FcA9 | 0.50 |  |
|  | mF7FcA10 | 0.47 |  |
|  | mF7FcA11 | 0.45 |  |

Measurement of diaphyseal wall thickness of femurs (cross sections) of mice to which mFZD7crd-hFcm recombinants have been administered and control mice 8-3. Necropsy Finding The femurs, sternums, and craniums of 4 mice to which the mFZD7crd-hFcm recombinants had been administered in Example 8-2 were observed at necropsy. As a result, whitening of the femur, whitening of the sternum, whitening of the cranium, whitening of the sternum, and a tendency of thickening node were observed as characteristic changes in mice to which the mFZD7crd-hFcm recombinants had been administered. The number of mice exhibiting changes is described below.

8-3-1. Femur

Whitening was observed in 3 mice among the 4 mice subjected to necropsy to which the mFZD7crd-hFcm recombinants had been administered.

8-3-2. Cranium

Whitening was observed in 2 mice among the 4 mice subjected to necropsy to which the mFZD7crd-hFcm recombinants had been administered.

8-3-3. Sternum

Whitening was observed in a mouse among the 4 mice subjected to necropsy to which the mFZD7crd-hFcm recombinants had been administered, and a tendency of thickening node was observed in 2 mice among such mice.

The above results suggest the possibility that whitening of the femur, whitening of the cranium, whitening of the sternum, and a tendency of thickening node were induced by administration of the mFZD7crd-hFcm recombinants.

8-4. Bone Morphometry

Tibial tissues were sampled at necropsy, samples of undemineralized tibial sections were prepared, and the resulting samples were subjected to toluidine blue staining. In order to prepare section samples, the tibia samples were embedded in GMA (glycolmethacrylate) resin in advance. The metaphyseal secondary cancellous bones of the obtained samples of undemineralized sections were subjected to measurement of the bone volume/tissue volume (BV/TV) as the structural parameter.

As a result of the measurement of the bone volume/tissue volume (BV/TV) of samples obtained from 5 control mice and 4 mice to which the mFZD7crd-hFcm recombinants had been administered, the increased BV/TV was observed at necropsy in the group to which the mFZD7-hFc recombinants had been administered compared with the control group. Accordingly, the increased bone volume/tissue volume was considered to have been induced by administration of the mFZD7crd-hFcm recombinants in the secondary cancellous bone of the tibial metaphysis (Table 3).

TABLE 3

| Groups | Animal No. | BV/TV (%) | Average (%) |
|---|---|---|---|
| Control | INT52 | 11.06 | 9.30 |
|  | INT53 | 8.96 |  |
|  | INT54 | 5.60 |  |
|  | INT55 | 15.95 |  |
|  | INT56 | 4.94 |  |
| mFZD7crd-hFcm | mF7FcA7 | 14.94 | 16.69 |
|  | mF7FcA9 | 20.26 |  |
|  | mF7FcA10 | 19.24 |  |
|  | mF7FcA11 | 12.30 |  |

Bone volume/tissue volume of secondary cancellous bone region of mice to which mFZD7crd-hFcm recombinants have been administered and that of tibial metaphyseal end of control mice Example 9

Preparation of USmFZD2crd-hFcm KI Chimeric Mouse

A pUSmFZD2crd-hFcm KI vector was prepared from mouse FZD2-cDNA (a 1,713-bp sequence comprising a region from an initiation codon to a termination codon, SEQ ID NO: 58) and human IgG1 Fc mutant-cDNA (SEQ ID NO: 3) in accordance with the method described in Example 1.

The mouse FZD2 signal sequence, a CRD (the cystein-rich-domain), and a region located downstream of a CRD comprising the 7-transmembrane domain in SEQ ID NO: 58 are marked by a single underline, a solid box, and a double underline, respectively, based on the information regarding the GenBank Accession Numbers: NM_020510.2 and NP_065256.1.

```
SEQ ID NO: 58:
ATGCGGGCCCGCAGCGCCCTGCCCCGCAGCGCCCTGCCCCGCCTGCTGCTGCCACTGCTGCTGCTGCCGGCCGCCGG

ACCGGCC

CAGTTCCACGGGGAGAAGGGCATCTCCATCCCGGACCACGGCTTCTGCCAGCCCATCTCCATCCCGCTGTGCACGGA

CATCGCCTACAACCAGACCATCATGCCCAACCTTCTTGGCCACACGAACCAGGAAGACGCGGGCCTGGAGGTGCATC

AGTTCTACCCGCTGGTGAAGGTGCAGTGCTCGCCCGAGCTGCGCTTCTTCCTGTGCTCCATGTACGCGCCGGTGTGC

ACAGTGCTGGAGCAGGCCATCCCGCCGTGCCGCTCCATCTGCGAGCGCGCGCGCCAAGGCTGCGAGGCGCTCATGAA

CAAGTTCGGCTTCCAATGGCCCGAGCGCCTCCGCTGCGAGCATTTCCCGCGTCACGGCGCGGAGCAGATCTGCGTGG

GCCAGAACCACTCGGAGGACGGAGCTCCTGCGCTA

CTCACCACCGCGCCACCTTCTGGGCTGCAGCCCGGCGCGGGTGGCACCCCGGGCGGCCCTGGCGGTGGTGGCTCGCC

ACCGCGTTACGCCACTCTGGAGCACCCTTTCCACTGTCCCCGCGTCCTCAAGGTGCCGTCCTATCTCAGCTATAAGT

TTCTGGGTGAGCGCGATTGTGCCGCGCCCTGCGAGCCCGCACGGCCCGACGGCTCTATGTTCTTCTCGCAAGAGGAG

ACTCGTTTTGCCCGTCTCTGGATCCTCACATGGTCGGTGTTGTGCTGCGCTTCCACTTTCTTCACGGTCACCACCTA

TTTAGTGGACATGCAGCGATTTCGCTACCCAGAGCGGCCCATCATCTTTCTGTCCGGCTGCTACACCATGGTGTCAG

TGGCCTACATTGCGGGCTTCGTTCTCCAGGAGCGCGTGGTATGCAATGAGCGCTTCTCAGAGGACGGTTATCGCACG

GTGGTGCAGGGCACTAAGAAAGAAGGCTGCACTATACTCTTCATGATGCTCTACTTCTTCAGCATGGCCAGCTCCAT

CTGGTGGGTGATTCTGTCCCTCACCTGGTTCCTGGCAGCCGGAATGAAGTGGGGCCACGAGGCCATCGAGGCCAATT

CGCAGTACTTCCACCTGGCCGCCTGGGCCGTGCCGGCCGTCAAAACCATCACCATCTTGGCCATGGGCCAGATCGAC

GGCGACCTGCTGAGCGGCGTGTGCTTCGTGGGCCTCAATAGCCTGGACCCGCTGCGGGGCTTCGTGCTGGCGCCGCT

CTTCGTATACCTGTTCATCGGTACATCCTTCCTGCTGGCCGGCTTCGTGTCACTCTTCCGCATCCGCACCATCATGA

AGCACGACGGCACCAAGACGGAGAAGCTGGAGAGGCTCATGGTGCGCATTGGCGTCTTCTCGGTGCTCTACACGGTA

CCGGCCACCATCGTCATCGCCTGCTACTTCTATGAGCAGGCCTTCCGCGAGCACTGGGAGCGCTCCTGGGTAAGCCA

GCACTGCAAGAGCCTAGCCATCCCCTGCCCGGCCCACTACACGCCCCGCATGTCGCCCGACTTCACAGTCTACATGA

TCAAATACCTCATGACGCTCATCGTGGGCATCACGTCGGGCTTCTGGATCTGGTCCGGCAAGACACTGCACTCGTGG

AGGAAGTTCTACACTCGTCTCACCAACAGCCGGCATGGCGAGACCACTGTGTGA
```

The amino acid sequence encoded by SEQ ID NO: 58 (570 amino acids, SEQ ID NO: 59) is shown below.

```
SEQ ID NO: 59:
MRARSALPRSALPRLLLPLLLLPAAGPA
```

```
QFHGEKGISIPDHGFCQPISIPLCTDIAYNQTIMPNLLGHTNQEDAGLEVHQFYPLVKVQCSPELRFFLCSMYAPVC
```

```
TVLEQAIPPCRSICERARQGCEALMNKFGFQWPERLRCEHFPRHGAEQICVGQNHSEDGAPAL
```

LTTAPPSGLQPGAGGTPGGPGGGGSPPRYATLEHPFHCPRVLKVPSYLSYKFLGERDCAAPCEPARPDGSIEFSQEE

TRFARLWILTWSVLCCASTFFTVTTYLVDMQRFRYPERPIIFLSGCYTMVSVAYIAGFVLQERVVCNERFSEDGYRT

VVQGTKKEGCTILFMMLYFFSMASSIWWVILSLTWFLAAGMKWGHEAIEANSQYFHLAAWAVPAVKTITILAMGQID

GDLLSGVCFVGLNSLDPLRGFVLAPLFVYLFIGTSFLLAGFVSLFRIRTIMKHDGTKTEKLERLMVRIGVFSVLYTV

PATIVIACYFYEQAFREHWERSWVSQHCKSLAIPCPAHYTPRMSPDFTVYMIKYLMTLIVGITSGFWIWSETLEISW

RKFYTRLTNSRHGETTV

A polynucleotide sequence comprising a region from the initiation codon to the termination codon of the pUSmFZD2crd-hFcm K1 vector expression unit (SEQ ID NO: 60; a 1,423-bp sequence comprising a mouse Igκ signal sequence containing an intron region (a region marked by a single underline) substituted with the mouse FZD2 signal sequence and the mouse FZD2crd-hFcm sequence located downstream thereof; wherein the region marked by a solid box represents the mouse Frizzled 2 extracellular cysteine-rich domain, and the region marked by a double underline represents hFcm) and the amino acid sequence encoded by the cDNA (SEQ ID NO: 61; a sequence comprising 393 amino acids; wherein the region marked by a single underline represents the mouse Igκ signal sequence, the region marked by a solid box represents the mouse Frizzled 2 extracellular cysteine-rich domain, and the region marked by a double underline represents hFcm) are shown below. Information regarding the mouse Igκ signal sequence containing an intron region was obtained from the UCSC mouse genome database as the genome sequence located upstream of MUSIGKVR1 obtained from the GenBank (Accession Number: K02159).

```
SEQ ID NO: 60:
ATGGAGACAGACACACTCCTGTTATGGGTACTGCTGCTCTGGGTTCCAGGTGAGAGTGCAGAGAAGTGTTGGATGCA
```

ACCTCTGTGGCCATTATGATACTCCATGCCTCTCTGTTCTTGATCACTATAATTAGGGCATTTGTCACTGGTTTTAA

GTTTCCCCAGTCCCCTGAATTTTCCATTTTCTCAGAGTGATGTCCAAAATTATTCTTAAAAATTTAAATAAAAAGGT

CCTCTGCTGTGAAGGCTTTTATACATATAT

AACAATAATCTTTGTGTTTATCATTCCAGGTTCCACTGGC

```
CAGTTCCACGGGGAGAAGGGCATCTCCATCCCGGACCACGGCTTCTGCCAGCCCATCTCCATCCCGCTGTGCACGGA
```

```
CATCGCCTACAACCAGACCATCATGCCCAACCTTCTTGGCCACACGAACCAGGAAGACGCGGGCCTGGAGGTGCATC
```

```
AGTTCTACCCGCTGGTGAAGGTGCAGTGCTCGCCCGAGCTGCGCTTCTTCCTGTGCTCCATGTACGCGCCGGTGTGC
```

```
ACAGTGCTGGAGCAGGCCATCCCGCCGTGCCGCTCCATCTGCGAGCGCGCGCGCCAAGGCTGCGAGGCGCTCATGAA
```

```
CAAGTTCGGCTTCCAATGGCCCGAGCGCCTCCGCTGCGAGCATTTCCCGCGTCACGGCGCGGAGCAGATCTGCGTGG
```

```
GCCAGAACCACTCGGAGGACGGAGCTCCTGCGCTA
```

GCCGAGCCTAGGTCTTCAGACAAAACTCACACATGCCCACCGTGCCCAGCACCTGAAGCCGAGGGGCCCCGTCAGT

CTTCCTCTTCCCCCCAAAACCCAAGGACACCCTCATGATCTCCCGGACCCCTGAGGTCACATGCGTGGTGGTGGACG

TGAGCCACGAAGACCCTGAGGTCAAGTTCAACTGGTACGTGGACGGCGTGGAGGTGCATAATGCCAAGACAAAGCCG

CGGGAGGAGCAGTACAACAGCACGTACCGTGTGGTCAGCGTCCTCACCGTCCTGCACCAGGACTGGCTGAATGGCAA

GGAGTACAAGTGCGCCGTCTCCAACAAAGCCCTCCCAGCCTCCATCGAGAAAACCATCTCCAAAGCCAAAGGGCAGC

CCCGAGAACCACAGGTGTACACCCTGCCCCCATCCCGGGATGAGCTGACCAAGAACCAGGTCAGCCTGACCTGCCTG

GTCAAAGGCTTCTATCCCAGCGACATCGCCGTGGAGTGGGAGAGCAATGGGCAGCCGGAGAACAACTACAAGACCAC

GCCTCCCGTGCTGGACTCCGACGGCTCCTTCTTCCTCTACAGCAAGCTCACCGTGGACAAGAGCAGGTGGCAGCAGG

GGAACGTCTTCTCATGCTCCGTGATGCATGAGGCTCTGCACAACCACTACACGCAGAAGAGCCTCTCCCTGTCTCCG

GGTAAATGA

SEQ ID NO: 61:
METDILLLWELLWVPGSTG

QFHGEKGISIPDHGFCQPISIPLCTDIAYNQTIMPNLLGHTNQEDAGLEVHQFYPLVKVQCSPELRFFLCSMYAPVC

TVLEQAIPPCRSICERARQGCEALMNKFGFQWPERLRCEHFPRHGAEQICVGQNHSEDGAPAL

AEPRSSDKTHTCPPCPAPEAEGAPSVFLFPPKPKDTLMISRTPEVTCVVVDVSHEDPEVKFNWYVDGVEVIINAKTKP

REEQYNSTYRVVSVLTVLHQDWLNGKEYKCAVSNKALPASIEKTISKAKGQPREPQVYTLPPSRDELTKNQVSLTCL

VKGFYPSDIAVEWESNGQPENNYKTTPPVLDSDGSFFLYSKLTVDKSRWQQGNVFSCSVMHEALHNHYTQKSLSLSP

GK

The USmFZD2crd-hFcm KI chimeric mice expressing a fusion protein of the mouse FZD2 extracellular cysteine-rich domain and human Fcm in a B-cell-specific manner are prepared with the use of the pUSmFZD2crd-hFcm KI vector in accordance with the method described in the Examples of WO 2006/78072.

Since the amino acid sequence of the FZD2 extracellular cysteine-rich domain of a human is identical to that of a mouse, the USmFZD2crd-hFcm KI chimeric mouse is substantially identical to the UShFZD2crd-hFcm KI chimeric mouse expressing a fusion protein of the human FZD2 extracellular cysteine-rich domain and human Fcm.

Further, control chimeric mice used in Example 10 were prepared in accordance with the method described in Example 11 of WO 2006/78072.

Example 10

Analysis of USmFZD2crd-hFcm KI Chimeric Mouse 10-1. Necropsy Finding
The chimeric mice prepared in Example 9 were subjected to necropsy at age of 16 weeks, and the spleen, the liver, the kidney, the adrenal gland, the stomach, the small intestine, the appendix, the large intestine, the pancreas, the mesenteric lymph node, the female/male reproductive organ, the thymic gland, the lung, the heart, the brain, the muscle, the skin, the femur, the sternum, the cranium, the spondylus, and the costa were observed. As a result, whitening of the femur, whitening of the sternum, whitening and hardening of the cranium, hardening of the spondylus, and hardening of the costa were observed as characteristic changes in the USmFZD2crd-hFcm KI chimeric mice compared with the control mice. The number of mice exhibiting changes is described below.
10-1-1. Femur
Whitening was observed more significant in 7 mice among the 12 USmFZD2crd-hFcm KI chimeric mice subjected to necropsy compared with 6 control mice.

10-1-2. Sternum
Whitening was observed more significant in 9 mice among the 12 USmFZD2crd-hFcm KI chimeric mice subjected to necropsy compared with 6 control mice.
10-1-3. Cranium
Whitening was observed more significant in 6 mice and hardening was observed more significant in 4 mice among the 12 USmFZD1crd-hFcm KI chimeric mice subjected to necropsy compared with 6 control mice.
10-1-4. Spondylus
Hardening was observed more significant in 2 mice among the 12 USmFZD2crd-hFcm KI chimeric mice subjected to necropsy compared with 6 control mice.
10-1-5. Costa
Hardening was observed more significant in 2 mice among the 12 USmFZD2crd-hFcm KI chimeric mice subjected to necropsy compared with 6 control mice.

The above results demonstrate that whitening of the femur, whitening of the sternum, whitening and hardening of the cranium, hardening of the spondylus, and hardening of the costa that are considered to result from the increased bone mass may have been induced by overexpression of the fusion protein of mouse FZD2 extracellular cysteine-rich domain and human Fc mutant.

10-2. Pathological Finding
In accordance with the method described in Example 8-2, the maximum diaphyseal wall thickness at sites 30%, 50%, and 80% away from the proximal end of the femur was measured.

Diaphyseal wall thickness of samples obtained from 6 control mice and from 12 USmFZD2crd-hFcm KI chimeric mice were measured at necropsy. As a result, the maximum diaphyseal wall thickness at a site 50% away from the proximal end and the minimum diaphyseal wall thickness at a site 30% away therefrom were larger than those of control samples (Table 4).

TABLE 4

| Gene Name | Mouse ID No. | Minimum diaphyseal wall thickness at site 30% away from proximal end (mm) | Average (mm) | Maximum diaphyseal wall thickness at site 50% away from proximal end (mm) | Average (mm) | Minimum diaphyseal wall thickness at site 50% away from proximal end (mm) | Average (mm) | Minimum diaphyseal wall thickness at site 80% away from proximal end (mm) | Average (mm) |
|---|---|---|---|---|---|---|---|---|---|
| Control | TAe1943 | 0.20 | 0.20 | 0.26 | 0.36 | 0.16 | 0.18 | 0.11 | 0.12 |
|  | TAe1945 | 0.20 |  | 0.31 |  | 0.20 |  | 0.16 |  |
|  | TAe1947 | 0.22 |  | 0.32 |  | 0.18 |  | 0.12 |  |
|  | TAe1949 | 0.20 |  | 0.44 |  | 0.18 |  | 0.10 |  |
|  | TAe1950 | 0.20 |  | 0.40 |  | 0.17 |  | 0.11 |  |
|  | TAe1951 | 0.20 |  | 0.40 |  | 0.17 |  | 0.11 |  |
| mFZD2crd-hFcm | USN-155FcA1 | 0.25 | 0.24 | 0.38 | 0.43 | 0.19 | 0.19 | 0.13 | 0.12 |
|  | USN-155FcA2 | 0.23 |  | 0.30 |  | 0.20 |  | 0.15 |  |
|  | USN-155FcA3 | 0.21 |  | 0.38 |  | 0.21 |  | 0.14 |  |
|  | USN-155FcA4 | 0.23 |  | 0.40 |  | 0.20 |  | 0.11 |  |
|  | USN-155FcA5 | 0.26 |  | 0.42 |  | 0.18 |  | 0.10 |  |
|  | USN-155FcA6 | 0.25 |  | 0.53 |  | 0.13 |  | 0.13 |  |
|  | USN-155FcB7 | 0.26 |  | 0.42 |  | 0.21 |  | 0.10 |  |
|  | USN-155FcB9 | 0.22 |  | 0.49 |  | 0.20 |  | 0.12 |  |
|  | USN-155FcB10 | 0.22 |  | 0.46 |  | 0.17 |  | 0.11 |  |
|  | USN-155FcB11 | 0.29 |  | 0.45 |  | 0.22 |  | 0.11 |  |
|  | USN-155FcB12 | 0.24 |  | 0.48 |  | 0.20 |  | 0.09 |  |
|  | USN-155FcB16 | 0.24 |  | 0.40 |  | 0.21 |  | 0.10 |  |

Measurements of diaphyseal wall thickness of femers (cross sections) of 16-week-old USmFZD2crd-hFcm KI chimeric mice and control mice The above results demonstrate that the thickened femoral diaphyseal wall may have been induced by overexpression of the fusion protein of mouse FZD2 extracellular cysteine-rich domain and human Fc mutant.

Example 11

Figure 13:
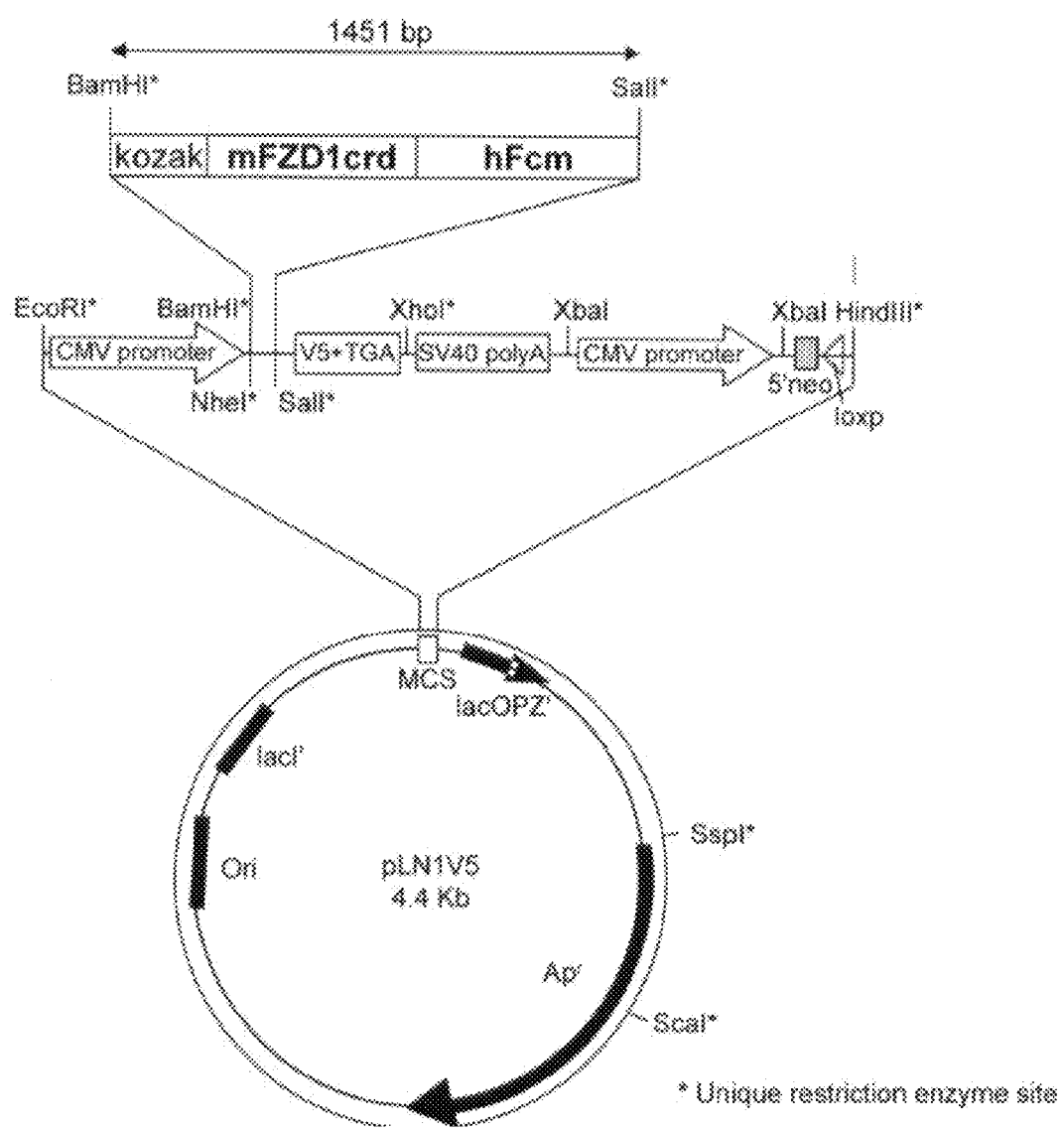
FIG. 13 shows a recombinant mFZD1crd-hFcm expression vector.

Expression and Preparation of Recombinant mFZD1crd-hFcm 11-1. Construction of Recombinant mFZD1crd-hFcm Expression Vector In accordance with the method described in Example 7-1, the recombinant mFZD1crd-hFcm expression vector was constructed using the PCR primers shown in SEQ ID NOs: 54, 55, 62, and 63 and, as templates, mouse Fzdl cDNA (SEQ ID NO: 11) and hFcm cDNA (SEQ ID NO: 3) (FIG. 13).

```
103Fc_BHIkozakFw:
                                           (SEQ ID NO: 62)
TAAA GGATCCCGGCCACC ATGGCTGAGGAGGCGGCGCC 103Fc_mFZD1G1SA_3 primer:
                                           (SEQ ID NO: 63)
GTCTGAAGACCTAGGCTCGGC GTGCTGCGGATTACTGGTCC
```

A polynucleotide sequence comprising a region from the initiation codon to the termination codon of recombinant mFZD1crd-hFcm cDNA (1,446 bp, SEQ ID NO: 64) and an amino acid sequence comprising a signal sequence of mFZD1-hFcm encoded by the cDNA (481 amino acids, SEQ ID NO: 65) are shown below. In SEQ ID NOs: 64 and 65, the underlined portion represents the signal sequence of mouse FZD1.

SEQ ID NO: 64:
ATGGCTGAGGAGGCGGCGCCTAGCGAGTCCCGGGCCGCCGGCCGGCTGAG

CTTGGAACTTTGTGCCGAAGCACTCCCGGGCCGGCGGAGGAGGTGGGGC

-continued
ACGAGGACACGGCCAGCCACCGCCGCCCCCGGGCTGATCCCCGGCGTTGG

GCTAGCGGGCTGCTGCTGCTGCTTTGGTTGCTGGAGGCTCCTCTGCTTTT

GGGGGTCCGAGCGCAGGCGGCGGGCCAGGTATCCGGGCCGGGCCAGCAAG

CCCCGCCGCCGCCCCAGCCCCAGCAGAGCGGGCAGCAGTACAACGGCGAA

CGGGGCATCTCCATCCCGGACCACGGCTACTGCCAGCCCATCTCCATCCC

GCTGTGCACGGACATCGCGTACAACCAGACCATCATGCCCAACCTGCTGG

GCCACACGAATCAGGAGGACGCCGGTCTGGAGGTGCACCAGTTCTACCCT

CTGGTGAAGGTGCAGTGCTCCGCCGAGCTCAAGTTCTTCCTGTGCTCCAT

GTACGCGCCTGTGTGCACCGTACTGGAGCAGGCGCTACCGCCCTGCCGCT

CCCTGTGCGAGCGCGCACGCCAGGGCTGCGAGGCGCTCATGAACAAGTTC

GGCTTCCAGTGGCCAGACACACTCAAGTGCGAGAAGTTCCCGGTGCACGG

CGCAGGAGAGCTGTGCGTGGGCCAGAACACGTCCGACAAAGGCACCCCAA

CTCCCTCCTTGCTACCAGAGTTCTGGACCAGTAATCCGCAGCACGCCGAG

CCTAGGTCTTCAGACAAAACTCACACATGCCCACCGTGCCCAGCACCTGA

AGCCGAGGGGGCCCCGTCAGTCTTCCTCTTCCCCCCAAAACCCAAGGACA

CCCTCATGATCTCCCGGACCCCTGAGGTCACATGCGTGGTGGTGGACGTG

AGCCACGAAGACCCTGAGGTCAAGTTCAACTGGTACGTGGACGGCGTGGA

GGTGCATAATGCCAAGACAAAGCCGCGGGAGGAGCAGTACAACAGCACGT

ACCGTGTGGTCAGCGTCCTCACCGTCCTGCACCAGGACTGGCTGAATGGC

AAGGAGTACAAGTGCGCCGTCTCCAACAAAGCCCTCCCAGCCTCCATCGA

GAAAACCATCTCCAAAGCCAAAGGGCAGCCCCGAGAACCACAGGTGTACA

CCCTGCCCCCATCCCGGGATGAGCTGACCAAGAACCAGGTCAGCCTGACC

TGCCTGGTCAAAGGCTTCTATCCCAGCGACATCGCCGTGGAGTGGGAGAG

CAATGGGCAGCCGGAGAACAACTACAAGACCACGCCTCCCGTGCTGGACT

-continued
```
CCGACGGCTCCTTCTTCCTCTACAGCAAGCTCACCGTGGACAAGAGCAGG

TGGCAGCAGGGGAACGTCTTCTCATGCTCCGTGATGCATGAGGCTCTGCA

CAACCACTACACGCAGAAGAGCCTCTCCCTGTCTCCGGGTAAATGA

SEQ ID NO: 65:
MAEEAAPSESRAAGRLSLELCAEALPGRREEVGHEDTASHRRPRADPRRW

ASGLLLLLWLLEAPLLLGVRAQAAGQVSGPGQQAPPPPQPQQSGQQYNGE

RGISIPDHGYCQPISIPLCTDIAYNQTIMPNLLGHTNQEDAGLEVHQFYP

LVKVQCSAELKFFLCSMYAPVCTVLEQALPPCRSLCERARQGCEALMNKF

GFQWPDTLKCEKFPVHGAGELCVGQNTSDKGTPTPSLLPEFWTSNPQHAE

PRSSDKTHTCPPCPAPEAEGAPSVFLFPPKPKDTLMISRTPEVTCVVVDV

SHEDPEVKFNWYVDGVEVHNAKTKPREEQYNSTYRVVSVLTVLHQDWLNG

KEYKCAVSNKALPASIEKTISKAKGQPREPQVYTLPPSRDELTKNQVSLT

CLVKGFYPSDIAVEWESNGQPENNYKTTPPVLDSDGSFFLYSKLTVDKSR

WQQGNVFSCSVMHEALHNHYTQKSLSLSPGK
```

11-2. Transient Expression of Recombinant mFZD1crd-hFcm Using Recombinant mFZD1crd-hFcm Expression Vector 11-2-1. Preparation of Expression Vector Used for Gene Introduction The recombinant mFZD1crd-hFcm expression vector obtained in Example 11-1 was introduced into *E. coli* DH5α, and DNA was prepared from the transformant cells using a plasmid purification kit (Qiagen plasmid Maxi kit; Qiagen, Japan).

11-2-2. Introduction of Vector into Cultured Cell and Secretory Expression

FreeStyle 293F cells (Invitrogen, Japan) are cultured in FreeStyle 293 expression medium (Invitrogen, Japan) at 37° C. in the presence of 5% $CO_2$ at 125 rpm to reach a cell density of $2 \times 10^5$ to $3 \times 10^6$ cells/ml. When culture was conducted using 1 liter of medium, 20 ml of Opti PRO SFM (Invitrogen, Japan) was added to 1 mg of the expression vector, and 17.5 ml of Opti PRO SFM was added to 2.5 ml of PEI (polyethylenimine). These solutions were mixed with each other immediately thereafter, and the resultant was incubated at room temperature for 10 minutes. Thereafter, the expression vector treated in the manner described above was added to a medium containing $1 \times 10^9$ cells/1 of FreeStyle 293F cells, and culture was conducted for 3 days.

11-3. Purification and Preparation of mFZD1crd-hFcm Recombinant 11-3-1. Pretreatment of Culture Supernatant The supernatant of the culture solution obtained in Example 11-2-2 was recovered, the supernatant was filtered through a 0.22 μm filter (0.22 μm GP Express Membrane 500 ml; Millipore, Japan) and then cooled to 4° C. (in a cold room).

11-3-2. Antibody Affinity Chromatography

The acidic buffer used is 1 liter of a solution comprising 3.895 g of citrate monohydrate (Nakalai Tesque, Inc., Japan, MW: 210.14), 0.38 g of trisodium citrate (Wako Pure Chemical Industries, Ltd., Japan, MW: 258.07), and 2.92 g of sodium chloride (Junsei Chemical Co., Ltd., Japan, MW: 58.44) dissolved in Milli-Q water. The neutralizing buffer used is 1 liter of a solution comprising 13.1 g of sodium dihydrogen phosphate dihydrate (Kanto Chemical Co., Inc., MW: 156.01), 41.5 g of disodium hydrogen phosphate dodecahydrate (Wako Pure Chemical Industries, Ltd., Japan, MW: 358.14), and 8.77 g of sodium chloride (Junsei Chemical Co., Ltd., MW: 58.44) dissolved in Milli-Q water.

The pretreated culture supernatant (1 liter) was applied to a protein G column (Hi Trap Protein G HP, 5 ml, GE Healthcare Bio-Sciences Corp., Japan) equilibrated with PBS (Dulecco's phosphate buffered saline, SIGMA). Thereafter, the column was washed with 25 ml or more PBS, then with 25 ml or more buffer prepared by adding NaCl to PBS to bring the NaCl concentration to 1.85 M, and with 30 ml of PBS again. After the completion of the washing procedure, 25 ml of acidic buffer was added to the column, and the target protein was recovered. The target protein was neutralized with a neutralizing buffer immediately after it was recovered. AKTAexplorer 10s (GE Healthcare Bio-Sciences Corp, Japan) was used in the separation and purification procedure. Endotoxin was removed before use.

11-3-3. Preparation of Purified Authentic Sample

The purified authentic sample obtained in Example 11-3-2 was concentrated using an ultrafilter membrane VIVASPIN20 10,000 MWCO PES (Sartorius Stedim Japan K. K., Japan). Thereafter, the buffer in the sample was substituted with PBS using NAP-25 Columns (GE Healthcare Bio-Sciences Corp, Japan). After the completion of the concentration and substitution procedures, the resultanting solution was filtered through a 0.22 μm filter (Millex GV; Millipore, Japan).

A protein concentration was determined by measuring a specific absorbance at 280 nm (A280 nm) (E1%, 1 cm=10.6).

Example 12

Analysis of Mouse to which Recombinant mFZD1crd-hFcm has been Administered 12-1. Administration to Mouse In accordance with the method described in Example 8-1, the recombinant mFZD1crd-hFcm obtained in Example 11-3 was administered to mice in order to evaluate physiological effects thereof on bone tissue.

Since the recombinant mFZD1crd-hFcm is a protein comprising the human antibody Fc region, the possibility of suppression of activity of the recombinant mFZD1crd-hFcm upon production of the neutralizing antibody in the body resulting from administration was considered. In order to reduce a risk of production of the neutralizing antibody, accordingly, homozygotes (97 KD mice, CLEA Japan, Inc., Proc. Natl. Acad. Sci., U.S.A., 97: 722-7, 2000) obtained via back-crossing of the immunoglobulin μ chain gene knockout mice lacking functional B lymphocytes and producing no antibodies into the MCH (ICR) strain (CLEA Japan, Inc.) were used. Mice were divided into groups based on body weights at age of 5 weeks on the previous day of the initiation of administration (i.e., day-1).

The recombinant mFZD1crd-hFcm was diluted with PBS to adjust a protein concentration to 5 mg/ml, and then administered into the tail veins of mice of the recombinant mFZD1crd-hFcm test group in amounts of 200 μl per mouse once every 10 days (seven times in total). As a control group for comparison of changes in bone tissue, a non-treatment group was designated. The day of the initial administration was designated as day 0, the recombinant was administered to the tail vein every 10 days up to day 60 (seven times in total), and mice were subjected to necropsy on day 70.

12-2. Necropsy Finding

The femurs, sternums, and craniums of 5 mice to which the recombinant mFZD1crd-hFcm had been administered were observed at necropsy. As a result, whitening and epiphyseal hypertrophy of the femur, whitening of the sternum, whitening and hardening of the cranium, and hardening of the costa were observed as characteristic changes in mice to which the recombinant mFZD1crd-hFcm had been administered compared with the control mice. The number of mice exhibiting changes is described below.

12-2-1. Femur

At necropsy, whitening was observed in 4 mice, a certain degree of whitening was observed in a mouse, epiphyseal hypertrophy was observed in another mouse among the 5 mice to which the mFZD1crd-hFcm recombinants had been administered, and a certain degree of whitening was observed in a mouse among 5 control mice.

12-2-2. Sternum

At necropsy, whitening was observed in 4 mice and a certain degree of whitening was observed in a mouse among the 5 mice to which the mFZD1crd-hFcm recombinants had been administered, and a certain degree of whitening was observed in a mouse among 5 control mice.

12-2-3. Cranium

At necropsy, whitening and hardening were observed in 4 mice and a certain degree of whitening and hardening was observed in a mouse among the 5 mice to which the mFZD1crd-hFcm recombinants had been administered, and no change was observed in all 5 control mice.

12-2-4. Costa

At necropsy, hardening was observed in a mouse among the 5 mice to which the recombinant mFZD1crd-hFcm had been administered, although no change was observed in all 5 control mice.

The above results demonstrate the possibility that whitening and epiphyseal hypertrophy of the femur, whitening of the sternum, whitening and hardening of the cranium, and hardening of the costa were induced by administration of the recombinant mFZD1crd-hFcm.

Example 13

13-1. Confirmation of Expression of the Fusion Protein of Mouse FZD7 Extracellular Cysteine-rich Domain and Human Fc Mutant in 4-, 8-, and 16-week-old USmFZD7crd-hFcm KI Chimeric Mice The concentrations of the fusions of the mouse FZD7 extracellular cysteine-rich domains and the human Fc mutants in the serum samples of the 4-week-old USmFZD7crd-hFcm KI chimeric mice (6 female mice), the 4-week-old control mice (6 female mice), the 8-week-old USmFZD7crd-hFcm KI chimeric mice (6 female mice), the 8-week-old control mice (6 female mice), the 16-week-old USmFZD7crd-hFcm KI chimeric mice (6 female mice and 6 male mice), and the 16-week-old control mice (6 female mice and 5 male mice) prepared in accordance with the method described in Example 1 were detected via ELISA by the method described in Example 2. Mice were raised while humidity, temperature, and light conditions were kept constant (temperature: 22° C.; humidity: 55%; and 12 hours light and 12 hours darkness) where they were allowed to freely eat feeds (CE-2, CLEA Japan, Inc.).

As a result, the average concentration among the 4-week-old female USmFZD7crd-hFcm KI chimeric mice was found to be 61.2 µg/ml, that among the 8-week-old female mice was found to be 220.4 µg/ml, that among the 16-week-old female mice was found to be 277.4 µg/ml, that among the 16-week-old male mice was found to be 253.3 µg/ml, and the concentrations in all control mice were lower than the detection limit.

The above results suggest that the fusion of the mouse FZD7 extracellular cysteine-rich domain and the human Fc mutant is expressed in the bodies of 4-week or older mice and circulated in the blood. The results also suggest that the concentration of the fusion is elevated with age.

13-2. Tibial Bone Morphometry Using 4-, 8-, and 16-week-old USmFZD7crd-hFcm KI Chimeric Mice 13-2-1. Bone Morphometry In order to obtain the data regarding the mineral apposition rate, the mineralization surface, and the bone formation rate, calcein (Product Number: 340-00433, Dojindo Laboratories, Japan) was dissolved in 2% sodium bicarbonate solution (Product Number: 37116-00, Kanto Chemical Co., Inc., Japan), and the prepared calcein solution (a calcium chelator) was administered subcutaneously at a dose of 16 mg/kg prior to necropsy. In the case of necropsy at age of 4 weeks, calcein was administered 3 days and 1 day before necropsy. In the case of necropsy at age of 8 weeks and 16 weeks, calcein was administered 6 days and 1 day before necropsy. Tibiae were sampled from 4-, 8-, and 16-week-old mice at necropsy, samples of undemineralized tibial sections were prepared, and the samples were then subjected to toluidine blue staining (TB staining), alkaline phosphatase staining (ALP staining), and tartrate-resistant acid phosphatase staining (TRAP staining). In order to prepare section samples, the tibia samples were embedded in GMA (glycolmethacrylate) resin in advance. The metaphyseal secondary cancellous bones of the obtained samples of undemineralized sections were subjected to measurement of the bone volume/tissue volume as the bone structure parameter (BV/TV), the osteoblast number/bone perimeter as the bone formation parameter (Ob.N/B.Pm), the osteoblast surface/bone surface (Ob.S/BS), the osteoid volume/bone volume (OV/BV), the mineral apposition rate (MAR), the mineralization surface/bone surface (MS/BS), the bone formation rate/bone surface (BFR/BS), the osteoclast number/bone perimeter as the bone absorption parameter (Oc.N/B.Pm), and the osteoclast surface/bone surface (Oc.S/BS).

13-2-2. Bone Volume/Tissue Volume

As a result of the measurement of the bone volume/tissue volume (BV/TV) of tibia samples obtained from 6 female control mice and 6 female USmFZD7crd-hFcm KI chimeric mice subjected to necropsy at ages of 4, 8, and 16 weeks, increases were observed in the bone volume/tissue volume of the group of USmFZD7crd-hFcm KI chimeric mice at ages of 4, 8, and 16 weeks compared with the control group. This suggests the possibility that the increased bone volume/tissue volume in the secondary cancellous bone of the tibial metaphysis was induced by overexpression of the mouse FZD7 extracellular cysteine-rich domain-human Fc mutant fusion constructs.

Further, tibia samples obtained from 5 male control mice and 6 male USmFZD7crd-hFcm KI chimeric mice subjected to necropsy at age of 16 weeks were subjected to measurement of the bone volume/tissue volume. As a result, the bone volume/tissue volume of the group of USmFZD7crd-hFcm KI chimeric mice was found to have been increased compared with that of the control group (with a significant difference). The results demonstrate the possibility that increased bone volume/tissue volume in the secondary cancellous bone of the tibial metaphyseal end was caused by overexpression of the fusion protein of mouse FZD7 extracellular cysteine-rich domain and human Fc mutant in male mice as well as in female mice (Table 5).

TABLE 5

| Age/sex/transgene | Bone volume/tissue volume (BV/TV) Average |
| --- | --- |
| 4 W ♀ USmFZD7crd-hFcm KI/Control | 11.8/7.4 |
| 8 W ♀ USmFZD7crd-hFcm KI/Control | 16.1/5.2 |
| 16 W ♀ USmFZD7crd-hFcm KI/Control | 18.5/4.5 |
| 16 W ♂ USmFZD7crd-hFcm KI/Control | 15.4/5.3 |

13-2-3. Osteoblast Number/Bone Perimeter, Osteoblast Surface/Bone Surface, and Osteoid Volume/Bone Volume The tibia samples obtained from 6 female control mice and 6 female USmFZD7crd-hFcm KI chimeric mice subjected to necropsy at ages of 4, 8, and 16 weeks were subjected to measurement of the osteoblast number/bone perimeter, the osteoblast surface/bone surface, and the osteoid volume/bone volume. As a result, the osteoblast number/bone perimeter and the osteoid volume/bone volume were found to be likely to decrease in the group of USmFZD7crd-hFcm KI chimeric mice at ages of 4 weeks and 8 weeks compared with the control group. This demonstrates that the osteoblast number/bone perimeter and the osteoid volume/bone volume in the secondary cancellous bone of the tibial metaphyseal end may not be substantially influenced or somewhat suppressed by overexpression of the fusion protein of mouse FZD7 extracellular cysteine-rich domain and human Fc mutant at young age. There was substantially no difference in terms of the osteoblast surface/bone surface between the recombinant mice and the control mice at ages of 4, 8, and 16 weeks.

As a result of measurement of the osteoblast number/bone perimeter, the osteoblast surface/bone surface, and the osteoid volume/bone volume of the tibia samples obtained from 5 male control mice and 6 male USmFZD7crd-hFcm KI chimeric mice subjected to necropsy at age of 16 weeks, substantially no difference was observed therebetween. This indicates that male mice are not substantially influenced by overexpression of the fusion protein of mouse FZD7 extracellular cysteine-rich domain and human Fc mutant fusion constructs as with the case of female mice (Table 6).

татBLE 6

| Age/sex/transgene | Osteoblast number/bone perimeter (Ob.N/B.Pm) Average | Osteoblast surface/bone surface (Ob.S/BS) Average | Osteoid volume/bone volume (OV/BV) Average |
| --- | --- | --- | --- |
| 4 W ♀ USmFZD7crd-hFcm KI/Control | 2219/2710 | 28.3/29.8 | 2.2/3 |
| 8 W ♀ USmFZD7crd-hFcm KI/Control | 1387/1963 | 20.2/23.9 | 1.1/2.3 |
| 16 W ♀ USmFZD7crd-hFcm KI/Control | 1255/1197 | 15.9/15.2 | 1.42/1.28 |
| 16 W ♂ USmFZD7crd-hFcm KI/Control | 733/626 | 9.7/7.5 | 0.26/0.38 |

13-2-4. Mineral Apposition Rate, Mineralization Surface, and Bone Formation Rate As a result of measurement of the mineral apposition rate, the mineralization surface, and the bone formation rate of the tibia samples obtained from 6 female control mice and 6 female USmFZD7crd-hFcm KI chimeric mice subjected to necropsy at ages of 4, 8, and 16 weeks, increase was observed in the mineral apposition rate only at age of 16 weeks, increase was observed in the mineralization surface/bone surface at ages of 4 and 8 weeks, and increase was observed in the bone formation rate at ages of 4, 8, and 16 weeks in the group of USmFZD7crd-hFcm KI chimeric mice compared with the control group. This indicates that mineralization of the secondary cancellous bone of the tibial metaphyseal end may have been accelerated by overexpression of the fusion protein of mouse FZD7 extracellular cysteine-rich domain and human Fc mutant.

As a result of measurement of the mineral apposition rate, the mineralization surface, and the bone formation rate of the tibia samples obtained from 5 male control mice and 6 male USmFZD7crd-hFcm KI chimeric mice subjected to necropsy at age of 16 weeks, further, increases were observed in the chimeric mice. This indicates that mineralization of the secondary cancellous bone of the tibial metaphyseal end may have been accelerated by overexpression of the fusion protein of mouse FZD7 extracellular cysteine-rich domain and human Fc mutant as with the case of femal mice (Table 7).

TABLE 7

| Age/sex/transgene | Mineral apposition rate (MAR) Average | Mineralization surface/bone surface (MS/BS) Average | Bone formation rate/bone surface (BFR/BS) Average |
| --- | --- | --- | --- |
| 4 W ♀ USmFZD7crd-hFcm KI/Control | 3.9/3.9 | 25.3/18.4 | 36.6/26.4 |
| 8 W ♀ USmFZD7crd-hFcm KI/Control | 2.5/2.5 | 19.5/15 | 18.3/14.2 |
| 16 W ♀ USmFZD7crd-hFcm KI/Control | 1.6/1.2 | 18.7/17.1 | 11.4/7.9 |
| 16 W ♂ USmFZD7crd-hFcm KI/Control | 1.2/0.9 | 17.7/11.3 | 7.9/3.8 |

13-2-5. Osteoclast Number/Bone Perimeter and Osteoclast Surface/Bone Surface

As a result of measurement of the osteoclast number/bone perimeter and the osteoclast surface/bone surface of the tibia samples obtained from 6 female control mice and 6 female USmFZD7crd-hFcm KI chimeric mice subjected to necropsy at age of 4, 8, and 16 weeks, no difference was observed therebetween. This indicates that the osteoclast number/bone perimeter and the osteoclast surface/bone surface of the secondary cancellous bone of the tibial metaphyseal end may not be substantially influenced by overexpression of the fusion protein of mouse FZD7 extracellular cysteine-rich domain and human Fc mutant.

As a result of measurement of the osteoclast number/bone perimeter and the osteoclast surface/bone surface of the tibia samples obtained from 5 male control mice and 6 male USmFZD7crd-hFcm KI chimeric mice subjected to necropsy at age of 16 weeks, further, no difference was observed therebetween. This indicates that the osteoclast number/bone perimeter and the osteoclast surface/bone surface of the secondary cancellous bone of the tibial metaphyseal end may not be influenced by overexpression of the fusion protein of mouse FZD7 extracellular cysteine-rich domain and human Fc mutant as with the case of female mice (Table 8).

TABLE 8

| Age/sex/transgene | Osteoclast number/ bone perimeter (Oc.N/B.Pm) Average | Osteoclast surface/ bone surface (OC.S/BS) Average |
|---|---|---|
| 4 W ♀ USmFZD7crd-hFcm KI/Control | 380.8/381.8 | 4.2/6.2 |
| 8 W ♀ USmFZD7crd-hFcm KI/Control | 265.7/289.9 | 4/4.6 |
| 16 W ♀ USmFZD7crd-hFcm KI/Control | 163.7/181.8 | 2.2/1.9 |
| 16 W ♂ USmFZD7crd-hFcm KI/Control | 115.5/112.9 | 1.5/1.4 |

13-3. Measurement of Bone Strength

The femur samples were obtained at necropsy and subjected to a three-point bending test. When conducting a test, the span of the support points was set as 6 mm, and a load was applied at the midpoint of the span to measure the maximum load (N).

As a result of measurement of the maximum load of femur samples obtained from 6 female control mice and 6 female USmFZD7crd-hFcm KI chimeric mice subjected to necropsy at ages of 4, 8, and 16 weeks, the measured values were found to have increased at both ages of 8 weeks and 16 weeks in the group of USmFZD7crd-hFcm KI chimeric mice compared with the control group. This indicates that the increased maximum load of the femur may have been caused by overexpression of the fusion protein of mouse FZD7 extracellular cysteine-rich domain and human Fc mutant.

As a result of measurement of the maximum load of femur samples obtained from 5 male control mice and 6 male USmFZD7crd-hFcm KI chimeric mice subjected to necropsy at age of 16 weeks, further, the values were found to have increased in the group of USmFZD7crd-hFcm KI chimeric mice compared with the control group. This indicates that an increase in the maximum load of the femur may have been induced by overexpression of the fusion protein of mouse FZD7 extracellular cysteine-rich domain and human Fc mutant as with the case of female mice (Table 9).

TABLE 9

| Age/sex/transgene | Maximum load (N) Average |
|---|---|
| 4 W ♀ USmFZD7crd-hFcm KI/Control | 11.1/11.3 |
| 8 W ♀ USmFZD7crd-hFcm KI/Control | 23.3/17.4 |
| 16 W ♀ USmFZD7crd-hFcm KI/Control | 35.3/26.6 |
| 16 W ♂ USmFZD7crd-hFcm KI/Control | 35.2/22.8 |

13-4. Analysis of Bone Structure (3-Dimensional Microfocus X-ray CT)

The left tibia samples were obtained at necropsy, and the internal structure of the cancellous bone region of the proximal tibial metaphysis was observed using a high-resolution microfocus X-ray CT scanner (micro-CT, Scan Xmate-L090, Comscantecno Co., Ltd., Japan) and the analytic software (TRY 3D-BON, Ratoc System Engineering Co., Ltd., Japan) in a non-invasive manner. The bone volume/tissue volume (BV/TV), the trabecular thickness (Tb. Th), the trabecular number (Tb. N), the trabecular separation (Tb. Sp), and the trabecular spacing (Tb. Spac) were measured.

The internal structure of the cancellous bone of the femur samples obtained from 6 female control mice and 6 female USmFZD7crd-hFcm KI chimeric mice subjected to necropsy at ages of 4, 8, and 16 weeks was observed via micro CT. As a result, the average bone volume/tissue volume, trabecular thickness, and trabecular number were found to have increased, and the average trabecular separation and trabecular spacing were found to have decreased in the group of USmFZD7crd-hFcm KI chimeric mice compared with the control group. In addition, the results obtained via micro CT using the femur samples obtained from 6 male control mice and 6 male USmFZD7crd-hFcm KI chimeric mice subjected to necropsy at age of 16 weeks were similar to those obtained from female mice at ages 4, 8, and 16 weeks. This suggests that the increased bone volume/tissue volume, the increased trabecular thickness, the increased trabecular number, the decreased trabecular separation, and the decreased trabecular spacing in the cancellous bone of the proximal tibial metaphysis may have been induced by overexpression of the fusion protein of mouse FZD7 extracellular cysteine-rich domain and human Fc mutant (Table 10).

TABLE 10

| Age/sex/transgene | Bone volume/tissue volume (BV/TV, %) Average | Trabecular thickness (Tb.Th, μm) Average | Trabecular number (Tb.N, 1/mm) Average | Trabecular separation (Tb.Sp, μm) Average | Trabecular spacing (Tb. Spac, μm) Average |
|---|---|---|---|---|---|
| 4 W ♀ USmFZD7crd-hFcm KI/4 W control | 22.9/12.3 | 32.1/27.5 | 7/4.3 | 111.2/216.8 | 143.3/244.3 |
| 8 W ♀ USmFZD7crd-hFcm KI/8 W control | 21.2/6.8 | 40.8/28.8 | 5.1/2.2 | 157.6/436.8 | 198.4/465.6 |
| 16 W ♀ USmFZD7crd-hFcm KI/16 W control | 22.1/5 | 51.2/32.5 | 4.2/1.5 | 190.6/797.4 | 241.9/830 |
| 16 W ♂ USmFZD7crd-hFcm KI/16 W control | 17.5/6 | 41.2/29.4 | 4.1/2 | 203/510.6 | 244.3/540 |

Example 14

14-1. Confirmation of Expression of the Fusion of Human FZD7 Extracellular Cysteine-Rich Domain and Human Fc Mutant in 8- and 12-week-old UShFZD7crd-hFcm KI Chimeric Mice The fusion of human FZD7 extracellular cysteine-rich domain and human Fc mutant existing in the serum samples of the 8-week-old UShFZD7crd-hFcm KI chimeric mice (6 female mice), the 8-week-old control mice (6 female mice), the 8-week-old UShFZD7crd-hFcm KI chimeric mice (6 male mice), the 8-week-old control mice (6 male mice), the 12-week-old UShFZD7crd-hFcm KI chimeric mice (6 male mice), and the 12-week-old control mice (6 male mice) prepared in accordance with the method described in Example 3 were detected via ELISA in accordance with the method described in Example 2. Mice were raised while humidity, temperature, and light conditions were kept constant (temperature: 22° C.; humidity: 55%; and 12 hours light and 12 hours darkness) where they were allowed to freely eat feeds (CE-2, CLEA Japan, Inc.).

As a result, the average concentration among the 8-week-old female mice was found to be 244.0 µg/ml, that among the 8-week-old male mice was found to be 190.2 µg/ml, that among the 12-week-old male mice was found to be 208.1 µg/ml, and the concentrations assayed with the use of the serum samples obtained from control mice were lower than the detection limit.

The above results suggest that the fusion protein of the human FZD7 extracellular cysteine-rich domain and the human Fc mutant are expressed in the bodies of 8-week-old or older mice and circulated in the blood.

14-2. Necropsy Finding of 8-week-old UShFZD7crd-hFcm KI Chimeric Mice

The chimeric mice prepared in Example 3 (6 female mice and 6 male mice) were subjected to necropsy at age of 8 weeks, and the spleen, the femur, the sternum, the cranium, the spondylus, and the costa were observed. As a result, whitening of the femur, whitening of the sternum, whitening and hardening of the cranium, and a certain degree of hardening of the costa were observed as characteristic changes in the UShFZD7crd-hFcm KI chimeric mice compared with the control mice (6 female mice and 6 male mice). In addition, spleen enlargement was observed in the UShFZD7crd-hFcm KI chimeric mice. The number of mice exhibiting changes is described below.

14-2-1. Necropsy Finding of Femur

Whitening was observed in 10 mice and a certain degree of whitening was observed in 2 mice among the 12 UShFZD7crd-hFcm KI chimeric mice subjected to necropsy compared with 12 control mice.

14-2-2. Necropsy Finding of Sternum

Whitening was observed in 10 mice and a certain degree of whitening was observed in 2 mice among the 12 UShFZD7crd-hFcm KI chimeric mice subjected to necropsy compared with 12 control mice.

14-2-3. Necropsy Finding of Cranium

Whitening was observed in 10 mice, a certain degree of whitening was observed in 2 mice, hardening was observed in a mouse, and a certain degree of hardening was observed in 9 mice among the 12 UShFZD7crd-hFcm KI chimeric mice subjected to necropsy compared with 12 control mice.

14-2-4. Necropsy Finding of Costa

A certain degree of hardening was observed in 5 mice among the 12 UShFZD7crd-hFcm KI chimeric mice subjected to necropsy compared with 12 control mice.

14-2-5. Necropsy Finding of Spleen

Tendency of spleen enlargement was observed in 6 mice among the 12 UShFZD7crd-hFcm KI chimeric mice subjected to necropsy compared with 12 control mice.

The above results indicate that whitening of the femur, whitening of the sternum, whitening and hardening of the cranium, and a certain degree of hardening of the costa may have been induced by overexpression of the human FZD7 extracellular cysteine-rich domain-human Fc mutant fusion constructs.

14-3. Measurement of Bone Strength of 8-week-old UShFZD7crd-hFcm KI Chimeric Mice The femur samples were obtained at necropsy and subjected to a three-point bending test. When conducting a test, the span of the support points was set as 6 mm, and a load was applied at the midpoint of the span to measure the maximum load (N).

As a result of measurement of the maximum load of femur samples obtained from 12 control mice and 12 UShFZD7crd-hFcm KI chimeric mice, the measured values were found to have increased in both female and male mice in the group of USmFZD7crd-hFcm KI chimeric mice compared with the control group. This indicates that the increased maximum load of the femur may have been induced by overexpression of the fusion protein of human FZD7 extracellular cysteine-rich domain and human Fc mutant (Table 11).

TABLE 11

| Age/sex/transgene | Maximum load (N) Average |
|---|---|
| 8 W ♀ UShFZD7crd-hFcm KI/Control | 22.5/19.3 |
| 8 W ♂ UShFZD7crd-hFcm KI/Control | 24.3/19.8 |

14-4. Analysis of Bone Structure of 8-week-old UShFZD7crd-hFcm KI Chimeric Mouse (3-Dimensional Microfocus X-ray CT)

The femur samples were obtained at necropsy, and the internal structure of the cancellous bone region of the distal femoral metaphysis was observed using a high-resolution microfocus X-ray CT scanner (micro-CT, Scan Xmate-L090, Comscantecno Co., Ltd.) and the analytic software (TRY 3D-BON, Ratoc System Engineering Co., Ltd.) in a non-invasive manner. The bone volume/tissue volume (BV/TV), the trabecular thickness (Tb. Th), the trabecular number (Tb. N), the trabecular separation (Tb. Sp), and the trabecular spacing (Tb. Spac) were measured.

As a result of observation of the internal structure of the cancellous bone region of the femur samples obtained from control mice (6 female mice and 6 male mice) and the UShFZD7crd-hFcm KI chimeric mice (6 female mice and 6 male mice) via micro-CT, the average bone volume/tissue volume, trabecular thickness, and trabecular number were found to have increased, and the average trabecular separation and trabecular spacing were found to have decreased in the group of UShFZD7crd-hFcm KI chimeric mice compared with the control group. It was thus suggested that the increased bone volume/tissue volume, the increased trabecular thickness, the increased trabecular number, the decreased trabecular separation, and the decreased trabecular spacing in the cancellous bone of the distal femoral metaphysis may have been induced by overexpression of the fusion protein of human FZD7 extracellular cysteine-rich domain and human Fc mutant (Table 12).

TABLE 12

| Age/sex/transgene | Average bone volume/tissue volume (BV/TV, %) Average | Trabecular thickness (Tb. Th, μm) Average | Trabecular number (Tb. N, 1/mm) Average | Trabecular separation (Tb. Sp, μm) Average | Trabecular spacing (Tb. Spac, μm) Average |
|---|---|---|---|---|---|
| 8 W ♀ UShFZD7crd-hFcm KI/8 W control | 25.1/7.6 | 43.1/28.2 | 5.7/2.6 | 130.8/367.5 | 174/395.7 |
| 8 W ♂ UShFZD7crd-hFcm KI/8 W control | 16.3/8.6 | 34.1/28.4 | 4.7/3.02 | 178.6/312.1 | 212.8/340.6 |

14-5. Necropsy Finding of 12-week-old UShFZD7crd-hFcm KI Chimeric Mouse

The chimeric mice prepared in Example 3 were subjected to necropsy (6 male mice) at age of 12 weeks, and the spleen, the femur, the sternum, the cranium, the spondylus, and the costa were observed. As a result, whitening of the femur, whitening of the sternum, whitening and hardening of the cranium, and a certain degree of hardening of the spondylus were observed as characteristic changes in the UShFZD7crd-hFcm KI chimeric mice compared with the control mice (6 male mice). In addition, a certain degree of tendency of spleen enlargement was observed in the UShFZD7crd-hFcm KI chimeric mice. The number of mice exhibiting changes is described below.

14-5-1. Necropsy Finding of Femur

Whitening was observed in a mouse and a certain degree of whitening was observed in 4 mice among the 6 UShFZD7crd-hFcm KI chimeric mice subjected to necropsy compared with 6 control mice.

14-5-2. Necropsy Finding of Sternum

Whitening was observed in a mouse and a certain degree of whitening was observed in a mouse among the 6 UShFZD7crd-hFcm KI chimeric mice subjected to necropsy compared with 6 control mice.

14-5-3. Necropsy Finding of Cranium

Whitening was observed in 2 mice, a certain degree of whitening was observed in 3 mice, hardening was observed in a mouse, and a certain degree of hardening was observed in a mouse among the 6 UShFZD7crd-hFcm KI chimeric mice subjected to necropsy compared with 6 control mice.

14-5-4. Necropsy Finding of Spondylus

A certain degree of hardening was observed in a mouse among the 6 UShFZD7crd-hFcm KI chimeric mice subjected to necropsy compared with 6 control mice.

14-5-5. Necropsy Finding of Spleen

Spleen enlargement was observed in a mouse among the 6 UShFZD7crd-hFcm KI chimeric mice subjected to necropsy compared with 6 control mice.

The above results indicate that whitening of the femur, whitening of the sternum, whitening and hardening of the cranium, and a certain degree of hardening of the spondylus may have been induced by overexpression of the fusion protein of human FZD7 extracellular cysteine-rich domain and human Fc mutant.

14-6. Pathological Finding of 12-week-old UShFZD7crd-hFcm KI Chimeric Mouse

The H&E stained femur and sternum pathological sections obtained from six 12-week-old control chimeric mice and six UShFZD7crd-hFcm KI chimeric mice were observed. As a result, the thickened femoral diaphyseal wall (FIGS. 14 and 15, Table 13), the increased cancellous bone (FIG. 16), and the increased sternal cancellous bone (FIG. 17) were observed in the UShFZD7crd-hFcm KI chimeric mice compared with control mice. The number of mice exhibiting changes is described below.

14-6-1. Femur

Figure 14:
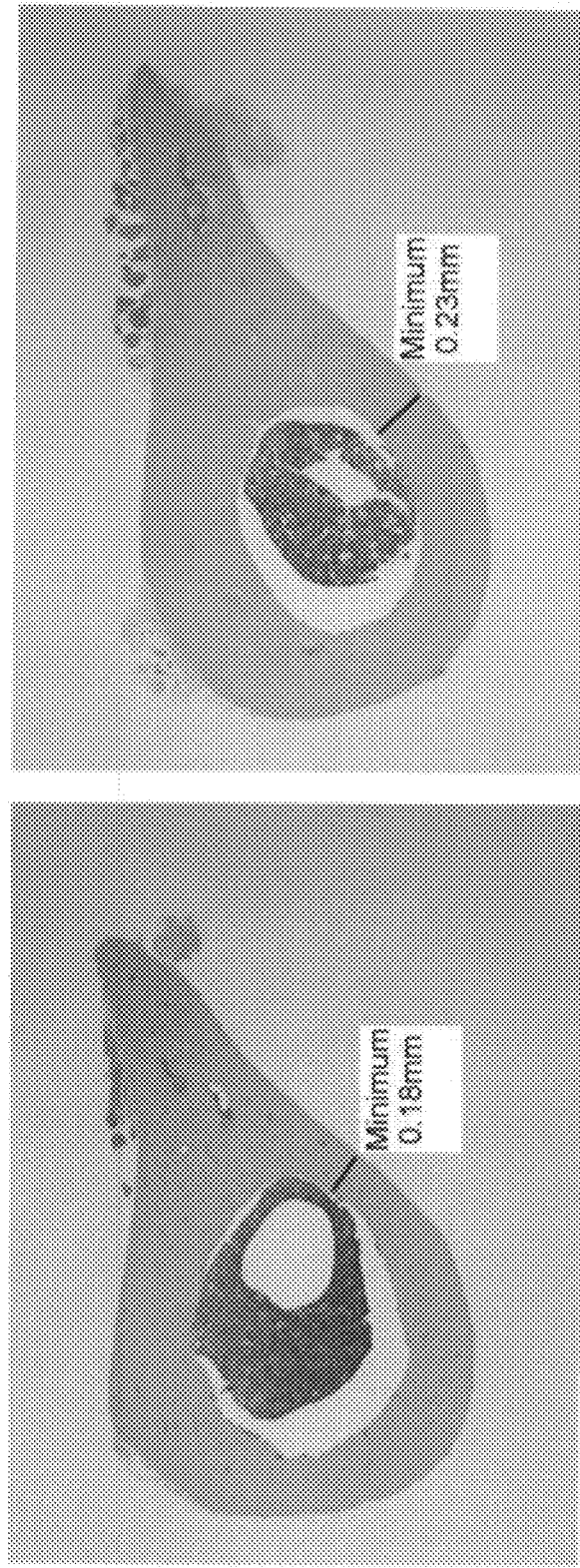
FIG. 14 shows images of H&E stained pathological sections of the femurs (at a site 30% away from the proximal end) of the 12-week-old UShFZD7crd-hFcm KI chimeric mouse (right diagram) and the control mouse (left diagram).
Figure 15:
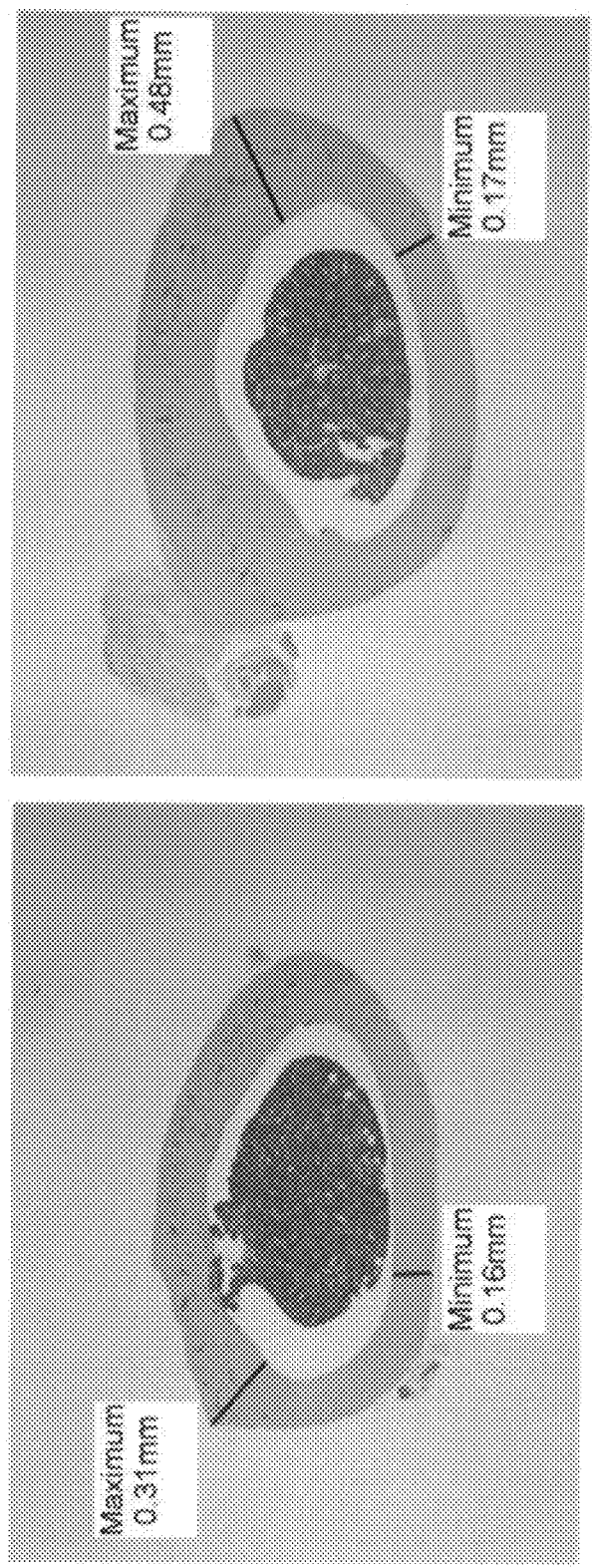
FIG. 15 shows images of H&E stained pathological sections of the femurs (at a site 50% away from the proximal end) of the 12-week-old UShFZD7crd-hFcm KI chimeric mouse (right diagram) and the control mouse (left diagram).
Figure 16:
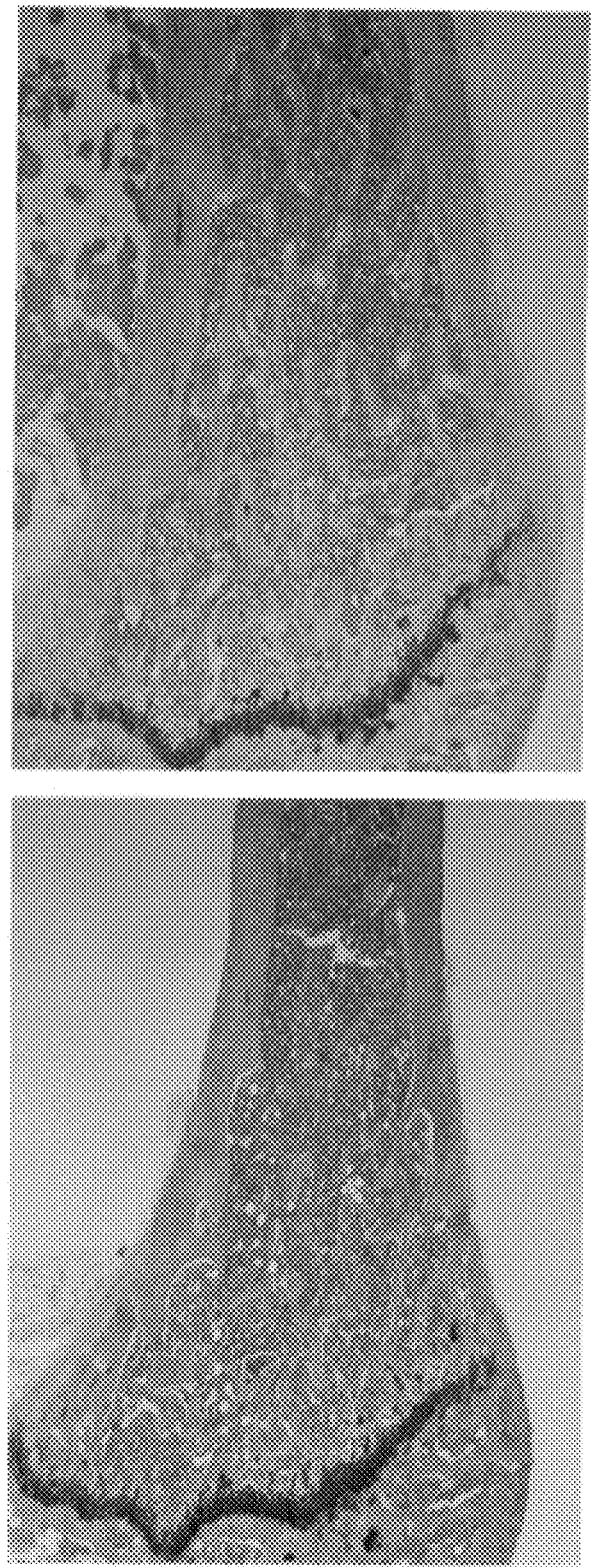
FIG. 16 shows images of H&E stained pathological sections of the femurs of the 12-week-old UShFZD7crd-hFcm KI chimeric mouse (right diagram) and the control mouse (left diagram).

The increased cancellous bone was observed in all the 6 UShFZD7crd-hFcm KI chimeric mice subjected to necropsy compared with 6 control mice (FIG. 16). Further, transected sections obtained from 3 femoral sites (i.e., sites 30%, 50%, and 80% away from the proximal end) were subjected to measurement of the diaphyseal wall thickness. As a result, the average minimum wall thickness at a site 30% away from the proximal end and the average maximum wall thickness at a site 50% away from the proximal end were found to be larger than those of the control group (FIGS. 14 and 15, Table 13).

TABLE 13

| Age/sex/transgene | Minimum diaphyseal wall thickness at site 30% away from proximal end (mm) Average | Maximum diaphyseal wall thickness at site 50% away from proximal end (mm) Average |
|---|---|---|
| 12 W ♂ UShFZD7crd-hFcm KI/12 W control | 0.22/0.19 | 0.47/0.34 |

14-6-2. Sternum

Figure 17:
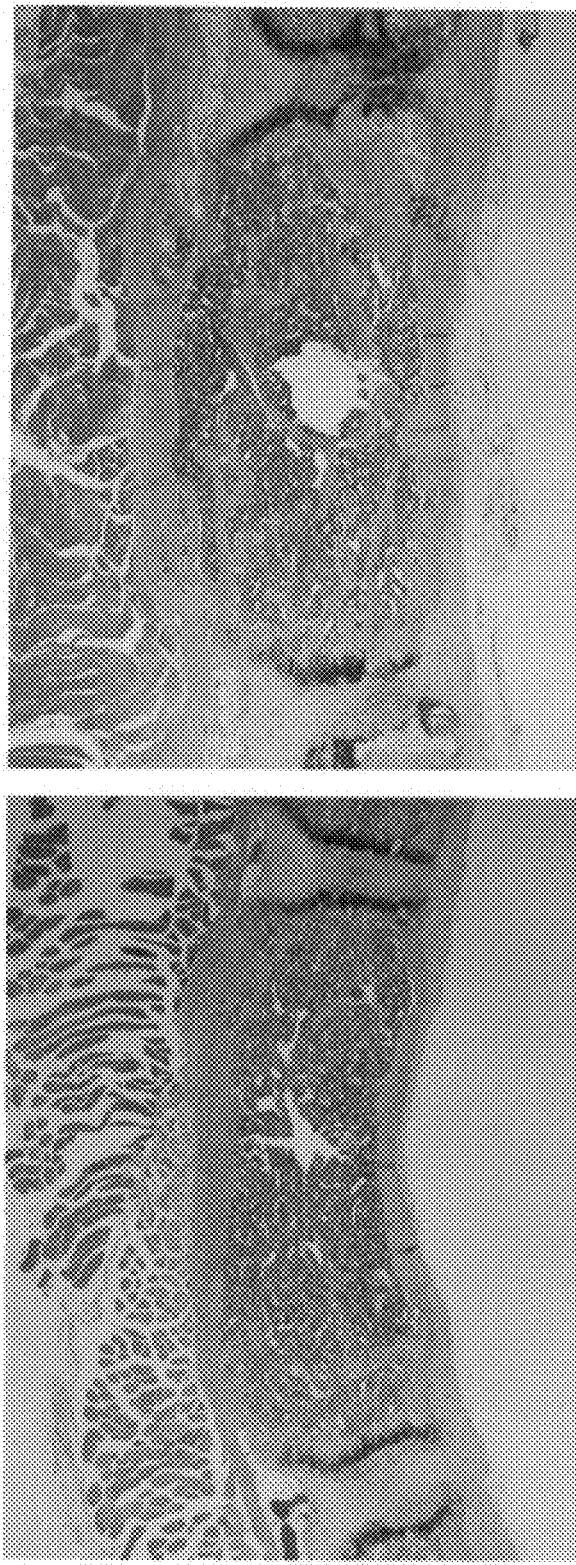
FIG. 17 shows images of H&E stained pathological sections of the sternums of the 12-week-old UShFZD7crd-hFcm KI chimeric mouse (right diagram) and the control mouse (left diagram).

The increased cancellous bone was observed in 5 mice among the 6 UShFZD7crd-hFcm KI chimeric mice subjected to necropsy compared with 6 control mice (FIG. 17).

The above results demonstrate that the thickened femoral diaphyseal wall, the increased cancellous bone, and the increased sternal cancellous bone may have been caused by overexpression of the fusion protein of human FZD7 extracellular cysteine-rich domain and human Fc mutant.

14-7. Biochemical Analysis of Serum

Six 12-week-old UShFZD7crd-hFcm KI male chimeric mice and 6 male control mice were exsanguinated under ether anesthesia to prepare serum samples. With the use of Hitachi 7180 (Hitachi Science Systems Ltd., Japan), serum samples were subjected to biochemical analysis (LDH activity, GOT activity, GPT activity, CK activity, ALP activity, AMY activity, LAP activity, LIP activity, T-CHO concentration, F-CHO concentration, LDL-CHO concentration, HDL-CHO concentration, TG concentration, PL concentration, GLU concentration, GA %, UA concentration, BUN concentration, CREA concentration, T-BIL concentration, D-BIL concentration, TP concentration, ALB concentration, A/G ratio, IP concentration, Ca concentration, Mg concentration, Na concentration, K concentration, Cl concentration, Fe concentration, UIBC concentration, and TIBC concentration). As a result, the values obtained with the use of UShFZD7crd-hFcm KI chimeric mice were not significantly different from those of the control mice.

Example 15

15-1. Preparation of Ovariectomized (OVX) Mouse Models

In order to evaluate the efficacy of the recombinant mFZD7crd-hFcm as a therapeutic agent for osteoporosis, ovariectomized (OVX) mouse models were prepared. Since the recombinant mFZD7crd-hFcm is a protein comprising the human antibody Fc region, the possibility of suppressing the activity of recombinant mFZD7crd-hFcm upon production of the neutralizing antibody in the body resulting from administration was considered. In order to reduce a risk of production of the neutralizing antibody, accordingly, homozygotes (97 KD mice, CLEA Japan, Inc., Proc. Natl. Acad. Sci., U.S.A., 97: 722-7, 2000) obtained via backcrossing of the immunoglobulin µ chain gene knockout mice lacking functional B lymphocytes and producing no antibodies into the MCH (ICR) strain (CLEA Japan, Inc.) were used for preparation of OVX mouse models. The dorsal regions of 10-week-old 97 KD mice were incised under anesthesia to remove both ovaries, or the mice were subjected to a sham operation of incision only without ovariectomy, followed by suturing.

15-2. Analysis of OVX Mouse Models to which Recombinant mFZD7crd-hFcm has been Administered

15-2-1. Administration to OVX Mouse Models

The recombinant mFZD7crd-hFcm was administered to the OVX mouse models prepared in Example 15-1 one week after the surgical operation in order to evaluate the efficacy of the recombinant mFZD7crd-hFcm in treatment of osteoporosis. As a test material, a bisphosphonate preparation (risedronate, Wako Pure Chemical Industries, Ltd., Product Number: 572-27451) was used for comparison, in addition to the recombinant mFZD7crd-hFcm, and a group to which both the recombinant mFZD7crd-hFcm and risedronate would be administered was further designated. The day at which administration was initiated was designated as day 0, and necropsy was carried out at day 69 and day 70. The recombinant mFZD7crd-hFcm was administered into the caudal veins (IV) in amounts of 1 mg/dose once every 10 days (seven times in total). Risedronate was administered subcutaneously (SC) in amounts of 5 µg/kg/dose three times in a week (30 times in total). Groups were designated as follows: a group subjected to sham operation without administration of a test substance (i.e., the sham/non-treatment group); a group subjected to OVX and administration of risedronate (i.e., the OVX/risedronate group); a group subjected to sham operation and administration of risedronate (i.e., the sham/risedronate group); a group subjected to OVX and administration of the recombinant mFZD7crd-hFcm (i.e., the OVX/mFZD7crd-hFcm group); a group subjected to sham operation and administration of the recombinant mFZD7crd-hFcm (i.e., the sham/mFZD7crd-hFcm group); a group subjected to OVX and administration of the recombinant mFZD7crd-hFcm and risedronate (i.e., the OVX/mFZD7crd-hFcm/risedronate group); and a group subjected to OVX without administration of a test substance (i.e., the OVX/non-treatment group). These groups were subjected to the administration experiment.

15-2-2. Necropsy Finding of OVX Mouse Models to which the Recombinant mFZD7crd-hFcm had been Administered The mice described in Example 15-2 were subjected to necropsy on day 69 and day 70, the femur, the sternum, the cranium, the costa, the spondylus, the spleen, and the uterus were observed. As a result, the sham/risedronate group, the OVX/mFZD7crd-hFcm group, the sham/mFZD7crd-hFcm group, and the OVX/mFZD7crd-hFcm/risedronate group exhibited characteristic changes in terms of whitening of the femur, whitening of the sternum, whitening and hardening of the cranium, hardening of the costa, and hardening of the spondylus (except for the sham/risedronate group) compared with the sham/non-treatment group. The number of mice exhibiting a certain degree of blackening in the spleen increased in the sham/mFZD7crd-hFcm group. Uterine involution was observed in the OVX/risedronate group, the OVX/mFZD7crd-hFcm group, the OVX/mFZD7crd-hFcm/risedronate group, and the OVX/non-treatment group. The number of mice exhibiting changes in the aforementioned organs is described below.

15-2-2-1. Necropsy Finding of Femur

While a certain degree of whitening was observed in 1 mouse among 10 mice of the sham/non-treatment group, whitening was observed in 1 mouse among 10 mice of the OVX/risedronate group, whitening was observed in 2 mice and a certain degree of whitening was observed in 4 mice among 10 mice of the sham/risedronate group, whitening was observed in 5 mice and a certain degree of whitening was observed in 4 mice among 10 mice of the OVX/mFZD7crd-hFcm group, whitening was observed in 8 mice and a certain degree of whitening was observed in 2 mice among 10 mice of the sham/mFZD7crd-hFcm group, whitening was observed in 7 mice and a certain degree of whitening was observed in 3 mice among 10 mice of the OVX/mFZD7crd-hFcm/risedronate group, and a certain degree of whitening was observed in a mouse among 10 mice of the OVX/non-treatment group.

15-2-2-2. Necropsy Finding of Sternum

While a certain degree of whitening was observed in 1 mouse among 10 mice of the sham/non-treatment group, a certain degree of whitening was observed in 2 mice among 10 mice of the OVX/risedronate group, whitening was observed in 4 mice and a certain degree of whitening was observed in 3 mice among 10 mice of the sham/risedronate group, whitening was observed in 4 mice and a certain degree of whitening was observed in 3 mice among 10 mice of the OVX/mFZD7crd-hFcm group, whitening was observed in 8 mice and a certain degree of whitening was observed in a mouse among 10 mice of the sham/mFZD7crd-hFcm group, whitening was observed in 8 mice and a certain degree of whitening was observed in 1 mouse among 10 mice of the OVX/mFZD7crd-hFcm/risedronate group, and a certain degree of whitening was observed in a mouse and deepening in color was observed in a mouse among 10 mice of the OVX/non-treatment group.

15-2-2-3. Necropsy Finding of Cranium

While a certain degree of whitening was observed in 1 mouse among 10 mice of the sham/non-treatment group, a certain degree of whitening was observed in 3 mice and a certain degree of hardening was observed in 1 mouse among 10 mice of the OVX/risedronate group, whitening was observed in 2 mice, a certain degree of whitening was observed in 6 mice, and a certain degree of hardening was observed in 2 mice among 10 mice of the sham/risedronate group, whitening was observed in 4 mice, a certain degree of whitening was observed in 3 mice, hardening was observed in 2 mice, and a certain degree of hardening was observed in 3 mice among 10 mice of the OVX/mFZD7crd-hFcm group, whitening was observed in 7 mice, a certain degree of whitening was observed in a mouse, hardening was observed in 5 mice, and a certain degree of hardening was observed in 4 mice among 10 mice of the sham/mFZD7crd-hFcm group, whitening was observed in 5 mice, a certain degree of whitening was observed in 2 mice, hardening was observed in 2 mice, and a certain degree of hardening was observed in 4 mice among 10 mice of the OVX/mFZD7crd-hFcm/risedronate group, and a certain degree of whitening was observed in 1 mouse and partial softening was observed in 2 mice among 10 mice of the OVX/non-treatment group.

15-2-2-4. Necropsy Finding of Costa

In comparison with the sham/non-treatment group (10 mice), hardening was observed in 1 mouse among 10 mice of the OVX/risedronate group, hardening was observed in 2 mice and a certain degree of hardening was observed in 1 mouse among 10 mice of the sham/risedronate group, hardening was observed in 2 mice and a certain degree of hardening was observed in 2 mice among 10 mice of the OVX/mFZD7crd-hFcm group, hardening was observed in 3 mice and a certain degree of hardening was observed in 2 mice among 10 mice of the sham/mFZD7crd-hFcm group, hardening was observed in 2 mice and a certain degree of hardening was observed in 2 mice among 10 mice of the OVX/mFZD7crd-hFcm/risedronate group, and partial softening was observed in 2 mice among 10 mice of the OVX/non-treatment group.

15-2-2-5. Necropsy Finding of Spondylus

In comparison with the sham/non-treatment group (10 mice), hardening was observed in 1 mouse and a certain degree of hardening was observed in a mouse among 10 mice of the OVX/mFZD7crd-hFcm group, hardening was observed in 4 mice among 10 mice of the sham/mFZD7crd-hFcm group, and hardening was observed in 2 mice and a certain degree of hardening was observed in 1 mouse among 10 mice of the OVX/mFZD7crd-hFcm/risedronate group.

15-2-2-6. Necropsy Finding of Spleen

In comparison with the sham/non-treatment group (10 mice), enlargement was observed in a mouse and blackening was observed in 1 mouse among 10 mice of the OVX/risedronate group, a tendency toward enlargement was observed in 1 mouse and a certain degree of blackening was observed in 1 mouse among 10 mice of the sham/risedronate group, a tendency toward enlargement was observed in 1 mouse and a certain degree of blackening was observed in 2 mice among 10 mice of the OVX/mFZD7crd-hFcm group, enlargement was observed in 1 mouse and a certain degree of blackening was observed in 6 mice among 10 mice of the sham/mFZD7crd-hFcm group, a tendency toward enlargement was observed in 1 mouse and a certain degree of blackening was observed in 2 mice among 9 mice of the OVX/mFZD7crd-hFcm/risedronate group, and a certain degree of blackening was observed in 1 mouse among 10 mice of the OVX/non-treatment group.

15-2-2-7. Necropsy Finding of Uterus

In comparison with the sham/non-treatment group (10 mice), involution was observed in 3 mice among 10 mice of the OVX/risedronate group, involution was observed in 4 mice and a tendency toward involution was observed in 2 mice among 10 mice of the OVX/mFZD7crd-hFcm group, involution was observed in 6 mice among 9 mice of the OVX/mFZD7crd-hFcm/risedronate group, and involution was observed in 3 mice and a tendency toward involution was observed in 2 mice among 10 mice of the OVX/non-treatment group.

The above results suggests the possibility that whitening of the femur, whitening of the sternum, whitening and hardening of the cranium, and hardening of the costa observed in the OVX/mFZD7crd-hFcm group and in the sham/mFZD7crd-hFcm group were induced by administration of the recombinant mFZD7crd-hFcm. The above results also suggest the possibility that whitening of the femur, whitening of the sternum, whitening and hardening of the cranium, and hardening of the costa observed in the OVX/risedronate group and in the sham/risedronate group were induced by administration of risedronate. The above results further suggest the possibility that whitening of the femur, whitening of the sternum, whitening and hardening of the cranium, and hardening of the costa observed in the OVX/mFZD7crd-hFcm/risedronate group were induced by administration of the mFZD7crd-hFcm recombinant and risedronate. Since hardening of the spondylus was observed exclusively in the OVX/mFZD7crd-hFcm group, the sham/mFZD7crd-hFcm group, and the OVX/mFZD7crd-hFcm/risedronate group, hardening of the spondylus may have been induced by administration of the recombinant mFZD7crd-hFcm. It was suggested that uterine involution observed only in the OVX treatment group was a change caused by OVX as reported in the literature (J. Bone Miner. Res., 20: 1085-92, 2005).

15-2-3. Pathological Finding

At necropsy conducted in Example 15-2-2, the right femur was sampled from each mouse, soaked and fixed in a 10% neutral buffered formalin solution (Wako Pure Chemical Industries, Ltd., Japan), and cut into round sections at sites 30% and 50% away from the proximal end to prepare H&E samples with lengthwise end surfaces. Changes in the cancellous bones at the ends were observed, and the maximum diaphyseal wall thickness at a site 30% away from the proximal end and the maximum/minimum diaphyseal wall thickness at a site 50% away from the proximal end were measured.

In accordance with the results of observation of changes in cancellous bones at the femoral ends, evaluation was made as follows: −: no change; ±; very mild; +: mild; ++; moderate; and +++; severe, and the results shown below were obtained.

While a very mild (±) decrease was observed in 2 mice and a mild (+) decrease was observed in 3 mice in the OVX/non-treatment group, a very mild (±) decrease was observed in 2 mice of the OVX/mFZD7crd-hFcm group. This indicates that a decrease in the cancellous bone resulting from OVX treatment is brought back to a normal state. While a very mild (±) increase was observed in 1 mouse and a very mild (±) decrease was observed in 2 mice of the sham/non-treatment group, a mild (+) increase was observed in 1 mouse of the sham/mFZD7crd-hFcm group.

As a result of the measurement of the minimum diaphyseal wall thickness at a site 30% away from the proximal end and the maximum/minimum diaphyseal wall thickness at a site 50% away from the proximal end, the average minimum diaphyseal wall thickness at a site 30% away from the proximal end and the average maximum/minimum diaphyseal wall thickness at a site 50% away from the proximal end of the sham/mFZD7crd-hFcm group increased compared with the sham/non-treatment group. Compared with the OVX/non-treatment group, the average minimum diaphyseal wall thickness at a site 30% away from the proximal end and the average maximum/minimum diaphyseal wall thickness at a site 50% away from the proximal end of the OVX/mFZD7crd-hFcm group increased. When the values of the OVX/mFZD7crd-hFcm group were compared with those of the sham/non-treatment group, the average maximum diaphyseal wall thickness at a site 50% away was equivalent to that of a group of normal control mice (i.e., the sham/non-treatment group), and the average minimum diaphyseal wall thickness at a site 30% away from the end and the average minimum diaphyseal wall thickness at a site 50% away from the end were found to be larger than those of the sham/non-treatment group (Table 14).

TABLE 14

| OVX non-treatment · OVX treatment/risedronate administration · recombinant administration · no recombinant administration | Minimum diaphyseal wall thickness at site 30% away from proximal end (mm) Average | Maximum diaphyseal wall thickness at site 50% away from proximal end (mm) Average | Minimum diaphyseal wall thickness at site 50% away from proximal end (mm) Average |
|---|---|---|---|
| Sham/risedronate group vs Sham/non-treatment group | 0.22/0.21 | 0.43/0.43 | 0.2/0.19 |
| Sham/mFZD7crd-hFcm group vs Sham/non-treatment group | 0.25/0.21 | 0.47/0.43 | 0.22/0.19 |
| OVX/risedronate group vs OVX/non-treatment group | 0.21/0.19 | 0.41/0.37 | 0.19/0.17 |
| OVX/mFZD7crd-hFcm group vs OVX/non-treatment group | 0.24/0.19 | 0.43/0.37 | 0.22/0.17 |
| OVX/mFZD7crd-hFcm/risedronate group vs OVX/non-treatment group | 0.24/0.19 | 0.47/0.37 | 0.23/0.17 |
| OVX/mFZD7crd-hFcm group vs Sham/non-treatment group | 0.24/0.21 | 0.43/0.43 | 0.22/0.19 |

The above results demonstrate that the recombinant mFZD7crd-hFcm has an activity of increasing the cancellous bone mass and an activity of increasing the diaphyseal wall thickness on the OVX treated mice as well as normal control mice (i.e., Sham/non-treatment mice).

15-2-4. Measurement of Cross-sectional Area of Femoral Cortical Bone

Figure 18:
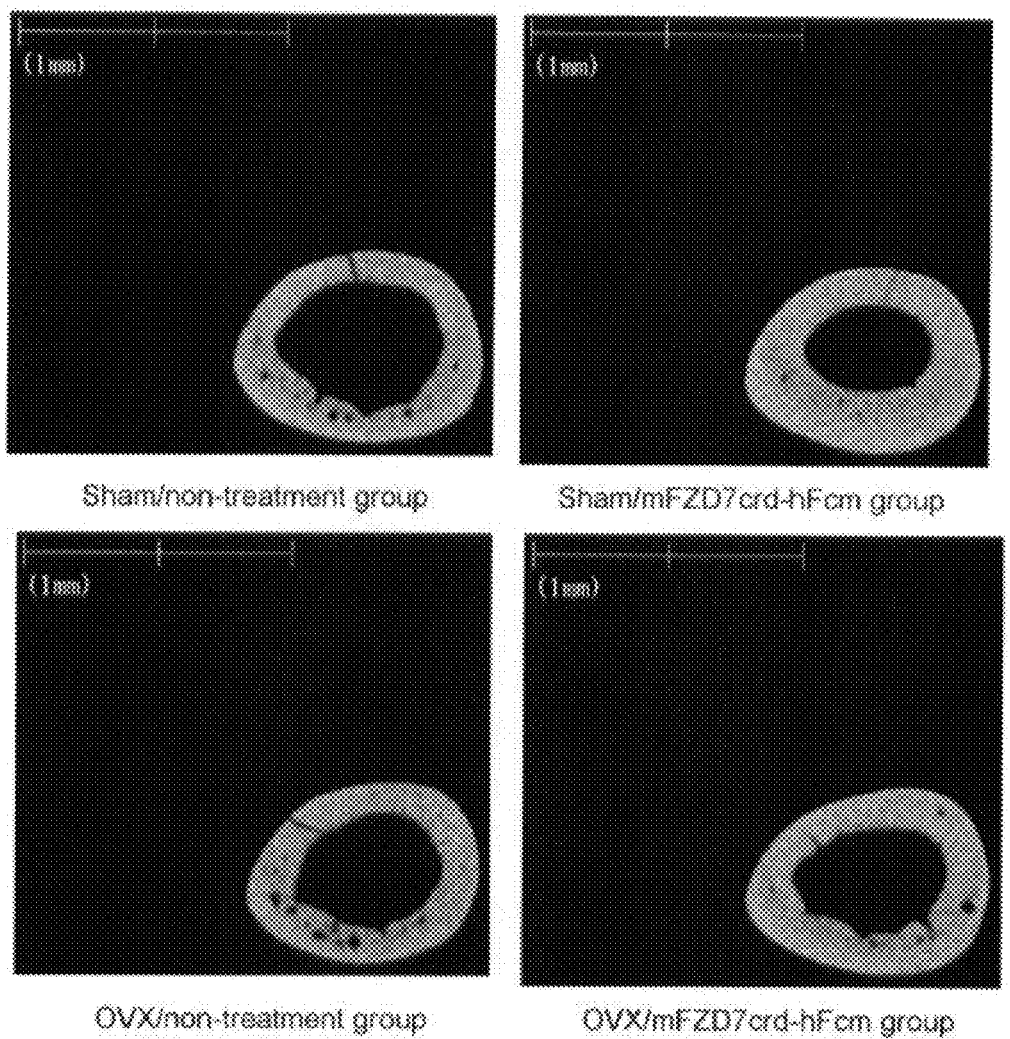
FIG. 18 shows 2D micro CT images of the femoral cortical bone (at a site 50% away from the proximal end) of the sham/non-treatment group (upper left diagram), the OVX/non-treatment group (lower left diagram), the sham/mFZD7crd-hFcm group (upper right diagram), and the OVX/mFZD7crd-hFcm group (lower right diagram).

The right femur was sampled from each mouse at necropsy conducted in Example 15-2-2, a site 50% away from the proximal end was subjected to 2D micro-CT photographing (FIG. 18), and the cross-sectional area of the cortical bone at a site 50% away from the proximal end was measured (the number of mice subjected to measurement: 10 mice of each group).

Compared with the sham/non-treatment group, the average of the sham/mFZD7crd-hFcm group increased. Compared with the OVX/non-treatment group, the average of the OVX/mFZD7crd-hFcm group also increased. When the value of the OVX/mFZD7crd-hFcm group was compared with that of the sham/non-treatment group, the average was found to be larger than that of the group of normal control mice (i.e., the sham/non-treatment group).

The above results demonstrate that the mFZD7crd-hFcm recombinant has the activity of increasing the cross-sectional area of the cortical bone on the OVX treated mice as well as normal control mice (i.e., sham/non-treatment mice) (Table 15).

TABLE 15

| OVX non-treatment · OVX treatment/risedronate administration · recombinant administration · no recombinant administration | Cross-sectional area of femoral cortical bone (mm$^2$) Average | Maximum load (N) Average |
|---|---|---|
| Sham/risedronate group vs Sham/non-treatment group | 1.36/1.23 | 35/33.1 |
| Sham/mFZD7crd-hFcm group vs Sham/non-treatment group | 1.43/1.23 | 39.2/33.1 |
| OVX/risedronate group vs OVX/non-treatment group | 1.23/1.11 | 33.7/30.6 |
| OVX/mFZD7crd-hFcm group vs OVX/non-treatment group | 1.29/1.11 | 36/30.6 |
| OVX/mFZD7crd-hFcm/risedronate group vs OVX/non-treatment group | 1.44/1.11 | 38.1/30.6 |
| OVX/mFZD7crd-hFcm group vs Sham/non-treatment group | 1.29/1.23 | 36/33.1 |

15-2-5. Measurement of Femoral Bone Strength

The right femur was sampled from each mouse at necropsy conducted in Example 15-2-2, and a three-point bending test was carried out (the number of mice subjected to measurement: 10 mice of each group). When conducting a test, the span of the support points was set as 6 mm, and a load was applied at the midpoint of the span to measure the maximum load (N).

In comparison with the sham/non-treatment group, the average of the sham/mFZD7crd-hFcm group increased. In comparison with the OVX/non-treatment group, the average of the OVX/mFZD7crd-hFcm group increased. When the values of the OVX/mFZD7crd-hFcm group were compared with those of the sham/non-treatment group, the average was found to be larger than that of the group of normal control mice (i.e., the sham/non-treatment group).

The above results demonstrate that the recombinant mFZD7crd-hFcm has the activity of increasing the femoral bone strength on the OVX treated mice as well as normal control mice (i.e., sham/non-treatment mice) (Table 15).

Example 16

16. Analysis of USmFZD1crd-hFcm KI Chimeric Mouse 16-1. Biochemical Analysis of Serum Fourteen 16-week-old USmFZD1crd-hFcm KI female chimeric mice, 6 USmFZD1crd-hFcm KI male chimeric mice, sixteen female control mice, and fourteen male control mice prepared in Example 4 were exsanguinated under ether anesthesia to prepare serum samples. With the use of Hitachi 7180 (Hitachi Science Systems Ltd., Japan), serum samples were subjected to biochemical analysis (LDH activity, GOT activity, GPT activity, CK activity, ALP activity, AMY activity, LAP activity, LIP activity, T-CHO concentration, F-CHO concentration, LDL-CHO concentration, HDL-CHO concentration, TG concentration, PL concentration, GLU concentration, GA %, UA concentration, BUN concentration, CREA concentration, T-BIL concentration, D-BIL concentration, TP concentration, ALB concentration, A/G ratio, IP concentration, Ca concentration, Mg concentration, Na concentration, K concentration, Cl concentration, Fe concentration, UIBC concentration, and TIBC concentration). As a result, the values obtained with the use of the USmFZD1crd-hFcm KI chimeric mice were not significantly different from those of the control mice.

16-2. Tibial Bone Morphometry Using 15-week-old USmFZD1crd-hFcm KI Chimeric Mouse 16-2-1. Bone Morphometry In order to obtain the data regarding the mineral apposition rate, the mineralization surface, and the bone formation rate, calcein (Product Number: 340-00433, Dojindo Laboratories, Japan) was dissolved in an aqueous solution of 2% sodium bicarbonate (Product Number: 37116-00, Kanto Chemical Co., Inc., Japan), and the prepared calcein solution (a calcium chelator) was administered subcutaneously at a dose of 16 mg/kg prior to necropsy. Administration was carried out 6 days and 1 day before necropsy. Tibiae were sampled at necropsy, samples of undemineralized tibial sections were prepared, and the samples were then subjected to toluidine blue staining (TB staining), alkaline phosphatase staining (ALP staining), and tartrate-resistant acid phosphatase staining (TRAP staining). In order to prepare section samples, the tibia samples were embedded in GMA (glycolmethacrylate) resin in advance. The metaphyseal secondary cancellous bones of the obtained samples of undemineralized sections were subjected to measurement of the bone volume/tissue volume as the bone structure parameter (BV/TV), the osteoblast number/bone perimeter as the bone formation parameter (Ob.N/B.Pm), the osteoblast surface/bone surface (Ob.S/BS), the osteoid/bone volume (OV/BV), the mineral apposition rate (MAR), the mineralization surface/bone surface (MS/BS), the bone formation rate/bone surface (BFR/BS), the osteoclast number/bone perimeter as the bone absorption parameter (Oc.N/B.Pm), and the osteoclast surface/bone surface (Oc.S/BS). In Example 16, all the control data were obtained from 16-week-old mice.

16-2-2. Bone Volume/Tissue Volume

As a result of the measurement of the bone volume/tissue volume (BV/TV) of tibia samples obtained from 6 female control mice and 6 female USmFZD1crd-hFcm KI chimeric mice subjected to necropsy, increases were observed in the bone volume/tissue volume of the group of USmFZD1crd-hFcm KI chimeric mice compared with the control group. This suggests the possibility that the increased bone volume/tissue volume in the secondary cancellous bone of the tibial metaphyseal end was induced by overexpression of the fusion protein of mouse FZD1 extracellular cysteine-rich domain and human Fc mutant.

Further, tibia samples obtained from 5 male control mice and 6 male USmFZD1crd-hFcm KI chimeric mice subjected to necropsy were subjected to measurement of the bone volume/tissue volume. As a result, the bone volume/tissue volume of the group of USmFZD1crd-hFcm KI chimeric mice was found to have increased compared with that of the control group. The results demonstrate the possibility that increased bone volume/tissue volume in the secondary cancellous bone of the tibial metaphyseal end was induced by overexpression of the fusion protein of mouse FZD1 extracellular cysteine-rich domain and human Fc mutant in male mice as well as in female mice (Table 16).

TABLE 16

| Age/sex/transgene | Bone volume (BV/TV) Average |
|---|---|
| 15 W♀ USmFZD1crd-hFcm KI/16 W control | 15.2/4.5 |
| 15 W♂ USmFZD1crd-hFcm KI/16 W control | 11.4/5.3 |

16-2-3. Osteoblast Number/Bone Perimeter, Osteoblast Surface/Bone Surface, and Osteoid Volume/Bone Volume The tibia samples obtained from 6 female control mice and 6 female USmFZD1crd-hFcm KI chimeric mice subjected to necropsy were subjected to measurement of the osteoblast number/bone perimeter, the osteoblast surface/bone surface, and the osteoid volume/bone volume. As a result, substantially no differences were observed between the chimeric mice and the control mice.

Further, tibia samples obtained from 5 male control mice and 6 male USmFZD1crd-hFcm KI chimeric mice subjected to necropsy were subjected to measurement of the osteoblast number/bone perimeter, the osteoblast surface/bone surface, and the osteoid volume/bone volume. As a result, substantially no differences were observed between the chimeric mice and the control mice. This indicates that male mice would not be influenced by overexpression of the fusion protein of mouse FZD1 extracellular cysteine-rich domain and human Fc mutant as with the case of female mice (Table 17).

TABLE 17

| Age/sex/transgene | Osteoblast number/bone perimeter (Ob.N/B.Pm) Average | Osteoblast surface/bone surface (Ob.S/BS) Average | Osteoid volume/bone volume (OV/BV) Average |
|---|---|---|---|
| 15 W♀ USmFZD1crd-hFcm KI/16 W control | 1167/1197 | 14.4/15.2 | 1.08/1.28 |
| 15 W♂ USmFZD1crd-hFcm KI/16 W control | 612.6/626 | 8/7.5 | 0.1/0.38 |

16-2-4. Mineral Apposition Rate, Mineralization Surface, and Bone Formation Rate As a result of measurement of the mineral apposition rate, the mineralization surface, and the bone formation rate of the tibia samples obtained from 6 female control mice and 6 female USmFZD1crd-hFcm KI chimeric mice subjected to necropsy, increases were observed in the mineral apposition rate, the mineralization surface, and the bone formation rate of the group of USmFZD1crd-hFcm KI chimeric mice compared with the control group. This indicates that mineralization of the secondary cancellous bone of the tibial metaphyseal end may have been accelerated by overexpression of the fusion protein of mouse FZD1 extracellular cysteine-rich domain and human Fc mutant.

As a result of measurement of the mineral apposition rate, the mineralization surface, and the bone formation rate of the tibia samples obtained from 5 male control mice and 6 male USmFZD1crd-hFcm KI chimeric mice subjected to necropsy, further, increases were observed in the chimeric mice in all items compared with control mice. This indicates that mineralization of the secondary cancellous bone of the tibial metaphyseal end may have been accelerated by overexpression of the fusion protein of mouse FZD1 extracellular cysteine-rich domain and human Fc mutant as with the case of femal mice (Table 18).

TABLE 18

| Age/sex/transgene | Mineral apposition rate (MAR) Average | Mineralization surface/bone surface (MS/BS) Average | Bone formation rate/bone surface (BFR/BS) Average |
|---|---|---|---|
| 15 W♀ USmFZD1crd-hFcm KI/16 W control | 1.4/1.2 | 21.2/17.1 | 10.7/7.9 |
| 15 W♂ USmFZD1crd-hFcm KI/16 W control | 1.1/0.9 | 17.5/11.3 | 7.5/3.8 |

16-2-5. Osteoclast Number/Bone Perimeter and Osteoclast Surface/Bone Surface

As a result of measurement of the osteoclast number/bone perimeter and the osteoclast surface/bone surface of the tibia samples obtained from 6 female control mice and 6 female USmFZD1crd-hFcm KI chimeric mice subjected to necropsy, the values of the chimeric mice were substantially equivalent to those of the control mice. This indicates that the osteoclast number/bone perimeter and the osteoclast surface/bone surface of the secondary cancellous bone of the tibial metaphyseal end may not be substantially influenced by overexpression of the fusion protein of mouse FZD1 extracellular cysteine-rich domain and human Fc mutant.

As a result of measurement of the osteoclast number/bone perimeter and the osteoclast surface/bone surface of the tibia samples obtained from 5 male control mice and 6 male USmFZD1crd-hFcm KI chimeric mice subjected to necropsy, further, the values of the chimeric mice were substantially equivalent to those of the control mice. This indicates that the osteoclast number/bone perimeter and the osteoclast surface/bone surface of the secondary cancellous bone of the tibial metaphyseal end may not be influenced by overexpression of the fusion protein of mouse FZD1 extracellular cysteine-rich domain and human Fc mutant as with the case of female mice (Table 19).

TABLE 19

| Age/sex/transgene | Osteoclast number/bone perimeter (Oc.N/B.Pm) Average | Osteoclast surface/ bone surface (OC.S/BS) Average |
|---|---|---|
| 15 W♀ USmFZD1crd-hFcm KI/16 W control | 169.9/181.8 | 2.7/1.9 |
| 15 W♂ USmFZD1crd-hFcm KI/16 W control | 112.9/112.9 | 1.5/1.4 |

16-3. Measurement of Bone Strength

The femur samples were obtained at necropsy and subjected to a three-point bending test. When conducting a test, the span of the support points was set as 6 mm, and a load was applied at the midpoint of the span to measure the maximum load (N).

As a result of measurement of the maximum load of femur samples obtained from 5 male control mice and 6 male USmFZD1crd-hFcm KI chimeric mice subjected to necropsy, the measured values were found to have increased in the group of USmFZD1crd-hFcm KI chimeric mice compared with the control group. This indicates that the increased maximum load of the femur may have been induced by overexpression of the fusion protein of mouse FZD1 extracellular cysteine-rich domain-human Fc mutant (Table 20).

TABLE 20

| Age/sex/transgene | Maximum load (N) Average |
|---|---|
| 15 W♂ USmFZD1crd-hFcm KI/16 W control | 33/22.8 |

16-4. Analysis of Bone Structure of 15-week-old USmFZD1crd-hFcm KI Chimeric Mice (3-Dimensional Microfocus X-ray CT)

The femur samples were obtained at necropsy, and the internal structure of the cancellous bone region of the distal femoral metaphysis was observed using a high-resolution microfocus X-ray CT scanner (micro-CT, Scan Xmate-L090, Comscantecno Co., Ltd., Japan) and the analytic software (TRY 3D-BON, Ratoc System Engineering Co., Ltd., Japan) in a non-invasive manner. The bone volume/tissue volume (BV/TV), the trabecular thickness (Tb. Th), the trabecular number (Tb. N), the trabecular separation (Tb. Sp), and trabecular spacing (Tb. Spac) were measured.

The internal structure of the cancellous bone of the femur samples obtained from control mice (6 female mice and 6 male mice) and USmFZD1crd-hFcm KI chimeric mice (6 female mice and 6 male mice) was observed via micro CT. As a result, the average bone volume/tissue volume, trabecular thickness, and trabecular number were found to have increased, and the average trabecular separation and trabecular spacing were found to have decreased in the group of USmFZD1crd-hFcm KI chimeric mice compared with the control group. This suggests that the increased bone volume/tissue volume, the increased trabecular thickness, the increased trabecular number, the decreased trabecular separation, and the decreased trabecular spacing in the cancellous bone of the distal femoral metaphysis may have been caused by overexpression of the fusion protein of mouse FZD1 extracellular cysteine-rich domain and human Fc mutant (Table 21).

TABLE 21

| Age/sex/transgene | Bone volume/tissue volume (BV/TV, %) Average | Trabecular thickness (Tb.Th, μm) Average | Trabecular number (Tb.N, 1/mm) Average | Trabecular separation (Tb. Sp, μm) Average | Trabecular spacing (Tb. Spac, μm) Average |
|---|---|---|---|---|---|
| 15 W♀ USmFZD1crd-hFcm KI/16 W control | 14.5/5 | 41.3/32.5 | 3.4/1.5 | 269.2/797.4 | 310.5/830 |
| 15 W♂ USmFZD1crd-hFcm KI/16 W control | 13.9/6 | 37.4/29.4 | 3.5/2 | 260.7/510.6 | 298.1/540 |

Example 17

17-1. Confirmation of Expression of Fusion Construct of Human FZD1 Extracellular Cysteine-rich Domain and Human Fc Mutant in 8- and 12-week-old UShFZD1crd-hFcm KI Chimeric Mice The fusion of human FZD1 extracellular cysteine-rich domain and human Fc mutant in the serum samples of the 8-week-old UShFZD1crd-hFcm KI chimeric mice (6 female mice and 6 male mice), the 8-week-old control mice (6 female mice and 6 male mice), the 12-week-old UShFZD1crd-hFcm KI chimeric mice (6 male mice), and the 12-week-old control mice (6 male mice) prepared in accordance with the method described in Example 6 was detected via ELISA in accordance with the method described in Example 2. Mice were raised while humidity, temperature, and light conditions were kept constant (temperature: 22° C.; humidity: 55%; and 12 hours light and 12 hours darkness) where they were allowed to freely eat feeds (CE-2, CLEA Japan, Inc.).

As a result, the average concentration among the 8-week-old female mice was found to be 525.5 μg/ml, that among the 8-week-old male mice was found to be 492.8 μg/ml, that among the 12-week-old male mice was found to be 452.8 μg/ml, and the concentrations assayed with the use of the serum samples obtained from all control mice were lower than the detection limit.

The above results suggest that the fusion protein of human FZD1 extracellular cysteine-rich domain and human Fc mutant is expressed in mouse bodies and circulated in the blood at age of 8 weeks.

17-2. Necropsy Finding of 8-week-old UShFZD1crd-hFcm KI Chimeric Mouse

The chimeric mice prepared in Example 6 were subjected to necropsy at age of 8 weeks (6 female mice and 6 male mice), and the spleen, the femur, the sternum, the cranium, the spondylus, and the costa were observed. As a result, whitening of the femur, whitening of the sternum, whitening and hardening of the cranium, and hardening of the costa were observed as characteristic changes in the UShFZD1crd-hFcm KI chimeric mice compared with the control mice. In addition, a certain degree of spleen enlargement was observed in the UShFZD1crd-hFcm KI chimeric mice. The number of mice exhibiting changes is described below.

17-2-1. Necropsy Finding of Femur

Whitening was observed in 5 mice and a certain degree of whitening was observed in 6 mice among the 12 UShFZD1crd-hFcm KI chimeric mice subjected to necropsy compared with the control group (6 female mice and 6 male mice).

17-2-2. Necropsy Finding of Sternum

Whitening was observed in 11 mice among the 12 UShFZD1crd-hFcm KI chimeric mice subjected to necropsy compared with the control group (6 female mice and 6 male mice).

17-2-3. Necropsy Finding of Cranium

Whitening was observed in 9 mice, a certain degree of whitening was observed in 3 mice, hardening was observed in 2 mice, and a certain degree of hardening was observed in 5 mice among the 12 UShFZD1crd-hFcm KI chimeric mice subjected to necropsy compared with the control group (6 female mice and 6 male mice).

17-2-4. Necropsy Finding of Costa

A certain degree of hardening was observed in 5 mice among the 12 UShFZD1crd-hFcm KI chimeric mice subjected to necropsy compared with the control group (6 female mice and 6 male mice).

17-2-5. Necropsy Finding of Spleen

A tendency toward enlargement was observed in 7 mice and a certain degree of blackening was observed in 8 mice among the 12 UShFZD1crd-hFcm KI chimeric mice subjected to necropsy compared with the control group (6 female mice and 6 male mice).

The above results indicate that whitening of the femur, whitening of the sternum, whitening and hardening of the cranium, whitening and hardening of the spondylus, and hardening of the costa may have been induced by overexpression of the fusion protein of human ZD1 extracellular cysteine-rich domain and human Fc mutant.

17-3. Measurement of Bone Strength of 8-week-old UShFZD1crd-hFcm KI Chimeric Mouse The femur samples were obtained at necropsy and subjected to a three-point bending test. When conducting a test, the span of the support points was set as 6 mm, and a load was applied at the midpoint of the span to measure the maximum load (N).

As a result of measurement of the maximum load of femur samples obtained from 12 control mice and 12 UShFZD1crd-hFcm KI chimeric mice, the measured values were found to have increased in both female and male mice in the group of UShFZD1crd-hFcm KI chimeric mice compared with the control group. This indicates that the increased maximum load of the femur may have been caused by overexpression of the fusion protein of human FZD1 extracellular cysteine-rich domain and human Fc mutant (Table 22).

TABLE 22

| Age/sex/transgene | Maximum load (N) Average |
|---|---|
| 8 W♀ UShFZD1crd-hFcm KI/Controls | 23.8/19.3 |
| 8 W♂ UShFZD1crd-hFcm KI/Controls | 27.6/19.8 |

17-4. Analysis of Bone Structure of 8-week-old UShFZD1crd-hFcm KI Chimeric Mouse (3-Dimensional Microfocus X-ray CT)

The femur samples were obtained at necropsy, and the internal structure of the cancellous bone region of the distal femoral metaphysis was observed using a high-resolution microfocus X-ray CT scanner (micro-CT, Scan Xmate-L090, Comscantecno Co., Ltd., Japan) and the analytic software (TRY 3D-BON, Ratoc System Engineering Co., Ltd., Japan) in a non-invasive manner. The bone volume/tissue volume (BV/TV), the trabecular thickness (Tb. Th), the trabecular number (Tb. N), the trabecular separation (Tb. Sp), and the trabecular spacing (Tb. Spac) were measured.

The internal structures of the cancellous bones of the femur samples obtained from control mice (6 female mice and 6 male mice) and UShFZD1crd-hFcm KI chimeric mice (6 female mice and 6 male mice) were observed via micro CT. As a result, the average bone volume/tissue volume, trabecular thickness, and trabecular number were found to have increased, and the average trabecular separation and trabecular spacing were found to have decreased in the group of UShFZD1crd-hFcm KI chimeric mice compared with the control group. This suggests that the increased volume/tissue volume, the increased trabecular thickness, the increased trabecular number, the decreased trabecular separation, and the decreased trabecular spacing in the cancellous bone of the distal femoral metaphysis may have been caused by overexpression of the fusion protein of human FZD1 extracellular cysteine-rich domain and human Fc mutant (Table 23).

TABLE 23

| Age/sex/transgene | Bone volume/tissue volume (BV/TV, %) Average | Trabecular thickness (Tb.Th, μm) Average | Trabecular number (Tb.N, 1/mm) Average | Trabecular separation (Tb.Sp, μm) Average | Trabecular spacing (Tb. Spac, μm) Average |
|---|---|---|---|---|---|
| 8 W♀ UShFZD1crd-hFcm KI/8 W control | 20.8/7.6 | 41/28.2 | 5.05/2.6 | 159.1/367.5 | 200.2/395.7 |

TABLE 23-continued

| Age/sex/transgene | Bone volume/tissue volume (BV/TV, %) Average | Trabecular thickness (Tb.Th, μm) Average | Trabecular number (Tb.N, 1/mm) Average | Trabecular separation (Tb.Sp, μm) Average | Trabecular spacing (Tb. Spac, μm) Average |
|---|---|---|---|---|---|
| 8 W♂ UShFZD1crd-hFcm KI/8 W control | 17.3/8.6 | 35.2/28.4 | 4.8/3.02 | 170.4/312.1 | 205.6/340.6 |

17-5. Necropsy Finding of 12-week-old UShFZD1crd-hFcm KI Chimeric Mouse

The chimeric mice prepared in Example 6 (6 male mice) were subjected to necropsy at age of 12 weeks, and the spleen, the femur, the sternum, the cranium, the spondylus, and the costa were observed. As a result, whitening of the femur, whitening of the sternum, whitening and hardening of the cranium, and a certain degree of hardening of the costa were observed as characteristic changes in the UShFZD1crd-hFcm KI chimeric mice compared with the control mice (6 male mice). The number of mice exhibiting changes is described below.

17-5-1. Necropsy Finding of Femur

A certain degree of whitening was observed in 5 mice among the 6 UShFZD1crd-hFcm KI chimeric mice subjected to necropsy compared with the control group (6 mice).

17-5-2. Necropsy Finding of Sternum

Whitening was observed in 3 mice and a certain degree of whitening was observed in 3 mice among the 6 UShFZD1crd-hFcm KI chimeric mice subjected to necropsy compared with the control group (6 mice).

17-5-3. Necropsy Finding of Cranium

Whitening was observed in a mouse, a certain degree of whitening was observed in 4 mice, hardening was observed in a mouse, and a certain degree of hardening was observed in 2 mice among the 6 UShFZD1crd-hFcm KI chimeric mice subjected to necropsy compared with the control group (6 mice).

17-5-4. Necropsy Finding of Costa

A certain degree of hardening was observed in 2 mice among the 6 UShFZD1crd-hFcm KI chimeric mice subjected to necropsy compared with the control group (6 mice).

The above results indicate that whitening of the femur, whitening of the sternum, whitening and hardening of the cranium, and a certain degree of hardening of the costa may have been caused by overexpression of the fusion protein of human FZD1 extracellular cysteine-rich domain and human Fc mutant.

17-6. Pathological Finding of 12-week-old UShFZD1crd-hFcm KI Chimeric Mouse

The H&E stained femur and sternum pathological sections obtained from six 12-week-old control chimeric mice and six UShFZD1crd-hFcm KI chimeric mice were observed. As a result, the thickened femoral diaphyseal wall (FIGS. 19 and 20, Table 24), the increased cancellous bone (FIG. 21), and the increased sternal cancellous bone (FIG. 22) were observed in the UShFZD1crd-hFcm KI chimeric mice compared with control mice. The number of mice exhibiting changes is described below.

17-6-1. Femur

Figure 19:
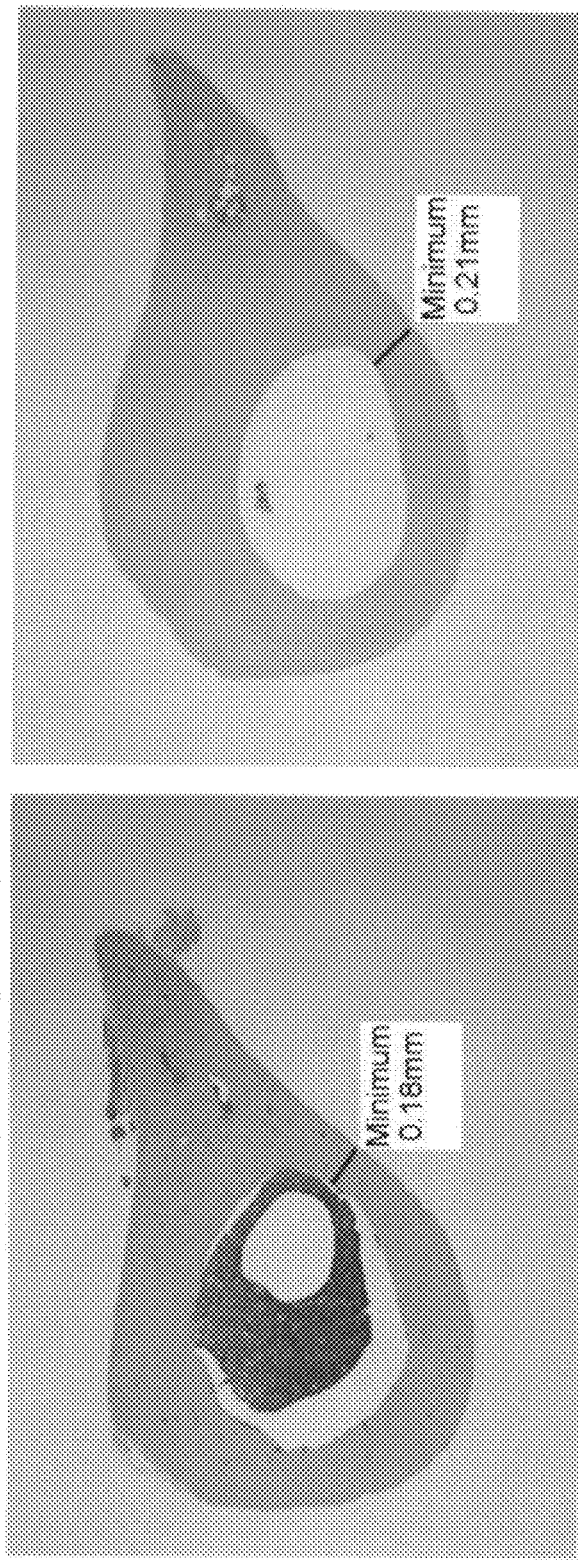
FIG. 19 shows images of H&E stained pathological sections of the femurs (at a site 30% away from the proximal end) of the 12-week-old UShFZD1crd-hFcm KI chimeric mouse (right diagram) and the control mouse (left diagram).
Figure 20:
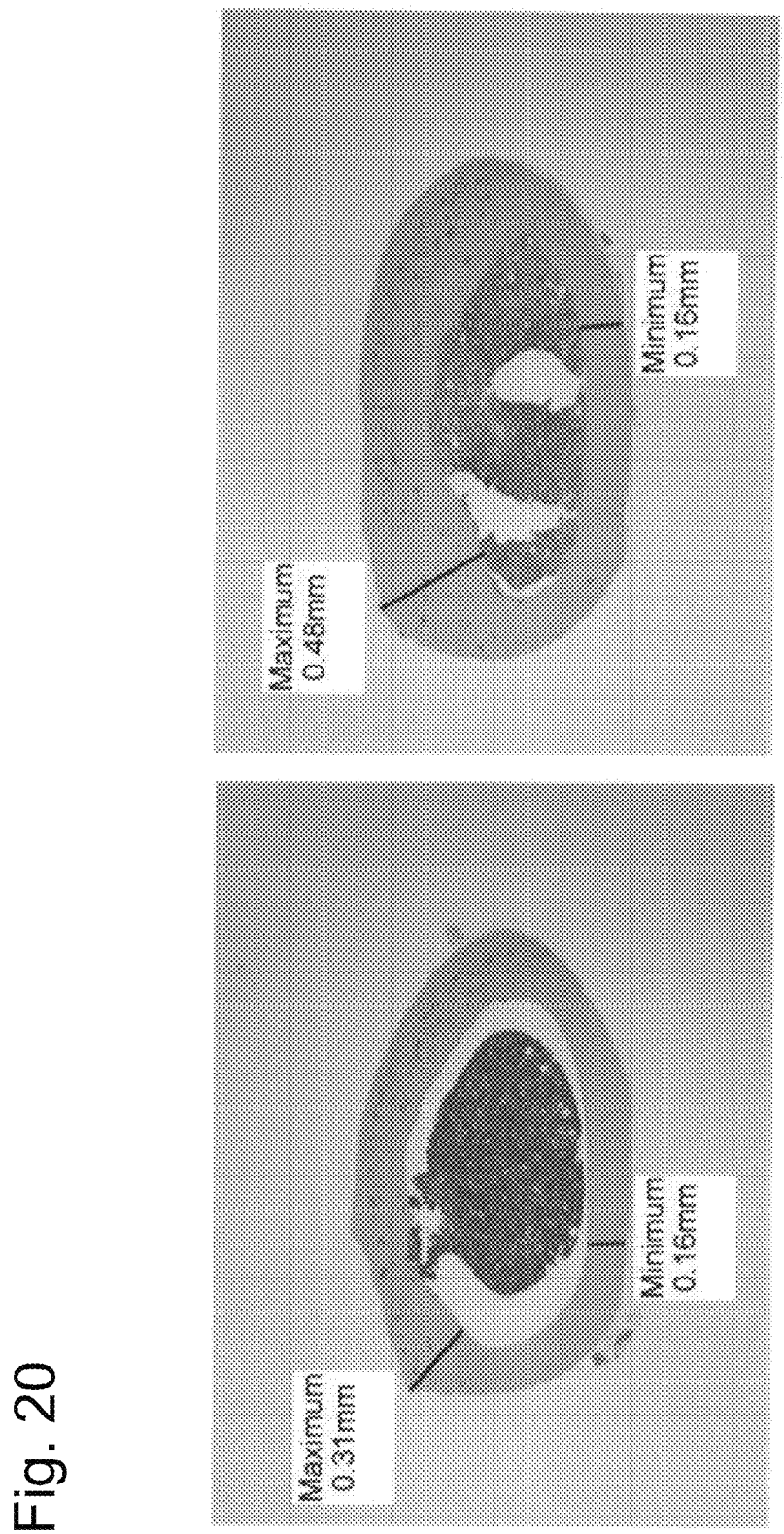
FIG. 20 shows images of H&E stained pathological sections of the femurs (at a site 50% away from the proximal end) of the 12-week-old UShFZD1crd-hFcm KI chimeric mouse (right diagram) and the control mouse (left diagram).
Figure 21:
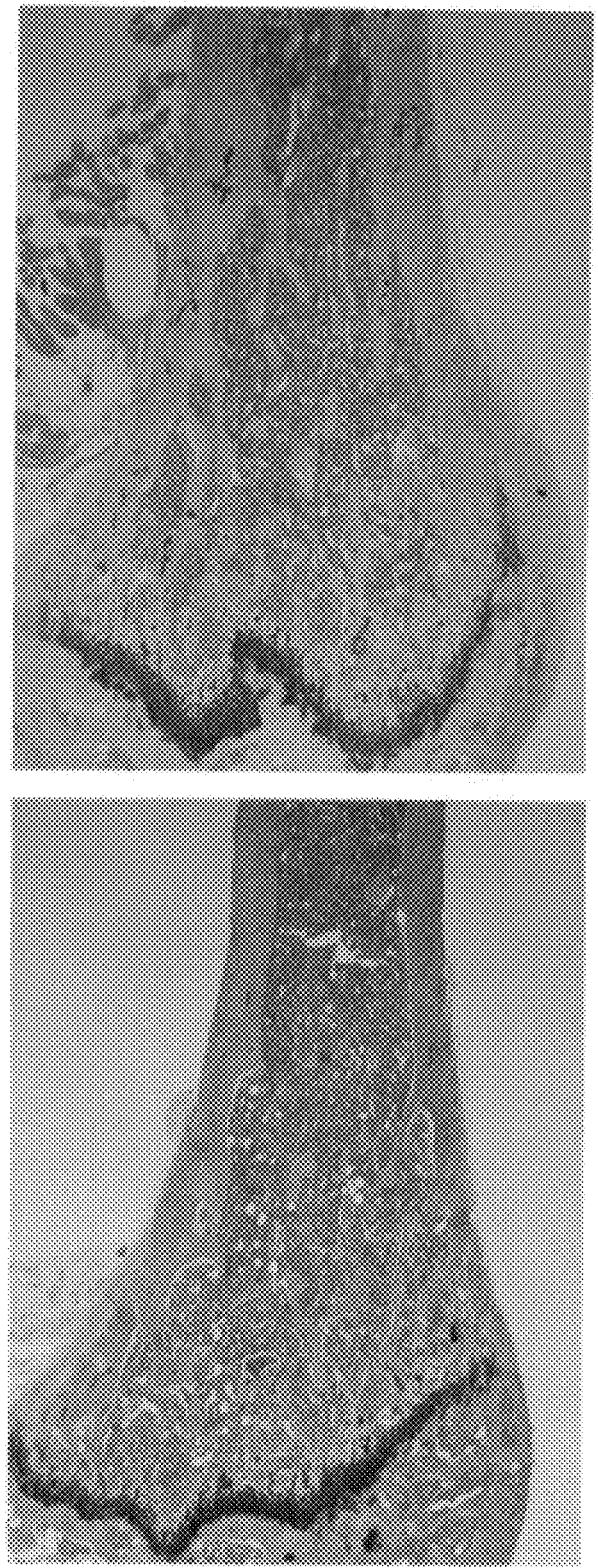
FIG. 21 shows images of H&E stained pathological sections of the femurs of the 12-week-old UShFZD1crd-hFcm KI chimeric mouse (right diagram) and the control mouse (left diagram).

The increased cancellous bone was observed in all the 6 UShFZD1crd-hFcm KI chimeric mice subjected to necropsy compared with 6 control mice. Further, transected sections obtained from 3 femoral sites (i.e., sites 30%, 50%, and 80% away from the proximal end) were subjected to measurement of the diaphyseal wall thickness. As a result, the average minimum wall thickness at a site 30% away from the proximal end and the average maximum wall thickness at a site 50% away from the proximal end were found to be larger than those of the control group (FIGS. 19 and 20, Table 24).

TABLE 24

| Age/sex/transgene | Minimum diaphyseal Wall thickness at site 30% away from proximal end (mm) Average | Maximum diaphyseal wall thickness at site 50% away from proximal end (mm) Average |
|---|---|---|
| 12 W♂ UShFZD1crd-hFcm KI/12 W control | 0.21/0.19 | 0.47/0.34 |

17-6-2. Sternum

Figure 22:
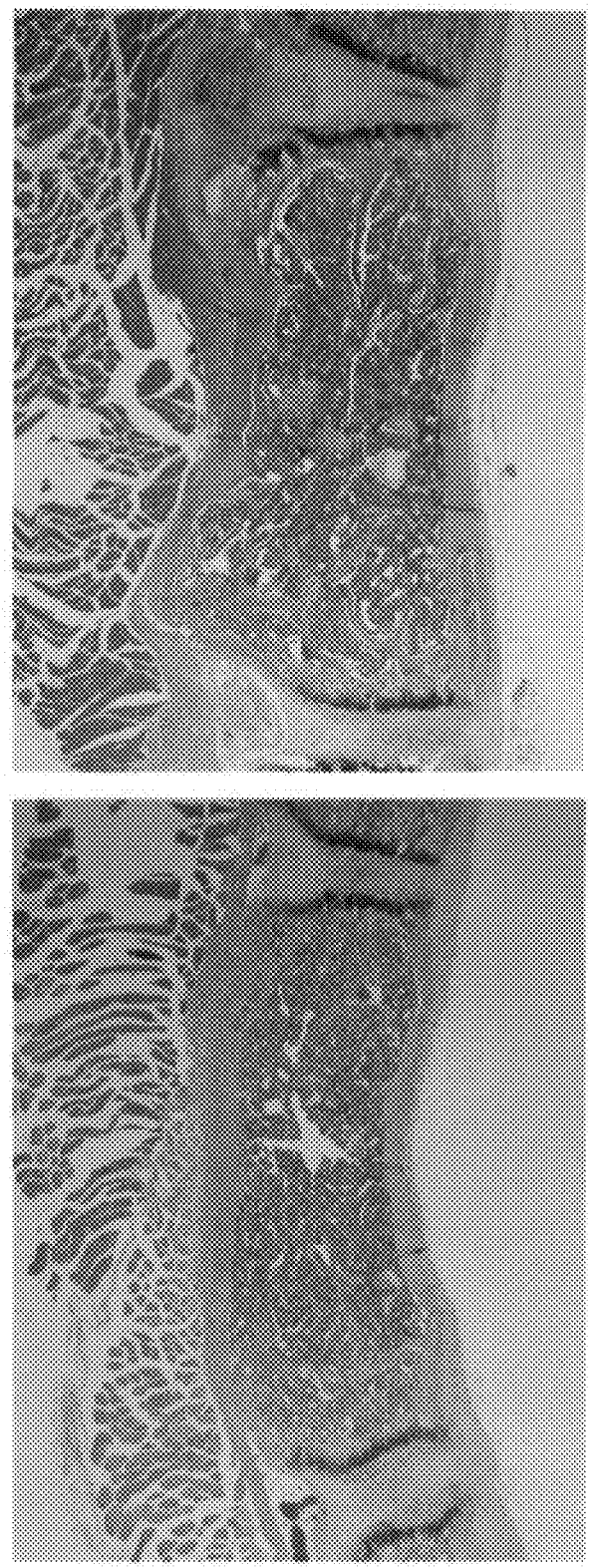
FIG. 22 shows images of H&E stained pathological sections of the sternums of the 12-week-old UShFZD1crd-hFcm KI chimeric mouse (right diagram) and the control mouse (left diagram).

The increased cancellous bone was observed in all of the 6 UShFZD1crd-hFcm KI chimeric mice subjected to necropsy compared with 6 control mice (FIG. 22).

The above results demonstrate that the thickened femoral diaphyseal wall, the increased cancellous bone, and the increased sternal cancellous bone may have been caused by overexpression of the fusion protein of human FZD1 extracellular cysteine-rich domain and human Fc mutant.

17-7. Biochemical Analysis of Serum

Six 12-week-old UShFZD1crd-hFcm KI male chimeric mice and 6 male control mice were exsanguinated under ether anesthesia to prepare serum samples. With the use of Hitachi 7180 (Hitachi Science Systems Ltd., Japan), serum samples were subjected to biochemical analysis (LDH activity, GOT activity, GPT activity, CK activity, ALP activity, AMY activity, LAP activity, LIP activity, T-CHO concentration, F-CHO concentration, LDL-CHO concentration, HDL-CHO concentration, TG concentration, PL concentration, GLU concentration, GA %, UA concentration, BUN concentration, CREA concentration, T-BIL concentration, D-BIL concentration, TP concentration, ALB concentration, A/G ratio, IP concentration, Ca concentration, Mg concentration, Na concentration, K concentration, Cl concentration, Fe concentration, UIBC concentration, and TIBC concentration). As a result, the values obtained with the use of the UShFZD1crd-hFcm KI chimeric mice were not significantly different from those of the control mice.

Example 18

The calvarial thickness of the cranium and the bone strength of the femur obtained from the mice to which the mFZD1crd-hFcm recombinant had been administered (described in Example 12) were measured.

18-1. Measurement of Calvarial Thickness of Cranium

Toluidine blue-stained cranium samples were prepared, and the calvarial thickness (μm) of the outer surface of the cranium to the parietal temporal suture (the squamous border) was measured while excluding the areas 0.6 mm each to the right and the left of the sagittal suture.

As a result of measurement of the calvarial thickness using 5 female control mice and 5 female mice to which the mFZD1crd-hFcm recombinant had been administered, the value of the mice to which the mFZD1crd-hFcm recombinant had been administered (average: 219.4 μm) was found to have increased compared with that of the control group (average: 213.9 μm). This suggests that the increased calvarial thickness of the cranium may have been caused by administration of the recombinant mFZD1crd-hFcm.

18-2. Measurement of Bone Strength of Femur

The femur samples were obtained at necropsy and subjected to a three-point bending test. When conducting a test, the span of the support points was set as 6 mm, and a load was applied at the midpoint of the span to measure the maximum load (N).

As a result of measurement of the maximum load of femur samples obtained from 5 female control mice and 5 female mice to which the recombinant mFZD1crd-hFcm had been administered, the measured values of the group of mice to which the recombinant mFZD1crd-hFcm had been administered were found to have increased (average: 31.3 N) compared with the values of the control group (average: 26.2 N). This indicates that the increased maximum load of the femur may have been caused by administration of the recombinant mFZD1crd-hFcm.

Example 19

Analysis Using USmFZD2crd-hFcm KI Chimeric Mouse Prepared in Accordance with the Method Described in Example 9

19-1. Blood Cell Analysis

Six 8-week-old USmFZD2crd-hFcm KI female chimeric mice, six 8-week-old USmFZD2crd-hFcm KI male chimeric mice, eleven 8-week-old female control mice, eleven 8-week-old male control mice, six 15-week-old USmFZD2crd-hFcm KI female chimeric mice, six 15-week-old USmFZD2crd-hFcm KI male chimeric mice, eleven 15-week-old female control mice, and eleven 15-week-old male control mice were subjected to orbital blood sampling using a glass capillary under ether anesthesia, and the obtained blood samples were subjected to blood component analysis using ADVIA120 (Bayer Medical Ltd., Japan) (blood components: erythrocyte counts, hemoglobin, hematocrit, MCH, MCHC, reticulocyte counts, leukocyte counts, blood platelet counts, lymphocyte counts, neutrophil counts, monocyte counts, eosinophil counts, and basophil counts). As a result, the values obtained with the use of the USmFZD2crd-hFcm KI chimeric mice were not significantly different from those of the control mice at ages of 8 weeks and 15 weeks.

19-2. Biochemical Analysis of Serum

Six USmFZD2crd-hFcm KI female chimeric mice, 6 USmFZD7crd-hFcm KI male chimeric mice, 9 female control mice, and 9 male control mice at age of 16 weeks were exsanguinated under ether anesthesia to prepare serum samples. With the use of Hitachi 7180 (Hitachi Science Systems Ltd., Japan), serum samples were subjected to biochemical analysis (LDH activity, GOT activity, GPT activity, CK activity, ALP activity, AMY activity, LAP activity, LIP activity, T-CHO concentration, F-CHO concentration, LDL-CHO concentration, HDL-CHO concentration, TG concentration, PL concentration, GLU concentration, GA %, UA concentration, BUN concentration, CREA concentration, T-BIL concentration, D-BIL concentration, TP concentration, ALB concentration, A/G ratio, IP concentration, Ca concentration, Mg concentration, Na concentration, K concentration, Cl concentration, Fe concentration, UIBC concentration, and TIBC concentration). As a result, the values obtained with the use of the USmFZD2crd-hFcm KI chimeric mice were not significantly different from those of the control mice.

19-3. Confirmation of Expression of the Fusion Protein of Mouse FZD2 Extracellular Cysteine-rich Domain and Human Fc Mutant in USmFZD2crd-hFcm KI Chimeric Mouse The concentration of the fusion protein of mouse FZD2 extracellular cysteine-rich domain and human Fc mutant existing in the serum samples of the 16-week-old USmFZD2crd-hFcm KI chimeric mice (6 female mice and 6 male mice) prepared in accordance with the method described in Example 2 was detected via ELISA. Mice were raised while humidity, temperature, and light conditions were kept constant (temperature: 22° C.; humidity: 55%; and 12 hours light and 12 hours darkness) where they were allowed to freely eat feeds (CE-2, CLEA Japan, Inc.).

As a result, the average concentration among the 16-week-old female USmFZD2crd-hFcm KI chimeric mice was found to be 31.5 μg/ml, that among the 16-week-old male mice was found to be 26.2 μg/ml, and the concentrations assayed with the use of control mice (6 female mice and 6 male mice) were lower than the detection limit.

The above results suggest that the fusion protein of FZD2 extracellular cysteine-rich domain and human Fc mutant is expressed in mouse bodies and circulated in the blood.

19-4. Tibial Bone Morphometry Using 18-week-old USmFZD2crd-hFcm KI Chimeric Mouse 19-4-1. Bone Morphometry In order to obtain the data regarding the mineral apposition rate, the mineralization surface, and the bone formation rate, calcein (Product Number: 340-00433, Dojindo Laboratories, Japan) was dissolved in an aqueous solution of 2% sodium bicarbonate (Product Number: 37116-00, Kanto Chemical Co., Inc., Japan), and the prepared calcein solution (a calcium chelator) was administered subcutaneously at a dose of 16 mg/kg prior to necropsy. Administration was performed 6 days and 1 day before necropsy. Tibiae were sampled at necropsy, the samples of undemineralized tibial sections were prepared, and the samples were then subjected to toluidine blue staining (TB staining), alkaline phosphatase staining (ALP staining), and tartrate-resistant acid phosphatase staining (TRAP staining). In order to prepare section samples, the tibia samples were embedded in GMA (glycolmethacrylate) resin in advance. The metaphyseal secondary cancellous bones of the obtained samples of undemineralized sections were subjected to measurement of the bone volume/tissue volume as the bone structure parameter (BV/TV), the osteoblast number/bone perimeter as the bone formation parameter (Ob.N/B.Pm), the osteoblast surface/bone surface (Ob.S/BS), the osteoid/bone volume (OV/BV), the mineral apposition rate (MAR), the mineralization surface/bone surface (MS/BS), the bone formation rate/bone surface (BFR/BS), the osteoclast number/bone perimeter as the bone absorption parameter (Oc.N/B.Pm), and the osteoclast surface/bone surface (Oc.S/BS). In Example 19-2 and subsequent examples, all the control data were obtained from 16-week-old mice.

19-4-2. Bone Volume/Tissue Volume

As a result of the measurement of the bone volume/tissue volume of tibia samples obtained from 6 female control mice and 3 female USmFZD2crd-hFcm KI chimeric mice subjected to necropsy, increases were observed in the bone volume/tissue volume of the group of USmFZD2crd-hFcm KI chimeric mice compared with the control group. This suggests the possibility that the increased bone volume/tissue volume of the secondary cancellous bone of the tibial metaphyseal end was caused by overexpression of the fusion protein of mouse FZD2 extracellular cysteine-rich domain and human Fc mutant.

Further, tibia samples obtained from 5 male control mice and 4 male USmFZD2crd-hFcm KI chimeric mice subjected to necropsy were subjected to measurement of the bone volume/tissue volume. As a result, the bone volume/tissue volume of the group of USmFZD2crd-hFcm KI chimeric mice was found to have increased compared with that of the control group. The results demonstrate the possibility that increased bone volume/tissue volume in the secondary cancellous bone of the tibial metaphyseal end was induced by overexpression of the mouse FZD2 extracellular cysteine-rich domain-human Fc mutant fusion constructs in male mice as well as in female mice (Table 25).

TABLE 25

| Age/sex/transgene | Bone volume/tissue volum (BV/TV) Average |
|---|---|
| 18 W ♀ USmFZD2crd-hFcm KI/16 W control | 15.3/4.5 |
| 18 W ♂ USmFZD2crd-hFcm KI/16 W control | 14.9/5.3 |

19-4-3. Osteoblast Number/Bone Perimeter, Osteoblast Surface/Bone Surface, and Osteoid/Bone Volume The osteoblast number/bone perimeter, the osteoblast surface/bone surface, and the osteoid/bone volume were measured using the tibia samples obtained from 6 female control mice and 3 female USmFZD2crd-hFcm KI chimeric mice subjected to necropsy. As a result, substantially no differences were observed between the chimeric mice and the control mice.

Further, the osteoblast number/bone perimeter, the osteoblast surface/bone surface, and the osteoid/bone volume were measured using the tibia samples obtained from 5 male control mice and 4 male USmFZD2crd-hFcm KI chimeric mice subjected to necropsy. As a result, substantially no differences were observed between the chimeric mice and the control mice. This indicates that male mice would not be influenced by overexpression of the fusion protein of mouse FZD2 extracellular cysteine-rich domain and human Fc mutant as with the case of female mice (Table 26).

TABLE 26

| Age/sex/transgene | Osteoblast number/bone perimeter (Ob.N/B.Pm) Average | Osteoblast surface/bone surface (Ob.S/BS) Average | Osteoid volume/bone volume (OV/BV) Average |
|---|---|---|---|
| 18 W ♀ USmFZD2crd-hFcm KI/16 W control | 1257.7/1197 | 15.5/15.2 | 1.3/1.28 |
| 18 W ♂ USmFZD2crd-hFcm KI/16 W control | 566.1/626 | 6.1/7.5 | 0.2/0.38 |

19-4-4. Mineral Apposition Rate, Mineralization Surface, and Bone Formation Rate As a result of measurement of the mineral apposition rate, the mineralization surface, and the bone formation rate of the tibia samples obtained from 6 female control mice and 3 female USmFZD2crd-hFcm KI chimeric mice subjected to necropsy, increases were observed in the mineral apposition rate, the mineralization surface, and the bone formation rate of the group of USmFZD2crd-hFcm KI chimeric mice compared with the control group. This indicates that mineralization of the secondary cancellous bone of the tibial metaphyseal end may have been accelerated by overexpression of the fusion protein of mouse FZD2 extracellular cysteine-rich domain and human Fc mutant.

As a result of measurement of the mineral apposition rate, the mineralization surface, and the bone formation rate of the tibia samples obtained from 5 male control mice and 4 male USmFZD1crd-hFcm KI chimeric mice subjected to necropsy, further, increases was observed in the mineralization surface compared with the control group (Table 27).

TABLE 27

| Age/sex/transgene | Mineral apposition rate (MAR) Average | Mineralization surface/bone surface (MS/BS) Average | Bone formation rate/bone surface (BFR/BS) Average |
|---|---|---|---|
| 18 W ♀ USmFZD2crd-hFcm KI/16 W control | 1.7/1.2 | 22.7/17.1 | 14.1/7.9 |
| 18 W ♂ USmFZD2crd-hFcm KI/16 W control | 0.8/0.9 | 13.4/11.3 | 4.2/3.8 |

19-4-5. Osteoclast Number/Bone Perimeter and Osteoclast Surface/Bone Surface

As a result of measurement of the osteoclast number/bone perimeter and the osteoclast surface/bone surface of the tibia samples obtained from 6 female control mice and 3 female USmFZD2crd-hFcm KI chimeric mice subjected to necropsy, both values were found to tend to decrease compared with the control group. This indicates that the osteoclast number/bone perimeter and the osteoclast surface/bone surface of the secondary cancellous bone of the tibial metaphyseal end may have been suppressed by overexpression of the fusion protein of mouse FZD2 extracellular cysteine-rich domain and human Fc mutant.

As a result of measurement of the osteoclast number/bone perimeter and the osteoclast surface/bone surface of the tibia samples obtained from 5 male control mice and 4 male USmFZD2crd-hFcm KI chimeric mice subjected to necropsy, both values were found to tend to decrease compared with the control group. This indicates that the osteoclast number/bone perimeter and the osteoclast surface/bone surface of the secondary cancellous bone of the tibial metaphyseal end may have been suppressed by overexpression of the fusion protein of mouse FZD2 extracellular cysteine-rich domain and human Fc mutant as with the case of female mice (Table 28).

TABLE 28

| Age/sex/transgene | Osteoclast number/bone perimete (Oc.N/B.Pm) Average | Osteoclast surface/bone surface (OC.S/BS) Average |
|---|---|---|
| 18 W ♀ USmFZD2crd-hFcm KI/16 W control | 112.6/181.8 | 1.6/1.9 |
| 18 W ♂ USmFZD2crd-hFcm KI/16 W control | 67.4/112.9 | 0.9/1.4 |

19-5. Measurement of Bone Strength

The femur samples were obtained at necropsy and subjected to a three-point bending test. When conducting a test, the span of the support points was set as 6 mm, and a load was applied at the midpoint of the span to measure the maximum load (N).

As a result of measurement of the maximum load of femur samples obtained from six 16-week-old female control mice and three 18-week-old USmFZD2crd-hFcm KI chimeric mice subjected to necropsy, the measured values were found to have increased in the group of USmFZD2crd-hFcm KI chimeric mice compared with the control group. This indicates that the increased maximum load of the femur may have been caused by overexpression of the fusion protein of mouse FZD2 extracellular cysteine-rich domain and human Fc mutant.

As a result of measurement of the maximum load of femur samples obtained from five 16-week-old male control mice and four 18-week-old male USmFZD2crd-hFcm KI chimeric mice subjected to necropsy, further, the measured values were found to have increased in the group of USmFZD2crd-hFcm KI chimeric mice compared with the control group. This indicates that the increased maximum load of the femur may have been induced by overexpression of the fusion protein of mouse FZD2 extracellular cysteine-rich domain and human Fc mutant as with the case of female mice (Table 29).

TABLE 29

| Age/sex/transgene | Maximum load (N) Average |
|---|---|
| 18 W♀ USmFZD2crd-hFcm KI/16 W control | 32.6/26.6 |
| 18 W♂ USmFZD2crd-hFcm KI/16 W control | 30.3/22.8 |

19-6. Analysis of Bone Structure of 18-week-old USmFZD2crd-hFcm KI Chimeric Mouse (3-Dimensional Microfocus X-ray CT)

The femur samples were obtained at necropsy, and the internal structure of the cancellous bone region of the distal femoral metaphysis was observed using a high-resolution microfocus X-ray CT scanner (micro-CT, Scan Xmate-L090, Comscantecno Co., Ltd., Japan) and the analytic software (TRY 3D-BON, Ratoc System Engineering Co., Ltd., Japan) in a non-invasive manner. The bone volume/tissue volume (BV/TV), the trabecular thickness (Tb. Th), the trabecular number (Tb. N), the trabecular separation (Tb. Sp), and trabecular spacing (Tb. Spac) were measured.

The internal structure of the cancellous bone of the femur samples obtained from 16-week-old control mice (6 female mice and 6 male mice) and 18-week-old USmFZD2crd-hFcm KI chimeric mice (3 female mice and 4 male mice) was observed via micro CT. The average bone volume/tissue volume, trabecular thickness, and trabecular number were found to have increased, and the average trabecular separation and trabecular spacing were found to have decreased in the group of USmFZD2crd-hFcm KI chimeric mice compared with the control group. This suggests that the increased bone volume/tissue volume, the increased trabecular thickness, the increased trabecular number, the decreased trabecular separation, and the decreased trabecular spacing in the cancellous bone of the distal femoral metaphysis may have been caused by overexpression of the fusion protein of mouse FZD2 extracellular cysteine-rich domain and human Fc mutant (Table 30).

TABLE 30

| Age/sex/transgene | Bone volume/tissue volume (BV/TV, %) Average | Trabecular thickness (Tb.Th, μm) Average | Trabecular number (Tb.N, 1/mm) Average | Trabecular separation (Tb.Sp, μm) Average | Trabecular spacing (Tb. Spac, μm) Average |
|---|---|---|---|---|---|
| 18 W♀ USmFZD2crd-hFcm KI/16 W control | 17.2/5 | 43.1/32.5 | 3.9/1.5 | 209.7/797.4 | 252.8/830 |
| 18 W♂ USmFZD2crd-hFcm KI/16 W control | 15.2/6 | 40.2/29.4 | 3.7/2 | 226.6/510.6 | 266.8/540 |

Example 20

Figure 23:
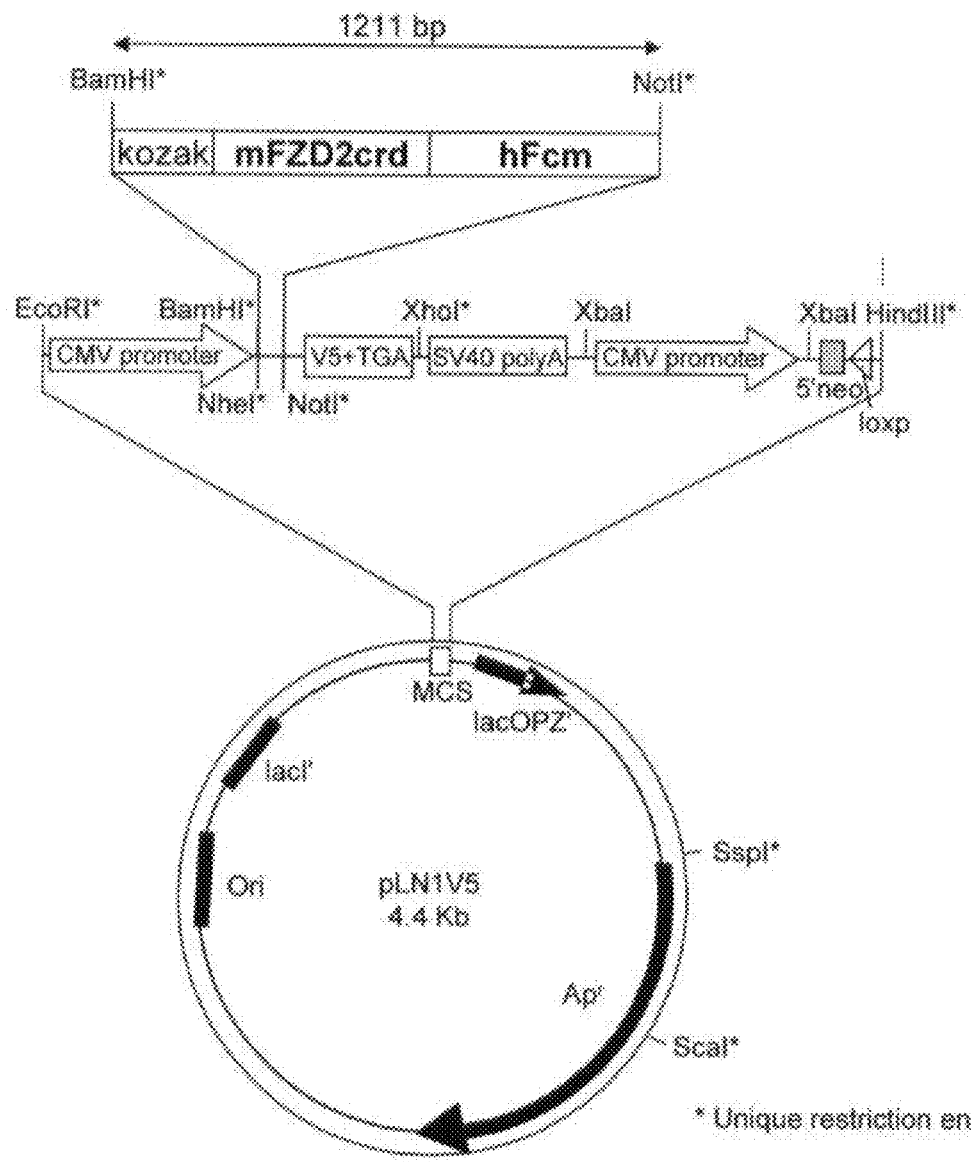
FIG. 23 shows a recombinant mFZD2crd-hFcm expression vector.

Expression and Preparation of Recombinant mFZD2crd-hFcm 20-1. Construction of Recombinant mFZD2crd-hFcm Expression Vector The recombinant mFZD2crd-hFcm expression vector was constructed using the PCR primers shown in SEQ ID NOs: 54, 66, 67, and 68 and, as templates, mouse FZD2 cDNA (SEQ ID NO: 58) and hFcm cDNA (SEQ ID NO: 3) in accordance with the method described in Example 7-1 (FIG. 23).

20-1-1. Construction of pLN1V5 Vector

Sense oligo DNA (V5S) having the BamHI, NheI, and SalI sites at the 5' terminus and the XhoI site at the 3' terminus (a V5 tag and a stop codon) and corresponding antisense oligo DNA (V5AS) were synthesized.

V5S:
(SEQ ID NO: 50)
GATCCGCTAGCGTCGACGGTAAGCCTATCCCTAACCCTCTCCTCGGTCTC

GATTCTACGTGAC

V5AS:
(SEQ ID NO: 51)
TCGAGTCACGTAGAATCGAGACCGAGGAGAGGGTTAGGGATAGGCTTACC

GTCGACGCTAGCG

Oligo DNA synthesized above was introduced into the BamHI-XhoI site on the pLN1 vector described in the report of Kakeda et al. (Gene Ther., 12, 852-856, 2005) to construct the pLN1 V5 vector.

20-1-2. Synthesis of mFZD2crd-hFcm DNA Fragment

155Fc_BHIkozakFw:
(SEQ ID NO: 66)
TAAAGGATCCCGGCCACCATGCGGGCCCGCAGCGCCCTGC

155Fc_mFZD2G1SA3 primer:
(SEQ ID NO: 67)
GTCTGAAGACCTAGGCTCGGCTAGCGCAGGAGCTCCGTCC G1SA_5 primer:
(SEQ ID NO: 54)
GCCGAGCCTAGGTCTTCAGAC hFc-NotI-Rv:
(SEQ ID NO: 68)
ATAGTTTAGCGGCCGCTCATTTACCCGGAGACAGG A reaction solution was prepared using Prime STAR HS DNA Polymerase (Takara Bio Inc., Japan) in accordance with the instructions, 10 pmol each primers shown in SEQ ID NOs: 66 and 67 and mouse FZD2 cDNA (SEQ ID NO: 58) as a template were added to 50 of the reaction solution, the resultant was incubated at 98° C. for 1 minute, an amplification cycle of 98° C. for 10 seconds, 62° C. for 5 seconds, and 72° C. for 40 seconds was repeated 30 times, and the resulting 543-bp amplified fragment was separated and recovered with 0.8% gel. The amplified fragment (BamHI mFZD2crd hFcm) was recovered from the gel using the QIAquick Gel Extraction Kit (Qiagen, Japan) in accordance with the instructions.

Similarly, a reaction solution was prepared using Prime STAR HS DNA Polymerase (Takara Bio Inc., Japan) in accordance with the instructions, 10 pmol each primers shown in SEQ ID NOs: 54 and 68 and hFcm cDNA (SEQ ID NO: 3) as a template were added to 50 µl of the reaction solution, the resultant was incubated at 98° C. for 1 minute, an amplification cycle of 98° C. for 10 seconds, 62° C. for 5 seconds, and 72° C. for 40 seconds was repeated 30 times, and the resulting 718-bp amplified fragment was separated and recovered with 0.8% gel. The amplified fragment (hFcm NotI) was recovered from the gel using the QIAquick Gel Extraction Kit (Qiagen, Japan) in accordance with the instructions.

The amplified DNA fragments obtained via the two above PCR procedures (i.e., BamHI mFZD2 hFcm and hFcm NotI) were added in amounts of 10 µl each, the solution was heated at 100° C. for 3 minutes, and the temperature was lowered to room temperature, followed by annealing of the hFcm region. Thereafter, 10 pmol each primers shown in SEQ ID NOs: 66 and 68 were added, an extension reaction was carried out at 72° C. for 5 minutes, the resultant was heated at 98° C. for 1 minute, an amplification cycle of 98° C. for 10 seconds, 62° C. for 5 seconds, and 72° C. for 1 minutes was repeated 30 times, and the resulting 1,240-bp amplified fragment was separated and recovered with 0.8% gel. The amplified fragment was recovered from the gel using the QIAquick Gel Extraction Kit (Qiagen, Japan) in accordance with the instructions.

20-1-3. Construction of mFZD2crd-hFcm Recombinant Expression Vector

The PCR-amplified fragment recovered in Example 20-1-2 was digested with the BamHI and NotI restriction enzymes (Roche Diagnostics, K. K., Japan), and the resultant was separated and recovered with 0.8% agarose gel. The enzyme-treated fragment was recovered from the gel using the QIAquick Gel Extraction Extraction Kit (Qiagen, Japan) in accordance with the instructions. The NotI site was added to the pLN1V5 vector prepared in Example 20-1-1 to prepare another vector, and the obtained enzyme-treated fragment was introduced into the BamHI•NotI site of the resulting vector to construct the mFZD2crd-hFcm recombinant expression vector (FIG. 23).

A polynucleotide sequence (1206 bp, SEQ ID NO: 69) comprising a region from the initiation codon to the termination codon of cDNA of the recombinant mFZD2crd-hFcm and an amino acid sequence (401 amino acids, SEQ ID NO: 70) comprising the signal sequence of mFZD2-hFcm encoded by the cDNA are shown below. In SEQ ID NOs: 69 and 70, the underlined portion represents the mouse FZD2 signal sequence.

```
SEQ ID NO: 69:
ATGCGGGCCCGCAGCGCCCTGCCCCGCAGCGCCCTGCCCCGCCTGCTGCTGCCAC

TGCTGCTGCTGCCGGCCGCCGGACCGGCCCAGTTCCACGGGGAGAAGGGCATCTC

CATCCCGGACCACGGCTTCTGCCAGCCCATCTCCATCCCGCTGTGCACGGACATC

GCCTACAACCAGACCATCATGCCCAACCTTCTTGGCCACACGAACCAGGAAGACG

CGGGCCTGGAGGTGCATCAGTTCTACCCGCTGGTGAAGGTGCAGTGCTCGCCCGA

GCTGCGCTTCTTCCTGTGCTCCATGTACGCGCCGGTGTGCACAGTGCTGGAGCAG

GCCATCCCGCCGTGCCGCTCCATCTGCGAGCGCGCGCGCCAAGGCTGCGAGGCGC

TCATGAACAAGTTCGGCTTCCAATGGCCCGAGCGCCTCCGCTGCGAGCATTTCCC

GCGTCACGGCGCGGAGCAGATCTGCGTGGGCCAGAACCACTCGGAGGACGGAGC

TCCTGCGCTAGCCGAGCCTAGGTCTTCAGACAAAACTCACACATGCCCACCGTGC

CCAGCACCTGAAGCCGAGGGGGCCCCGTCAGTCTTCCTCTTCCCCCCAAAACCCA

AGGACACCCTCATGATCTCCCGGACCCCTGAGGTCACATGCGTGGTGGTGGACGT

GAGCCACGAAGACCCTGAGGTCAAGTTCAACTGGTACGTGGACGGCGTGGAGGT

GCATAATGCCAAGACAAAGCCGCGGGAGGAGCAGTACAACAGCACGTACCGTGT

GGTCAGCGTCCTCACCGTCCTGCACCAGGACTGGCTGAATGGCAAGGAGTACAA

GTGCGCCGTCTCCAACAAAGCCCTCCCAGCCTCCATCGAGAAAACCATCTCCAAA

GCCAAAGGGCAGCCCCGAGAACCACAGGTGTACACCCTGCCCCCATCCCGGGAT
```

-continued

```
GAGCTGACCAAGAACCAGGTCAGCCTGACCTGCCTGGTCAAAGGCTTCTATCCCA

GCGACATCGCCGTGGAGTGGGAGAGCAATGGGCAGCCGGAGAACAACTACAAGA

CCACGCCTCCCGTGCTGGACTCCGACGGCTCCTTCTTCCTCTACAGCAAGCTCACC

GTGGACAAGAGCAGGTGGCAGCAGGGGAACGTCTTCTCATGCTCCGTGATGCAT

GAGGCTCTGCACAACCACTACACGCAGAAGAGCCTCTCCCTGTCTCCGGGTAAAT

GA
```

SEQ ID NO: 70:
MRARSALPRSALPRLLLPLLLLPAAGPAQFHGEKGISIPDHGFCQPISIPLCTDIAYNQTI

MPNLLGHTNQEDAGLEVHQFYPLVKVQCSPELRFFLCSMYAPVCTVLEQAIPPCRSIC

ERARQGCEALMNKFGFQWPERLRCEHFPRHGAEQICVGQNHSEDGAPALAEPRSSD

KTHTCPPCPAPEAEGAPSVFLFPPKPKDTLMISRTPEVTCVVVDVSHEDPEVKFNWYV

DGVEVHNAKTKPREEQYNSTYRVVSVLTVLHQDWLNGKEYKCAVSNKALPASIEKT

ISKAKGQPREPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSLSPGK 20-2. Transient Expression of Recombinant mFZD2crd-hFcm Using Recombinant mFZD2crd-hFcm Expression Vector 20-2-1. Preparation of Expression Vector Used for Gene Introduction The recombinant mFZD2crd-hFcm expression vector obtained in Example 20-1-3 was introduced into E. coli DH5α, and DNA was prepared from the transformant cells using a plasmid purification kit (Qiagen plasmid Maxi kit, Qiagen, Japan).

20-2-2. Introduction of Vector into Cultured Cell and Secretory Expression

FreeStyle CHO-S cells (Invitrogen, Japan) were cultured in FreeStyle CHO expression medium (Invitrogen, Japan) at 37° C. in the presence of 5% $CO_2$ at 125 rpm to reach a cell density of $1 \times 10^5$ to $4 \times 10^6$ cells/ml. When culture was conducted using 1 liter of medium, 20 ml of Opti PRO SFM (Invitrogen, Japan) was added to 1 mg of the expression vector, and 12.5 ml of Opti PRO SFM (Invitrogen, Japan) was added to 7.5 ml of polyethyleneimine (PEI). These solutions were mixed with each other immediately thereafter, and the resultant was incubated at room temperature for 10 minutes. Thereafter, the expression vector treated in the manner described above was added to a medium containing $2 \times 10^9$ cells/1 of FreeStyle CHO-S cells, and culture was conducted for 3 days.

20-3. Purification and Preparation of Recombinant mFZD2crd-hFcm 20-3-1. Pretreatment of Culture Supernatant After culture, the supernatant was recovered, filtered through a 0.22 μm filter (TC Filter Unit, PES, Nalgene), and then cooled to 4° C. (in a low-temperature chamber). When cryopreserved, the resultant was thawed and then filtered through a 0.22 μm filter again.

20-3-2. Antibody Affinity Chromatography

The acidic buffer used is 1 liter of a solution comprising 3.43 g of citrate monohydrate (Nakalai Tesque, Inc., Japan, MW: 210.14), 0.90 g of trisodium citrate (Wako Pure Chemical Industries, Ltd., MW: 258.07), and 8.77 g of sodium chloride (Junsei Chemical Co., Ltd., MW: 58.44) dissolved in Milli-Q water. The neutralizing buffer used is 1 liter of a solution comprising 13.1 g of sodium dihydrogen phosphate dihydrate (Kanto Chemical Co., Inc., MW: 156.01), 41.5 g of disodium hydrogen phosphate dodecahydrate (Wako Pure Chemical Industries, Ltd., MW: 358.14), and 8.77 g of sodium chloride (Junsei Chemical Co., Ltd., MW: 58.44) dissolved in Milli-Q water.

The pretreated culture supernatant (1 liter) was applied to a protein A column (Hi Trap Protein A HP, 5 ml, GE Healthcare Bio-Sciences Corp., Japan) equilibrated with PBS (Dulecco's phosphate buffered saline, SIGMA). Thereafter, the column was washed with 25 ml or more PBS, and the column was washed again with 30 ml of PBS. After the completion of the washing procedure, 25 ml of acidic buffer was added to the column, and the target protein was recovered. AKTAexplorer 10s (GE Healthcare Bio-Sciences Corp, Japan) was used in the separation and purification procedure. Endotoxin was removed before use.

20-3-3. Preparation of Purified Authentic Sample

The purified authentic sample obtained in Example 20-3-2 was concentrated using an ultrafilter membrane VIVAS-PIN20 10,000 MWCO PES (Sartorius Stedim Japan K. K., Japan). Thereafter, the buffer in the sample was substituted with PBS using NAP-25 Columns (GE Healthcare Bio-Sciences Corp, Japan). After the completion of the concentration and substitution procedure, the resultanting solution was filtered through a 0.22 μm filter (Millex GV, Millipore, Japan). The concentration procedure was carried out in a clean bench to the extent possible. All the procedures conducted in Example 20-3 other than those conducted in a clean bench were carried out in a low-temperature chamber (+4° C.) or on ice. A protein concentration was determined by measuring a specific absorbance at 280 nm (A280 nm) (E1%, 1 cm=9.7).

Example 21

Figure 24:
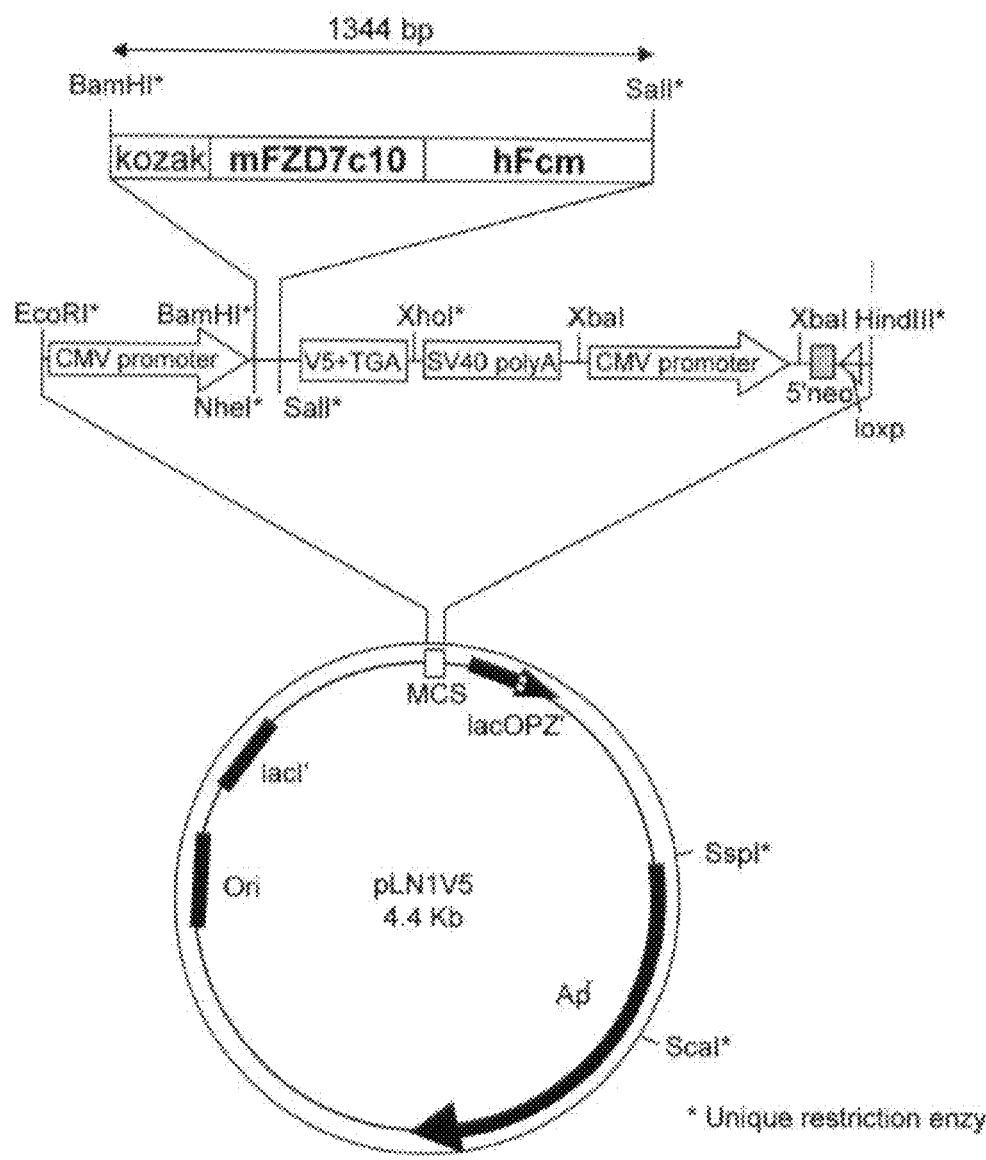
FIG. 24 shows a recombinant mFZD7c10-hFcm expression vector.

Expression and Preparation of Recombinant mFZD7c10-hFcm 21-1. Construction of Recombinant mFZD7c10-hFcm Expression Vector The recombinant mFZD7c10-hFcm expression vector was constructed using the PCR primers shown in SEQ ID NOs: 55 and 71 and, as templates, mouse FZD7 cDNA (SEQ ID NO: 1) and hFcm cDNA (SEQ ID NO: 3) in accordance with the method described in Example 7-1 (FIG. 24).

21-1-1. Construction of pLN1V5 Vector

Sense oligo DNA (V5S) having the BamHI, NheI, and SalI sites at the 5' terminus and the XhoI site at the 3' terminus (a V5 tag and a stop codon) and corresponding antisense oligo DNA (V5AS) were synthesized.

```
V5S:
                                            (SEQ ID NO: 50)
GATCCGCTAGCGTCGACGGTAAGCCTATCCCTAACCCTCTCCTCGGTCTC

GATTCTACGTGAC

V5AS:
                                            (SEQ ID NO: 51)
TCGAGTCACGTAGAATCGAGACCGAGGAGAGGGTTAGGGATAGGCTTACC

GTCGACGCTAGCG
```

Oligo DNA synthesized above was introduced into the BamHI-XhoI site on the pLN1 vector described in the article of Kakeda et al. (Gene Ther., 12, 852-856, 2005) to construct the pLN1V5 vector.

21-1-2. Synthesis of mFZD7c10-hFcm DNA Fragment

```
pLN1V5-BHIkozakFw:
                                            (SEQ ID NO: 71)
TAAAGGATCCCGGCCACCATGGAGACAGACACACTCCTG SalIG1SARv:
                                            (SEQ ID NO: 55)
TAAAGTCGACTCATTTACCCGGAGACAGGG
```

A reaction solution was prepared using Prime STAR HS DNA Polymerase (Takara Bio Inc., Japan) in accordance with the instructions, 10 pmol each primers shown in SEQ ID NOs: 71 and 55 and, as a template, the fusion DNA construct encoding the fusion protein of mouse Igk signal sequence, Frizzled 7 mouse CRD, and mutant human IgG1-derived Fc protein prepared in accordance with the method described in Example 1 were added to 50 µl of the reaction solution, the mixture was incubated at 98° C. for 10 seconds, an amplification cycle of 98° C. for 10 seconds, 57° C. for 5 seconds, and 72° C. for 2 minutes was repeated 20 times, and the resulting 1,367-bp amplified fragment was separated and recovered with 0.8% gel. The amplified fragment (BamHI mFZD7c10hFcm SalI) was recovered from the gel using the QIAquick Gel Extraction Kit (Qiagen, Japan) in accordance with the instructions.

21-1-3. Construction of Recombinant mFZD7c10-hFcm Expression Vector

The PCR-amplified fragment recovered in Example 21-1-2 was digested with the BamHI and SalI restriction enzymes (Roche Diagnostics, Japan), and the resultant was separated and recovered with 0.8% agarose gel. The enzyme-treated fragment was recovered from the gel using the QIAquick Gel Extraction Kit (Qiagen, Japan) in accordance with the instructions. The obtained enzyme-treated fragment was introduced into the BamHI•SalI site of the pLN1V5 vector prepared in Example 21-1-1 to construct the mFZD7c10-hFcm recombinant expression vector (FIG. 24).

The polynucleotide sequence (1339 bp, SEQ ID NO: 72) comprising a region from the initiation codon to the termination codon of cDNA of the recombinant mFZD7c10-hFcm, and the amino acid sequence (365 amino acids, SEQ ID NO: 73) comprising the mouse Igk signal sequence encoded by the cDNA, are shown below. In SEQ ID NOs: 72 and 73, the underlined portion represents the mouse Igk signal sequence, the region marked by the solid box represents the cysteine-rich domain comprising N-terminal cysteine 1 to cysteine 10 of the mouse Frizzled 7 extracellular region protein (the minimum CRD region), and the region marked by the double underline represents hFcm.

```
SEQ ID NO: 72:
ATGGAGACAGACACACTCCTGTTATGGGTACTGCTGCTCTGGGTTCCAGGTGAGAGTGCAGAGAAGTGTT

GGATGCAACCTCTGTGGCCATTATGATACTCCATGCCTCTCTGTTCTTGATCACTATAATTAGGGCATTT

GTCACTGGTTTTAAGTTTCCCCAGTCCCCTGAATTTTCCATTTTCTCAGAGTGATGTCCAAAATTATTCT

TAAAAATTTAAATAAAAAGGTCCTCTGCTGTGAAGGCTTTTATACATATATAACAATAATCTTTGTGTTT

ATCATTCCAGGTTCCACTGGCTGCCAGCCCATCTCCATCCCGTTGTGCACGGATATCGCCTACAACCAGA

CCATCCTGCCCAACCTGCTGGGCCACACGAACCAAGAGGACGCGGGCCTCGAGGTGCACCAGTTCTACCC

TCTGGTAAAGGTGCAGTGTTCTCCTGAGCTACGCTTCTTCTTATGCTCTATGTACGCACCCGTGTGCACC

GTGCTCGACCAAGCCATTCCTCCGTGCCGTTCCTTGTGCGAGCGCGCCCGACAGGGCTGCGAGGCGCTCA

TGAACAAGTTCGGCTTCCAGTGGCCAGAGCGGTTGCGCTGCGAGAACTTCCCAGTGCACGGTGCCGGCGA

GATCTGCGCCGAGCCTAGGTCTTCAGACAAAACTCACACATGCCCACCGTGCCCAGCACCTGAAGCCGAG

GGGGCCCCGTCAGTCTTCCTCTTCCCCCCAAAACCCAAGGACACCCTCATGATCTCCCGGACCCCTGAGG

TCACATGCGTGGTGGTGGACGTGAGCCACGAAGACCCTGAGGTCAAGTTCAACTGGTACGTGGACGGCGT

GGAGGTGCATAATGCCAAGACAAAGCCGCGGGAGGAGCAGTACAACAGCACGTACCGTGTGGTCAGCGTC

CTCACCGTCCTGCACCAGGACTGGCTGAATGGCAAGGAGTACAAGTGCGCCGTCTCCAACAAAGCCCTCC

CAGCCTCCATCGAGAAAACCATCTCCAAAGCCAAAGGGCAGCCCCGAGAACCACAGGTGTACACCCTGCC

CCCATCCCGGGATGAGCTGACCAAGAACCAGGTCAGCCTGACCTGCCTGGTCAAAGGCTTCTATCCCAGC
```

```
GACATCGCCGTGGAGTGGGAGAGCAATGGGCAGCCGGAGAACAACTACAAGACCACGCCTCCCGTGCTGG

ACTCCGACGGCTCCTTCTTCCTCTACAGCAAGCTCACCGTGGACAAGAGCAGGTGGCAGCAGGGGAACGT

CTTCTCATGCTCCGTGATGCATGAGGCTCTGCACAACCACTACACGCAGAAGAGCCTCTCCCTGTCTCCG

GGTAAATGA
```

SEQ ID NO: 73:
```
METDTLLLWVLLLWVPGSTGCQPISIPLCTDIAYNQTILPNLLGHTNQEDAGLEVHQFYPLVKVQCSPEL

RFFLCSMYAPVCTVLDQAIPPCRSLCERARQGCEALMNKFGFQWPERLRCENFPVHGAGEICAEPRSSDK

THTCPPCPAPEAEGAPSVFLFPPKPKDTLMISRTPEVTCVVVDVSHEDPEVKFNWYVDGVEVHNAKTKPR

EEQYNSTYRVVSVLTTVLHOALNGKEYKCAVSNKALPASIEKTISKAKGQPREPQVYTLPPSRDELTKNQ

VSLTCLVKGFYPSDIAVEWESNGQPENNYKTTPPVLDSDGSFFLYSKLTVDKSRWQQGNVFSCSVMHEAL

HNHYTQKSLSLSPGK
```

21-2. Transient Expression of Recombinant mFZD7c10-hFcm Using Recombinant mFZD7c10-hFcm Expression Vector 21-2-1. Preparation of Expression Vector Used for Gene Introduction The recombinant mFZD7c10-hFcm expression vector obtained in Example 21-1-3 was introduced into *E. coli* DH5α, and DNA was prepared from the transformant using a plasmid purification kit (Qiagen plasmid Maxi kit, Qiagen, Japan).

21-2-2. Introduction of Vector into Cultured Cell and Secretory Expression

FreeStyle 293F cells (Invitrogen Japan K. K.) are cultured in FreeStyle 293 expression medium (Invitrogen Japan K. K.) at 37° C. in the presence of 5% $CO_2$ at 125 rpm to reach a cell density of $2\times10^5$ to $3\times10^6$ cells/ml. When culture was conducted using 1 liter of medium, 35 ml of the Opti-MEM I reduced serum medium (Invitrogen, Japan) was added to 1 mg of the expression vector, 33.7 ml of the Opti-MEM I reduced serum medium (Invitrogen, Japan) was added to 1.3 ml of the 293 fectin transfection reagent (Invitrogen, Japan), and the resulting solutions were incubated at room temperature for 5 minutes. These solutions were mixed with each other after incubation, and the resultant was further incubated at room temperature for 20 to 30 minutes. Thereafter, the expression vector treated in the manner described above was added to a medium containing $1\times10^9$ cells/l of FreeStyle 293F cells, and culture was conducted for 3 days.

21-3. Purification and Preparation of Recombinant mFZD7c10-hFcm 21-3-1. Pretreatment of Culture Supernatant After culture, the supernatant was recovered, filtered through a 0.22 μm filter (TC Filter Unit, PES, Nalgene), and then cooled to 4° C. (in a low-temperature chamber). When cryopreserved, the resultant was thawed and then filtered through a 0.22 μm filter again.

21-3-2. Antibody Affinity Chromatography

The acidic buffer used is 1 liter of a solution comprising 3.895 g of citrate monohydrate (Nakalai Tesque, Inc., Japan, MW: 210.14), 0.38 g of trisodium citrate (Wako Pure Chemical Industries, Ltd., MW: 258.07), and 8.77 g of sodium chloride (Junsei Chemical Co., Ltd., MW: 58.44) dissolved in Milli-Q water. The neutralizing buffer used is 1 liter of a solution comprising 13.1 g of sodium dihydrogen phosphate dihydrate (Kanto Chemical Co., Inc., MW: 156.01), 41.5 g of disodium hydrogen phosphate dodecahydrate (Wako Pure Chemical Industries, Ltd., MW: 358.14), and 8.77 g of sodium chloride (Junsei Chemical Co., Ltd., MW: 58.44) dissolved in Milli-Q water.

The pretreated culture supernatant (1 liter) was applied to a protein G column (Hi Trap Protein G HP, 5 ml, GE Healthcare Bio-Sciences Corp., Japan) equilibrated with PBS (Dulecco's phosphate buffered saline, SIGMA). Thereafter, the column was washed with 25 ml or more PBS, the column was then washed with 25 ml or more buffer prepared by adding NaCl to PBS to bring the NaCl concentration to 1.85 mol/l, and the column was washed again with 30 ml of PBS. After the completion of the washing procedure, 25 ml of acidic buffer was added to the column, and the target protein was recovered. The target protein was neutralized immediately after recovery with the use of a neutralizing buffer. AKTAexplorer 10s (GE Healthcare Bio-Sciences Corp, Japan) was used in the separation and purification procedure. Endotoxin was removed before use.

21-3-3. Preparation of Purified Authentic Sample

The buffer in the purified authentic sample obtained in Example 21-3-2 was substituted with PBS using an ultrafilter membrane VIVASPIN20 10,000 MWCO PES (Sartorius Stedim Japan K. K., Japan), and then concentrated. After the completion of the concentration and substitution procedure, the resultant was filtered through a 0.22 μm filter (Millex GV, Millipore, Japan). The concentration procedure was carried out in a clean bench to the extent possible. All the procedures conducted in Example 21-3 other than those conducted in a clean bench were carried out in a low-temperature chamber (+4° C.) or on ice. The final purification product was subjected to SDS-PAGE (CBB staining), and monomers were detected under reducing conditions. A protein concentration was determined by measuring a specific absorbance at 280 nm (A280 nm) (E1%, 1 cm=10.5).

Example 22

Analysis of Mouse to which Recombinant mFZD7c10-hFcm had been Administered 22-1. Administration of Recombinant mFZD7c10-hFcm In order to evaluate the efficacy of the recombinant mFZD7c10-hFcm, the recombinant mFZD7c10-hFcm was administered to mice. Since the recombinant mFZD7c10-hFcm is a protein comprising the human antibody Fc region, the possibility of suppressing the activity of the recombinant mFZD7c10-hFcm upon production of the neutralizing antibody in the body resulting from administration was considered. In order to reduce a risk of production of the neutralizing antibody, accordingly, the homozygote (the 97 KD mouse, CLEA Japan, Inc., Proc. Natl. Acad. Sci., U.S.A., 97: 722-7, 2000) obtained via back-crossing of the immunoglobulin μ chain gene knockout mice lacking functional B lymphocytes and producing no antibodies into the MCH (ICR) strain (CLEA Japan, Inc.) was used for the administration experiment. During the administration period, 97 KD mice were raised while humidity, temperature, and light conditions were kept constant (temperature: 22° C.; humidity: 55%; 12 hours of light and 12 hours of darkness) where they were allowed to freely eat feeds (CE-2, CLEA Japan, Inc.). Mice were divided into four groups (each group consisting of 5 mice) based on body weights at age of 6 weeks on the previous day of the initiation of administration (i.e., day-1). The recombinant mFZD7c10-hFcm was diluted with PBS to adjust the protein concentration to 5 mg/ml, and the resultant was cryopreserved, the cryopreserved product was thawed at the time of use, and the resulting solution was administered through the caudal vein to the group of the mFZD7c10-hFcm recombinant administration in amounts of 200 μl per mouse at 1 mg/dose once every 10 days (7 times in total) (q10d7). As a control group, a non-treatment group was designated. The day of the initial administration was designated as day 0, the recombinant protein was administered to the caudal vein every 10 days up to day 60 (seven times in total), and all mice were subjected to necropsy on day 70.

22-2. Measurement of Bone Strength

The right femur samples were obtained at necropsy and subjected to a three-point bending test. When conducting a test, the span of the support points was set as 6 mm, and a load was applied at the midpoint of the span to measure the maximum load (N).

As a result of measurement of the maximum load of femur samples obtained from 5 control mice and 5 mice to which the mFZD7c10-hFcm recombinant had been administered, the measured values were found to have increased in the group of mice to which the mFZD7c10-hFcm recombinant had been administered (average: 28) compared with the values of the control group (average: 26). This indicates that the increased maximum load of the femur may have been induced by administration of the mFZD7c10-hFcm recombinant.

22-3. Analysis of Bone Structure of Mouse to which Recombinant mFZD7c10-hFcm had been Administered (3-Dimensional Microfocus X-ray CT)

Figure 25:
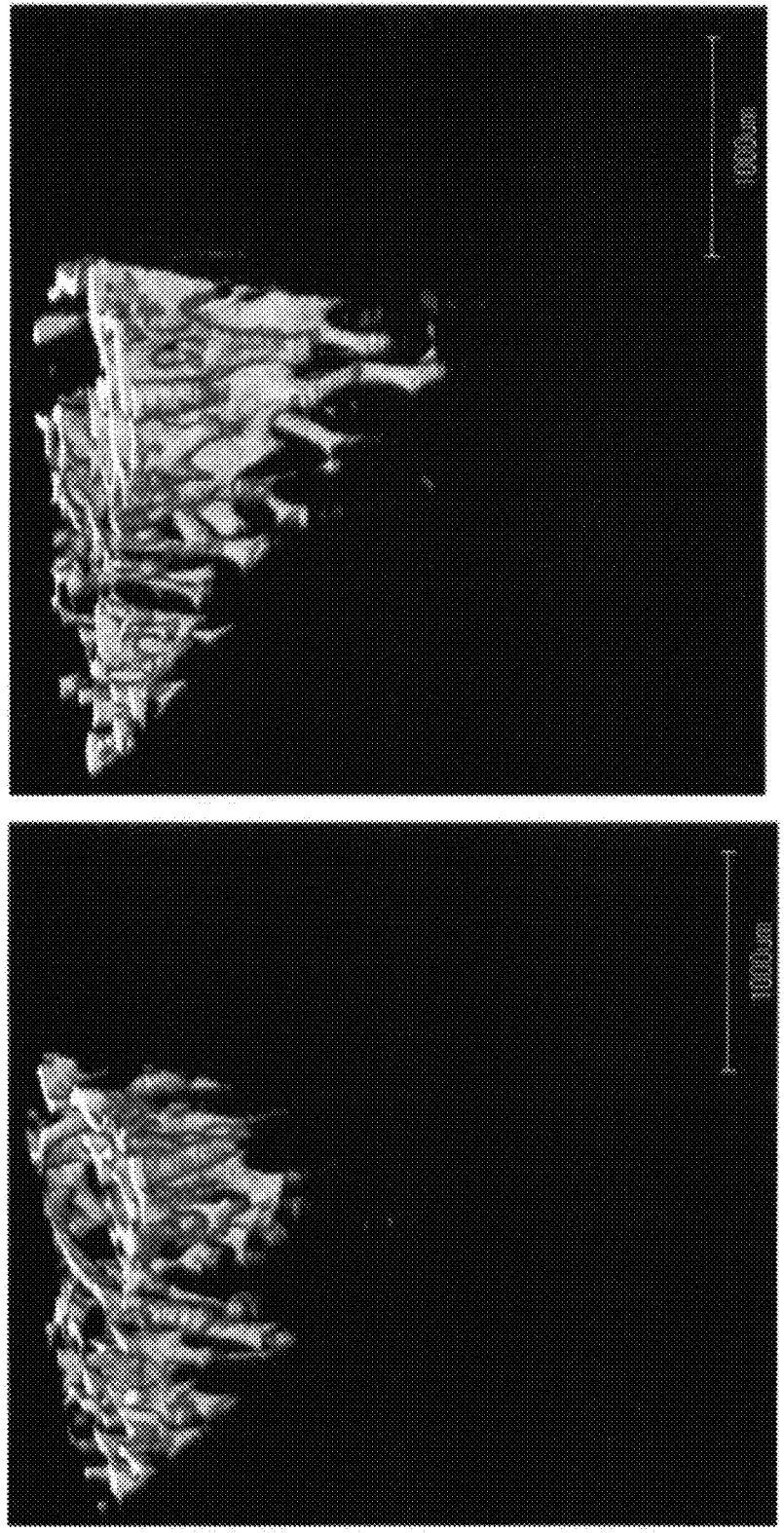
FIG. 25 shows 3D micro CT images of tibial cancellous bones of a mouse to which a recombinant mFZD7c10-hFcm protein has been administered (right diagram) and the control mouse (left diagram).

The left tibia samples were obtained at necropsy, and the internal structure of the cancellous bone region of the proximal tibial metaphysis was observed using a high-resolution microfocus X-ray CT scanner (micro-CT, Scan Xmate-L090, Comscantecno Co., Ltd., Japan) and the analytic software (TRY 3D-BON, Ratoc System Engineering Co., Ltd., Japan) in a non-invasive manner. The bone volume/tissue volume (BV/TV), the trabecular thickness (Tb. Th), the trabecular number (Tb. N), the trabecular separation (Tb. Sp), and trabecular spacing (Tb. Spac) were measured (FIG. 25).

The internal structure of the cancellous bone of the tibia samples obtained from 5 control mice and 5 mice to which the mFZD7c10-hFcm recombinant had been administered was observed via micro CT. As a result, the average bone volume/tissue volume, trabecular thickness, and trabecular number were found to have increased, and the average trabecular separation and trabecular spacing were found to have decreased in the group of mice to which the recombinant mFZD7c10-hFcm had been administered compared with the control group. This suggests that the increased bone volume/tissue volume, the increased trabecular thickness, the increased trabecular number, the decreased trabecular separation, and the decreased trabecular spacing in the cancellous bone of the proximal tibial metaphysis may have been induced by administration of the recombinant mFZD7c10-hFcm (Table 31).

TABLE 31

| Recombinant administration/ no recombinant administration | Bone volume/tissue volume (BV/TV, %) Average | Trabecular thickness (Tb.Th, μm) Average | Trabecular number (Tb.N, 1/mm) Average | Trabecular separation (Tb.Sp, μm) Average | Trabecular spacing (Tb. Spac, μm) Average |
|---|---|---|---|---|---|
| mFZD7c10-hFcm group vs non-treatment group | 8.2/6.7 | 39.4/35.1 | 2/1.8 | 451.7/519.4 | 491.1/554.5 |

All publications, patents, and patent applications cited herein are incorporated herein by reference in their entirety.

INDUSTRIAL APPLICABILITY

The present invention can increase bone mass, bone density, and/or bone strength. Accordingly, bone diseases resulting from osteoporosis, osteoarthritis, articular rheumatism, or malignant tumors, and various diseases and disorders associated therewith can be treated without causing side effects.

SEQUENCE LISTING FREE TEXT

SEQ ID NOs: 3 and 4: Human IgG1 Fc mutants
SEQ ID NO: 5: DNA encoding a fusion protein
SEQ ID NO: 6: Fusion protein
SEQ ID NO: 9: DNA encoding a fusion protein
SEQ ID NO: 10: Fusion protein
SEQ ID NO: 13: DNA encoding a fusion protein
SEQ ID NO: 14: Fusion protein
SEQ ID NO: 17: DNA encoding a fusion protein
SEQ ID NO: 18: Fusion protein
SEQ ID NOs: 27 to 31: Fusion proteins
SEQ ID NOs: 38 to 43: DNAs encoding fusion proteins
SEQ ID NOs: 50 and 51: Sense oligo DNAs
SEQ ID NOs: 52 to 55: Primers
SEQ ID NO: 56: DNA encoding a fusion protein
SEQ ID NO: 57: Fusion protein
SEQ ID NOs: 62 and 63: Primers
SEQ ID NO: 64: DNA encoding a fusion protein
SEQ ID NO: 65: Fusion protein
SEQ ID NOs: 66 to 68: Primers
SEQ ID NO: 69: DNA encoding a fusion protein
SEQ ID NO: 70: Fusion protein
SEQ ID NO: 71: Primer
SEQ ID NO: 72: DNA encoding a fusion protein
SEQ ID NO: 73: Fusion protein

The invention claimed is:

1. A method for increasing bone mass, bone density and/or bone strength, comprising:
administering to a mammalian animal with a bone disease an effective amount of a pharmaceutical composition which comprises, as an active ingredient, a protein comprising an extracellular cystein-rich domain comprising the amino acid sequence of SEQ ID NO: 26, to increase bone mass, bone density and/or bone strength; wherein the method excludes treatment of malignant tumors of bone.

2. The method according to claim 1, wherein the mammalian animal is a human.

3. The method according to any one of claim 1, wherein the protein is a fragment of an extracellular region of a Frizzled 2 receptor, wherein said fragment comprises the extracellular cysteine-rich domain.

4. The method according to claim 1, wherein the extracellular cysteine-rich domain comprises an amino acid sequence spanning from the 1st cysteine residue on the N-terminal side to the 10th cysteine residue in the amino acid sequence of an extracellular region protein of the Frizzled 2 receptor.

5. The method according to claim 3, wherein the protein comprises the amino acid sequence of SEQ ID NO: 25.

6. The method according to claim 1, wherein the protein is a recombinant protein.

7. The method according to claim 1, wherein the protein is a fusion protein of the extracellular cysteine-rich domain or a mutant thereof and a mammalian immunoglobulin Fc protein or a mutant thereof prepared so that antibody dependent cellular cytotoxicity (ADCC) and complement dependent cytotoxicity (CDC) activities are lowered.

8. The method according to claim 7, wherein Fc protein comprises the amino acid sequence of SEQ ID NO: 4.

9. The method according to claim 7, wherein the fusion protein comprises the amino acid sequence as shown in any of SEQ ID NO: 31.

10. The method according to claim 1, wherein the protein is chemically modified.

11. The method according to claim 10, wherein the chemical modification is a binding of one or more polyethylene glycol molecules.

12. The method according to claim 10, wherein the chemical modification is a binding of one or more sugar chains.

13. The method according to claim 1, wherein the composition is simultaneously or continuously administered in combination with another therapeutic agent for increasing bone mass, bone density and/or bone strength.

* * * * *